(12) United States Patent
Kaiser et al.

(10) Patent No.: US 9,186,181 B2
(45) Date of Patent: Nov. 17, 2015

(54) METHOD AND APPARATUS FOR DISTRACTING A JOINT

(71) Applicant: Pivot Medical, Inc., Sunnyvale, CA (US)

(72) Inventors: William Kaiser, San Jose, CA (US); Julian Nikolchev, Portola Valley, CA (US); Brett M. Page, Sunnyvale, CA (US); Ed Carcamo, Millbrae, CA (US)

(73) Assignee: Pivot Medical, Inc., Sunnyvale, CA (US)

( * ) Notice: Subject to any disclaimer, the term of this patent is extended or adjusted under 35 U.S.C. 154(b) by 190 days.

(21) Appl. No.: 13/843,808

(22) Filed: Mar. 15, 2013

(65) Prior Publication Data

US 2014/0066939 A1  Mar. 6, 2014

Related U.S. Application Data

(63) Continuation-in-part of application No. 12/726,268, filed on Mar. 17, 2010, now Pat. No. 8,900,243, and a continuation-in-part of application No. 13/292,002, filed on Nov. 8, 2011, now Pat. No. 8,956,365.

(Continued)

(51) Int. Cl.
*A61B 17/58* (2006.01)
*A61B 17/60* (2006.01)
(Continued)

(52) U.S. Cl.
CPC .............. *A61B 17/66* (2013.01); *A61B 17/025* (2013.01); *A61B 2017/00557* (2013.01); *A61B 2017/0275* (2013.01); *A61F 2002/30754* (2013.01)

(58) Field of Classification Search
USPC ................ 606/57, 63, 90, 105, 192–198, 282
See application file for complete search history.

(56) References Cited

U.S. PATENT DOCUMENTS 3,840,014 A  10/1974  Ling et al.
3,875,595 A  4/1975  Froning
(Continued)

FOREIGN PATENT DOCUMENTS

DE  25 01 080  7/1976
EP  0 507 645  10/1992
(Continued)

OTHER PUBLICATIONS

Byrd, Operative Hip Arthroscopy, 2005, 146-147.
(Continued)

*Primary Examiner* — Sameh Boles
(74) *Attorney, Agent, or Firm* — Pandiscio & Pandiscio

(57) ABSTRACT

A method for creating space in a joint formed at the convergence of two bones, comprising applying force to a body part so as to separate the two bones from one another by a distance which is greater than the distance that they are normally separated from one another when the joint is in a healthy state, whereby to distract the joint and create an intrajoint space; inserting an assembly of three balloons into the intrajoint space while the assembly is in a contracted condition; expanding the assembly of three balloons within the intrajoint space; and reducing the force applied to the body part so that the joint is supported on the assembly of three balloons, with the two bones remaining separated from one another by a distance which is greater than the distance that they are normally separated from one another when the joint is in a healthy state.

17 Claims, 109 Drawing Sheets

Related U.S. Application Data

(60) Provisional application No. 61/210,315, filed on Mar. 17, 2009, provisional application No. 61/268,340, filed on Jun. 11, 2009, provisional application No. 61/278,744, filed on Oct. 9, 2009, provisional application No. 61/336,284, filed on Jan. 20, 2010, provisional application No. 61/411,179, filed on Nov. 8, 2010, provisional application No. 61/452,477, filed on Mar. 14, 2011, provisional application No. 61/492,640, filed on Jun. 2, 2011, provisional application No. 61/702,630, filed on Sep. 18, 2012.

(51) Int. Cl.
*A61F 2/00* (2006.01)
*A61B 17/66* (2006.01)
*A61B 17/02* (2006.01)
*A61B 17/00* (2006.01)
*A61F 2/30* (2006.01)

(56) References Cited

U.S. PATENT DOCUMENTS

| | | |
|---|---|---|
| 4,467,479 A | 8/1984 | Brody |
| 4,669,106 A | 5/1987 | Ammerman |
| 4,772,266 A | 9/1988 | Groshong |
| 4,874,375 A | 10/1989 | Ellison |
| 4,928,670 A | 5/1990 | DeLorenzo |
| 4,968,316 A | 11/1990 | Hergenroeder |
| 4,983,165 A | 1/1991 | Loilerman |
| 4,995,875 A | 2/1991 | Coes |
| 5,019,042 A | 5/1991 | Sahota |
| 5,071,410 A | 12/1991 | Pazell |
| 5,171,297 A | 12/1992 | Barlow et al. |
| 5,176,683 A | 1/1993 | Kimsey et al. |
| 5,213,112 A | 5/1993 | Niwa et al. |
| 5,234,455 A | 8/1993 | Mulhollan |
| 5,290,220 A | 3/1994 | Guhl |
| 5,342,386 A | 8/1994 | Trotta |
| 5,344,459 A | 9/1994 | Swartz |
| 5,411,475 A | 5/1995 | Atala et al. |
| 5,411,517 A | 5/1995 | Guignard |
| 5,704,372 A | 1/1998 | Moll et al. |
| 5,725,545 A | 3/1998 | Bircoll |
| 5,738,629 A | 4/1998 | Moll et al. |
| 5,803,902 A | 9/1998 | Sienkiewicz et al. |
| 5,817,123 A | 10/1998 | Kieturakis et al. |
| 5,820,595 A | 10/1998 | Parodi |
| 5,827,289 A | 10/1998 | Reiley et al. |
| 5,827,318 A | 10/1998 | Bonutti |
| 5,888,220 A | 3/1999 | Felt et al. |
| 6,017,305 A | 1/2000 | Bonutti |
| 6,123,718 A | 9/2000 | Tu et al. |
| 6,171,236 B1 | 1/2001 | Bonutti |
| 6,187,023 B1 | 2/2001 | Bonutti |
| 6,217,548 B1 | 4/2001 | Tsugita et al. |
| 6,468,289 B1 | 10/2002 | Bonutti |
| 6,482,209 B1 | 11/2002 | Engh et al. |
| 6,575,979 B1 | 6/2003 | Cragg |
| 6,616,673 B1 | 9/2003 | Stone et al. |
| 6,620,181 B1 | 9/2003 | Bonutti |
| 6,855,149 B2 | 2/2005 | Dye |
| 6,859,661 B2 | 2/2005 | Tuke |
| 6,860,892 B1 | 3/2005 | Tanaka et al. |
| 7,166,121 B2 | 1/2007 | Reiley et al. |
| 7,189,229 B2 | 3/2007 | Lopath et al. |
| 7,201,756 B2 | 4/2007 | Ross et al. |
| 7,216,385 B2 | 5/2007 | Hill |
| 7,217,273 B2 | 5/2007 | Bonutti |
| 7,226,462 B2 | 6/2007 | Tanaka et al. |
| 7,241,303 B2 | 7/2007 | Reiss et al. |
| 7,300,448 B2 | 11/2007 | Criscuolo et al. |
| 7,488,337 B2 | 2/2009 | Saab et al. |
| 8,491,567 B2 | 7/2013 | Magnin et al. |
| 2001/0001128 A1 | 5/2001 | Holman et al. |
| 2001/0001315 A1 | 5/2001 | Bates et al. |
| 2002/0151880 A1 | 10/2002 | Lafontaine |
| 2002/0177866 A1 | 11/2002 | Weikel et al. |
| 2003/0004460 A1 | 1/2003 | Bedell |
| 2003/0033017 A1 | 2/2003 | Lotz et al. |
| 2003/0220698 A1 | 11/2003 | Mears et al. |
| 2004/0059290 A1 | 3/2004 | Palasis |
| 2004/0098015 A1 | 5/2004 | Weikel et al. |
| 2004/0106861 A1 | 6/2004 | Leither |
| 2004/0116848 A1 | 6/2004 | Gardeski et al. |
| 2004/0138754 A1 | 7/2004 | Lang et al. |
| 2004/0236342 A1 | 11/2004 | Ferree et al. |
| 2004/0249360 A1 | 12/2004 | Spehalski |
| 2005/0267482 A1 | 12/2005 | Hyde, Jr. |
| 2006/0015171 A1 | 1/2006 | Armstrong |
| 2006/0184246 A1 | 8/2006 | Zwirkowski |
| 2006/0259063 A1 | 11/2006 | Bates et al. |
| 2006/0293685 A1 | 12/2006 | Stone et al. |
| 2006/0293750 A1 | 12/2006 | Sherman et al. |
| 2007/0173946 A1 | 7/2007 | Bonutti |
| 2007/0213759 A1 | 9/2007 | Osborne et al. |
| 2007/0219561 A1 | 9/2007 | Lavallee et al. |
| 2007/0255394 A1 | 11/2007 | Ryan |
| 2007/0265635 A1 | 11/2007 | Torrie et al. |
| 2007/0288095 A1 | 12/2007 | Wirtel et al. |
| 2008/0019004 A1 | 1/2008 | Hansen |
| 2008/0045967 A1 | 2/2008 | Lubinus et al. |
| 2008/0109004 A1 | 5/2008 | Da Rold et al. |
| 2009/0112214 A1* | 4/2009 | Philippon et al. ............... 606/90 |
| 2009/0299282 A1 | 12/2009 | Lau et al. |
| 2009/0312807 A1 | 12/2009 | Boudreault et al. |
| 2010/0312179 A1 | 12/2010 | Nikolchev et al. |

FOREIGN PATENT DOCUMENTS

| | | |
|---|---|---|
| FR | 1 061 009 | 4/1954 |
| FR | 2 734 146 | 11/1996 |
| WO | WO 92/22259 | 12/1993 |
| WO | WO 97/27897 | 8/1997 |
| WO | WO 99/59669 | 11/1999 |
| WO | WO 00/23009 | 4/2000 |
| WO | WO 01/45601 | 6/2001 |
| WO | WO 2005/048812 | 6/2005 |
| WO | WO 2007/080454 | 7/2007 |
| WO | WO 2007/092841 | 8/2007 |
| WO | WO 2009/042429 | 4/2009 |
| WO | WO 2009/152470 | 12/2009 |
| WO | WO 2010/097724 | 2/2010 |
| WO | WO 2010/107949 | 9/2010 |
| WO | WO 2012/064786 | 5/2012 |

OTHER PUBLICATIONS

Ganz et al., Surgical dislocation of the adult hip, The Journal of Bone and Joint Surgery, Nov. 2001, vol. 83-B, No. 8, 1119-1124.

Aydin et al., A New Noninvasive Controlled Intra-articular Ankle Distraction Technique on a Cadaver Model, Arthroscopy: The Journal of Arthroscopic and Related Surgery, Aug. 2006. vol. 22, No. 8, 905.e1-905.e3.

Burman, Arthroscopy or the Direct Visuaiization of Joints: An Experimental Cadaver Study, The Journal of Bone and Joint Surgery, Oct. 1931, vol. XIII, No. 4, 669-695.

Dienst, Chapter 11: Hip Arthroscopy Without Traction, 2005, pp. 170 and 174.

Dienst et al., Hip Arthroscopy Without Traction: In Vivo Anatomy of the Peripheral Hip Joint cavity, Arthrotscopy: The Journal of Arthroscopic and Related Surgery, Nov.-Dec. 2001, vol. 17, No. 9, 924-931.

Sartoretti et al., Angioplasty Balloon Catheters Used for Distraction of the Ankle Joint, Arthroscopy: The Journal of Arthroscopic and Related Surgery, Feb. 1996, vol. 12, No. 1, 82-86.

Shetty et al., Hip arthroscopy: current concepts and review of literature, Br J Sports Med, 2007, 41, 64-68.

(56) References Cited

OTHER PUBLICATIONS

Tan et al., Contribution of Acetabular Labrum to Articulating Surface Area and Femoral Head Coverage in Adult Hip Joints: An Anatomic Study in Cadavers, The American Journal of Orthopedics, Nov. 2001, vol. XXX. No. 11, 809-812.

Dienst et al., Effects of Traction, Distension, and Joint Position on Distraction of the Hip Joint. An Experimental Study in Cadavers, Arthrosoopy: The Journal of Arthroscopic and Related Surgery. Oct. 2002, vol. 18. No. 8, 865-871.

* cited by examiner

CAM-TYPE FEMOROACETABULAR IMPINGEMENT (FAI)
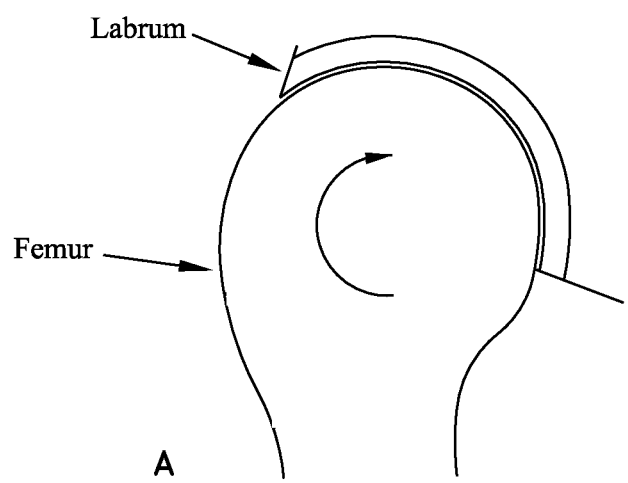
CAM INJURY TO THE LABRUM
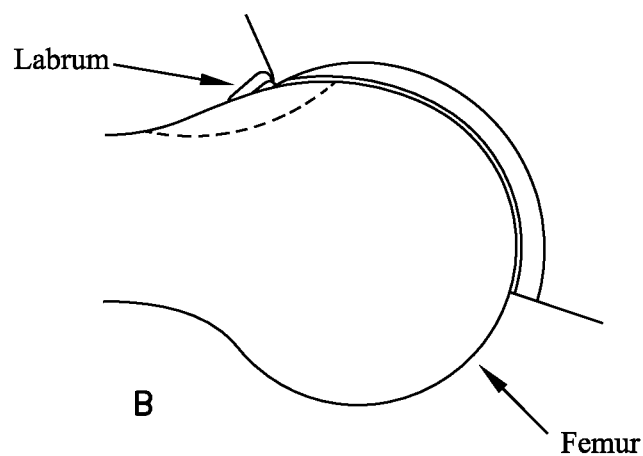
FIG. 13

PINCER-TYPE FEMOROACETABULAR IMPINGEMENT (FAI)
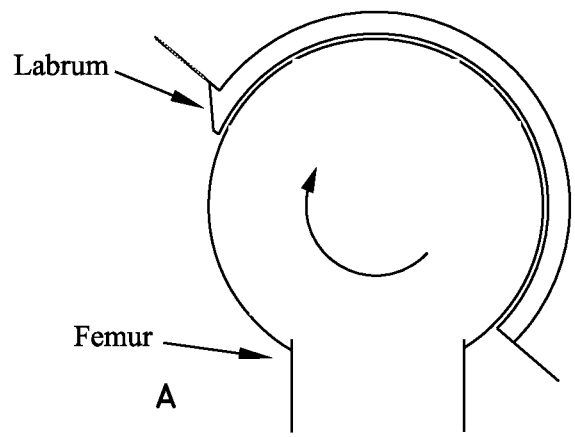
PINCER INJURY TO THE LABRUM
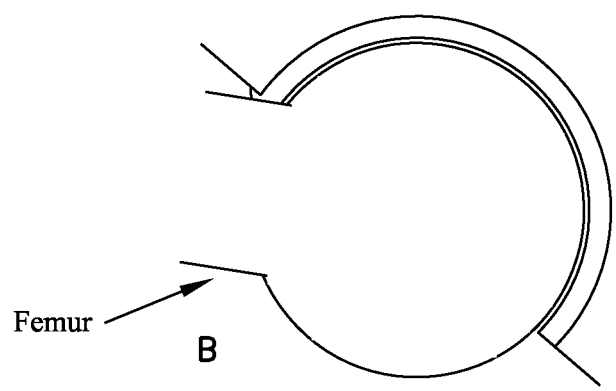
FIG. 14

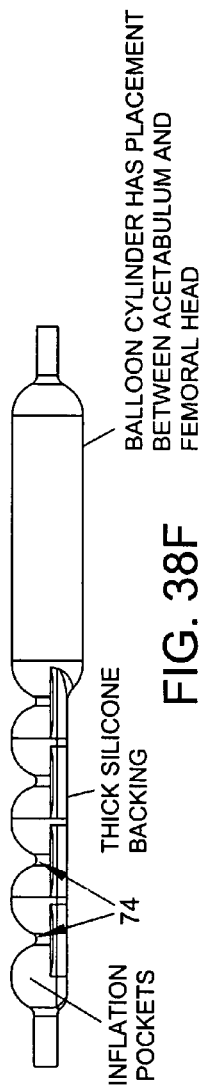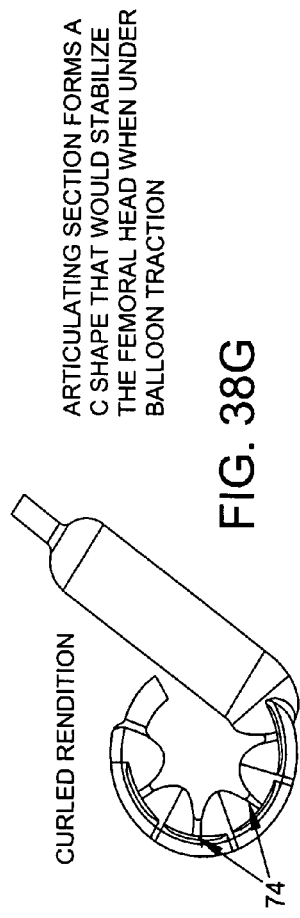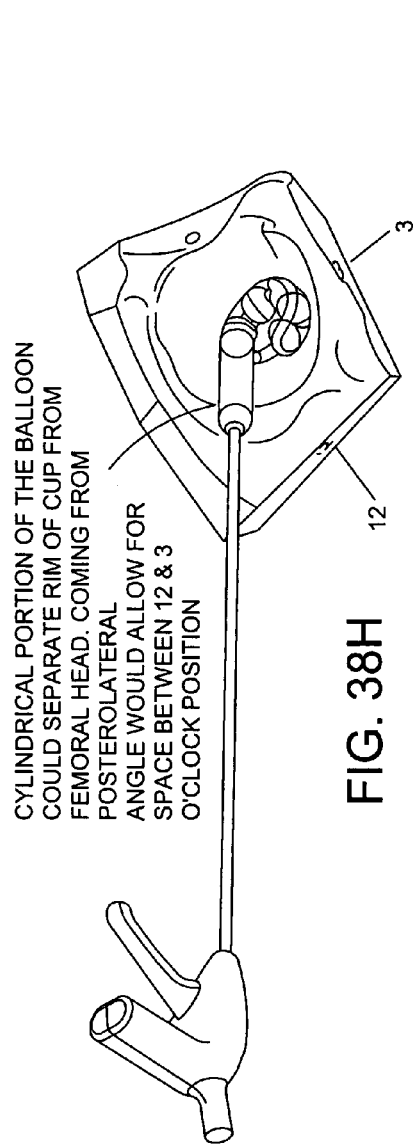

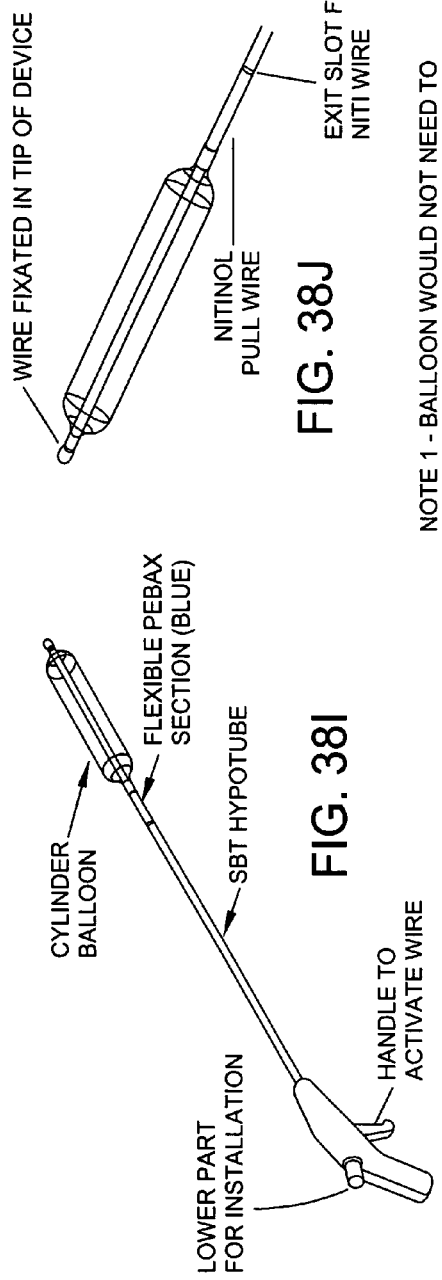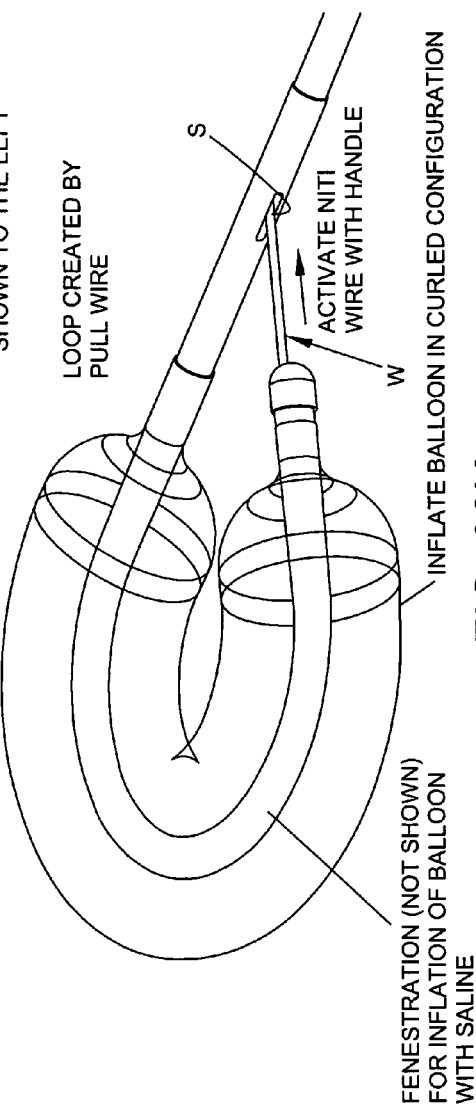

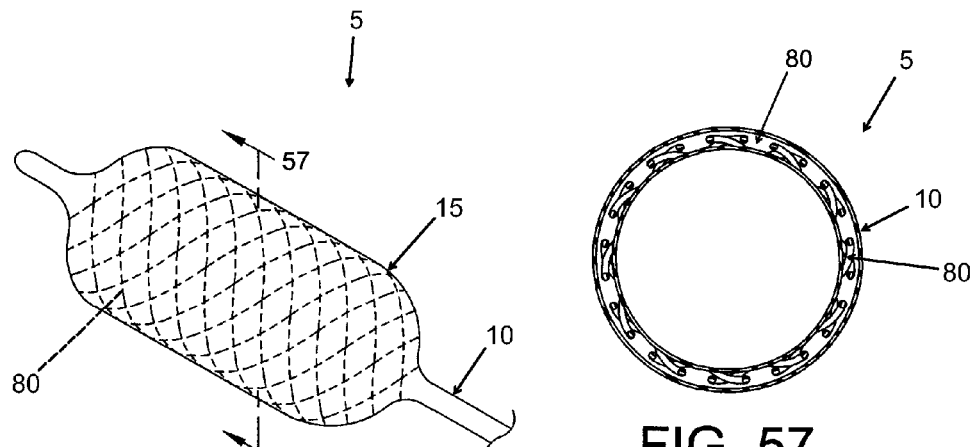
FIG. 56
FIG. 57
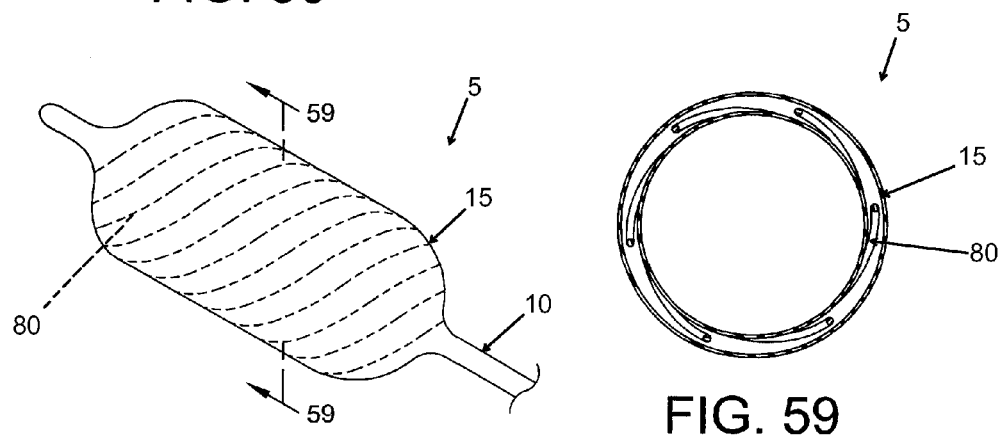
FIG. 58
FIG. 59
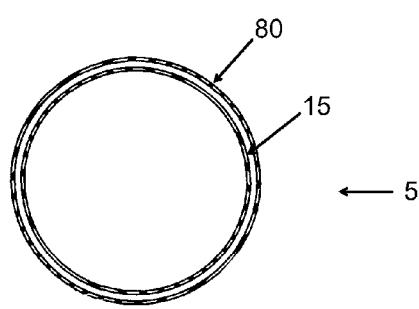
FIG. 60

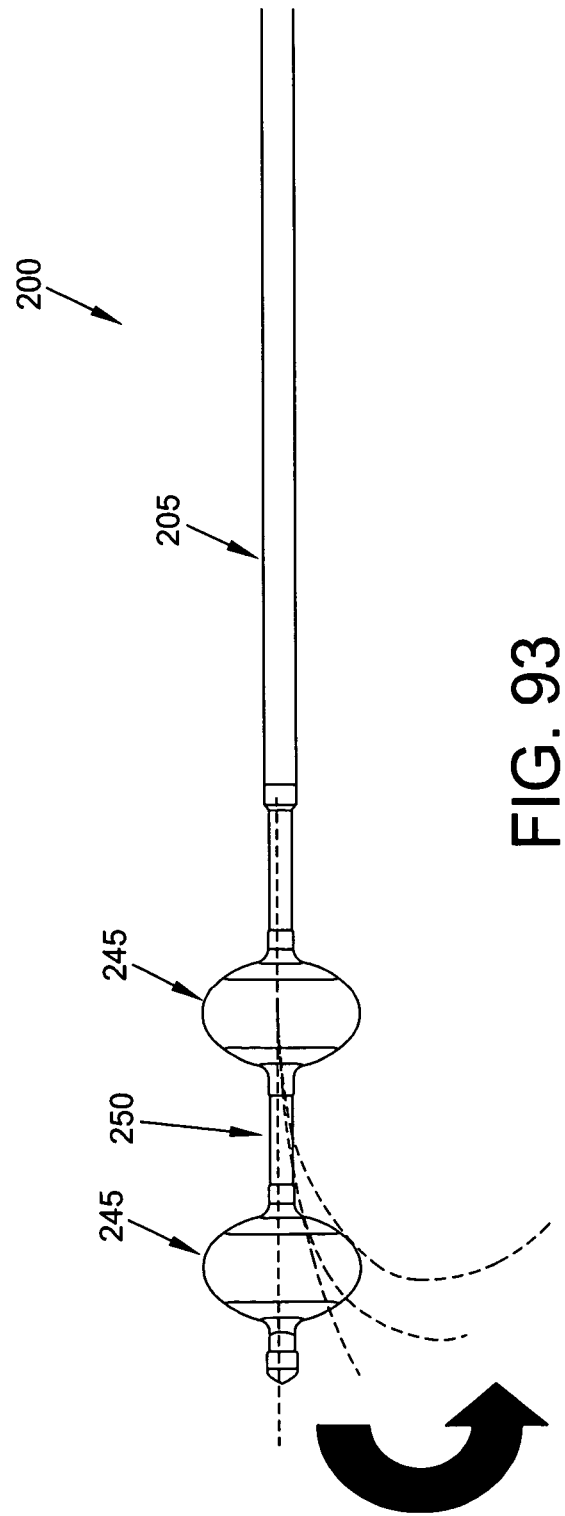

METHOD AND APPARATUS FOR DISTRACTING A JOINT

REFERENCE TO PENDING PRIOR PATENT APPLICATIONS

This patent application:

(i) is a continuation-in-part of prior U.S. patent application Ser. No. 12/726,268, filed Mar. 17, 2010 by Julian Nikolchev et al. for METHOD AND APPARATUS FOR DISTRACTING A JOINT, INCLUDING THE PROVISION AND USE OF A NOVEL JOINT-SPACING BALLOON CATHETER AND A NOVEL INFLATABLE PERINEAL POST, which claims benefit of: (a) prior U.S. Provisional Patent Application Ser. No. 61/210,315, filed Mar. 17, 2009 by Julian Nikolchev et al. for JOINT SPACING BALLOON CATHETER; (b) prior U.S. Provisional Patent Application Ser. No. 61/268,340, filed Jun. 11, 2009 by Julian Nikolchev et al. for METHOD AND APPARATUS FOR DISTRACTING A JOINT, INCLUDING THE PROVISION AND USE OF A NOVEL JOINT-SPACING BALLOON CATHETER AND A NOVEL INFLATABLE PERINEAL POST; (c) prior U.S. Provisional Patent Application Ser. No. 61/278,744, filed Oct. 9, 2009 by Julian Nikolchev et al. for METHOD AND APPARATUS FOR DISTRACTING A JOINT, INCLUDING THE PROVISION AND USE OF A NOVEL JOINT-SPACING BALLOON CATHETER AND A NOVEL INFLATABLE PERINEAL POST; and (d) prior U.S. Provisional Patent Application Ser. No. 61/336,284, filed Jan. 20, 2010 by Julian Nikolchev et al. for METHOD AND APPARATUS FOR DISTRACTING A JOINT, INCLUDING THE PROVISION AND USE OF A NOVEL JOINT-SPACING BALLOON CATHETER AND A NOVEL INFLATABLE PERINEAL POST;

(ii) is a continuation-in-part of prior U.S. patent application Ser. No. 13/292,002, filed Nov. 8, 2011 by William Kaiser et al. for METHOD AND APPARATUS FOR DISTRACTING A JOINT, which in turn claims benefit of (a) prior U.S. Provisional Patent Application Ser. No. 61/411,179, filed Nov. 8, 2010 by William Kaiser et al. for METHOD AND APPARATUS FOR DISTRACTING A JOINT, INCLUDING THE PROVISION AND USE OF A NOVEL JOINT-SPACING BALLOON CATHETER AND A NOVEL INFLATABLE PERINEAL POST; (b) claims benefit of prior U.S. Provisional Patent Application Ser. No. 61/452,477, filed Mar. 14, 2011 by Hal David Martin et al. for METHOD AND APPARATUS FOR DISTRACTING A JOINT, INCLUDING THE PROVISION AND USE OF A NOVEL JOINT-SPACING BALLOON CATHETER AND A NOVEL INFLATABLE PERINEAL POST; and (c) claims benefit of prior U.S. Provisional Patent Application Ser. No. 61/492,640, filed Jun. 2, 2011 by William Kaiser et al. for METHOD AND APPARATUS FOR DISTRACTING A JOINT, INCLUDING THE PROVISION AND USE OF A NOVEL JOINT-SPACING BALLOON CATHETER AND A NOVEL INFLATABLE PERINEAL POST; and (iii) claims benefit of prior U.S. Provisional Patent Application Ser. No. 61/702,630, filed Sep. 18, 2012 by William Kaiser et al. for METHOD AND APPARATUS FOR DISTRACTING A JOINT.

The ten (10) above-identified patent applications are hereby incorporated herein by reference.

FIELD OF THE INVENTION

This invention relates to surgical methods and apparatus in general, and more particularly to surgical methods and apparatus for treating a hip joint.

BACKGROUND OF THE INVENTION

The Hip Joint in General

The hip joint is a ball-and-socket joint which movably connects the leg to the torso. The hip joint is capable of a wide range of different motions, e.g., flexion and extension, abduction and adduction, medial and lateral rotation, etc. See FIGS. 1A, 1B, 1C and 1D.

With the possible exception of the shoulder joint, the hip joint is perhaps the most mobile joint in the body. Significantly, and unlike the shoulder joint, the hip joint carries substantial weight loads during most of the day, in both static (e.g., standing and sitting) and dynamic (e.g., walking and running) conditions.

The hip joint is susceptible to a number of different pathologies. These pathologies can have both congenital and injury-related origins. In some cases, the pathology can be substantial at the outset. In other cases, the pathology may be minor at the outset but, if left untreated, may worsen over time. More particularly, in many cases, an existing pathology may be exacerbated by the dynamic nature of the hip joint and the substantial weight loads imposed on the hip joint.

The pathology may, either initially or thereafter, significantly interfere with patient comfort and lifestyle. In some cases, the pathology can be so severe as to require partial or total hip replacement. A number of procedures have been developed for treating hip pathologies short of partial or total hip replacement, but these procedures are generally limited in scope due to the significant difficulties associated with treating the hip joint.

A better understanding of various hip joint pathologies, and also the current limitations associated with their treatment, can be gained from a more thorough understanding of the anatomy of the hip joint.

Anatomy of the Hip Joint

The hip joint is formed at the junction of the leg and the hip. More particularly, and looking now at FIG. 2, the head of the femur is received in the acetabular cup of the hip, with a plurality of ligaments and other soft tissue serving to hold the bones in articulating condition.

More particularly, and looking now at FIG. 3, the femur is generally characterized by an elongated body terminating, at its top end, in an angled neck which supports a hemispherical head (also sometimes referred to as "the ball"). As seen in FIGS. 3 and 4, a large projection known as the greater trochanter protrudes laterally and posteriorly from the elongated body adjacent to the neck of the femur. A second, somewhat smaller projection known as the lesser trochanter protrudes medially and posteriorly from the elongated body adjacent to the neck. An intertrochanteric crest (FIGS. 3 and 4) extends along the periphery of the femur, between the greater trochanter and the lesser trochanter.

Looking next at FIG. 5, the hip socket is made up of three constituent bones: the ilium, the ischium and the pubis. These three bones cooperate with one another (they typically ossify into a single "hip bone" structure by the age of 25 or so) in order to collectively form the acetabular cup. The acetabular cup receives the head of the femur.

Both the head of the femur and the acetabular cup are covered with a layer of articular cartilage which protects the underlying bone and facilitates motion. See FIG. 6.

Various ligaments and soft tissue serve to hold the ball of the femur in place within the acetabular cup. More particularly, and looking now at FIGS. 7 and 8, the ligamentum teres extends between the ball of the femur and the base of the acetabular cup. As seen in FIGS. 8 and 9, a labrum is disposed about the perimeter of the acetabular cup. The labrum serves to increase the depth of the acetabular cup and effectively establishes a suction seal between the ball of the femur and the rim of the acetabular cup, thereby helping to hold the head of the femur in the acetabular cup. In addition to the foregoing, and looking now at FIG. 10, a fibrous capsule extends between the neck of the femur and the rim of the acetabular cup, effectively sealing off the ball-and-socket members of the hip joint from the remainder of the body. The foregoing structures (i.e., the ligamentum teres, the labrum and the fibrous capsule) are encompassed and reinforced by a set of three main ligaments (i.e., the iliofemoral ligament, the ischiofemoral ligament and the pubofemoral ligament) which extend between the femur and the perimeter of the hip socket. See, for example, FIGS. 11 and 12, which show the iliofemoral ligament, with FIG. 11 being an anterior view and FIG. 12 being a posterior view.

Pathologies of the Hip Joint

As noted above, the hip joint is susceptible to a number of different pathologies. These pathologies can have both congenital and injury-related origins.

By way of example but not limitation, one important type of congenital pathology of the hip joint involves impingement between the neck of the femur and the rim of the acetabular cup. In some cases, and looking now at FIG. 13, this impingement can occur due to irregularities in the geometry of the femur. This type of impingement is sometimes referred to as cam-type femoroacetabular impingement (i.e., cam-type FAI). In other cases, and looking now at FIG. 14, the impingement can occur due to irregularities in the geometry of the acetabular cup. This latter type of impingement is sometimes referred to as pincer-type femoroacetabular impingement (i.e., pincer-type FAI). Impingement can result in a reduced range of motion, substantial pain and, in some cases, significant deterioration of the hip joint.

By way of further example but not limitation, another important type of congenital pathology of the hip joint involves defects in the articular surface of the ball and/or the articular surface of the acetabular cup. Defects of this type sometimes start out fairly small but often increase in size over time, generally due to the dynamic nature of the hip joint and also due to the weight-bearing nature of the hip joint. Articular defects can result in substantial pain, induce and/or exacerbate arthritic conditions and, in some cases, cause significant deterioration of the hip joint.

By way of further example but not limitation, one important type of injury-related pathology of the hip joint involves trauma to the labrum. More particularly, in many cases, an accident or sports-related injury can result in the labrum being torn away from the rim of the acetabular cup, typically with a tear running through the body of the labrum. See FIG. 15. These types of injuries can be very painful for the patient and, if left untreated, can lead to substantial deterioration of the hip joint.

The General Trend Toward Treating Joint Pathologies Using Minimally-Invasive, and Earlier, Interventions The current trend in orthopedic surgery is to treat joint pathologies using minimally-invasive techniques. Such minimally-invasive, "keyhole" surgeries generally offer numerous advantages over traditional, "open" surgeries, including reduced trauma to tissue, less pain for the patient, faster recuperation times, etc.

By way of example but not limitation, it is common to re-attach ligaments in the shoulder joint using minimally-invasive, "keyhole" techniques which do not require laying open the capsule of the shoulder joint. By way of further example but not limitation, it is common to repair torn meniscal cartilage in the knee joint, and/or to replace ruptured ACL ligaments in the knee joint, using minimally-invasive techniques.

While such minimally-invasive approaches can require additional training on the part of the surgeon, such procedures generally offer substantial advantages for the patient and have now become the standard of care for many shoulder joint and knee joint pathologies.

In addition to the foregoing, in view of the inherent advantages and widespread availability of minimally-invasive approaches for treating pathologies of the shoulder joint and knee joint, the current trend is to provide such treatment much earlier in the lifecycle of the pathology, so as to address patient pain as soon as possible and so as to minimize any exacerbation of the pathology itself. This is in marked contrast to traditional surgical practices, which have generally dictated postponing surgical procedures as long as possible so as to spare the patient from the substantial trauma generally associated with invasive surgery.

Treatment for Pathologies of the Hip Joint

Unfortunately, minimally-invasive treatments for pathologies of the hip joint have lagged far behind minimally-invasive treatments for pathologies of the shoulder joint and the knee joint. This is generally due to (i) the constrained geometry of the hip joint itself, and (ii) the nature and location of the pathologies which must typically be addressed in the hip joint.

More particularly, the hip joint is generally considered to be a "tight" joint, in the sense that there is relatively little room to maneuver within the confines of the joint itself. This is in marked contrast to the shoulder joint and the knee joint, which are generally considered to be relatively "spacious" joints (at least when compared to the hip joint). As a result, it is relatively difficult for surgeons to perform minimally-invasive procedures on the hip joint.

Furthermore, the pathways for entering the interior of the hip joint (i.e., the natural pathways which exist between adjacent bones and/or delicate neurovascular structures) are generally much more constraining for the hip joint than for the shoulder joint or the knee joint. This limited access further complicates effectively performing minimally-invasive procedures on the hip joint.

In addition to the foregoing, the nature and location of the pathologies of the hip joint also complicate performing minimally-invasive procedures on the hip joint. By way of example but not limitation, consider a typical detachment of the labrum in the hip joint. In this situation, instruments must generally be introduced into the joint space using an angle of approach which is offset from the angle at which the instrument addresses the tissue. This makes drilling into bone, for example, significantly more complicated than where the angle of approach is effectively aligned with the angle at which the instrument addresses the tissue, such as is frequently the case in the shoulder joint. Furthermore, the working space within the hip joint is typically extremely limited, further complicating repairs where the angle of approach is not aligned with the angle at which the instrument addresses the tissue.

As a result of the foregoing, minimally-invasive hip joint procedures are still relatively difficult to perform and relatively uncommon in practice. Consequently, patients are typically forced to manage their hip pain for as long as possible, until a resurfacing procedure or a partial or total hip replacement procedure can no longer be avoided. These procedures are generally then performed as a highly-invasive, open procedure, with all of the disadvantages associated with highly-invasive, open procedures.

As a result, there is, in general, a pressing need for improved methods and apparatus for treating pathologies of the hip joint.

Current Approaches for Hip Joint Distraction

During arthroscopic hip surgery, it is common to distract the hip joint so as to provide increased workspace within the joint. More particularly, during arthroscopic hip surgery, it is common to unseat the ball of the femur from the socket of the acetabular cup so as to provide (i) improved access to the interior of the joint, (ii) additional workspace within the interior of the joint, and (iii) increased visibility for the surgeon during the procedure. This hip joint distraction is normally accomplished in the same manner that the hip joint is distracted during a total hip replacement procedure, e.g., by applying an external distraction device to the lower end of the patient's leg near the ankle and then using the external distraction device to pull the leg distally with substantial force so as to unseat the ball of the femur from the acetabular cup.

However, since the distracting force is applied to the lower end of the patient's leg, this approach necessitates that the distracting force be applied across substantially the entire length of the leg. As a result, the intervening tissue (i.e., the tissue located between where the distracting force is applied and the ball of the femur) must bear the distracting load for the entire time that the hip joint is distracted.

In practice, it has been found that the longer the distracting load is maintained on the leg, the greater the trauma imposed on the intervening tissue. Specifically, it has been found that temporary or even permanent neurological damage can occur if the leg is distracted for too long using conventional distraction techniques.

As a result, the standard of care in the field is for the surgeon to limit the duration of distraction during arthroscopic hip surgery to 90 minutes or less in order to minimize damage to the intervening tissue due to joint distraction. In some situations, this can mean that desirable therapeutic procedures may be curtailed, or even eliminated entirely, in order to keep the duration of the distraction to 90 minutes or less. And even where the duration of the distraction is kept to 90 minutes or less, significant complications can nonetheless occur for many patients.

In addition to the foregoing, in current hip distraction, it is common to use a perineal post to facilitate hip distraction. More particularly, and looking now at FIG. 16, a perineal post is generally positioned between the legs of the patient so that the medial side of the femur which is to be distracted lies against the perineal post. After the patient's leg is pulled distally (i.e., in the direction of the pulling vector $V_P$), the leg is adducted so as to lever the leg against the perineal post, which moves the neck and ball of the femur in the direction of the lateral vector $V_L$; the combination of these two displacements is $V_D$ (i.e., the resultant vector of the vectors of $V_L$ and $V_P$). This ensures that the ball of the femur is unseated from the acetabular cup in the desired direction (i.e., in the direction of the resultant vector $V_D$).

Unfortunately, it has been found that the use of a perineal post can contribute to the damage done to the intervening tissue when the leg is distracted too long. This is because the perineal post can press against the pudendal nerve and/or the sciatic nerve (as well as other anatomy) when such distraction occurs. Thus, if the distraction is held too long, neurological damage can occur. This is another reason that the standard of care in the field is for the surgeon to limit the duration of distraction during arthroscopic hip surgery to 90 minutes or less. Additionally, the perineal post can exert pressure on the blood vessels in the leg, and it has been shown that blood flow in these vessels (e.g., the femoral vein, etc.) may be significantly reduced, or in some cases completely occluded, while the hip is in distraction, thus placing the patient in danger of forming deep vein thrombosis or developing other complications.

Additionally, current hip distraction using an external distraction device limits the extent to which the leg can be manipulated under distraction during hip arthroscopy, since a substantial pulling force must be maintained on the distal end of the leg throughout the duration of the distraction. Due to this, and due to the fact that there are typically only 2-4 portals available for surgical access into the interior of the hip joint, visualization and access to hip joint pathology and anatomy is frequently hindered while the leg is being externally distracted. This can limit the extent of surgical procedures available to the surgeon, and can prevent some procedures from being attempted altogether. Procedures such as mosaicplasty and autologous cartilage injection are examples of procedures which require access to extensive areas of the articular surfaces of the femoral head, but which are typically not performed arthroscopically because of the aforementioned access limitations when the leg is being distracted using an external distraction device.

Thus, there is a need for a new and improved approach for distracting the hip joint which addresses the foregoing problems.

SUMMARY OF THE INVENTION

These and other objects of the present invention are addressed by the provision and use of a new method and apparatus for distracting a joint.

Among other things, the present invention provides a novel method for distracting a joint and for maintaining distraction of a joint, wherein the novel method minimizes damage to intervening tissue while maintaining distraction of the joint. In addition, the novel method allows visualization of areas in the hip joint that were not previously visible using a conventional hip distraction approach.

The present invention also provides novel apparatus for distracting a joint and for maintaining distraction of a joint, wherein the novel apparatus comprises a novel joint-spacing balloon catheter for maintaining the distraction of a joint.

In one preferred form of the invention, there is provided a method for creating space in a joint formed at the convergence of two bones, the method comprising:

applying force to a body part so as to separate the two bones from one another by a distance which is greater than the distance that they are normally separated from one another when the joint is in a healthy state, whereby to distract the joint and create an intrajoint space;
  inserting at least one balloon into the intrajoint space while the at least one balloon is in a contracted condition;
  expanding the at least one balloon within the intrajoint space; and
  reducing the force applied to the body part so that the joint is supported on the at least one balloon, with the two bones remaining separated from one another by a distance which is greater than the distance that they are normally separated from one another when the joint is in a healthy state.

In another preferred form of the invention, there is provided a joint-spacing balloon catheter comprising:
  a shaft having a distal end and a proximal end;
  first and second balloons mounted to the distal end of the shaft, the first balloon being disposed distal to, and spaced from, the second balloon, with the portion of the shaft between the first and second balloons being flexible; and
  a handle attached to the proximal end of the shaft.

In another preferred form of the invention, there is provided apparatus for maintaining space within a joint, the apparatus comprising:
  a cannula for providing a corridor to an interior space, the distal end of the cannula comprising a beveled surface; and
  a joint-spacing balloon catheter comprising:
  a shaft having a distal end and a proximal end;
  first and second balloons mounted to the distal end of the shaft, the first balloon being disposed distal to, and spaced from, the second balloon, with the portion of the shaft between the first and second balloons being flexible; and
  a handle attached to the proximal end of the shaft.

In another preferred form of the invention, there is provided a method for creating space in a joint formed at the convergence of two bones, the method comprising:
  applying force to a body part so as to separate the two bones from one another by a distance which is greater than the distance that they are normally separated from one another when the joint is in a healthy state, whereby to distract the joint and create an intrajoint space;
  inserting an assembly of three balloons into the intrajoint space while the assembly of three balloons is in a contracted condition;
  expanding the assembly of three balloons within the intrajoint space; and
  reducing the force applied to the body part so that the joint is supported on the assembly of three balloons, with the two bones remaining separated from one another by a distance which is greater than the distance that they are normally separated from one another when the joint is in a healthy state.

In another preferred form of the invention, there is provided a joint-spacing balloon catheter comprising:
  a shaft having a distal end and a proximal end;
  first, second and third balloons mounted to the distal end of the shaft, the first balloon being disposed distal to, and spaced from, the second balloon, with the portion of the shaft between the first and second balloons being flexible, and the second balloon being disposed distal to, and spaced from, the third balloon, with the portion of the shaft between the second and third balloons being flexible; and
  a handle attached to the proximal end of the shaft.

In another preferred form of the invention, there is provided a method for treating a patient, the method comprising:
  providing a balloon catheter comprising a shaft having a distal tip and a balloon mounted to the shaft proximal to the distal tip;
  inserting the balloon into a joint space while the balloon is in a contracted condition;
  securing the distal tip of the shaft to a portion of the shaft proximal to the balloon; and
  expanding the balloon within the joint space.

In another preferred form of the invention, there is provided apparatus for treating a patient, the apparatus comprising:
  a balloon catheter comprising a shaft having a distal tip and a balloon mounted to the shaft proximal to the distal tip;
  wherein the distal tip of the shaft is securable to a portion of the shaft proximal to the balloon.

In another preferred form of the invention, there is provided a method for treating a patient, the method comprising:
  injecting a fluid into the capsule of a joint so as to disrupt the natural seal of the joint.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 13 is a schematic view showing cam-type femoroacetabular impingement (FAI);

FIG. 14 is a schematic view showing pincer-type femoroacetabular impingement (FAI);

FIG. 23' is a schematic view showing a peel-away sheath covering a joint-spacing balloon catheter formed in accordance with the present invention;

FIGS. 38A and 38B, 38C-38E and 38F-38H are schematic views showing how the balloon(s) of the joint-spacing balloon catheter may comprise a crease, whereby to facilitate bending of the balloon(s), e.g., so as to conform to the curvature of a joint;

FIGS. 38I-38P are schematic views showing how the joint-spacing balloon catheter can be provided with a tip retention mechanism, such that a substantially cylindrical balloon can be retained in an arcuate or semi-toroidal configuration at the distal end of the joint-spacing balloon catheter;

FIGS. 56-60 and 60A-60D are schematic views showing how a balloon of the joint-spacing balloon catheter may incorporate puncture protection within its structure;

FIGS. 91-93, 93A, 94-99 and 99A are schematic views showing a preferred construction for the joint-spacing balloon catheter of the present invention;

DETAILED DESCRIPTION OF THE PREFERRED EMBODIMENTS

Novel Joint-Spacing Balloon Catheter

In one form of the present invention, there is provided a novel joint-spacing balloon catheter for use in distracting a joint, and more particularly for maintaining the distraction of a previously-distracted joint, as will hereinafter be discussed in detail.

Figure 17:
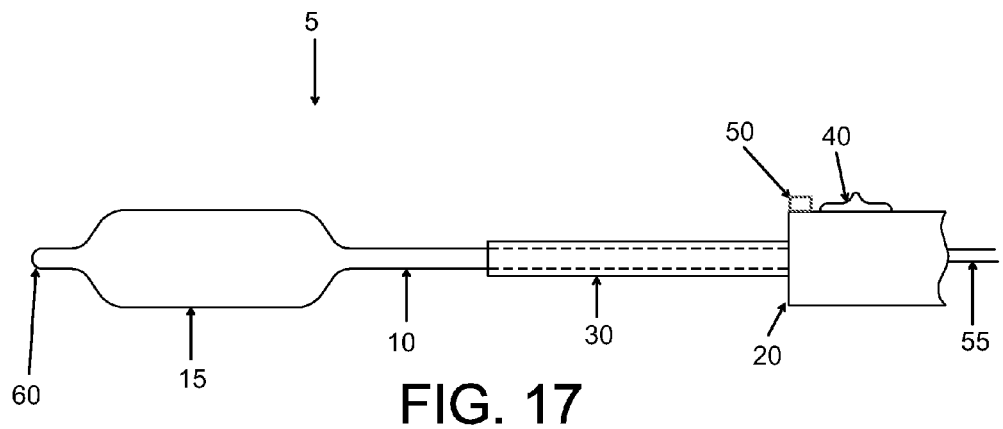
FIGS. 17-19 are schematic views showing a novel joint-spacing balloon catheter formed in accordance with the present invention.
Figure 18:
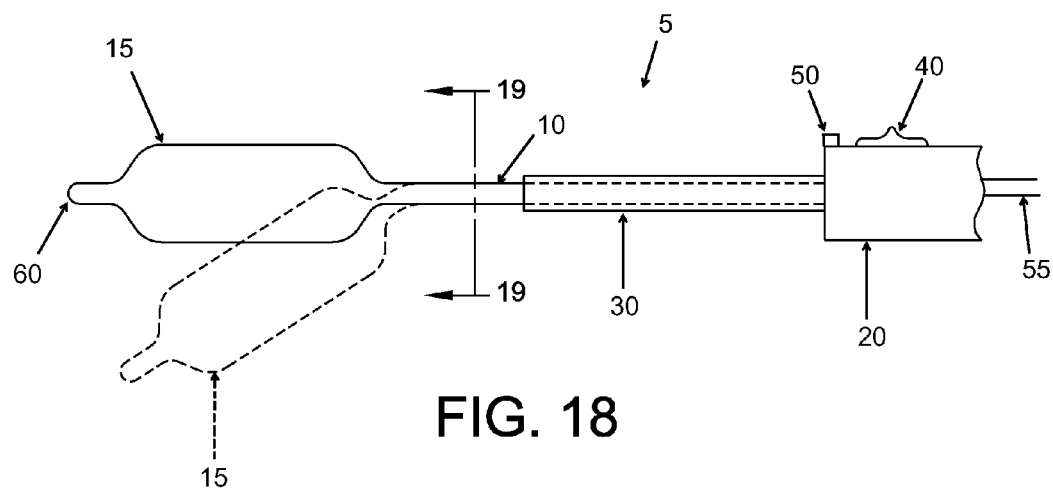
Figure 19:
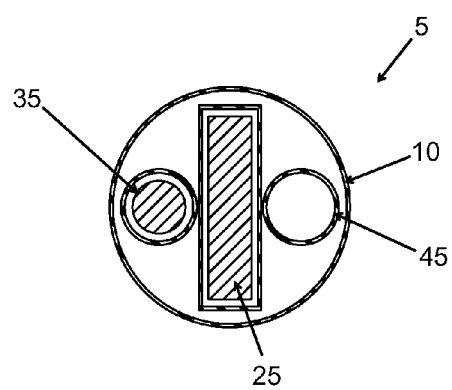

More particularly, in this form of the invention, and looking next at FIGS. 17-19, there is shown a novel joint-spacing balloon catheter 5 formed in accordance with the present invention. Novel joint-spacing balloon catheter 5 generally comprises an elongated shaft 10 having a balloon 15 disposed at its distal end and a handle 20 disposed at its proximal end. If desired, and as will hereinafter be discussed, multiple balloons 15 may be disposed on the distal end of elongated shaft 10.

Elongated shaft 10 is preferably flexible, and preferably includes an internal stiffener 25 extending along at least a portion of its length so as to facilitate proper positioning of balloon 15 during use. Internal stiffener 25 may comprise a round or rectangular wire (e.g., such as is shown in FIG. 19), and may be made out of a metal (e.g., stainless steel, Nitinol, etc.) or a polymer. If internal stiffener 25 comprises a rectangular wire, the short axis (of the cross-section) of the wire can provide flexibility (e.g., to enable the distal end of the joint-spacing balloon catheter 5 to navigate around the curvature of the femoral head), whereas the long axis (of the cross-section) of the wire can provide stiffness to better control the position of the balloon in the joint space. If desired, elongated shaft 10 may also include a substantially rigid overshaft 30 adjacent to handle 20 so as to further stiffen the proximal end of elongated shaft 10, whereby to provide better control for the positioning of balloon 15. Rigid overshaft 30 can be a stainless steel tube, a hard polymer tube, etc. Rigid overshaft 30 may be about 10 cm to about 30 cm in length, but is preferably about 12.5 cm to about 22.5 cm in length. A steering cable 35 is provided for steering the direction of the distal end of shaft 10, whereby to steer the direction of balloon 15. More particularly, steering cable 35 (FIG. 19) extends through elongated shaft 10 between the distal end of elongated shaft 10 and a steering control mechanism 40 provided on handle 20. By manipulating steering control mechanism 40, the user is able to steer the direction of the distal end of shaft 10, and hence the direction of balloon 15, e.g., in the manner shown in FIG. 18. More particularly, steering control mechanism 40 and steering cable 35 are adapted to cause shaft 10 to bend, preferably in the manner of an arc, which can facilitate positioning of balloon 15 in a joint, e.g., in the central compartment of the hip joint, behind the ball of the femur. This arc can be a radius of about 5 mm to about 10 cm, but is preferably a radius of about 1 cm to about 5 cm. Steering cable 35 may be stainless steel, and may further comprise a low friction coating (e.g., polytetrafluoroethylene (PTFE)) so as to reduce friction and/or wear. Alternatively, steering cable 35 may slide in a low friction lumen (e.g., in a PTFE tube).

Balloon 15 is preferably selectively inflatable/deflatable via an inflation/deflation lumen 45 (FIG. 19) extending through elongated shaft 10 and handle 20. An inflation/deflation control mechanism 50 is interposed between inflation/deflation lumen 45 and a supply port 55 which is connected to an appropriate fluid reservoir (not shown). By manipulating inflation/deflation control mechanism 50, the user is able to inflate/deflate balloon 15 as desired. Inflation/deflation control mechanism 50 may comprise a stopcock, a valve, a pump and/or other fluid control mechanisms. Balloon 15 preferably includes an atraumatic tip 60 at its distal end.

Inflation/deflation control mechanism 50 may comprise a valve which controls flow to and from balloon 15. By way of example but not limitation, the valve may be a simple open/close type of valve. If joint-spacing balloon catheter 5 comprises two or more balloons (see below), and if each balloon can be independently inflated/deflated, the inflation/deflation control mechanism 50 may comprise a multiple position valve. By way of example but not limitation, where the joint-spacing balloon catheter comprises two balloons 15, and where inflation/deflation control mechanism 50 comprises a multiple position valve, in a first position, the valve closes flow to both balloons; in a second position, the valve opens flow to the first balloon but closes flow to the second balloon; in a third position, the valve opens flow to the second balloon but closes flow to the first balloon; and in a fourth position, the valve opens flow to both balloons. Alternatively, inflation/deflation control mechanism 50 may regulate the amount of fluid in a balloon 15 (i.e., adding fluid to, or withdrawing fluid from, balloon 15 so that balloon 15 contains a pre-determined quantity of fluid) and/or regulate the pressure of the fluid in a balloon 15 (i.e., increasing or decreasing the pressure of the fluid in balloon 15 so that the fluid in the balloon has a pre-determined pressure).

On account of the foregoing, joint-spacing balloon catheter 5 may have its balloon 15 set to its deflated state via inflation/deflation control mechanism 50, the deflated balloon may be advanced to a remote site using handle 20 and steering control mechanism 40, and then joint-spacing balloon catheter 5 may have its balloon set to its inflated state by further manipulating inflation/deflation control mechanism 50, whereby to enable balloon 15 to support tissue and maintain the distraction of a previously-distracted joint, as will hereinafter be discussed in detail.

Novel Method for Distracting a Joint

In another form of the present invention, there is provided a novel method for distracting a joint, preferably the hip joint, and preferably using novel joint-spacing balloon catheter 5.

Figure 1A:
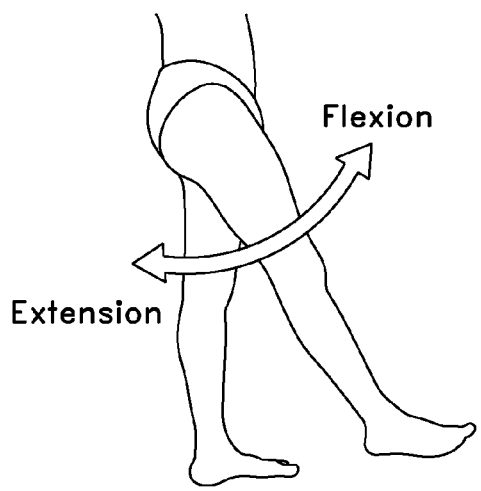
FIGS. 1A-1D are schematic views showing various aspects of hip motion.
Figure 1B:
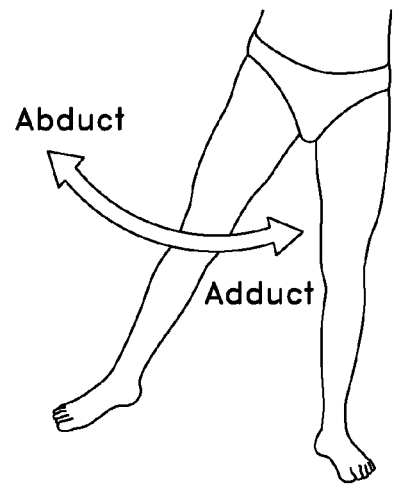
Figure 1C:
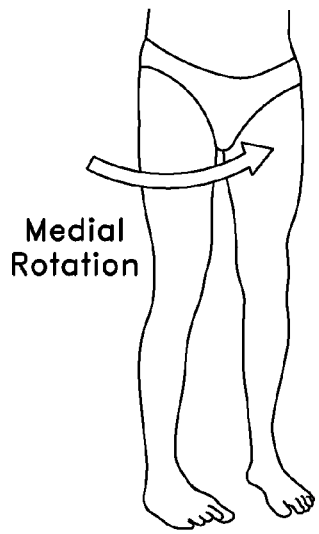
Figure 1D:
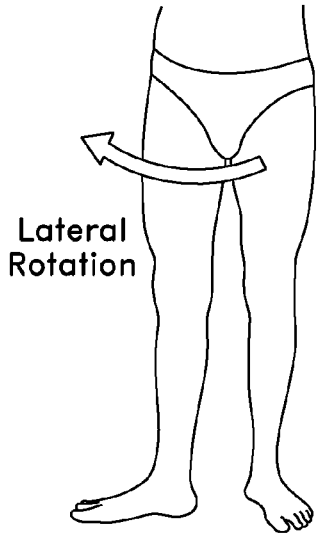
Figure 2:
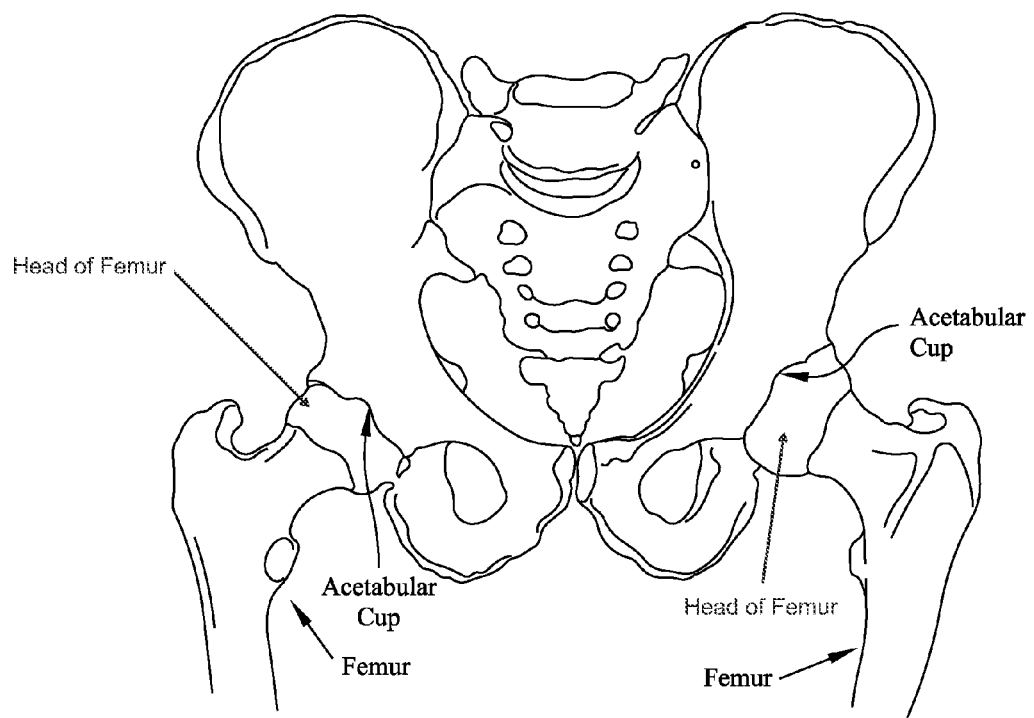
FIG. 2 is a schematic view showing the bone structure in the region of the hip joints.
Figure 3:
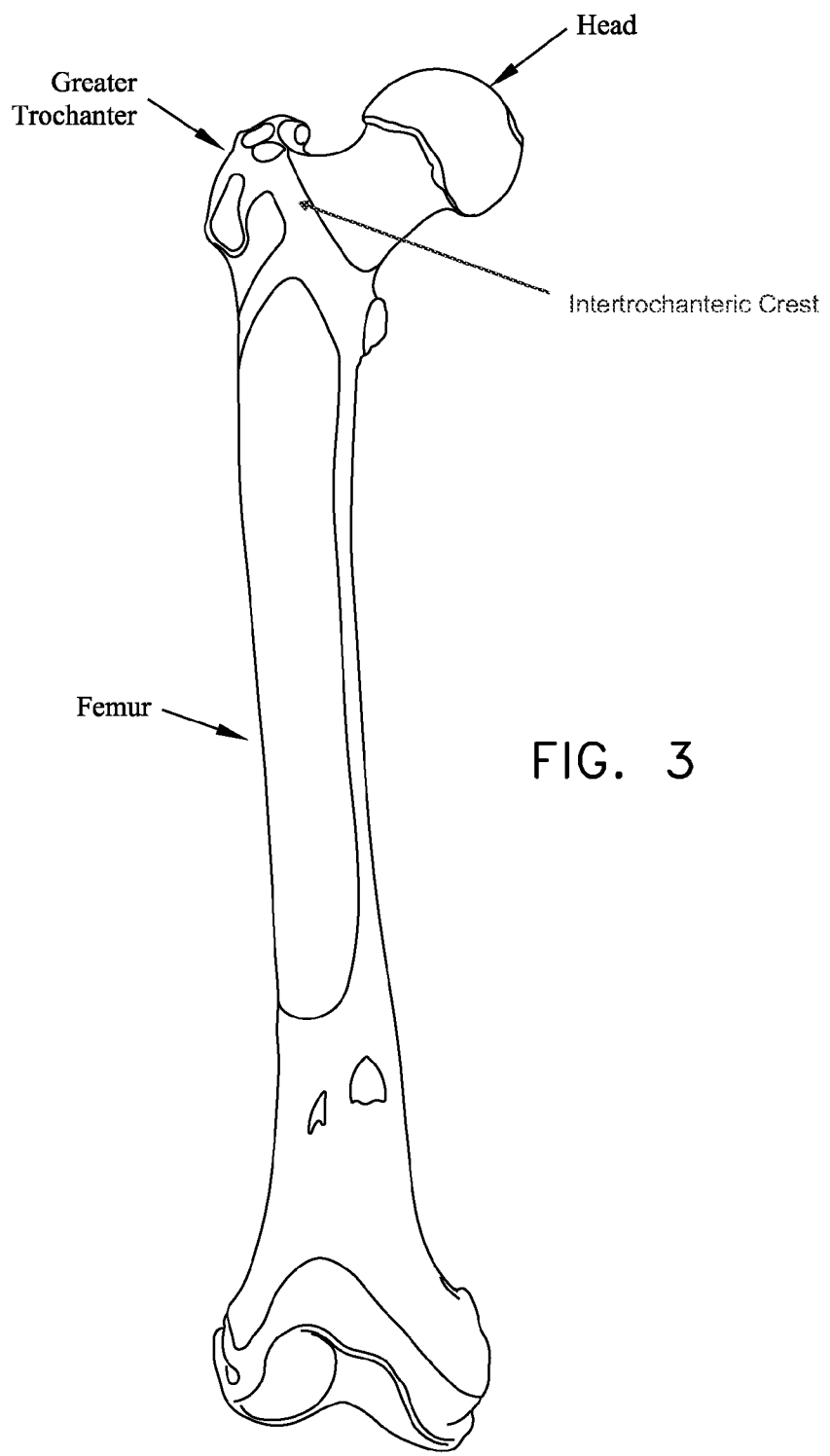
FIG. 3 is a schematic anterior view of the femur.
Figure 4:
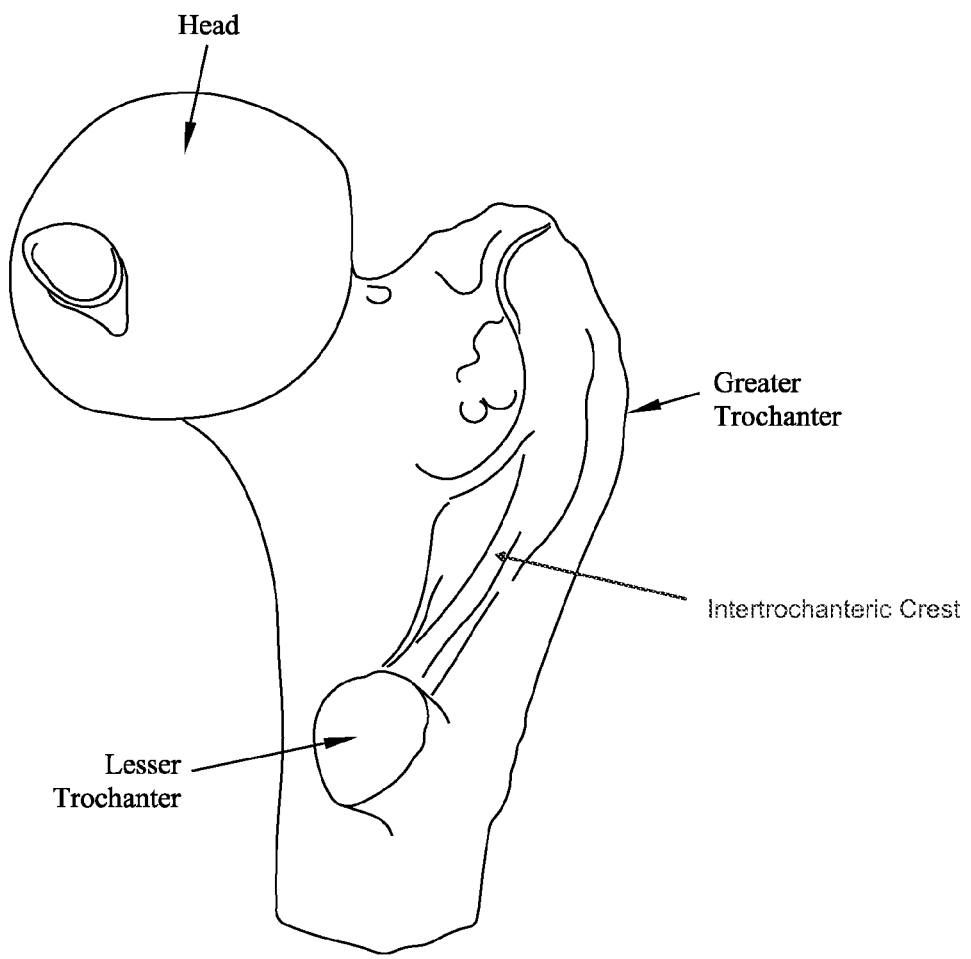
FIG. 4 is a schematic posterior view of the top end of the femur.
Figure 5:
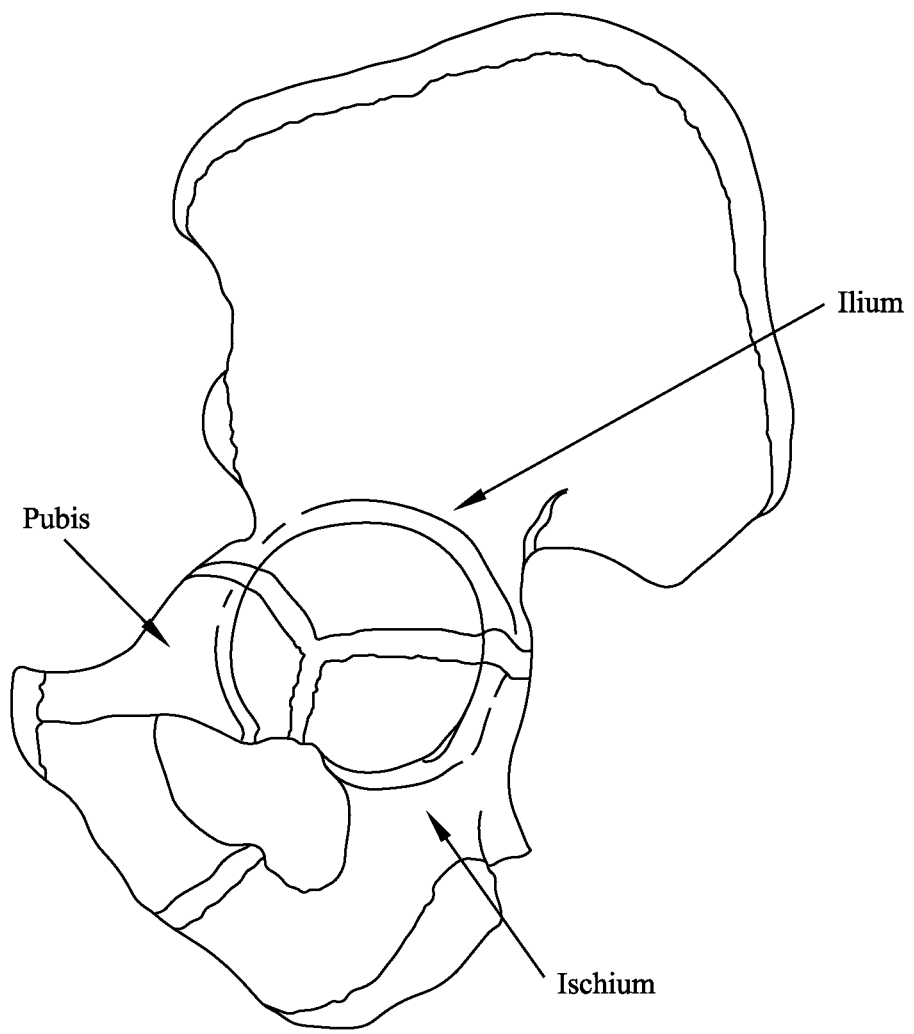
FIG. 5 is a schematic view of the pelvis.
Figure 6:
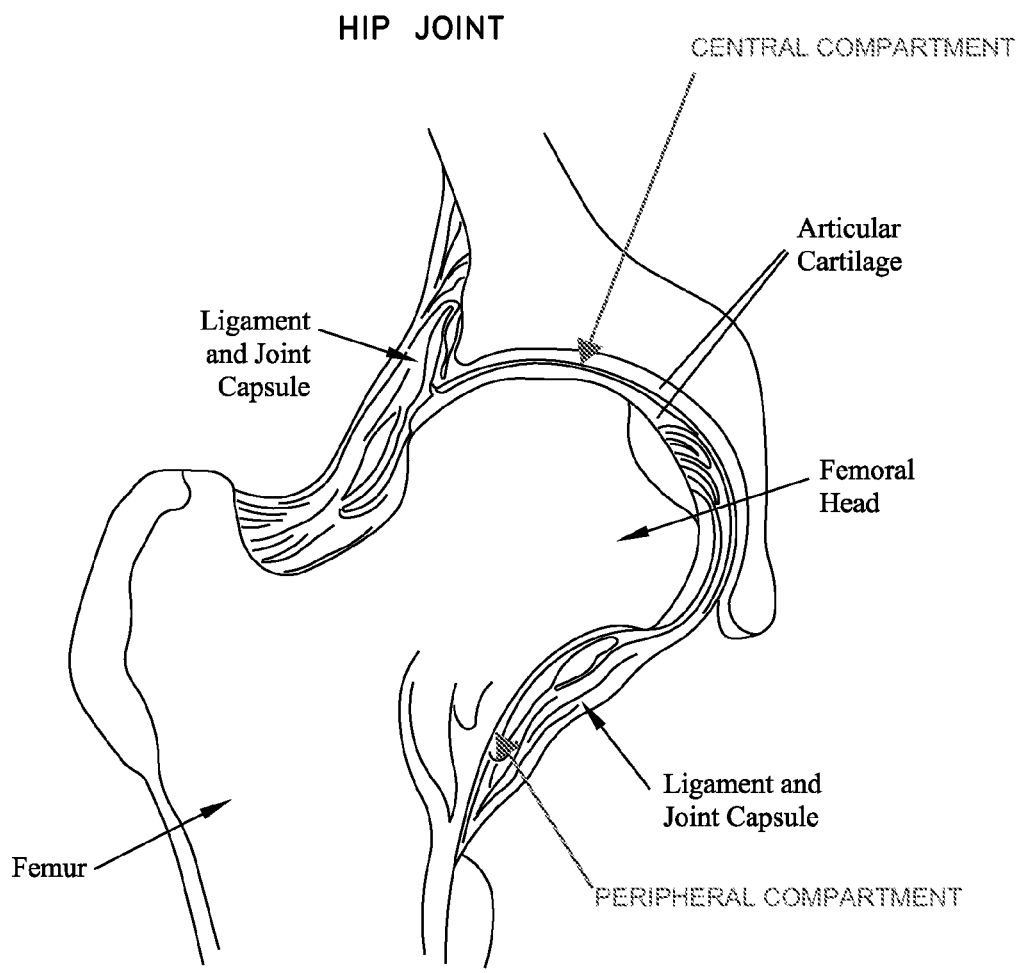
FIGS. 6-12 are schematic views showing the bone and soft tissue structure of the hip joint.
Figure 7:
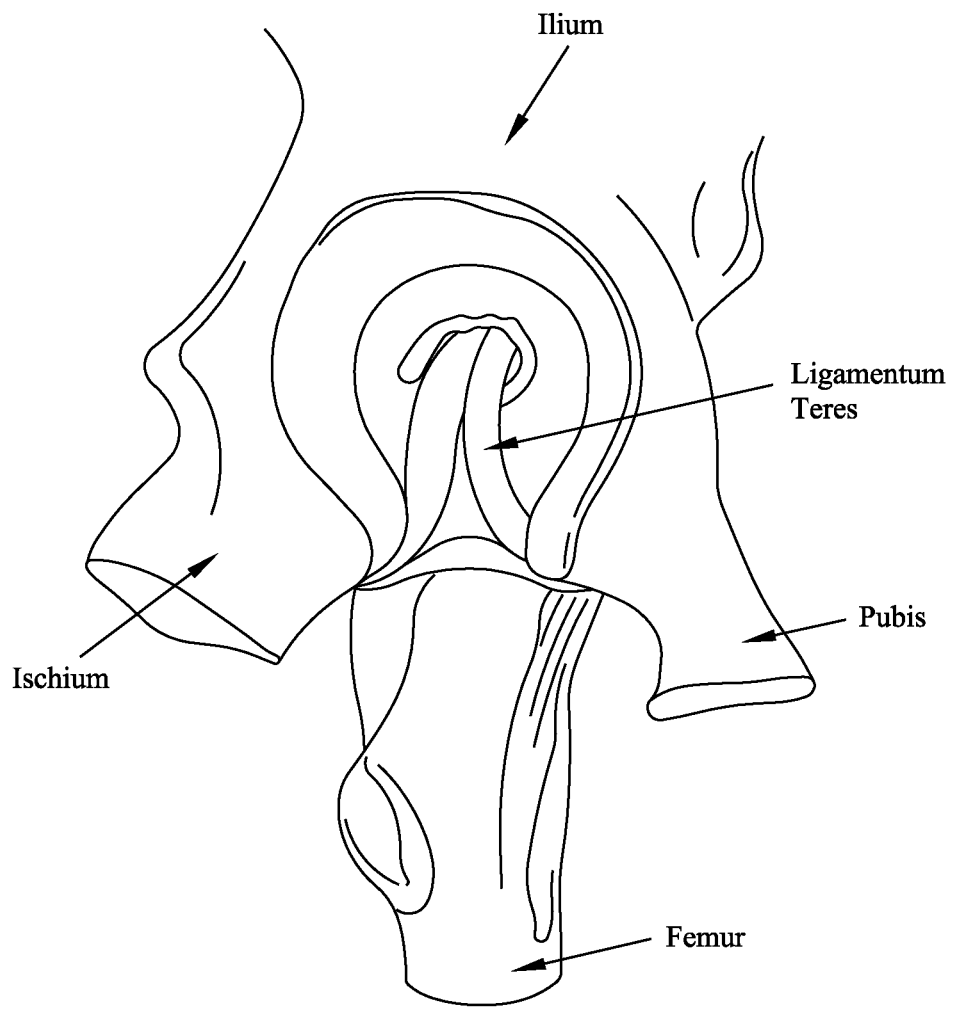
Figure 8:
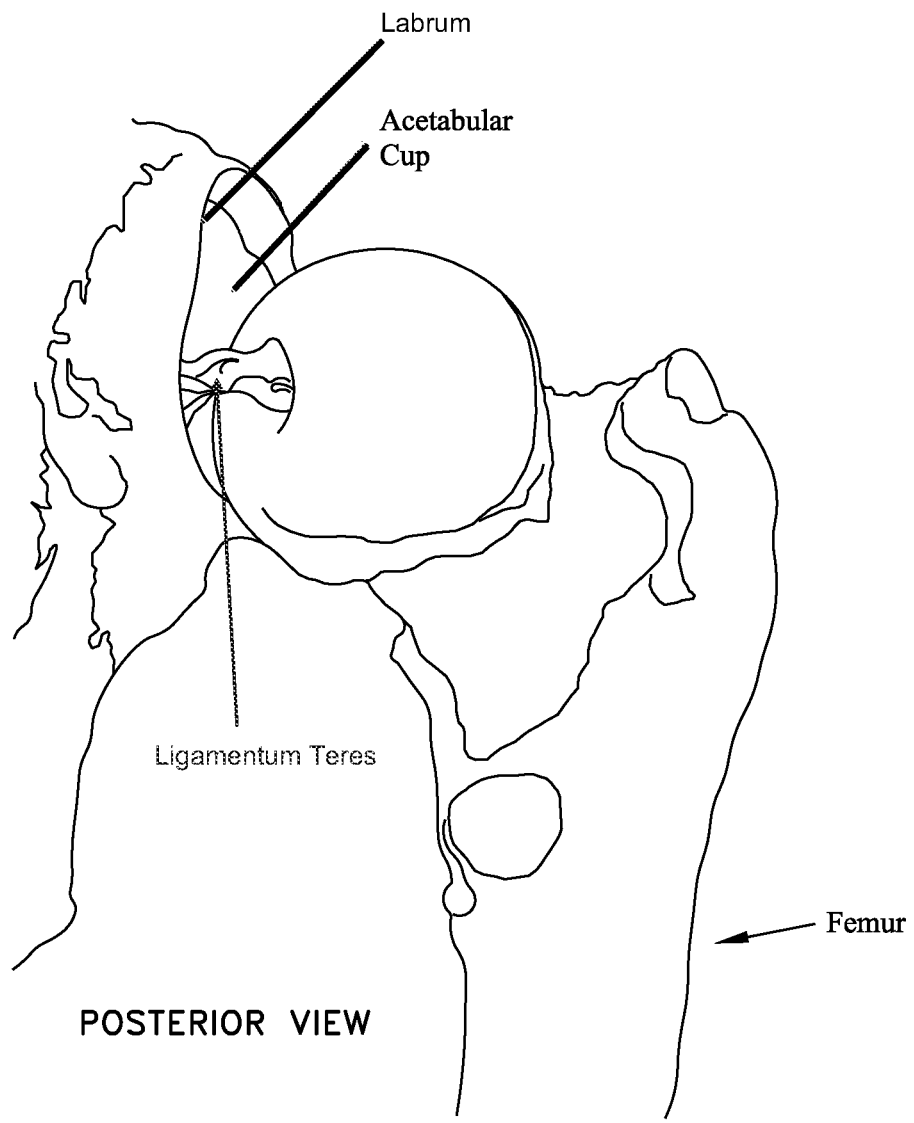
Figure 9:
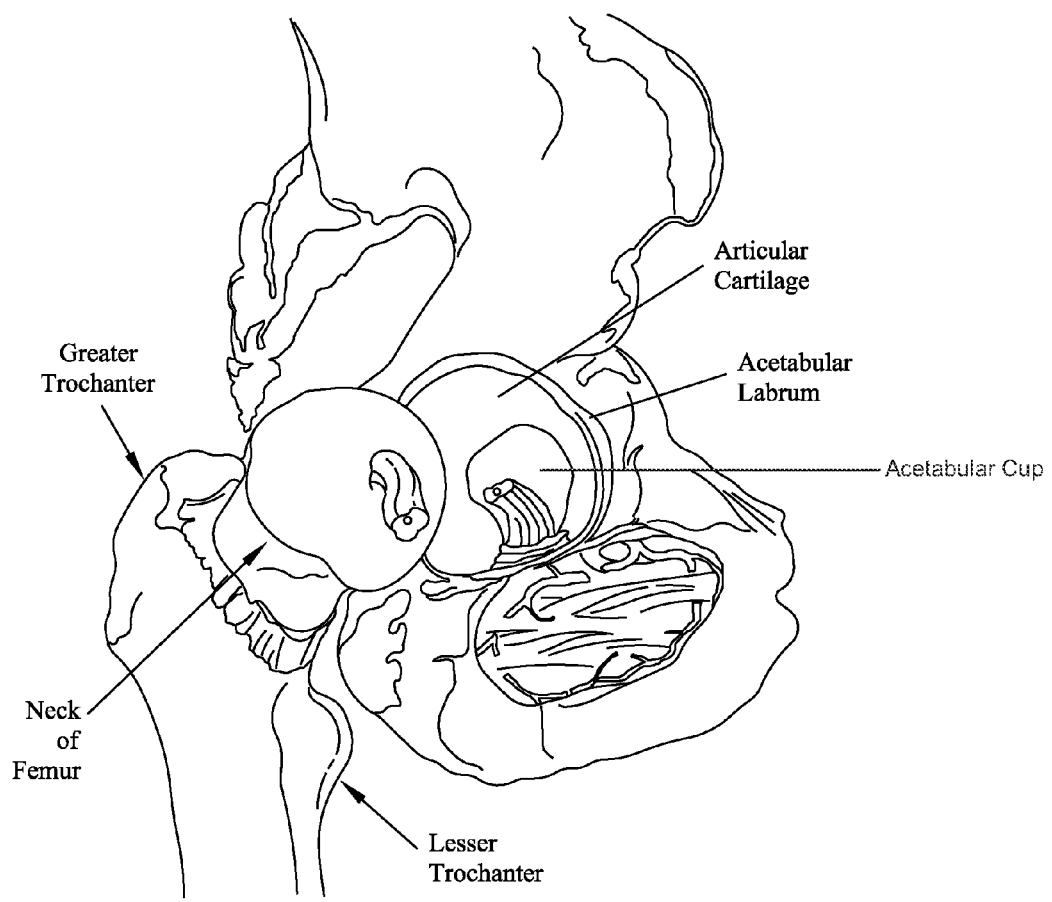
Figure 10:
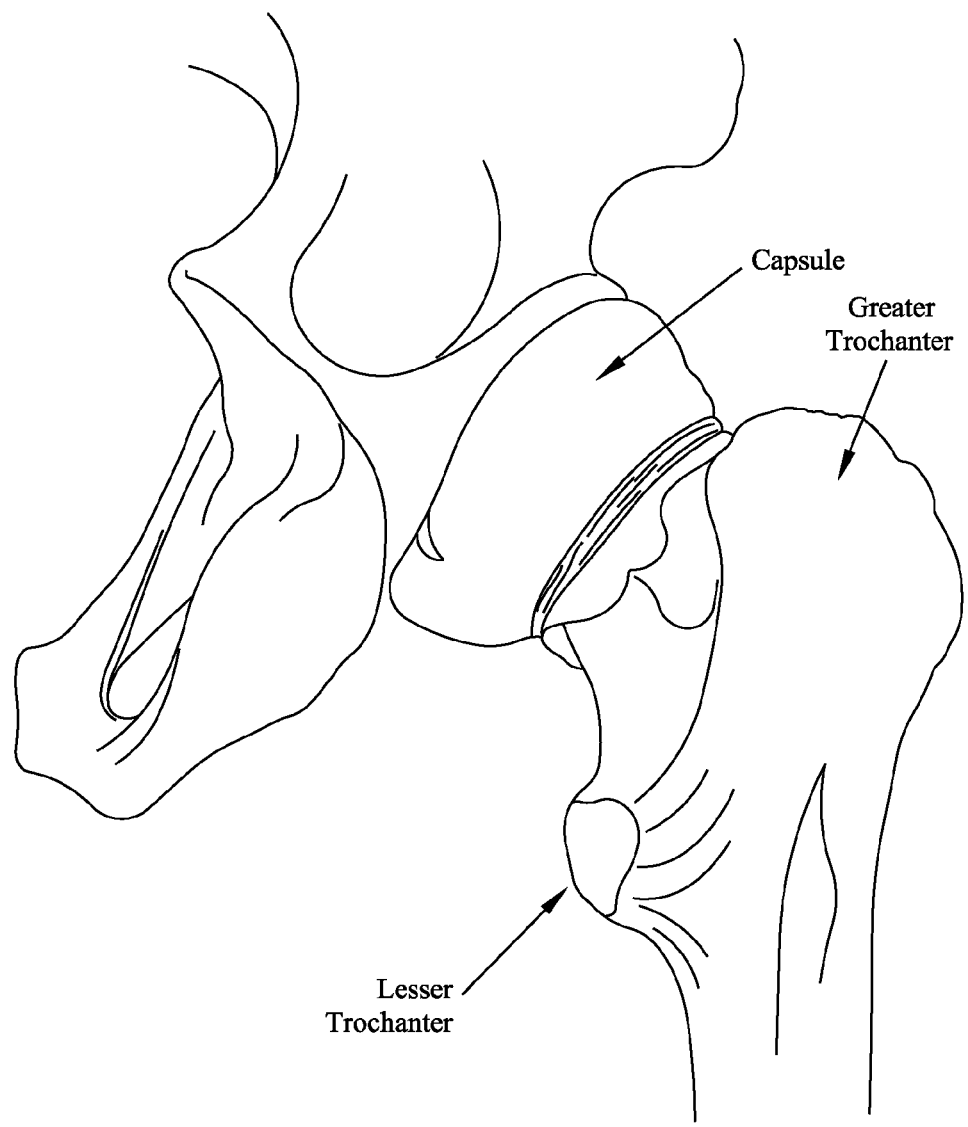
Figure 11:
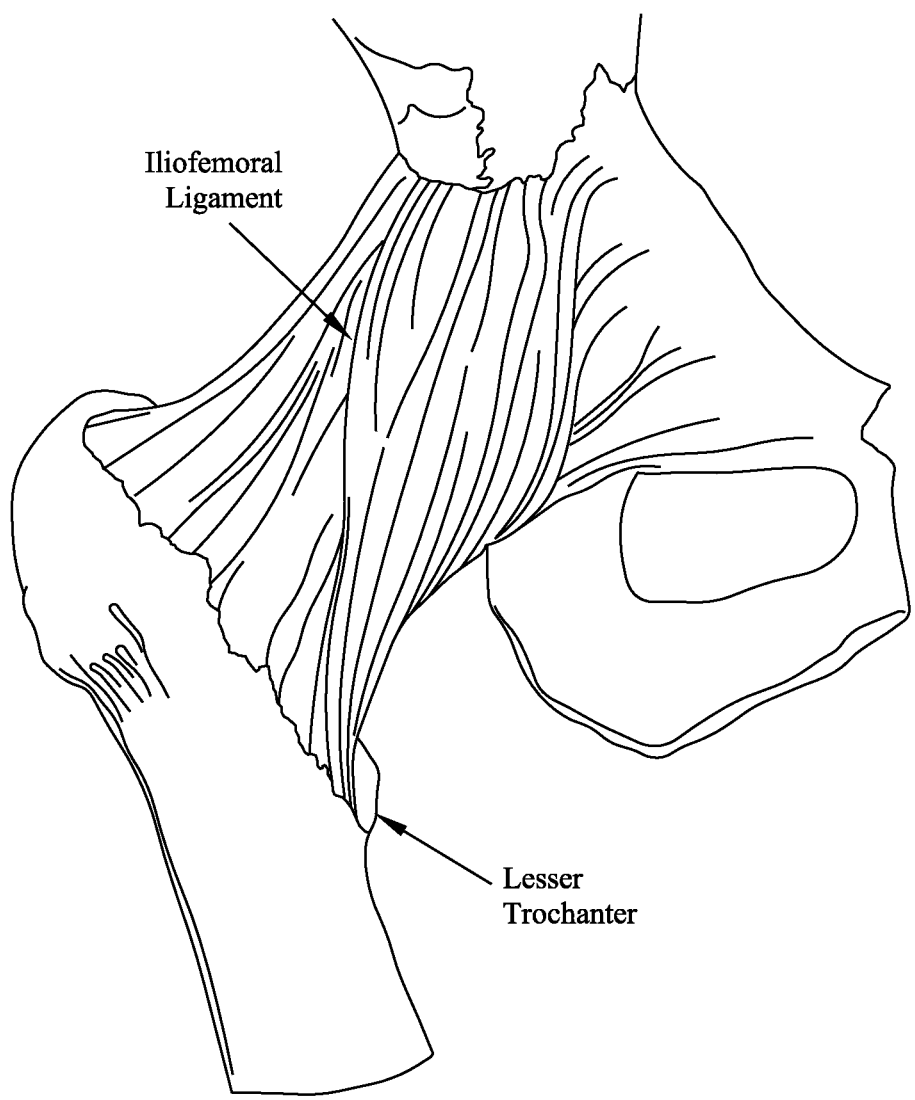
Figure 12:
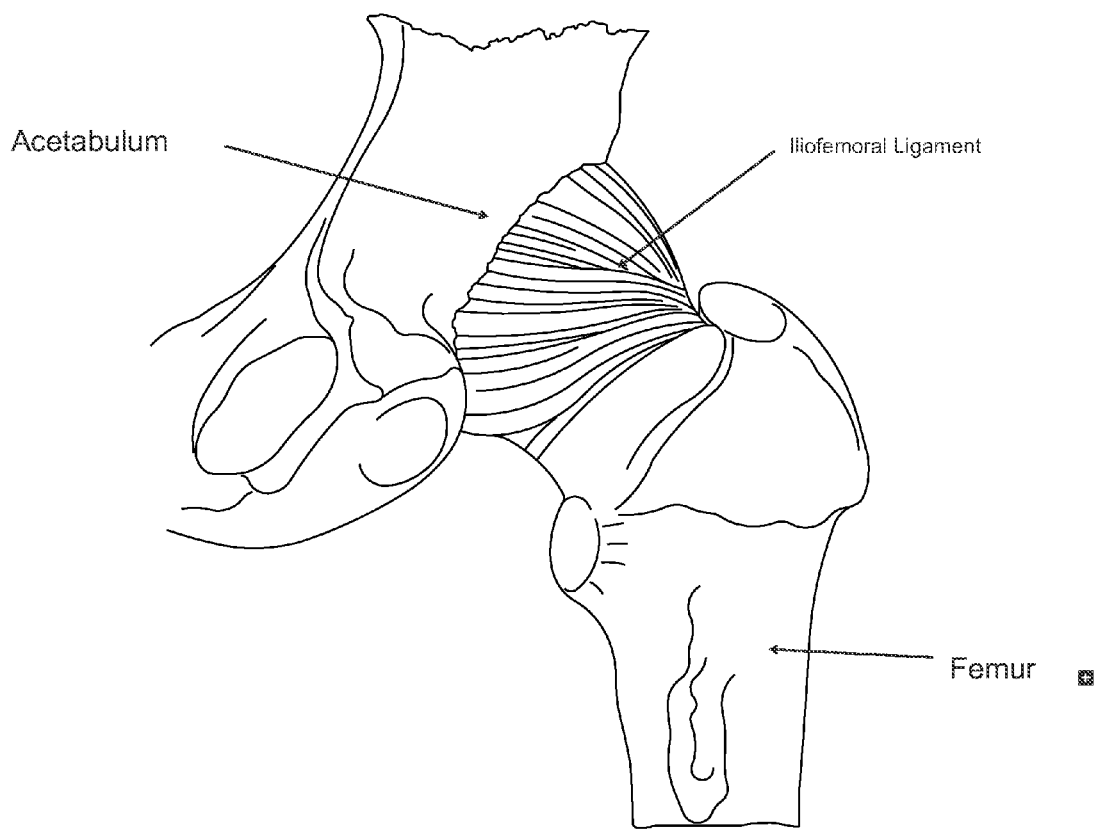
Figure 15:
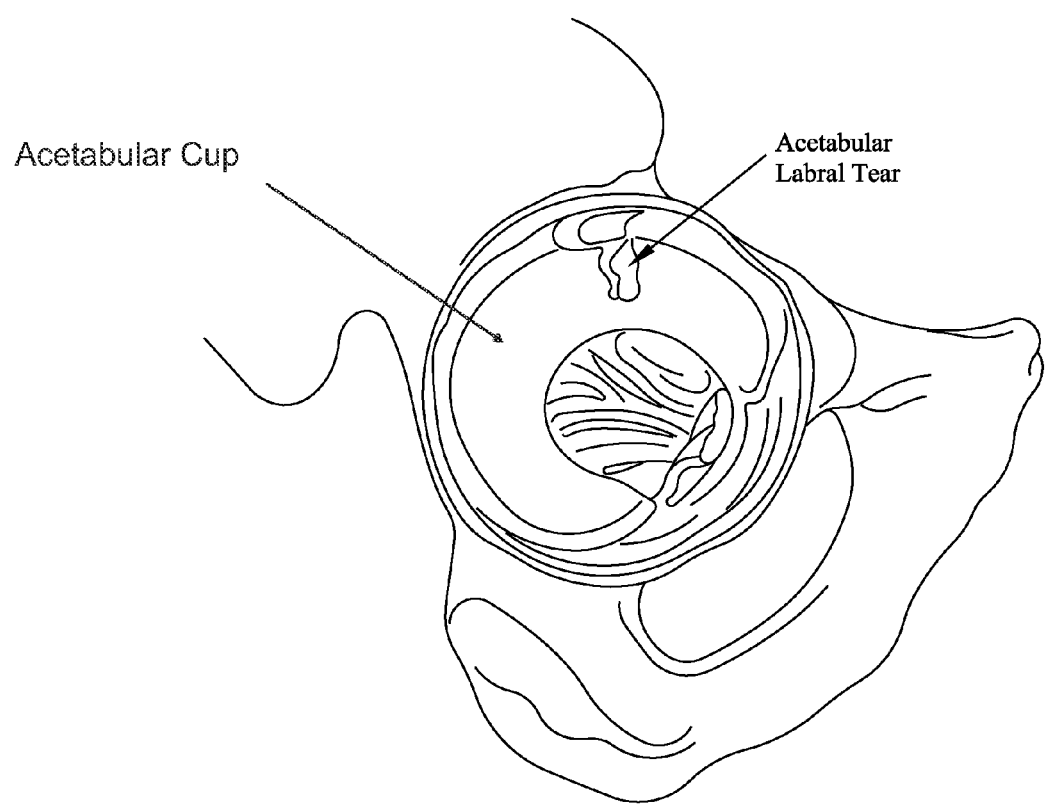
FIG. 15 is a schematic view showing a labral tear.
Figure 16:
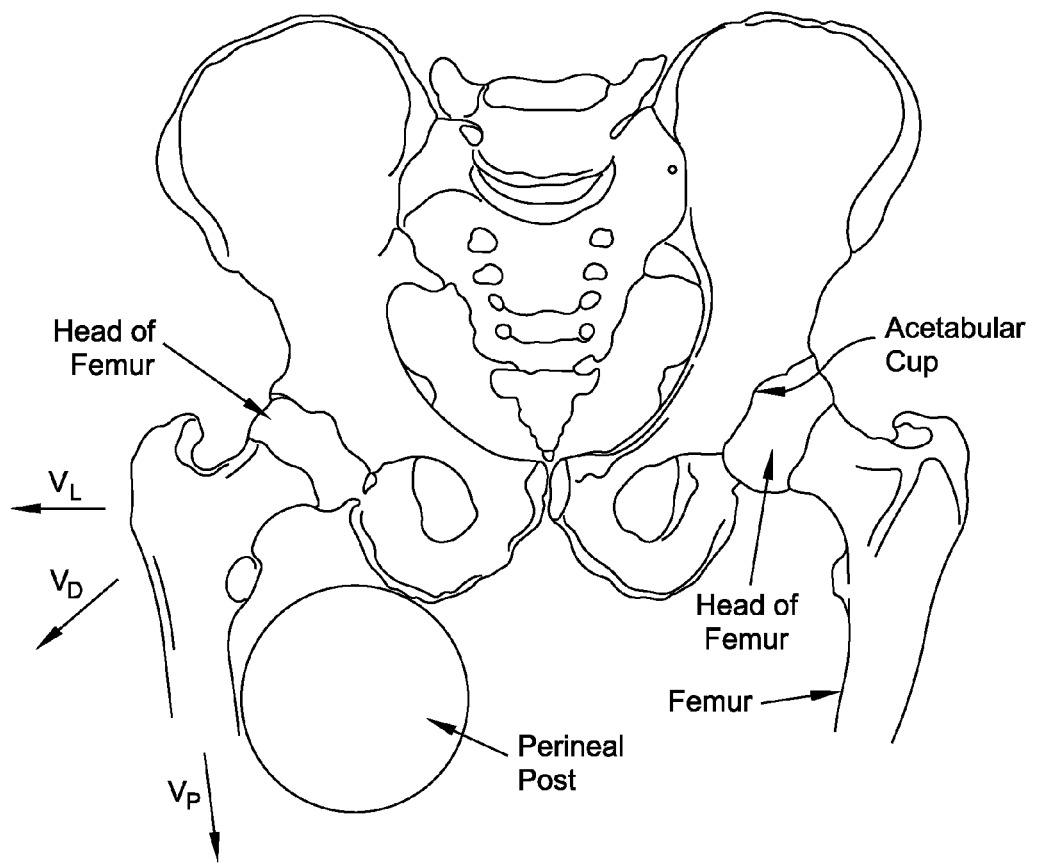
FIG. 16 is a schematic view showing how a perineal post is used in conjunction with an external traction device to distract the hip joint in a conventional hip distraction.
Figure 20:
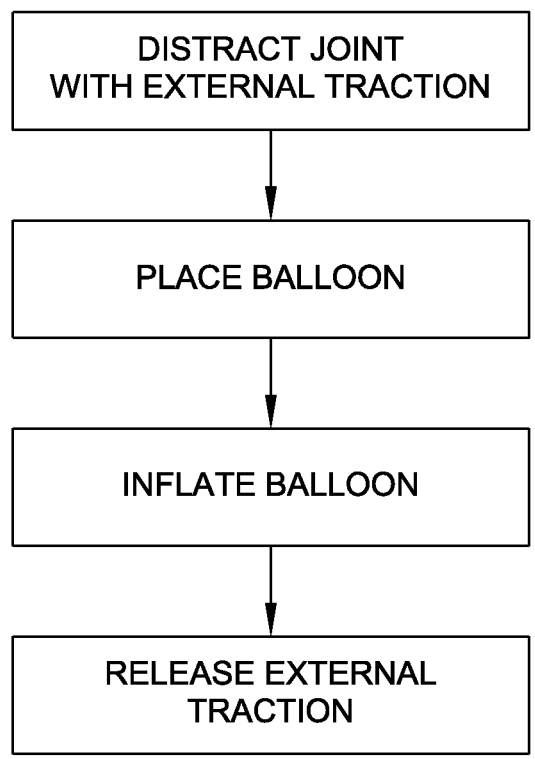
FIG. 20 is a schematic flowchart showing one novel aspect of a novel method for distracting a joint.

More particularly, in this form of the invention, and looking now at FIG. 20, the hip joint is first distracted using a standard leg distraction technique, e.g., by positioning a perineal post between the patient's legs, applying an external distraction device to the distal end of the leg and using the external distraction device to pull on the distal end of the leg with a substantial force, and then adducting the leg so as to unseat the ball of the femur from the acetabular cup, in the manner described above and shown in FIG. 16. This action separates the head of the femur from the acetabular cup by a distance which is greater than the distance that they are normally separated from one another when the joint is in a healthy state, whereby to distract the joint and create a substantial intrajoint space. By way of example but not limitation, the head of the femur may be separated from the acetabular cup by a distance of approximately 10-20 mm or more, and preferably in the range of approximately 15 mm.

Next, joint-spacing balloon catheter 5, with its balloon 15 set in its deflated state, is inserted into the space created between the ball of the femur and the acetabular cup. This may be done under direct visualization (i.e., using an endoscope inserted into the distracted joint), or under fluoroscopy, or both.

Figure 21:
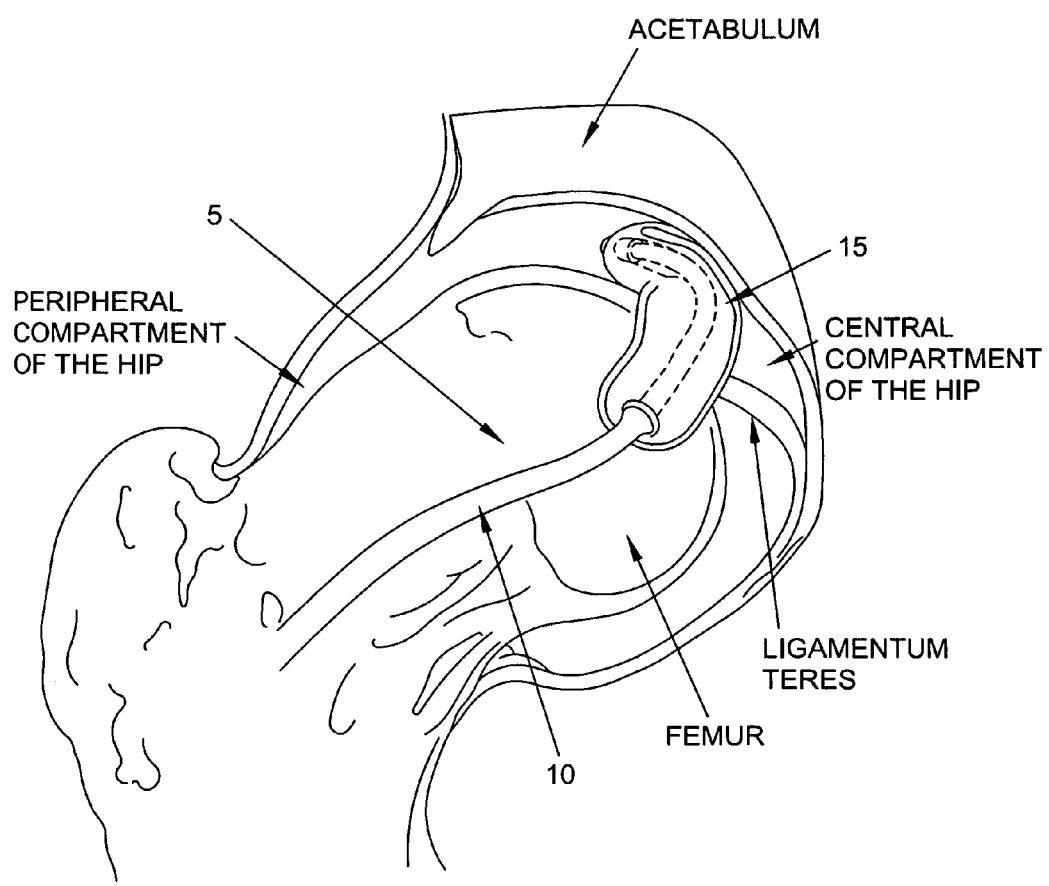
FIG. 21 is a schematic view showing the novel joint-spacing balloon catheter of FIGS. 17-19 being deployed within a hip joint.

Then balloon 15 is inflated. See FIG. 21.

Next, the distal force which was previously applied to the distal end of the leg is partially or fully released. Release of the full distraction force has the beneficial effect of completely eliminating the tension load imposed on the intervening tissue of the leg, whereas a partial release of the distraction force only partially eliminates the tension load imposed on the intervening tissue of the leg—however, even such partial release of the distraction force can still meaningfully reduce the tension load imposed on the intervening tissue of the leg, and it provides a safeguard in the event that balloon 15 should prematurely deflate, e.g., mid-procedure. The aforementioned partial or full release of the external distraction force allows the ball of the femur to seat itself on the inflated balloon, with the balloon acting as a spacer so as to maintain a desired spacing between the ball of the femur and the acetabular cup. This action keeps the head of the femur separated from the acetabular cup by a distance which is greater than the distance that they are normally separated from one another when the joint is in a healthy state, whereby to maintain a substantial intrajoint space which provides the surgeon with excellent access to the central compartment of the hip joint. By way of example but not limitation, the head of the femur may be maintained separated from the acetabular cup by a distance of approximately 10-20 mm or more, and preferably in the range of approximately 15 mm. Thus, joint distraction is maintained even though a substantial distraction force is no longer being applied to the distal end of the leg with an external distraction device. Since joint distraction can be reliably maintained without the risk of damage to the intervening tissue from a substantial externally-applied distraction force, the traditional concern to complete procedures in 90 minutes or less is substantially diminished, and complications from joint distraction are greatly reduced. This is a very significant improvement over the prior art.

With respect to the foregoing method of the present invention, it should also be appreciated that once the joint-spacing balloon catheter 5 is supporting the load of the femoral head (i.e., maintaining the space between the femoral head and acetabular cup), the balloon can be further inflated or deflated so as to increase or decrease the space between the femoral head and acetabular cup.

With the joint so distracted, the arthroscopic surgery can then proceed in the normal fashion. Among other things, this includes accessing the central compartment with instruments, performing therapy on the labrum, treating femoroacetabular impingement, treating articular cartilage within the central compartment of the hip joint, etc.

Figure 22:
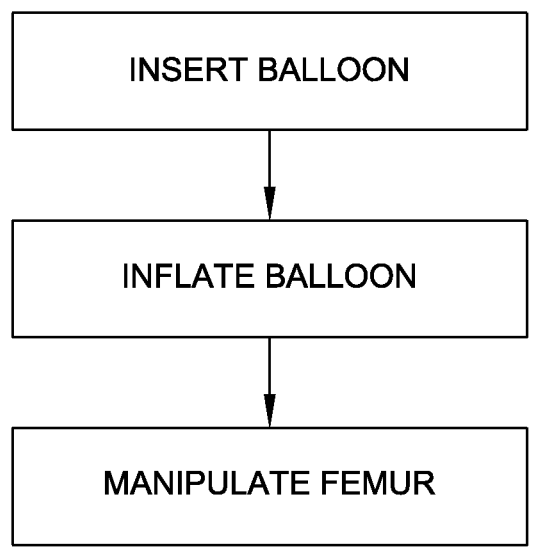
FIG. 22 is a schematic flowchart showing another novel aspect of a novel method for distracting a joint.
Figure 23:
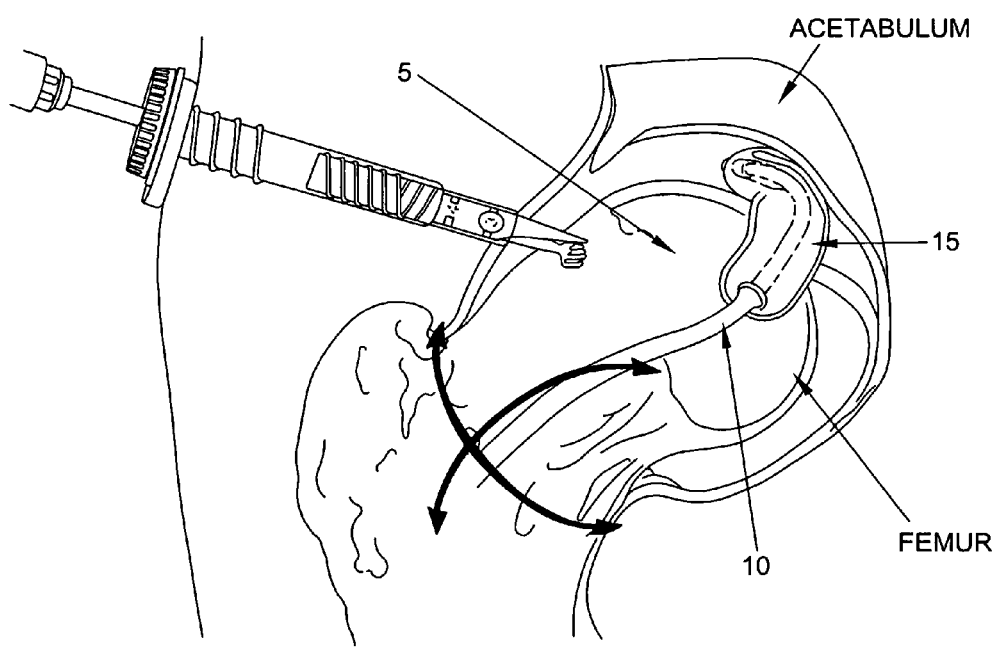
FIG. 23 is a schematic view showing how the leg of a patient may be manipulated once the ball of the femur is being supported on the inflated balloon of the joint-spacing balloon catheter, and once the external distracting force previously applied to the distal end of the leg has been released.
Figure 23:
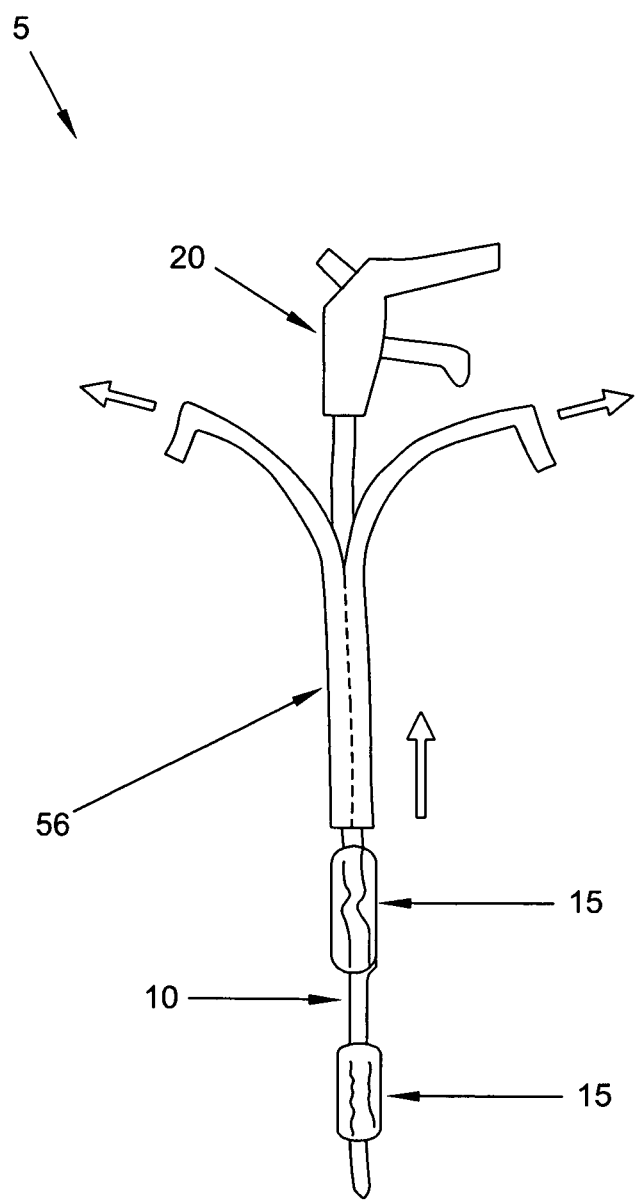

Significantly, and in accordance with another novel aspect of the present invention (see FIG. 22), the use of joint-spacing balloon catheter 5 can enable the leg to be manipulated while the joint is in a distracted state. More particularly, it has been discovered that, once balloon 15 has been inflated within the joint and the pulling force applied to the distal end of the leg by an external distraction device has been partially or fully released, so that the head of the femur is resting on the balloon, the leg can be moved about (i.e., pivoted) on the balloon. Manipulation can include flexion and extension, adduction and abduction, as well as internal and external rotation. See, for example, FIG. 23. This manipulation of the leg while the joint is in a distracted, balloon-supported state enables more of the joint anatomy and pathology to be visualized and accessed, for superior surgical results. By contrast, a patient's leg cannot be manipulated in this manner when the leg is being distracted in a conventional manner, i.e., by a pulling force applied to the distal end of the leg by an external distraction device. Therefore, procedures can be performed using the present invention which cannot be performed using conventional distraction techniques. This is a very significant improvement over the prior art.

Additionally, some procedures which would normally require the creation of an additional portal to access pathology can be accomplished without the creation of the additional portal, thereby reducing the visible scar and potential morbidity of the additional portal. This is also a significant improvement over the prior art.

At the conclusion of the arthoscopic surgery, a distal force is re-applied to the distal end of the leg (e.g., via the external distraction device) so as to take the load off the inflated balloon, the balloon is deflated, and then the joint-spacing balloon catheter is removed from the interior of the joint. Alternatively, the balloon may be deflated and removed from the joint without the re-application of a distal force to the leg by an external distraction device.

Finally, the distal force applied to the distal end of the leg is released, so as to allow the ball of the femur to re-seat itself in its normal position within the acetabular cup.

With respect to the foregoing method of the present invention, it should be appreciated that joint-spacing balloon catheter 5 can be specifically located in the joint space so as to preferentially bias the position of the femoral head relative to the acetabulum when the pulling force on the distal end of the leg is relaxed and the ball of the femur transfers its load to (i.e., is seated on) the inflated balloon. For example, positioning joint-spacing balloon catheter 5 so that balloon 15 is more posterior in the joint causes the femoral head to settle in a more anterior position, which can improve visualization and access to the posterior acetabular rim.

With respect to the foregoing method of the present invention, it should also be appreciated that joint-spacing balloon catheter 5 can be placed in the joint space so as to provide better visualization and access to the peripheral compartment of the hip.

Thus it will be seen that the present invention provides a safe and simple way to significantly reduce trauma to intervening tissue in the leg when practicing leg distraction, since a substantial distally-directed force only needs to be applied to the distal end of the patient's leg long enough for the deflated balloon to be positioned in the distracted joint and for the balloon to thereafter be inflated—the distally-directed distraction force does not need to be maintained on the distal end of the patient's leg during the surgery itself. As a result, trauma to the intervening tissue is greatly reduced, and the surgeon no longer needs to limit the duration of distraction to 90 minutes or less in order to avoid damage to the intervening tissue. This is a very significant improvement over the prior art.

In addition, the use of the present invention enables more of the joint anatomy and pathology to be visualized and accessed, since supporting the ball of the femur on an inflated balloon allows the initial external distraction to be relaxed, and allows the leg to be manipulated on the inflated balloon while the joint is in a distracted state. By contrast, the leg cannot be manipulated in this manner while the leg is being distracted in a conventional manner, i.e., by a pulling force applied to the distal end of the leg by an external distraction device. Therefore, arthroscopic procedures can be performed using the present invention which cannot be performed using conventional distraction techniques. This is a very significant improvement over the prior art.

Additionally, some procedures which would normally require the creation of an additional portal to access pathology can be accomplished without the creation of the additional portal, thereby reducing the visible scar and potential morbidity of the additional portal. This is also a significant improvement over the prior art.

Further Details of the Joint-Spacing Balloon Catheter

It will be appreciated that balloon 15 preferably serves as a both a spacer to allow access to the central compartment of the hip joint and as a pivot support to allow the manipulation of the femur while the joint is distracted. Balloon 15 is constructed so as to be atraumatic in order to avoid damaging the anatomy, including the cartilage surfaces of the joint. At the same time, and as will hereinafter be discussed in further detail, balloon 15 may be appropriately textured and/or sculpted in order to help maintain its position within the joint, preferentially to enhance engagement with either one of the acetabulum or femur, while still allowing the opposing bone to move smoothly over the balloon surface.

In one preferred form of the invention, elongated shaft 10 has an outer diameter of about 0.040" (or less) to about 0.250" (or more). An outer diameter of approximately 0.120" to 0.200" is preferred for many hip applications.

If desired, a retractable and/or removable sheath may be provided over shaft 10 in order to cover balloon 15 prior to inflation. This sheath may be a peel-away design, as is commonly used in vascular catheter systems. See, for example, FIG. 23' which shows a peel-away sheath 56 covering the distal end of elongated shaft 10 (including covering two balloons 15 provided on the distal end of the elongated shaft). A peel-away sheath construction enables the sheath to be removed during or after delivery of the balloon(s) to the desired site. The retractable and/or removable sheath may comprise a polymer. The polymer may be of a low friction type so as to facilitate smooth advancement of the sheath through the anatomy during delivery (e.g., the sheath may be formed out of PTFE or expanded-PTFE or nylon).

And if desired, the distal end of shaft 10 can be pre-shaped with a bend so as to give joint-spacing balloon catheter 5 a directional bias at its distal end.

Furthermore, if desired, and looking now at FIGS. 23A-23D, an outer guiding member 57 may be provided for directing joint-spacing balloon catheter 5 to a location within the joint. More particularly, in this form of the invention, outer guiding member 57 comprises a central lumen 58 sized to slidably receive joint-spacing balloon catheter 5—the outer guiding member is advanced into position within the joint, and then joint-spacing balloon catheter 5 is advanced down the central lumen 58 of outer guiding member 57 and then out the distal end of outer guiding member 57 so that the distal end of joint-spacing balloon catheter 5 is properly disposed within the interior of the joint.

Figures 23A, 23B:
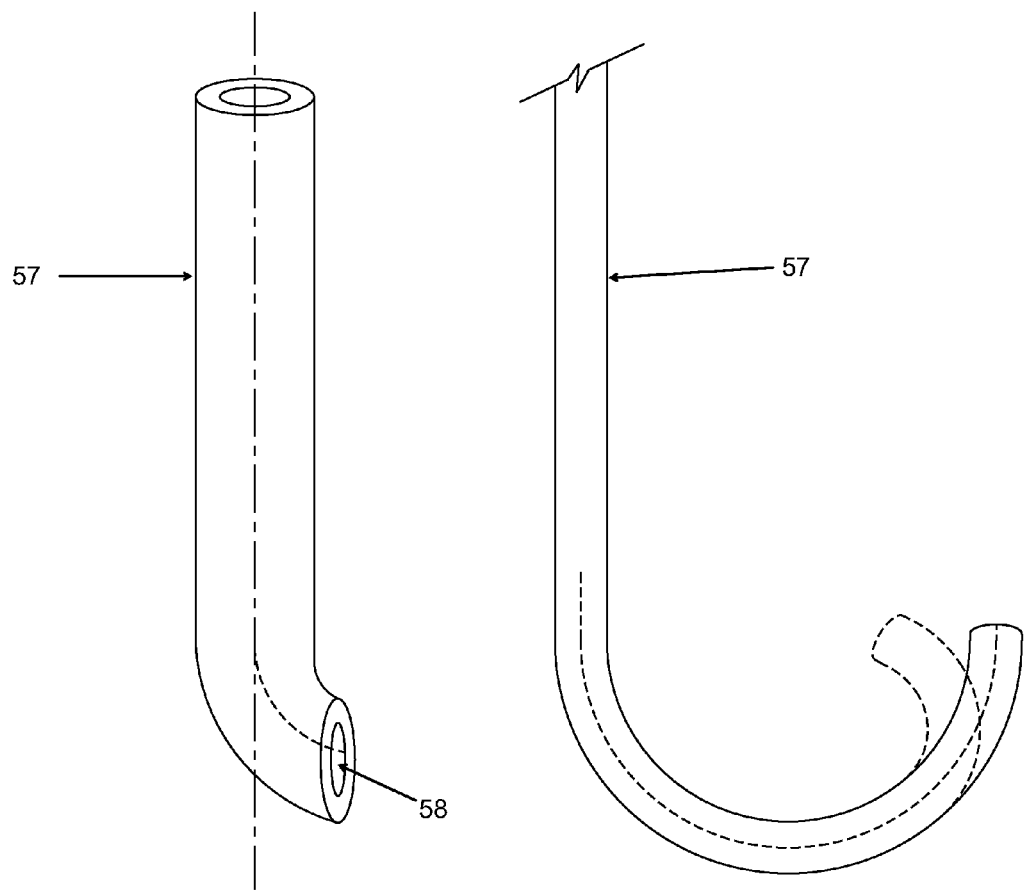
FIGS. 23A-23D are schematic views showing an outer guiding member which may be used to deploy the joint-spacing balloon catheter within the joint.
Figure 23C:
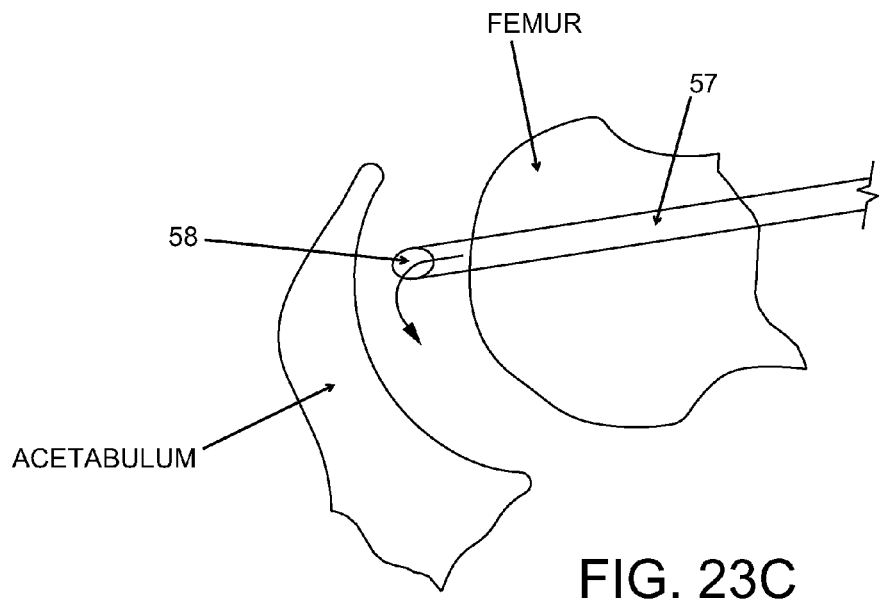
Figure 23D:
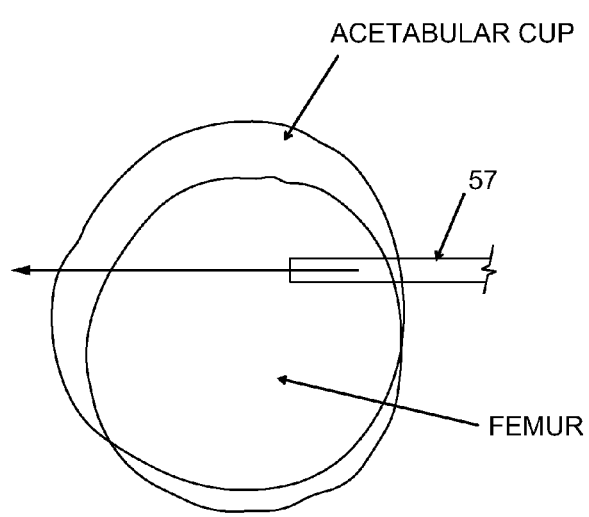

More particularly, FIG. 23A is a schematic view showing an outer guiding member 57 which may be used to deploy joint-spacing balloon catheter 5 within the joint. In many instances, the portal through the skin does not directly align with a desired location within the joint space (e.g., with the acetabular rim region of the hip joint). Outer guiding member 57 has a curve at its distal end which can be aligned with the desired location within the joint space, thus facilitating delivery of joint-spacing balloon catheter 5 to the desired joint space. The joint-spacing balloon catheter 5 is advanced through the central lumen 58 of outer guiding member 57 and exits in a direction which better facilitates navigating the distal end of the joint-spacing balloon catheter to the desired joint space, e.g., around the femoral head. The joint-spacing balloon catheter 5 may have a pre-shaped distal end that further enables guidance into the joint space. Alternatively, joint-spacing balloon catheter 5 could be steerable as discussed above. In one preferred form of the invention, outer guiding member 57 is positioned in the patient such that the distal tip of outer guiding member 57 is at or near the entrance to the central compartment of the hip (FIGS. 23C and 23D). Alternatively, the distal end of outer guiding member 57 can be placed within the central compartment of the hip. The distal tip of outer guiding member 57 is oriented in the desired direction for proper placement of the balloon. Joint-spacing balloon catheter 5 is then advanced through the central lumen 58 of outer guiding member 57 and into the joint space until balloon 15 is in the desired location (the arrows in FIGS. 23C and 23D indicate direction of balloon catheter delivery). The outer guiding member can be used to help adjust the final balloon position. The outer guiding member 57 can be left in place during the procedure to help tether the joint-spacing balloon catheter in position within the joint. Additionally, outer guiding member 57 can provide a conduit to remove the joint-spacing balloon catheter from the body.

In one preferred form of the invention, balloon 15 is preferably approximately 28 mm in diameter, although it can also range from about 10 mm (or less) in diameter to about 50 mm (or more) in diameter if desired. Furthermore, in one preferred form of the invention, the length of balloon 15 is preferably approximately 50 mm, although it can also range from about 10 mm (or less) in length to about 75 mm (or more) in length if desired. In this respect, it will be appreciated that balloons of various sizes may be used to address patients of different sizes, variations in anatomy, and/or different pathologies.

Balloon 15 may be inflated with a pressure of up to about 1000 psi, and is preferably inflated with a pressure of up to about 200 psi, and is most preferably inflated with a pressure of up to about 100 psi. In this respect it will be appreciated that it is generally accepted that a force of about 50-80 lbs. is sufficient to distract the hip joint. In order for joint-spacing balloon catheter 5 to support this force, it must provide sufficient pressure over a sufficient surface area (force=pressure×area). Although a number of different balloon sizes and operating pressures can be envisioned, there are limitations on the balloon size and pressure to consider. On the one hand, the balloon must be large enough to cover a sufficient amount of cartilage such that the pressure on the cartilage is lower than that which would damage the cartilage. On the other hand, the balloon must be small enough so as to permit access to, and visualization of, the operative areas. Hence, there is an optimal range of balloon size and operating pressure, and this optimal range is dependent on tissue dynamics.

In one preferred form of the invention, balloon 15 is fabricated so as to be semi-compliant, although it can also be fabricated so as to be compliant or non-compliant if desired. Examples of semi-compliant balloon materials include polyurethane, nylon and polyether block amide (PEBAX). An example of a compliant balloon material is silicone rubber. An example of a non-compliant balloon material is polyethylene terapthalate (PET). A compliant or semi-compliant balloon is generally preferred over a non-compliant balloon since it will deform under load to the shape of the surface which the balloon is contacting in order to help distribute load onto that surface. A semi-compliant balloon is generally most preferred since it will retain some aspects of its pre-load shape even when under load, which can be helpful in directing or maintaining bone positioning, particularly when the leg is being manipulated while in a distracted state. The thickness of the balloon material is preferably in the range of about 0.001" to about 0.020", and is most preferably between about 0.002" and about 0.012". The durometer of the balloon material is preferably in the range of about 30 Shore A to about 85 Shore D, and is most preferably between about 40 Shore D and about 85 Shore D.

If desired, the surfaces of balloon 15 can be textured (e.g., with dimples, ridges, etc.) or covered with another material (e.g., a coating or covering) so as to prevent slippage of the balloon along cartilage when the balloon is being used to support a joint. At the same time, this surface texture or non-slip covering is configured so as to engage the cartilage without causing cartilage damage. In one preferred form of the invention, only a portion of the outer surface of the balloon is textured or covered with a non-slip material. For example, the portion of the balloon which faces the acetabulum may be textured or covered with a non-slip material, but the portion of the balloon which faces the femoral head may be non-textured or non-covered, so as to keep the surface facing the acetabulum from slipping while allowing the surface facing the femoral head to slide relative to the femoral head. In another preferred form of the invention, a majority of the balloon surface is textured or covered with a non-slip material. In yet another preferred form of the invention, two or more different textures or non-slip coverings are provided on the outer surface of the balloon, e.g., depending on the particular cartilage surface which they are intended to engage.

In yet another embodiment of the invention, the balloon is covered with a low friction material which enables slippage of a joint surface on the balloon. The low friction material may cover some or all of the balloon surface.

The balloon may comprise both low slippage and low friction coverings if desired.

Furthermore, if desired, fluoroscopic markings can be incorporated into or disposed on elongated shaft 10, or incorporated into or disposed on balloon 15, or incorporated into or disposed on another part of joint-spacing balloon catheter 5, so as to render the apparatus visible under X-ray. Such fluoroscopic markings may comprise radiopaque ink applied to the apparatus, radiopaque bands applied to the apparatus, radiopaque material incorporated in the construction of the apparatus, and/or a radiopaque fluid used to inflate the balloon (such as a contrast agent). By way of example but not limitation, a radiopaque band material could comprise platinum. By way of further example but not limitation, a radiopaque fluid could comprise a contrast agent such as Dodecafluoropentane.

Figure 91:
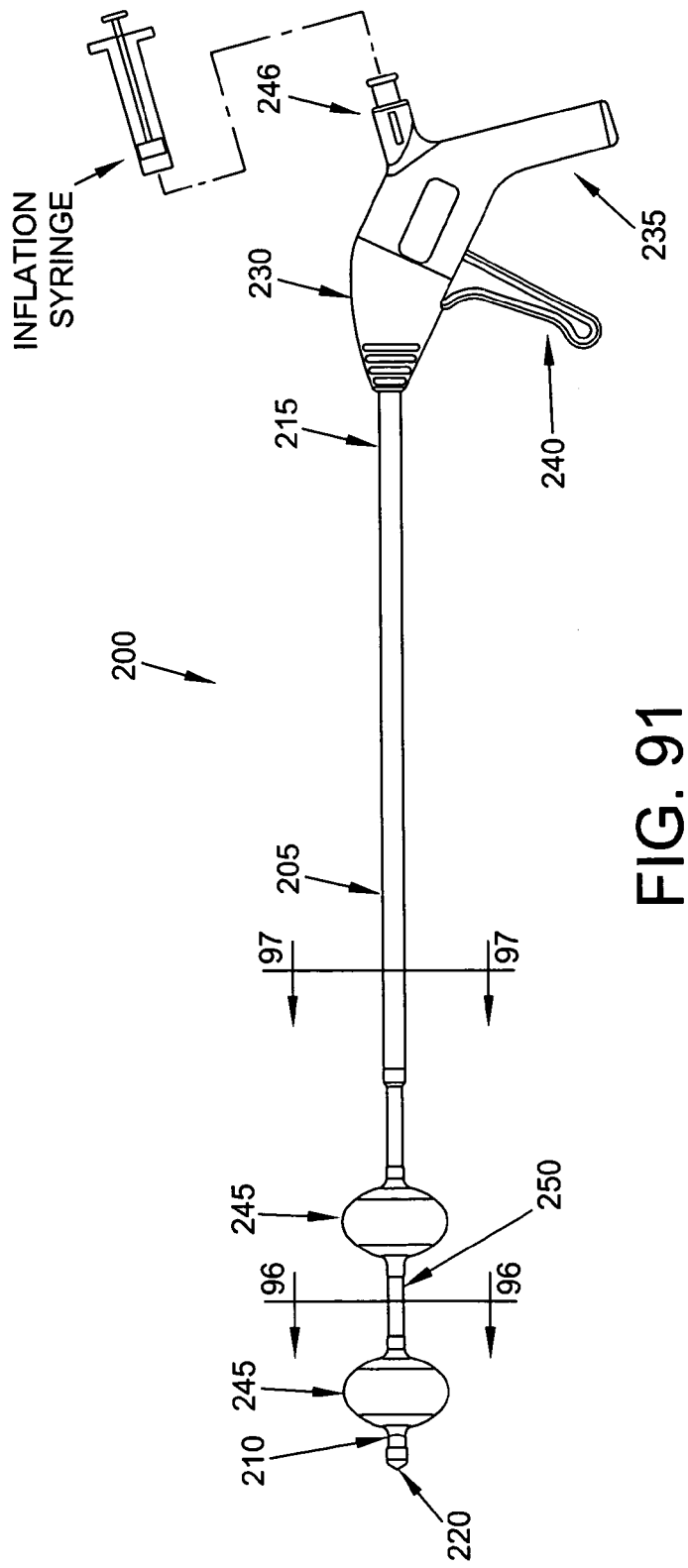

In one preferred form of the invention, balloon 15 is preferably inflated with a liquid medium, e.g., saline; however, it could also be inflated with a gaseous medium, e.g., air. Among other things, the balloon can be inflated with a high viscosity fluid. This latter construction may be beneficial in the event of a balloon puncture as it would slow the pace of balloon deflation. If desired, a fluid could be used which changes viscosity when subject to changes in temperature, electrical charge, magnetic field, or other means. Alternatively, the balloon can be filled with a compound which increases in viscosity when exposed to saline. This latter construction can be advantageous in certain circumstances, e.g., in the event of a balloon puncture, the escaping fluid would react with the saline present in the joint and could at least partially seal the puncture hole in the balloon.

Where balloon 15 is inflated with a gaseous medium, and that gaseous medium is air, inflation/deflation control mechanism 50 may comprise a pump, and supply port 55 may be open to the atmosphere.

Where balloon 15 is inflated with a liquid medium, the joint-spacing balloon catheter 5 may further comprise an inflation mechanism (not shown in FIGS. 17 and 18, but shown as an inflation syringe in FIG. 91). The inflation mechanism can be a syringe, a pump, an indeflator, or other commonly used liquid inflation mechanisms. In general, a simple hand-operated syringe mechanism of the sort shown in FIG. 91 is generally preferred. The inflation mechanism may separately connect to the supply port 55, e.g., via a Luer-type fitting.

The inflation time of the balloon is preferably less than 2 minutes, and more preferably less than 1 minute, and more preferably less than 30 seconds.

Figure 24:
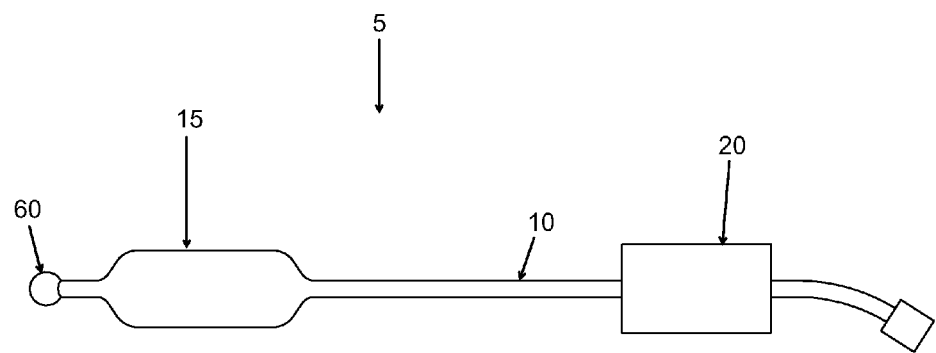
FIGS. 24-28 are schematic views showing how one or more expandable elements may be used to tether the joint-spacing balloon catheter to the capsule of the joint.
Figure 27:
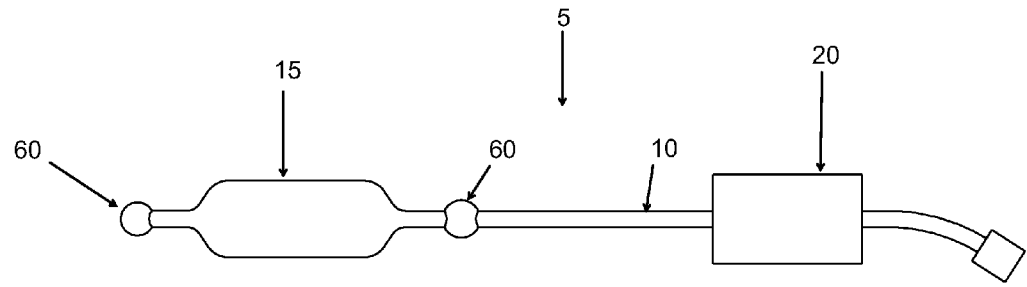
Figure 25:
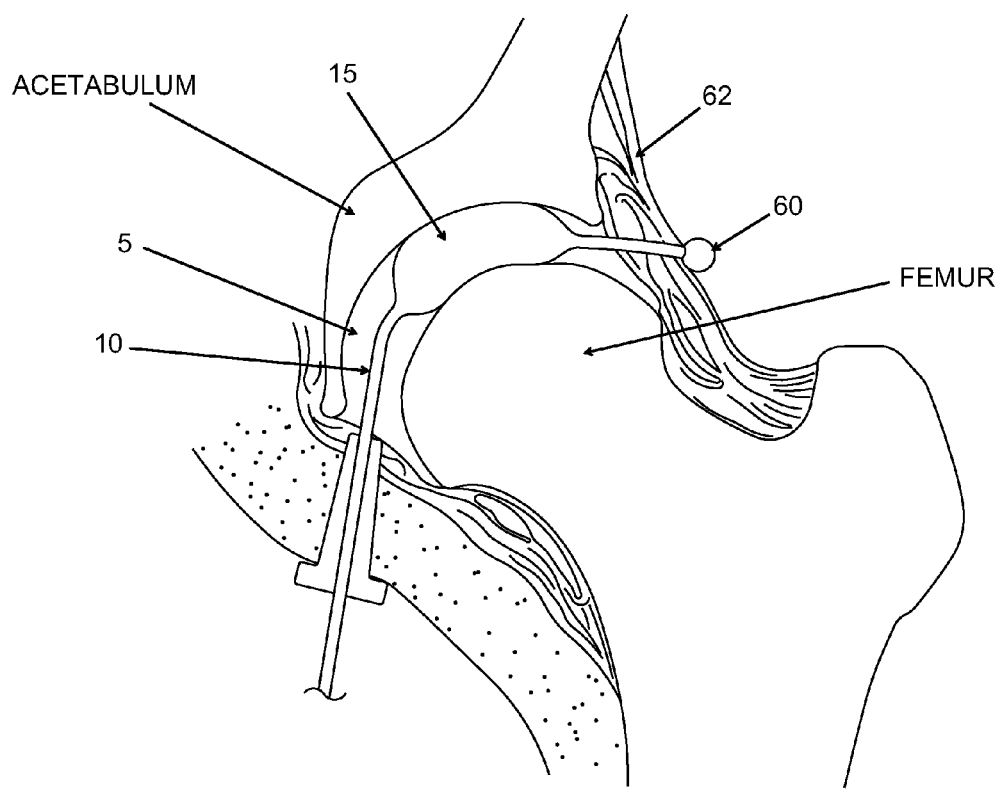
Figure 26:
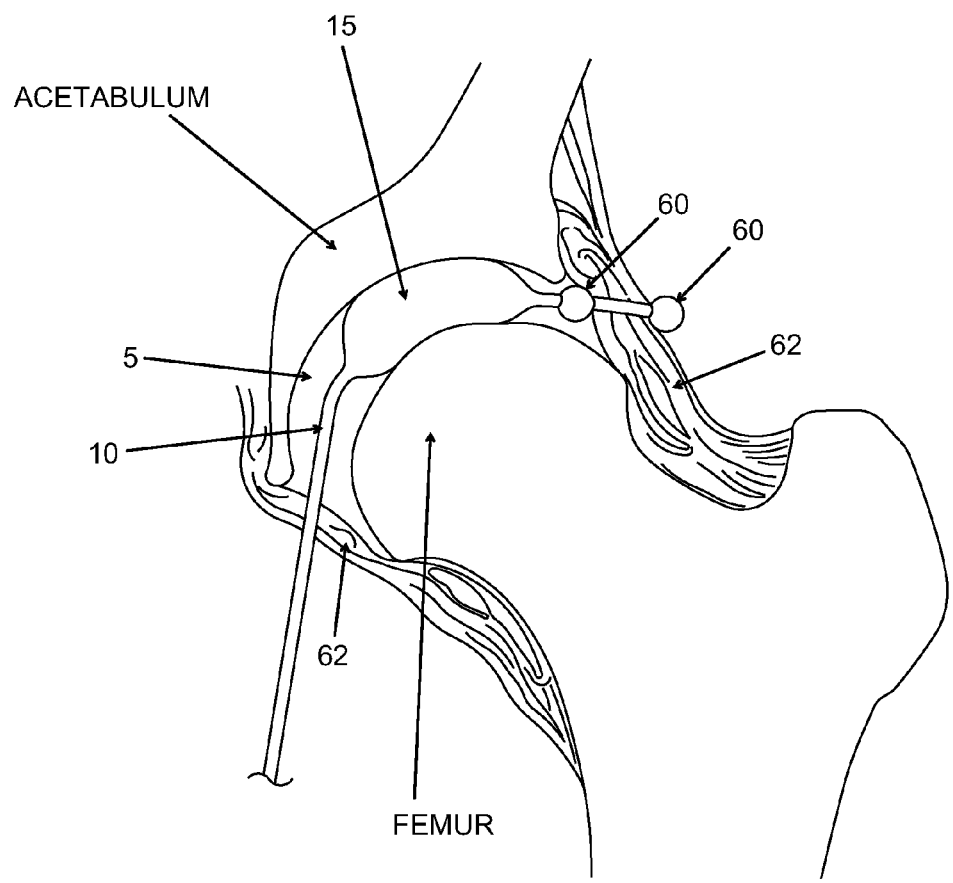
Figure 28:
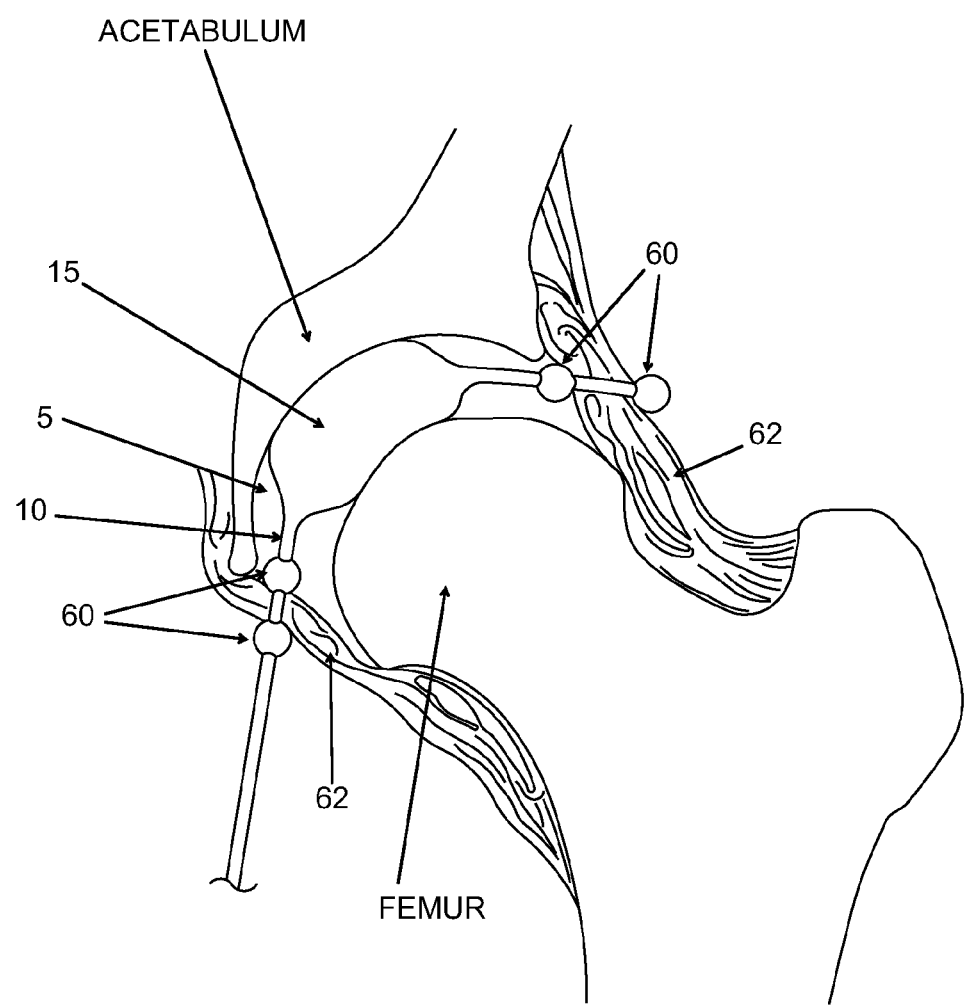

In one aspect of the invention, and looking now at FIGS. 24-28, joint-spacing balloon catheter 5 further comprises one or more expandable elements 60 in addition to balloon 15. These expandable elements 60 can be another balloon, a collapsible braid, and/or some other structure which can expand when desired to a larger lateral dimension. Expandable element 60 can be used to releasably secure joint-spacing balloon catheter 5 to the joint capsule. In one embodiment, and as shown in FIG. 24, an expandable element 60 is located at the distal end of the joint-spacing balloon catheter. This expandable element 60 is laterally expanded once the distal end of the balloon catheter (and the expandable element 60) has passed through the capsule 62 (FIG. 25) at the far side of the joint, so that the expandable element is deployed on the far side of the capsule, whereby to stabilize balloon 15 within the joint. In another embodiment, a second expandable element 60 is provided proximal to the first expandable element 60 but distal to balloon 15 (FIG. 26) and is expanded adjacent to the internal surface of the far capsule so that the far side of the capsule is sandwiched between the two expandable elements 60, whereby to further stabilize balloon 15 within the joint. In this respect it should be appreciated that the two expandable elements 60 may or may not be expanded simultaneously. In yet another embodiment, and looking now at FIG. 27, one or more expandable elements 60 are disposed proximal to the balloon 15, to tether the joint-spacing balloon catheter to capsule 62 at the proximal portion of the joint, such as is shown in FIG. 28.

Figure 28A:
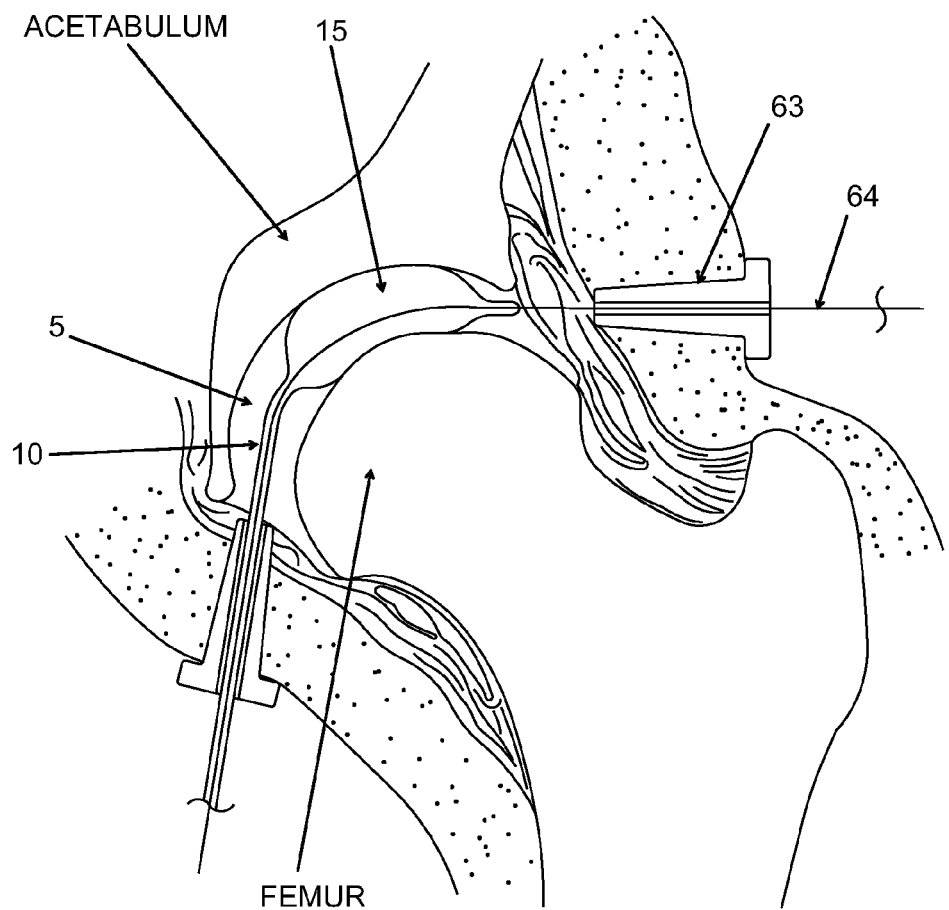
FIG. 28A is a schematic view showing another means for stabilizing the joint-spacing balloon catheter within a joint.

In another embodiment (FIG. 28A), a second cannula 63 is used to secure the distal end of joint-spacing balloon catheter 5 relative to the anatomy. More particularly, in this form of the invention, the distal tip of joint-spacing balloon catheter 5, (or a flexible element 64 which extends from the distal end of the joint-spacing balloon catheter, e.g., a guidewire) is passed into the second cannula 63. The flexible element could be a wire, a suture, a ribbon, a catheter, a braid, or some other construction which is flexible or semi-flexible. The flexible element 64 can be received within the second cannula and/or, if desired, gripped within the second cannula. A gripping feature (not shown) could be provided in the second cannula to achieve this result. Alternatively, the flexible element 64 could pass entirely through the second cannula, e.g., in the manner shown in FIG. 28A. In any case, this construction results in the tip of joint-spacing balloon catheter 5 being partially (e.g., laterally) or fully (e.g., laterally and longitudinally) stabilized in position by the second cannula 63.

Figure 29:
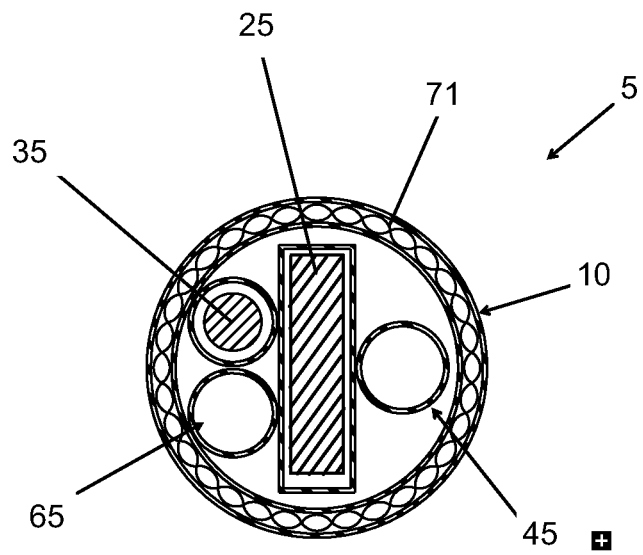
FIGS. 29 and 30 are schematic views showing how additional lumens may be provided in the elongated shaft of the joint-spacing balloon catheter in order to accommodate additional structures, e.g., guidewires, obturators, working instruments, optical fibers, etc.
Figure 30:
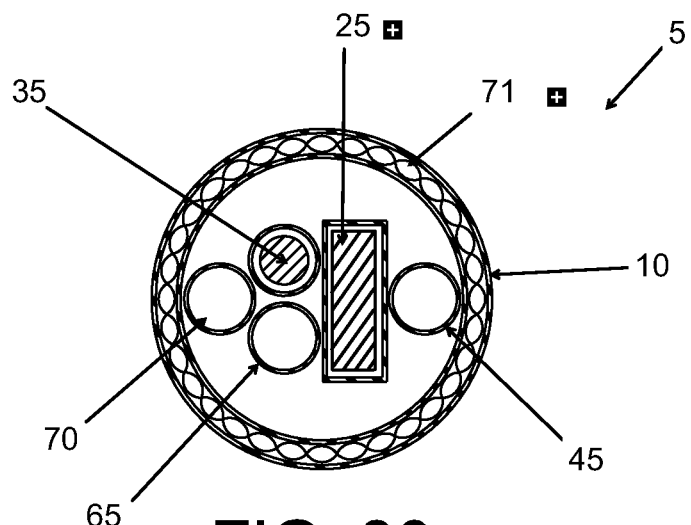

Additionally, and looking now at FIG. 29, another lumen 65 can be provided in elongated shaft 10 to accommodate a guidewire, obturator, light fiber, electrical wire, or the like, or as an additional inflation lumen, etc. And, as shown in FIG. 30, further lumen(s) 70 can be provided for working instruments, etc. If desired, a pre-shaped guidewire or obturator can be placed through one of the lumens of elongated shaft 10 in order to bias the tip direction of the joint-spacing balloon catheter 5 as the joint-spacing balloon catheter is advanced over the pre-shaped guidewire or obturator. Alternatively, a second steerable wire (not shown) can be placed through one of the lumens, so as to enable steering of the balloon catheter in a second direction.

To improve resistance to kinking, or to provide the shaft with the desired stiffness and torsional characteristics, a braid or coil 71 (FIG. 30) may be incorporated into the catheter. The braid or coil could comprise a stainless steel wire, a Nitinol wire, etc. Braid or coil 71 may be incorporated in any section of joint-spacing balloon catheter 5, but is preferably located in at least the flexible section of the catheter.

Figure 31:
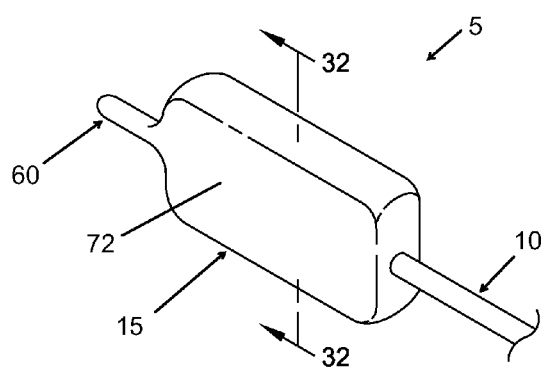
FIGS. 31-35 are schematic views showing alternative configurations for the balloon of the joint-spacing balloon catheter.
Figure 32:
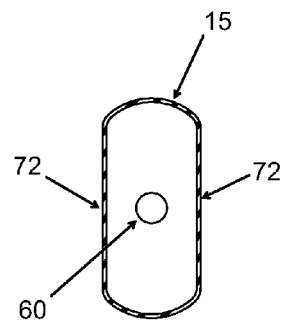
Figure 35:
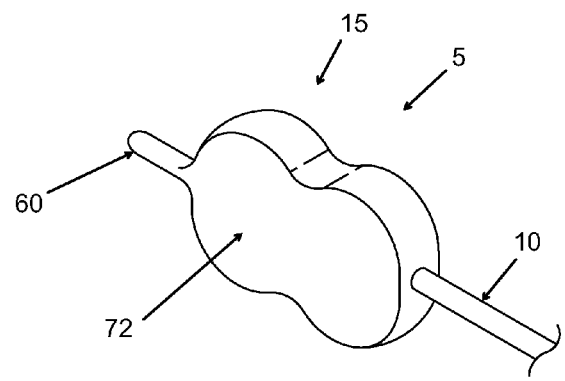
Figure 33:
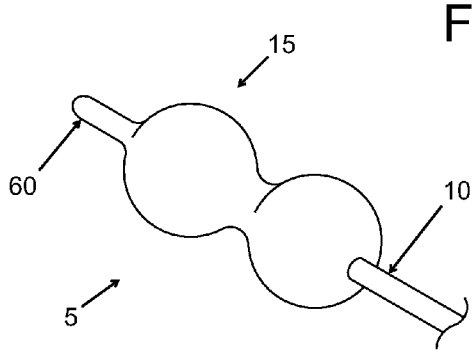
Figure 34:
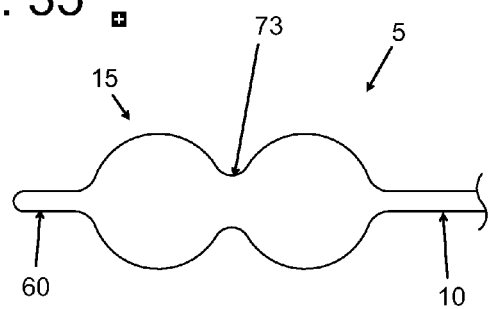

In FIGS. 17 and 18, balloon 15 is shown with a generally cylindrical configuration. However, if desired, balloon 15 can have different configurations. Thus, for example, and looking now at FIGS. 31 and 32, balloon 15 can comprise a pair of opposing flat surfaces 72; or, and looking now at FIGS. 33 and 34, balloon 15 can have an hourglass shape which includes an intermediate section 73 of reduced diameter; or, and looking now at FIG. 35, balloon 15 can have a generally hourglass shape with a pair of opposing flat surfaces 72. The aforementioned hourglass shapes, although depicted symmetrical, can also be asymmetric. For example, one end of the hourglass-shaped balloon may be of a larger dimension (length, diameter, etc.) than the other end of the hourglass-shaped balloon.

Figure 36:
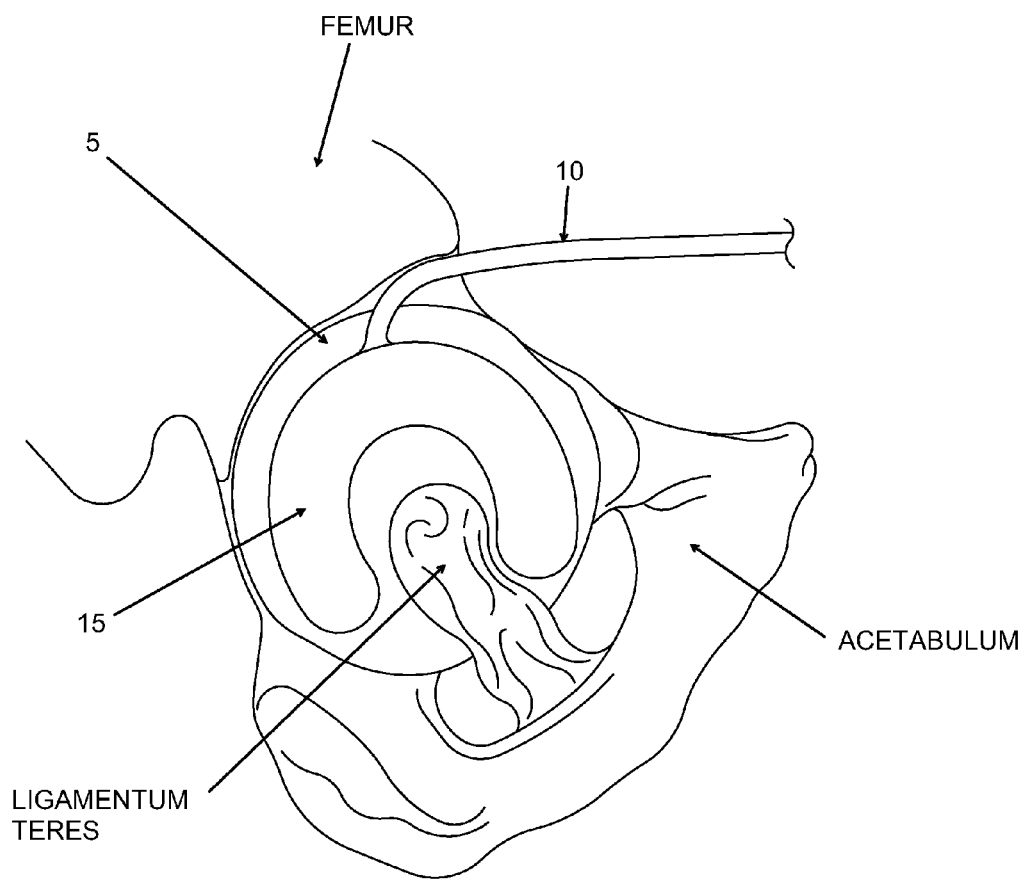
FIGS. 36-38 are schematic views showing additional alternative configurations for the balloon of the joint-spacing balloon catheter.
Figure 37:
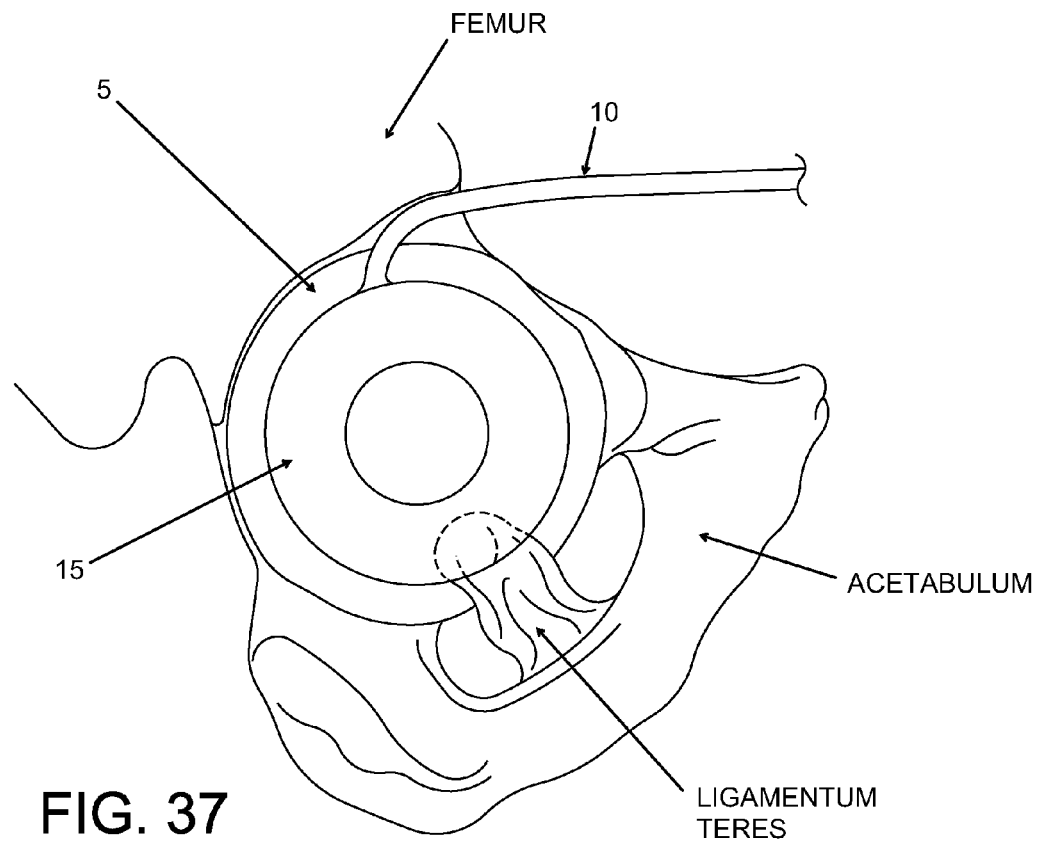
Figure 38:
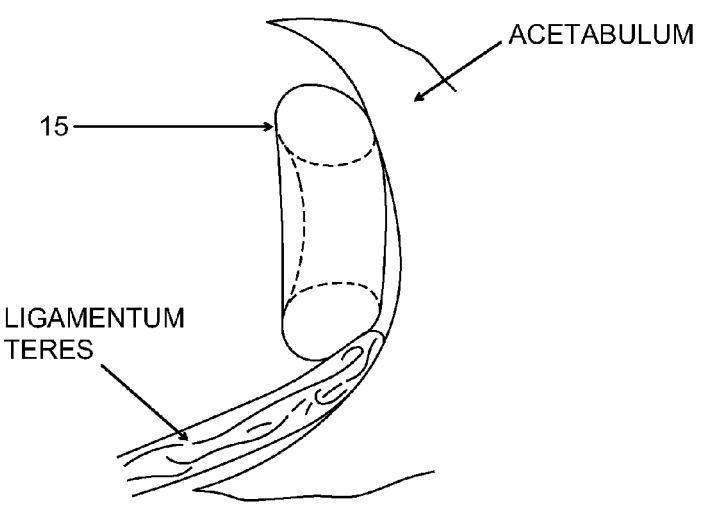

Balloon 15 may also be in the form of an arc or other curvature (i.e., a geometry where one side has a greater curvature than the other side), or some other shape (e.g., U-shaped), so as to fit around the ligamentum teres. See FIG. 36. Additionally, balloon 15 could have the shape of a torus, so as to provide a seat for the ball of the femur. See FIGS. 37 and 38.

Figure 38A:
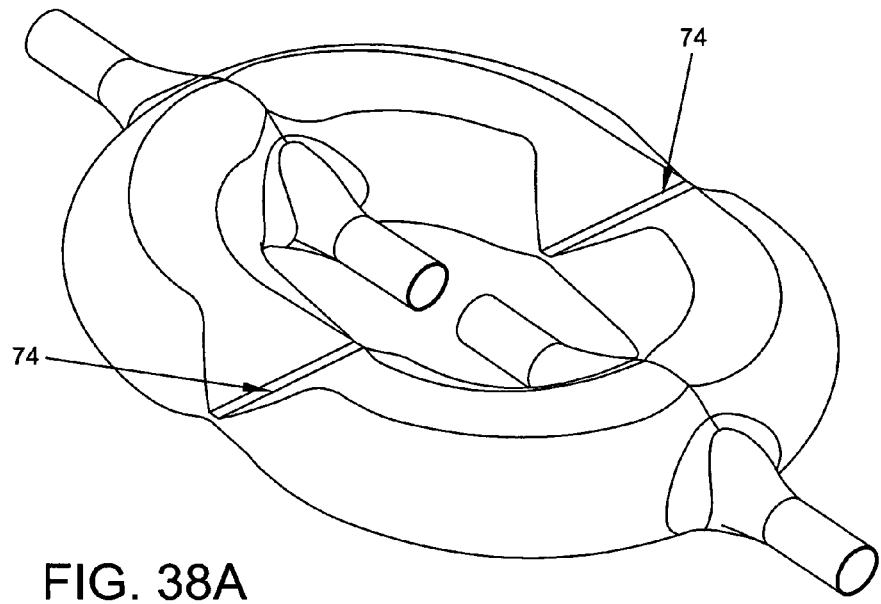
Figure 38B:
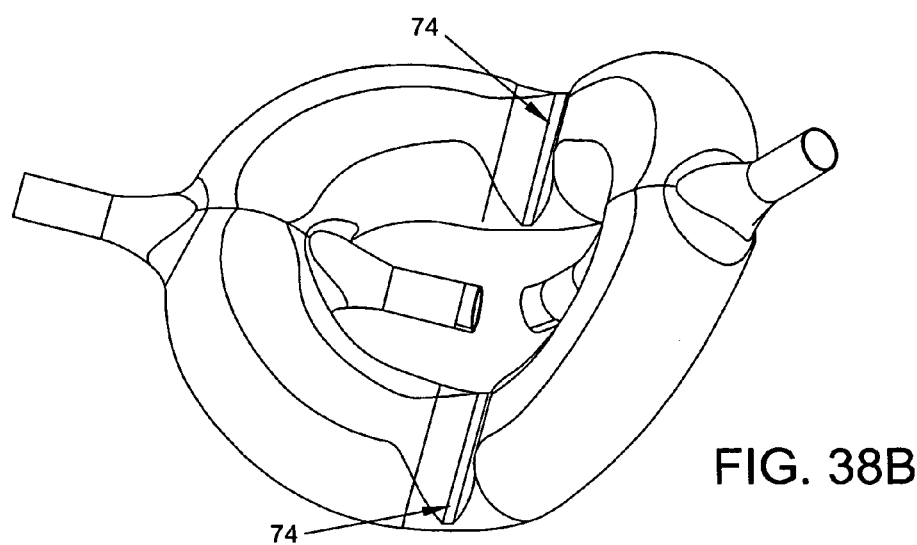

If desired, and looking now at FIGS. 38A and 38B, and/or 38C-38E, and/or 38F-38H, balloon(s) 15 may be provided with one or more creases 74 so as to facilitate folding of the balloon, e.g., whereby to allow the balloon(s) to better conform to the curvature of the head of the femur and the acetabular cup and/or to facilitate articulation of the shaft and disposition of the balloon(s) to a desired geometry.

Now looking at FIGS. 38A and 38B, joint-spacing balloon catheter 5 may comprise a toroidal-shaped balloon with a crease 74 extending across the balloon, preferably across approximately the middle of the balloon. Once the toroidal-shaped balloon is disposed between the femoral head and acetabular cup and inflated, crease 74 enables the toroidal-shaped balloon to fold, whereby to conform to the femoral head and/or to the acetabular cup. As discussed above, the toroidal-shaped balloon can be mounted onto elongated shaft 10 (not shown in FIGS. 38A and 38B for clarity), so as to allow the toroidal-shaped balloon to be delivered to the interior of the joint and inflated.

Figure 38C:
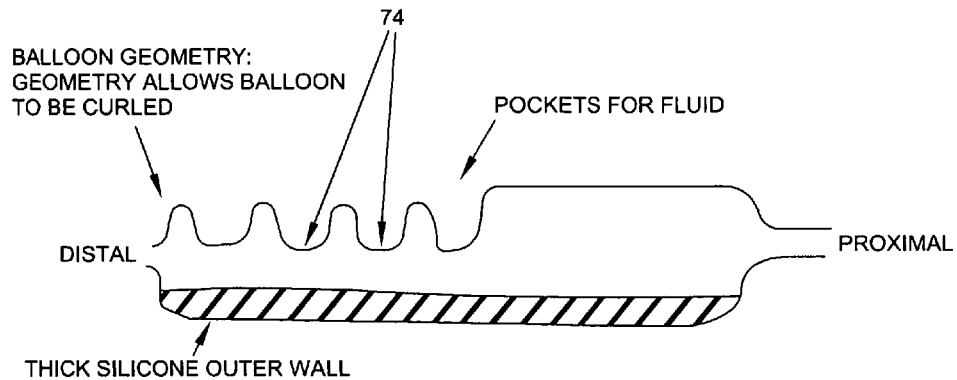
Figure 38D:
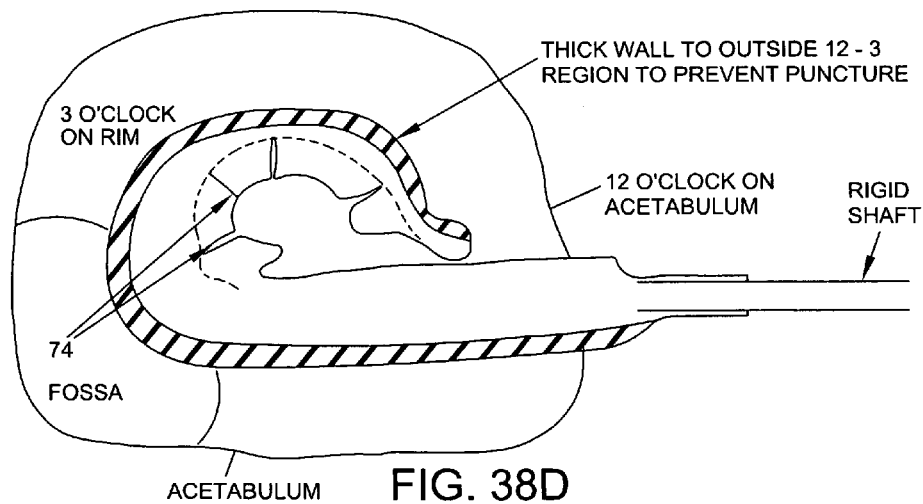
Figure 38E:
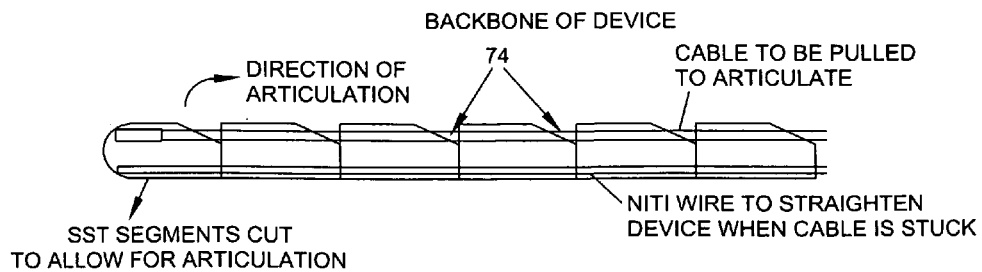

Now looking at FIGS. 38C-38E, joint-spacing balloon catheter 5 may comprise a balloon with multiple creases 74. Creases 74 are located at the balloon locations where folding is preferred. In this embodiment, the outside surface of the folded balloon comprises a thicker wall to increase the puncture resistance of joint-spacing balloon catheter 5. Once inflated in the joint, the outside surface of the balloon faces the acetabular rim and hence the location where instruments—if they come into contact with joint-spacing balloon catheter 5—are likely to contact the balloon.

FIGS. 38F-38H show a construction similar to that of FIGS. 38C-38E, however, in this embodiment of the invention, joint-spacing balloon catheter 5 comprises a plurality of balloons forming a folding balloon assembly. FIG. 38H depicts joint-spacing balloon catheter 5 of FIGS. 38F-38G positioned in the acetabular cup and inflated. Joint-spacing balloon catheter 5 is preferably introduced into the joint through the PL (posterolateral) portal with at least a portion of the balloon residing in the acetabular fossa. A proximal portion of joint-spacing balloon catheter 5 may rest on the acetabular rim as depicted in FIG. 38H.

Figure 38L:
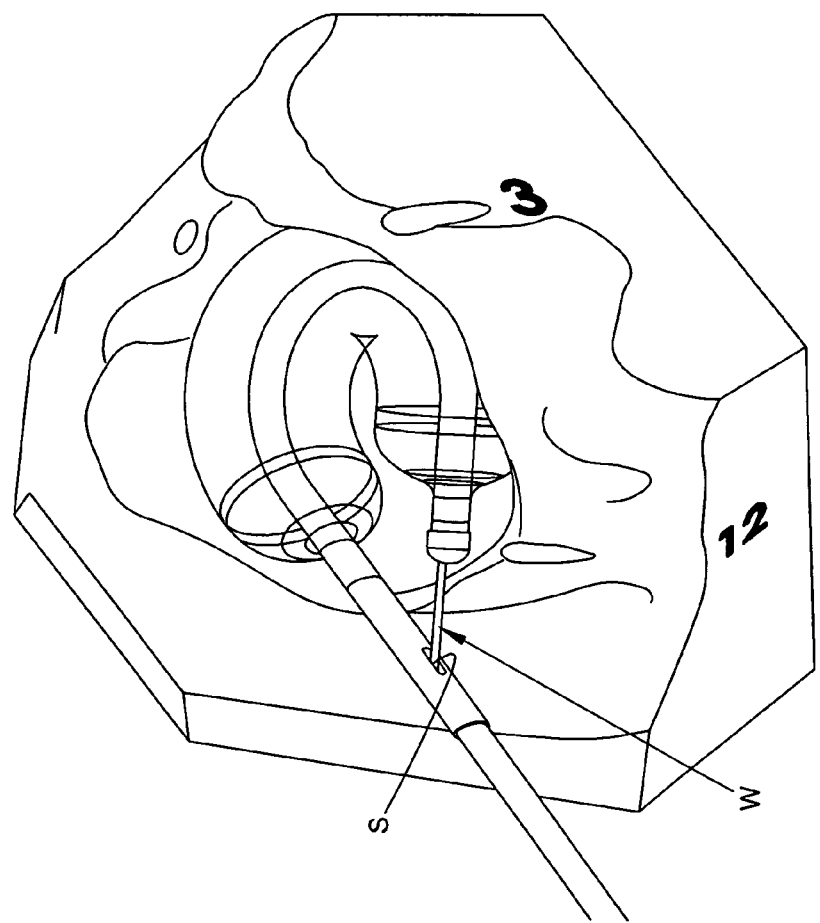
Figure 38M:
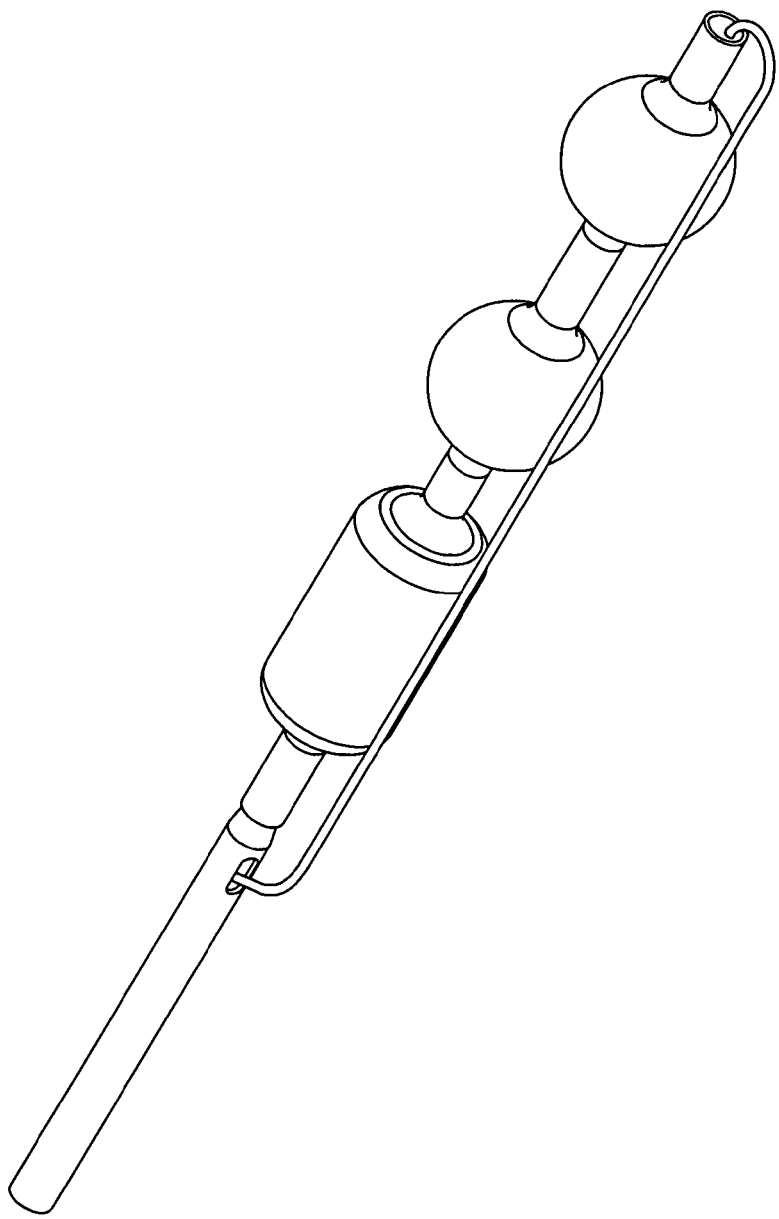
Figure 38N:
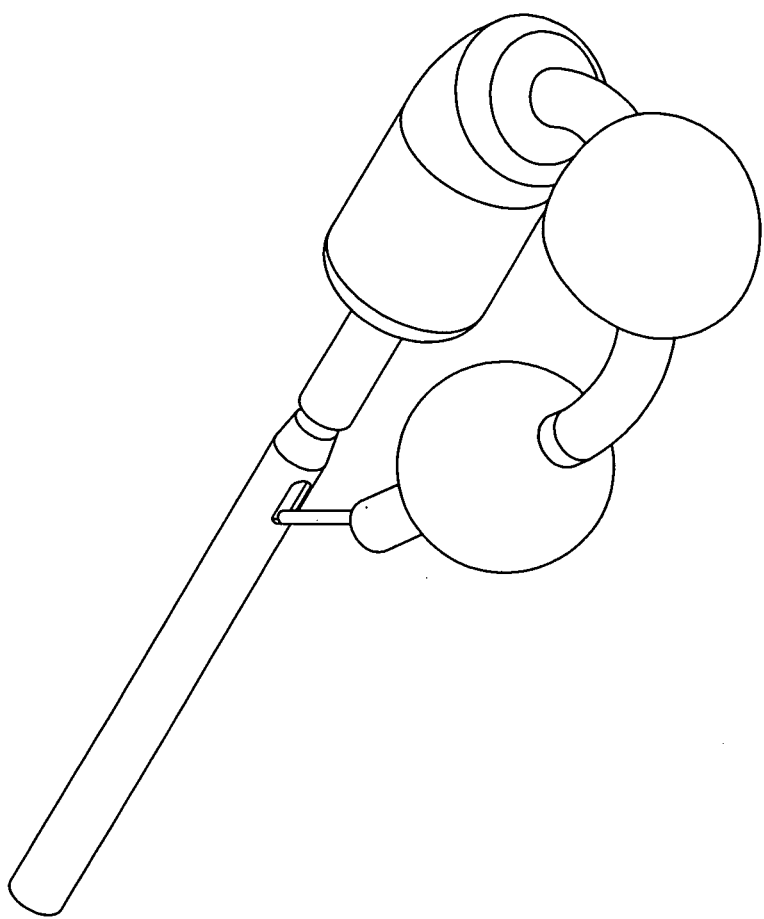
Figure 38O:
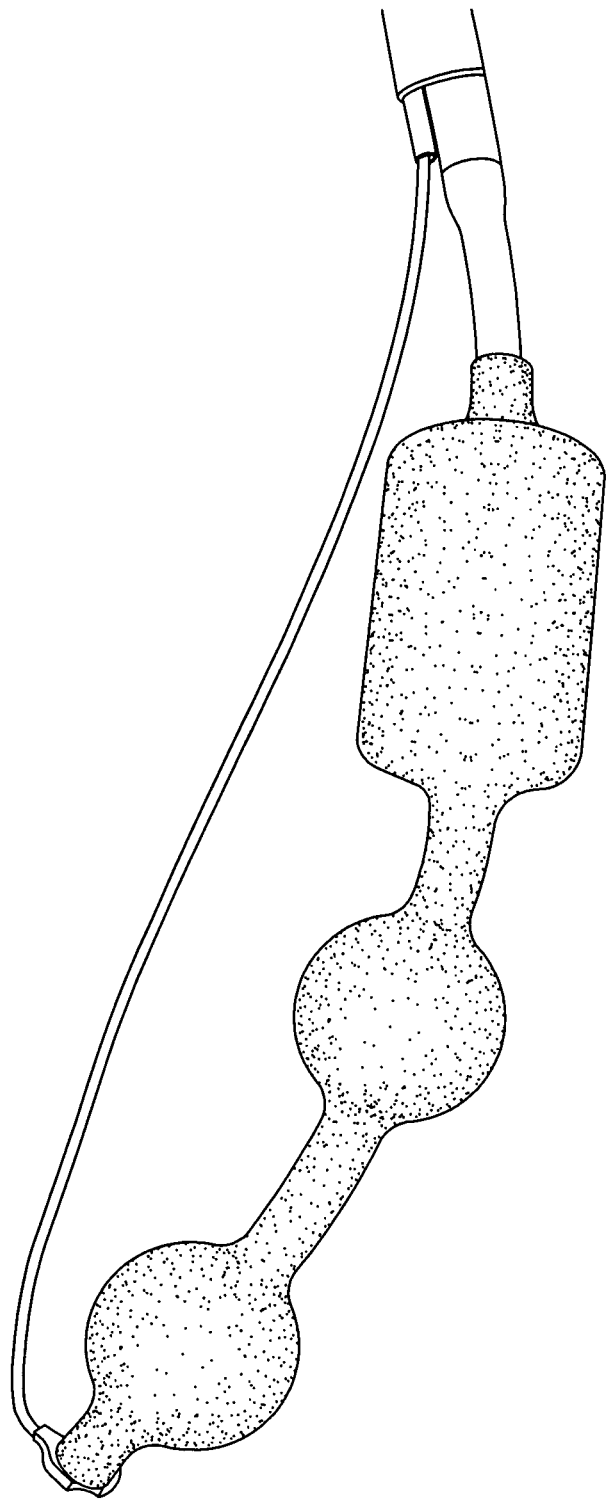
Figure 38P:
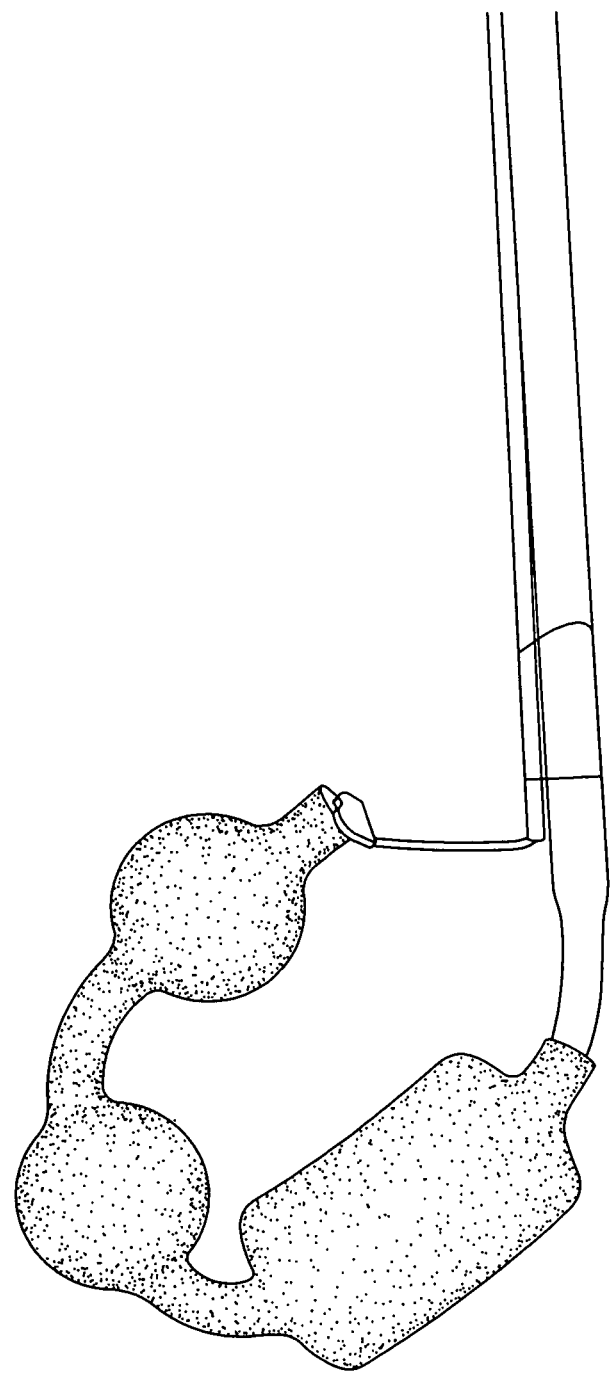

Furthermore, if desired, joint-spacing balloon catheter 5 can be provided with a tip retention mechanism, such that the distal tip of joint-spacing balloon catheter 5 is secured to the shaft of joint-spacing balloon catheter 5. By way of example but not limitation, where joint-spacing balloon catheter 5 comprises a substantially cylindrical balloon, the substantially cylindrical balloon can be retained in an arcuate or semi-toroidal configuration at the distal end of the joint-spacing balloon catheter. By way of further example but not limitation, in this form of the invention, and looking now at FIGS. 38I-38L, joint-spacing balloon catheter 5 can be provided with (i) a wire W which is projectable out of the distal end of the joint-spacing balloon catheter 5, and (ii) a seat S disposed proximal to balloon 15, such that upon appropriate articulation of elongated shaft 10, wire W can be projected out of the distal end of elongated shaft 10 and into seat S so as to lock the substantially cylindrical balloon in an arcuate or semi-toroidal configuration at the distal end of the joint-spacing balloon catheter. Seat S is preferably located on or near the overshaft 30 (see FIGS. 17-19) of elongated shaft 10. FIG. 38L depicts joint-spacing balloon catheter 5 with a tip retention mechanism, with the balloon (held in an arcuate or semi-toroidal configuration by virtue of seating wire W in seat S) disposed in the acetabulum and inflated (the femoral head is not shown in FIG. 38L for clarity).

In an alternative embodiment, and looking now at FIGS. 38M-38P, the joint-spacing balloon catheter 5 can be provided with (i) a suture which is coupled to the distal end of the joint-spacing balloon catheter 5, and (ii) a suture lumen disposed proximal to balloon 15, such that upon appropriate articulation of elongated shaft 10, the suture can be drawn proximally to pull the distal end of elongated shaft 10 proximally to form the substantially cylindrical balloon in an arcuate or semi-toroidal configuration. In one embodiment, the joint-spacing balloon catheter 5 does not have articulation; the suture can both articulate the distal end and draw it proximally to form an arcuate or semi-toroidal configuration. It will be apparent to one skilled in the art that a tip retention mechanism can be incorporated into the other balloon shapes and multiple balloon configurations.

In a preferred method of use, the joint-spacing balloon catheter 5 (with the aforementioned tip retention mechanism) is introduced into the joint space and positioned in the desired location within the acetabular cup. The tip retention mechanism is then actuated so that the joint-spacing balloon catheter 5 forms an arcuate or semi-toroidal configuration, and the joint-spacing balloon catheter 5 is inflated. By securing the tip of the catheter to the shaft, the position of the balloon of the joint-spacing balloon catheter 5 can be better controlled, and is less likely to migrate relative to the overshaft 30. Additionally, securing the tip of the catheter to the shaft enables the balloon to assume an arcuate or semi-toroidal configuration, whereby to better provide stability to the femoral head (i.e., the femoral head is less likely to shift relative to the acetabular cup due to forces acting on the femoral head).

Figure 40:
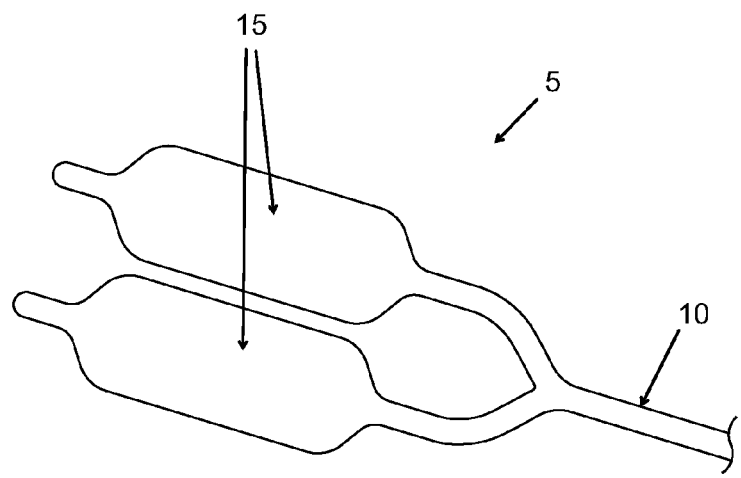
FIGS. 39-52 are schematic views showing that the joint-spacing balloon catheter may comprise multiple balloons, with those multiple balloons being arranged in a variety of configurations.
Figure 39:
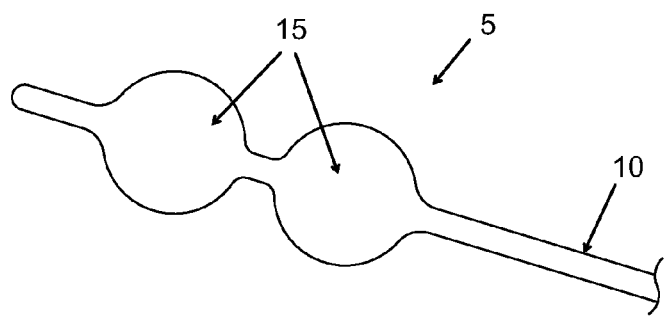
Figure 44:
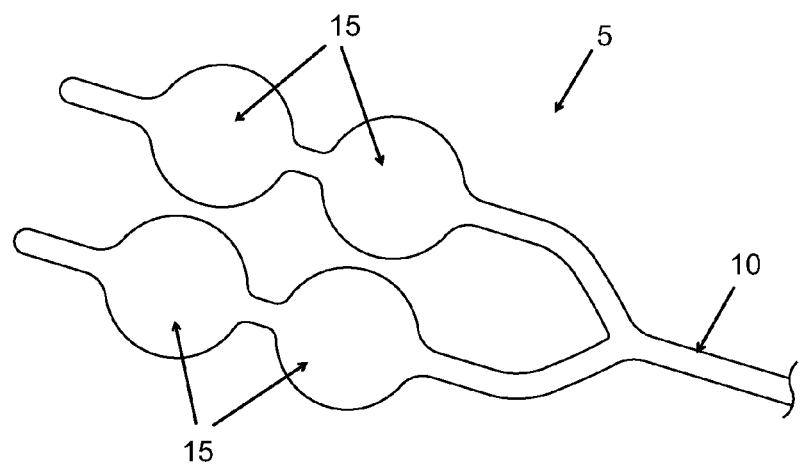
Figure 41:
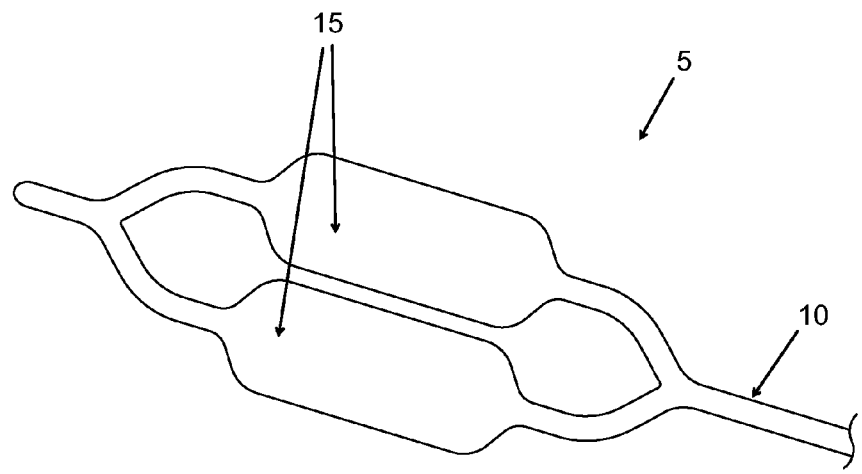
Figure 42:
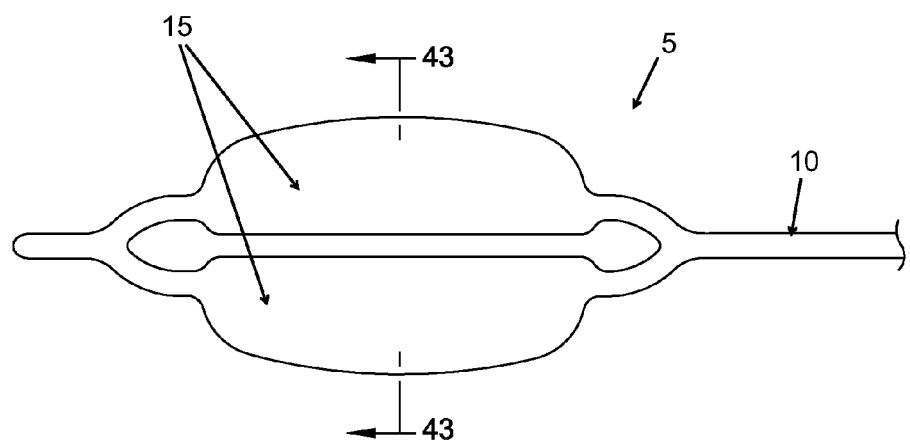
Figure 43:
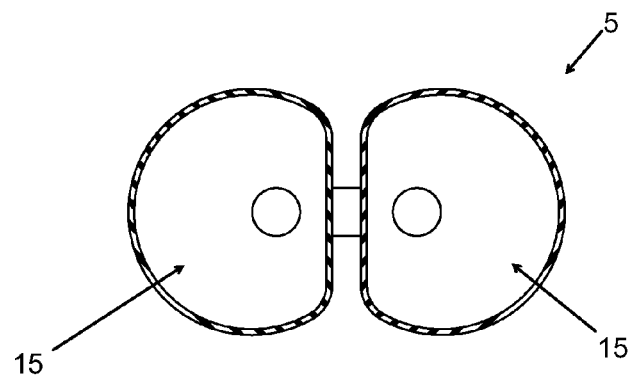
Figure 45:
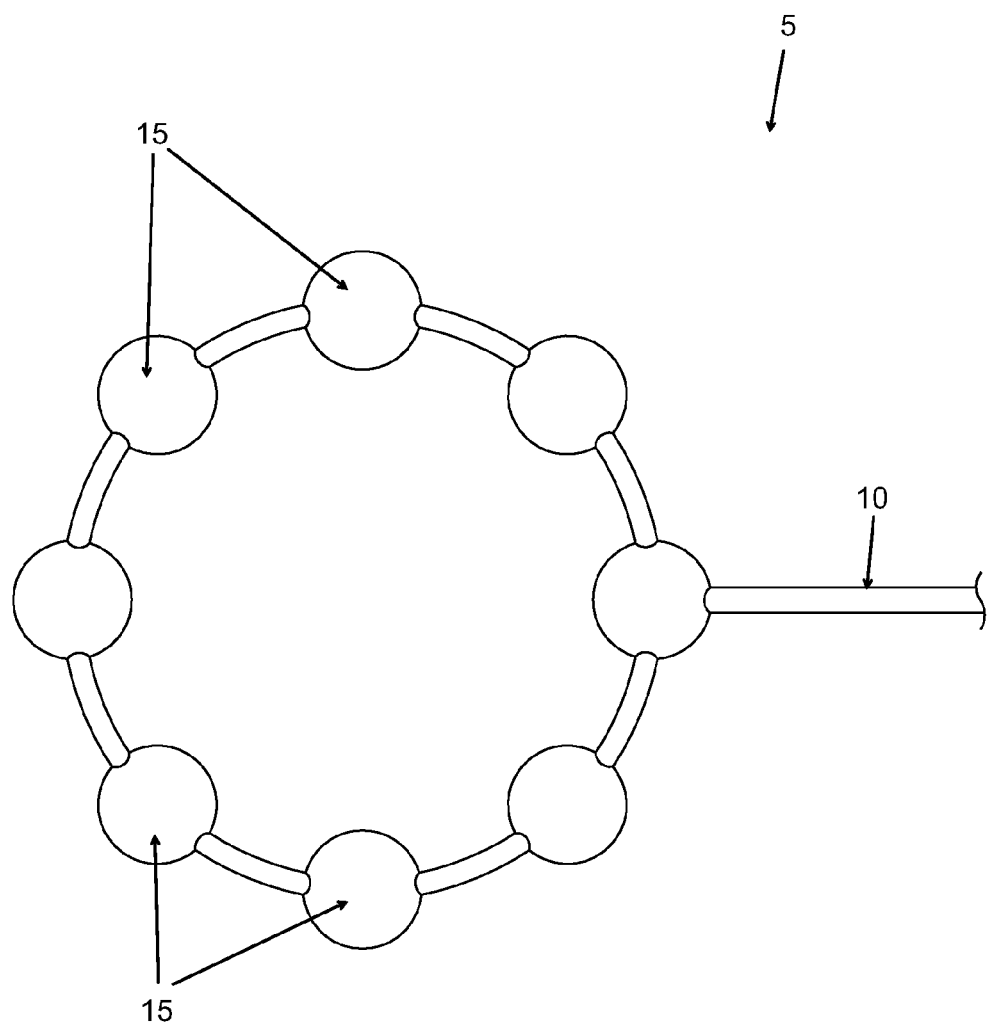
Figure 46:
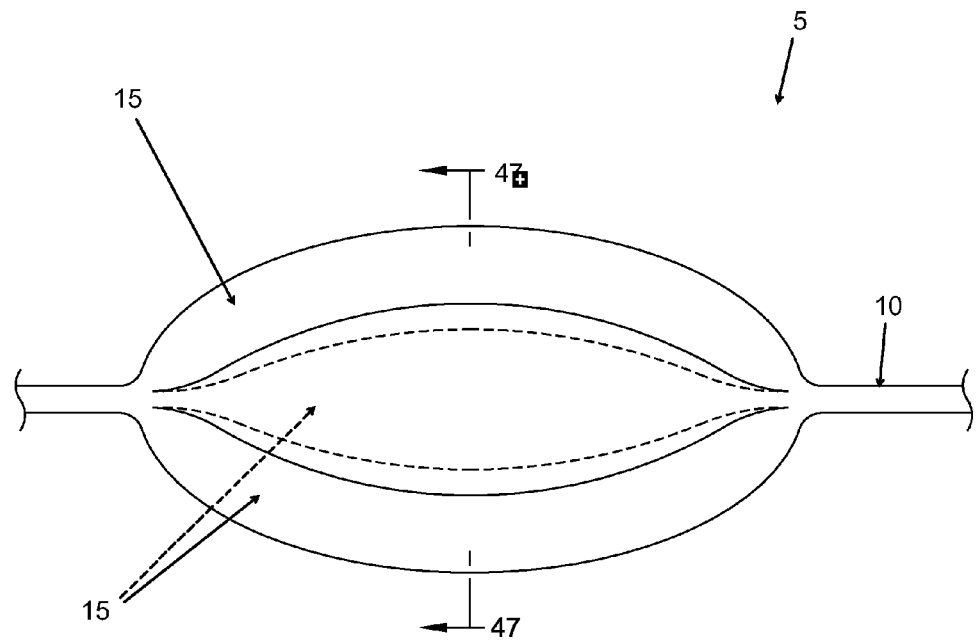
Figure 47:
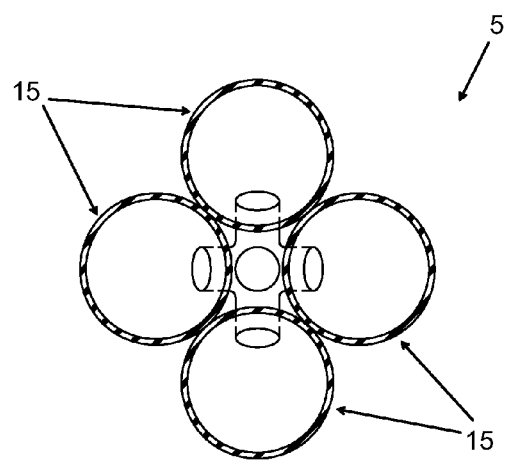
Figure 48:
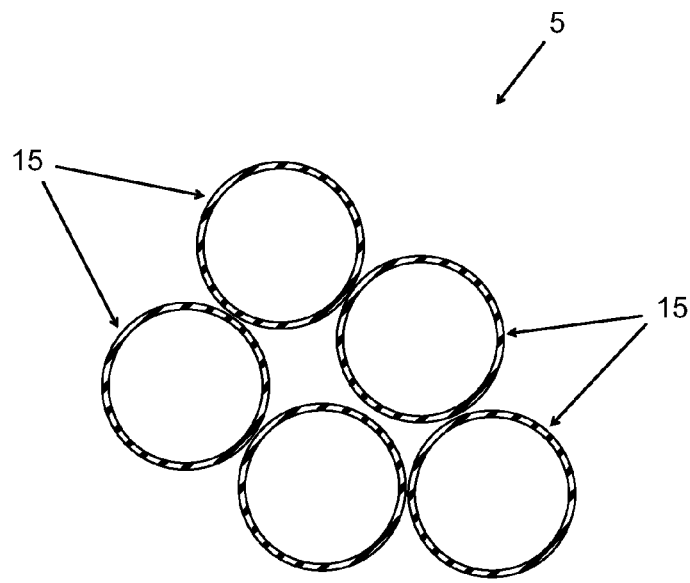
Figure 49:
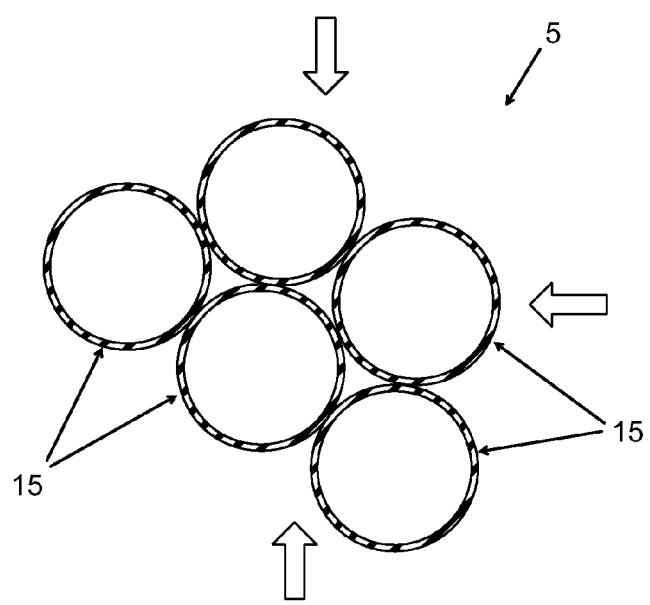
Figure 50:
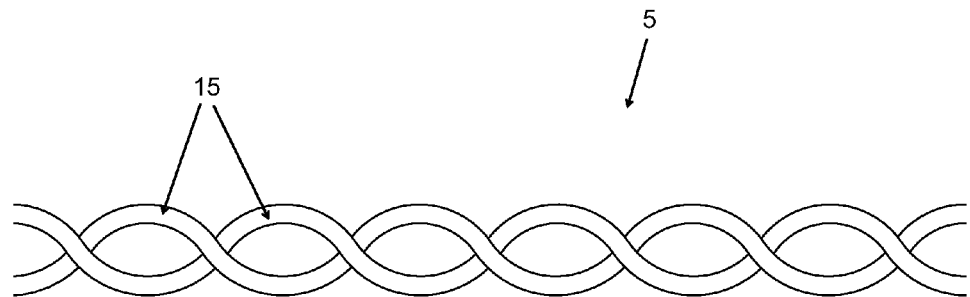
Figure 51:
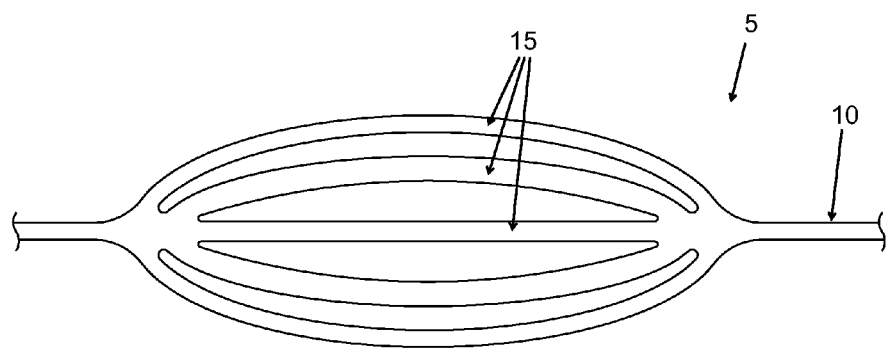
Figure 52:
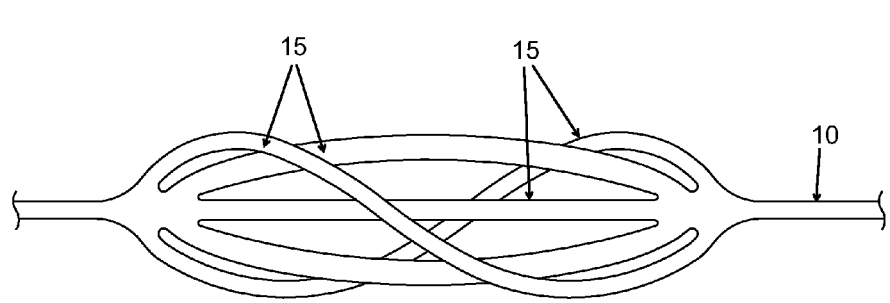

It is also possible to provide joint-spacing balloon catheter 5 with more than one balloon 15. Where more than one balloon is provided, the balloons can be disposed in series (i.e., end-to-end, such as is shown in FIG. 39), or in parallel (such as shown in FIGS. 40 and 41), with or without complementary geometries (such as shown in FIGS. 42 and 43), or combinations of such geometries (such as shown in FIG. 44), or toroidal (such as is shown in FIG. 45), etc. The shafts of the multiple balloons may be separated at their distal end (such as is shown in FIG. 40) or may be joined at their distal ends (such as is shown in FIG. 41). The multiple balloons may be of the same construction, or they may be of different constructions. For example, the multiple balloons may be of different sizes, shapes, materials, compliances, coatings, surface textures, coverings, colors, and/or other aspects of construction. Additionally, the multiple balloons may be inflated to different pressures and/or volumes.

By way of example but not limitation, in one preferred form of the invention, joint-spacing balloon catheter 5 comprises two balloons disposed in series, with the proximal balloon being larger than the distal balloon. In another preferred form of the invention, joint-spacing balloon catheter 5 comprises two balloons disposed in series, with the distal balloon being larger than the proximal balloon.

These multiple balloons 15 can also be disposed in a mutually-supporting configuration, such as is shown in FIGS. 46-52. By arranging the multiple balloons 15 in a mutually-supporting configuration, the multiple balloons 15 may better conform to the acetabulum and femoral surfaces, which can be beneficial in order to reduce the pressure on the cartilage and/or to help maintain the balloons in position within the joint space (i.e., to prevent slipping). In this form of the invention, a balloon catheter 5 could have an assembly of balloons 15 that would collectively act as a compliant or semi-compliant device even though the individual balloons are themselves non-compliant, or vice versa. An additional benefit of arranging the multiple balloons 15 in a mutually-supporting configuration is that if one of the balloons deflates, the other balloons can still maintain a substantial portion of the joint space. In one preferred construction, the balloons 15 can slide against each other so as to spread out, e.g., so as to spread out in a lateral direction. Where joint-spacing balloon catheter 5 comprises multiple balloons 15, preferably, a separate inflation/deflation lumen is provided for each balloon, so that each balloon can be separately inflated or deflated to a desired degree and/or at a desired time, although a single inflation/deflation lumen could be used to simultaneously inflate/deflate more than one balloon. By permitting each balloon of a group of balloons to be selectively inflated, the surgeon can influence the manner in which the ball of the femur is supported relative to the acetabular cup. In one preferred manner of use, each of the balloons may be inflated to a different volume (and/or pressure) than others of the balloons. This approach can be used to impart a specific shape to the overall balloon structure, whereby to influence the manner in which distraction is maintained. Also, some of the balloons 15 can be made compliant, and others of the balloons can be made non-compliant, so as to achieve a desired pressure distribution and/or shape for the overall balloon structure.

Figure 53:
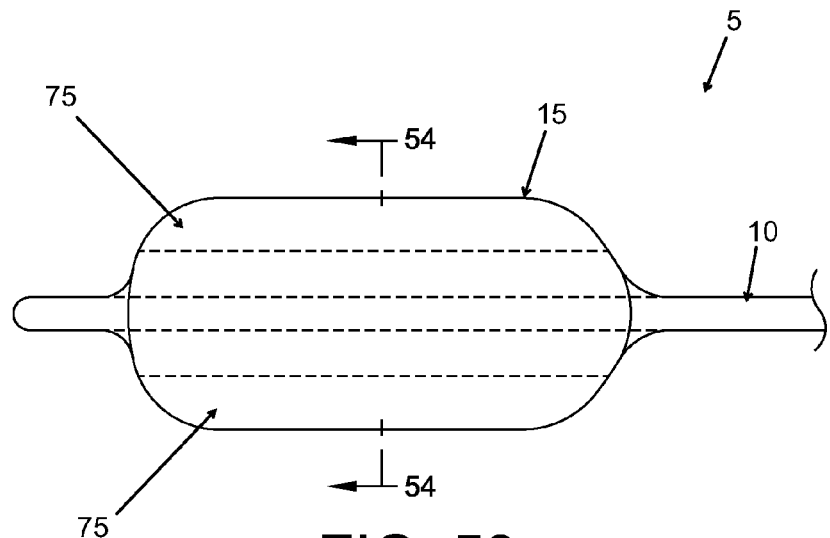
FIGS. 53-55 are schematic views showing how a balloon of the joint-spacing balloon catheter may comprise a plurality of separate chambers, with those chambers being arranged in a variety of configurations.
Figure 54:
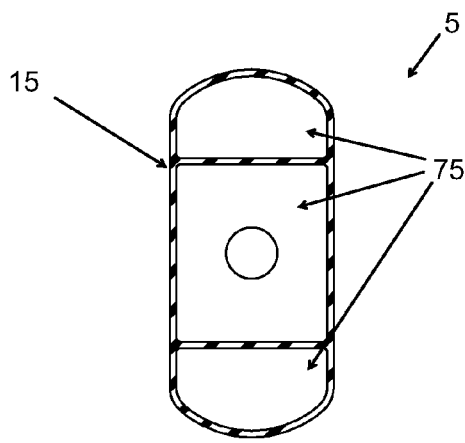
Figure 55:
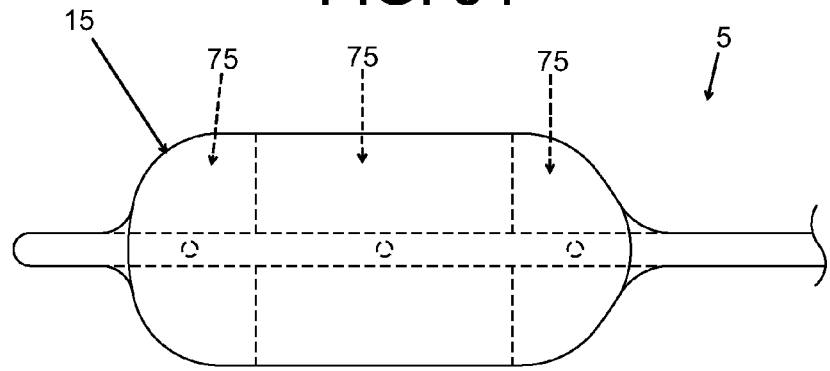
Figure 60A:
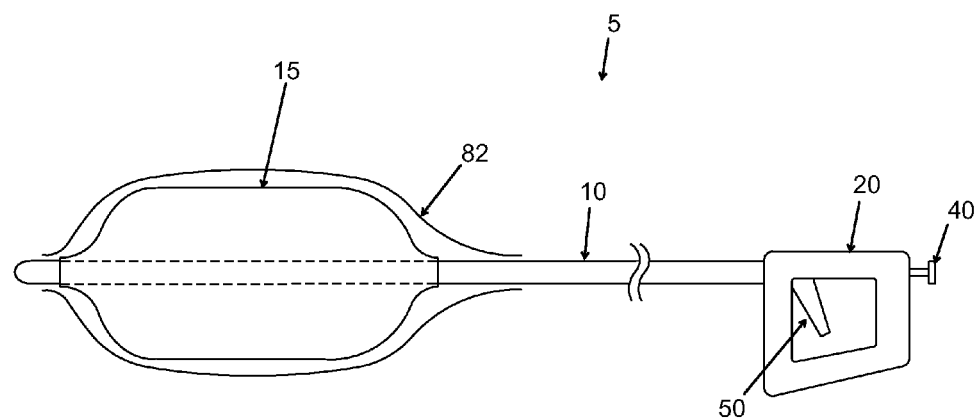
Figure 60B:
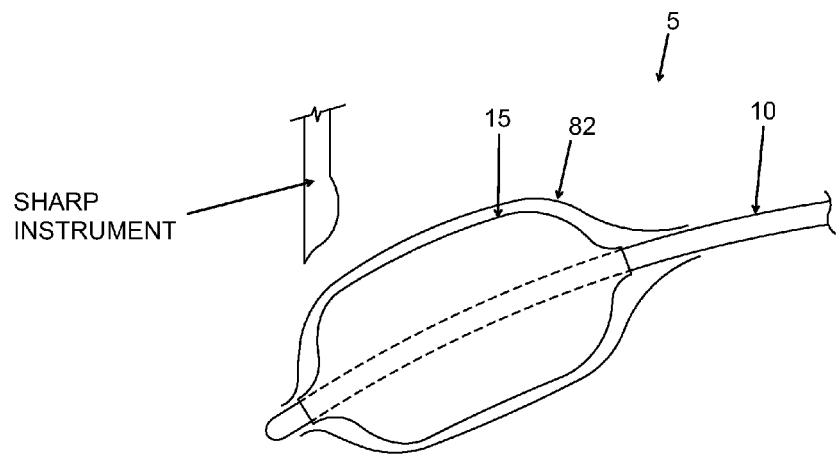
Figure 60C:
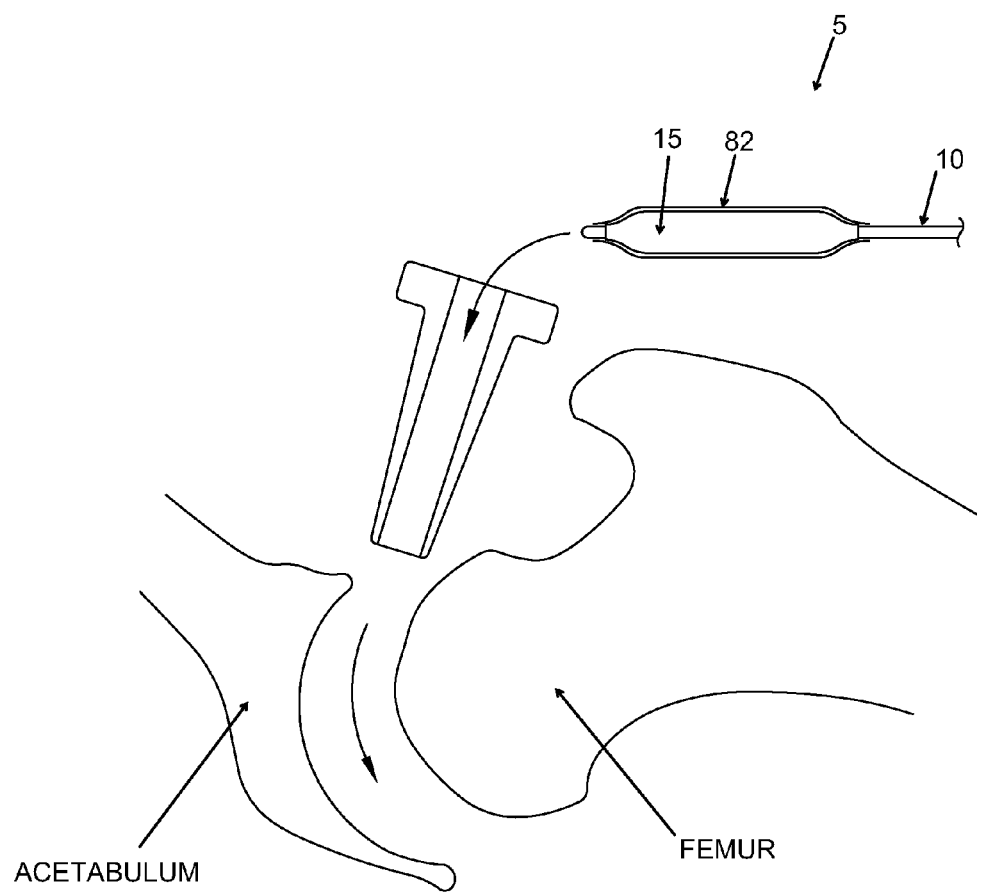
Figure 60D:
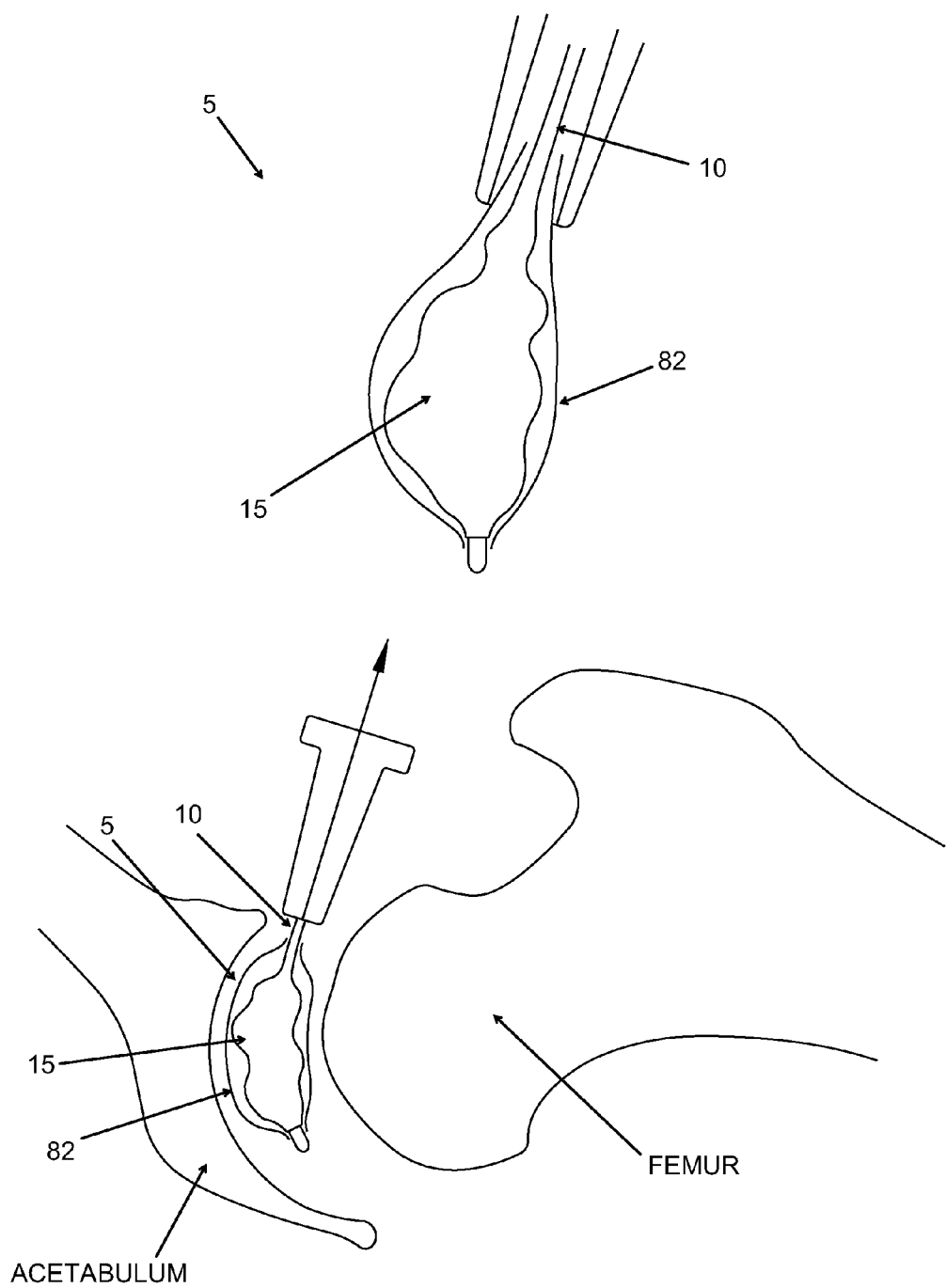

It is also possible to provide each of the balloons 15 with a plurality of separate internal chambers 75 (FIGS. 53-55). Preferably each of these separate chambers 75 can be selectively inflated so as to influence the manner in which the ball of the femur is supported relative to the acetabular cup. Thus, in this sort of construction, selective inflation of the various chambers can be used to adjust the position of the ball of the femur within the acetabular cup when the external distraction force applied to the distal end of the leg is relaxed. The use of multiple chambers may also provide a safer design. More particularly, in the event that one of the chambers 75 is punctured during a procedure, the use of multiple chambers 75 may permit some joint distraction to be maintained, thus reducing the chances that, for example, an instrument will be wedged between the femoral head and acetabulum.

If desired, balloons 15 can be formed so as to be puncture resistant in order to minimize the possibility of inadvertently deflating the balloon, e.g., with an errant surgical instrument. To this end, and looking now at FIG. 56-59, a balloon 15 can embed, or sandwich, a puncture-resistant structure 80 (e.g., a coil or mesh or strand or braid formed out of Nitinol, or stainless steel, or a polymer, etc.) between two layers of material (preferably a non-abrasive elastomer). Alternatively, the puncture-resistant structure 80 could be placed on one side of, or embedded within, a single sheet of material, such as is shown in FIG. 60. This puncture-resistant structure 80 may be a separate element added to the outer wall of the balloon or a coating applied to the outer wall of the balloon. The puncture-resistant structure 80 may also be a layer of material within the side wall of the balloon; for example, the outer layer may be a puncture-resilient material (such as polyurethane) to enhance puncture resistance, while the inner layer material (e.g., PET) maintains the balloon pressure. In one preferred construction, puncture-resistant structure 80 covers a substantial portion of the balloon surface. In another preferred construction, the puncture-resistant structure 80 covers a smaller portion of the balloon surface; in this instance, the surface incorporating the puncture-resistant structure 80 is disposed on the side of the balloon where instruments (which could puncture the balloon) are used.

Furthermore, if desired, and looking now at FIGS. 60A-60D, the distal end of joint-spacing balloon catheter 5 could include a shroud 82 disposed over balloon 15. Shroud 82 may be formed out of a puncture-resistant material so as to protect balloon 15 from inadvertent puncture. Additionally, and/or alternatively, shroud 82 could be formed so as to define the volume created within the joint when balloon 15 is inflated. This construction can be advantageous where balloon 15 is formed out of a compliant material and it is desired to control the manner in which space is created within the joint, i.e., by using a non-compliant or semi-compliant shroud 82. Additionally, and/or alternatively, shroud 82 could be formed out of a material which provides slippage (e.g., it can be formed out of PTFE or ePTFE). This can be beneficial in a number of ways. First, it can facilitate easier delivery of the balloon into the joint, including passage through the entry cannula. In a similar way, shroud 82 can also facilitate easier removal of the joint-spacing balloon catheter from the joint, including through the entry cannula. By having enhanced slippage properties, shroud 82 can also facilitate joint manipulation on the balloon. The shroud's geometry (e.g., tapered ends) can also facilitate delivery of the joint-spacing balloon catheter into, and removal of the joint-spacing balloon catheter from, the joint space. This may be particularly beneficial if the balloon catheter goes through an entry cannula.

Alternatively, the shroud 82 could be formed out of a material which prevents slippage on the joint surface (e.g., a low durometer elastomer). This can be beneficial to enable the balloon to remain stationary on the joint surfaces once it has been placed in the joint space. Additionally, and/or alternatively, shroud 82 can be constructed so as to provide better endoscopic visualization of the balloon; for example, shroud 82 can be an opaque color.

Figure 61:
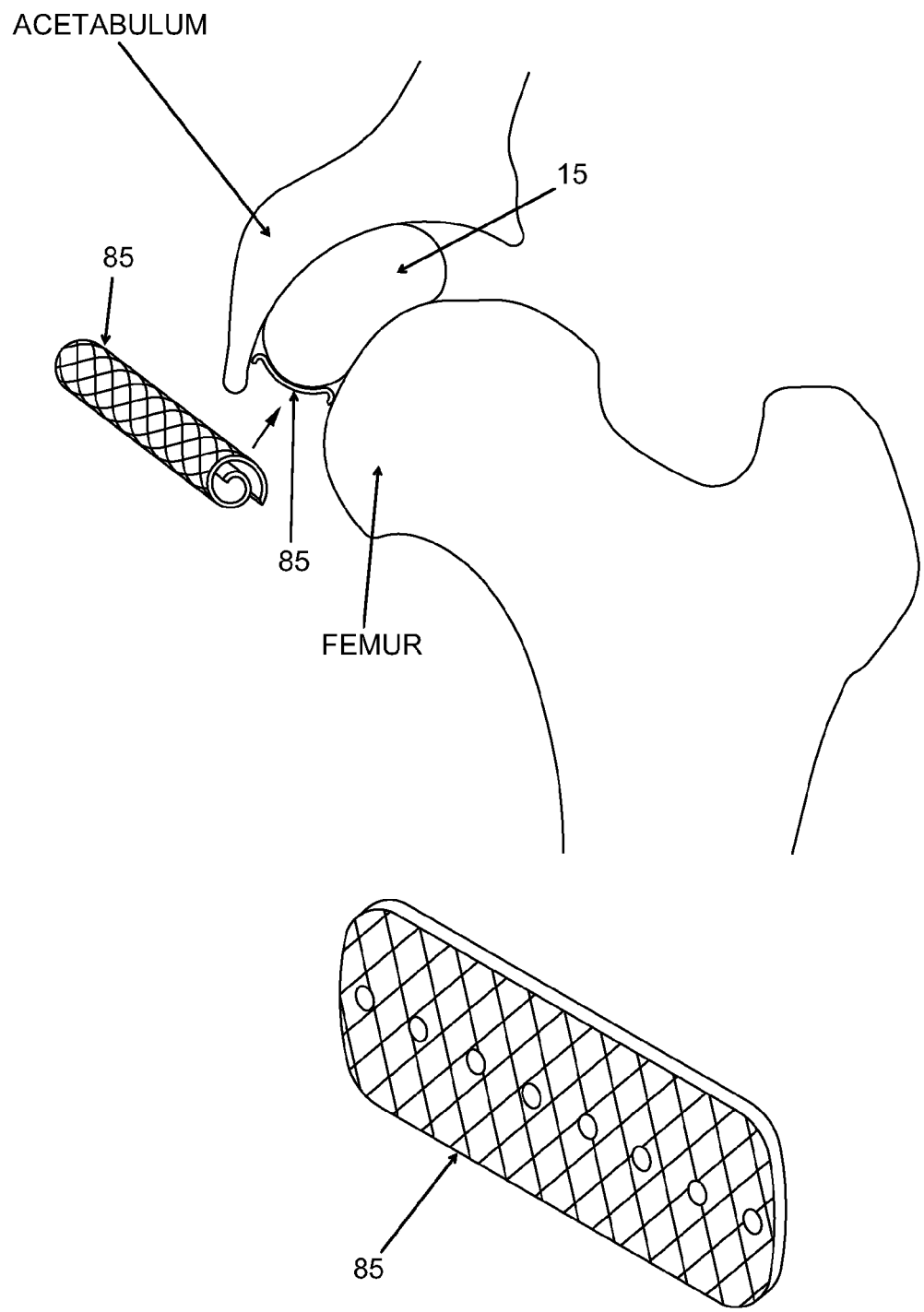
FIGS. 61-63 are schematic views showing how a associated structure may be used in conjunction with the joint-spacing balloon catheter so as to provide puncture protection for a balloon of the joint-spacing balloon catheter.
Figure 62:
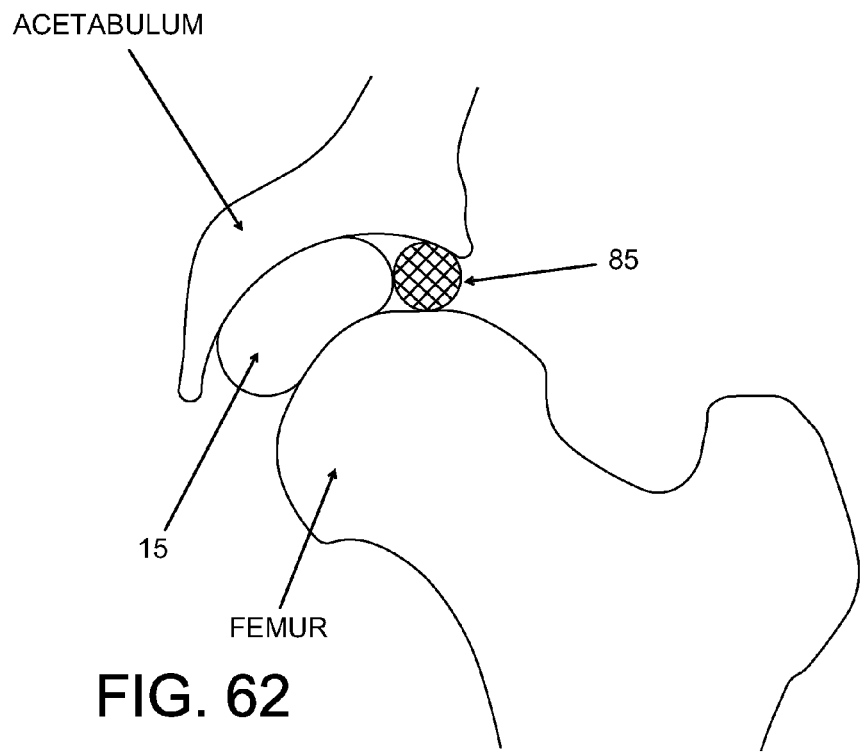
Figure 63:
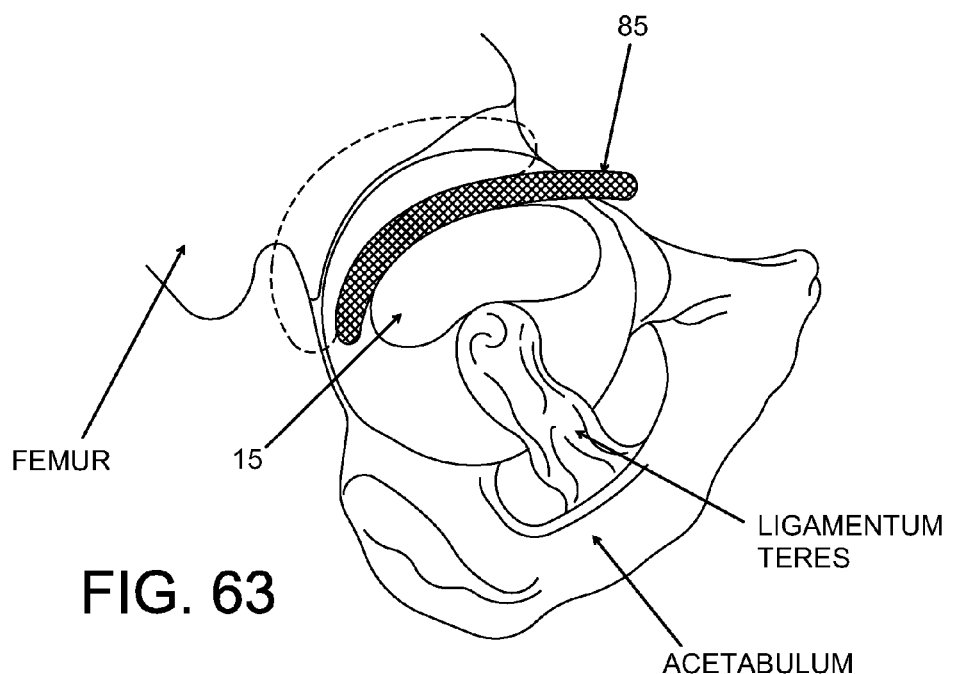
Figure 64:
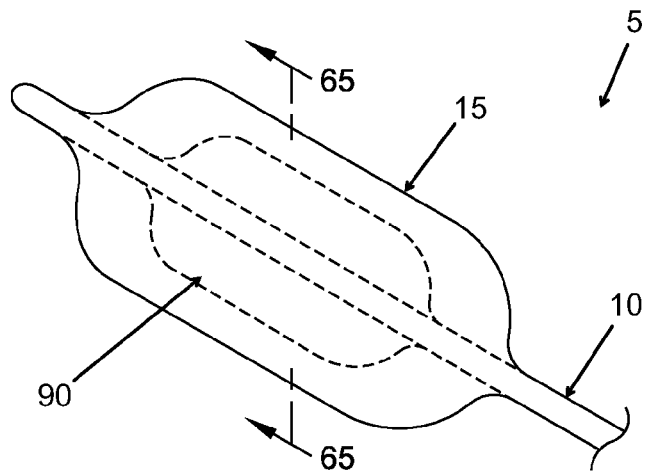
FIGS. 64-72 are schematic views showing how a supplemental structure may be provided within a balloon of the joint-spacing balloon catheter so as to provide fail-safe support in the event that the balloon should lose its integrity.
Figure 65:
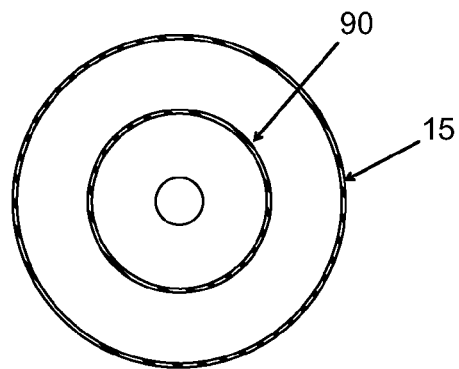
Figure 66:
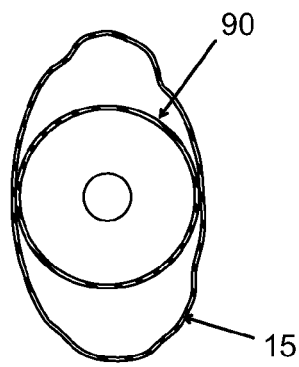
Figure 67:
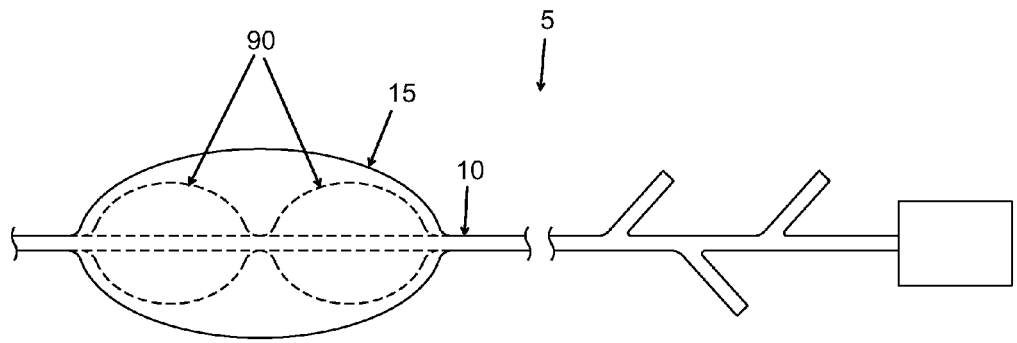
Figure 68:
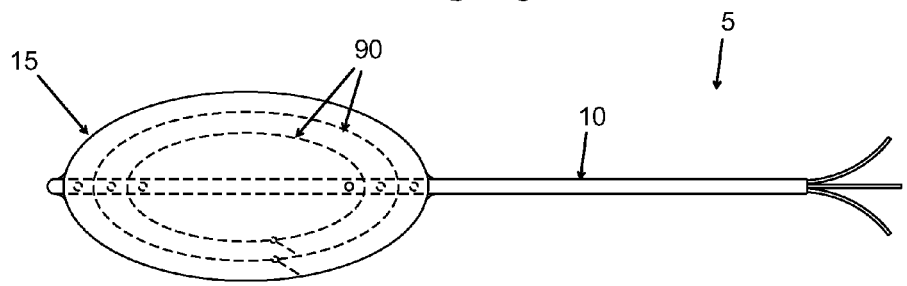

Alternatively, and looking now at FIGS. 61-63, a shield 85 could be placed alongside balloon 15 so as to protect the balloon from being punctured from that direction. Shield 85 is preferably introduced into the joint after the balloon has been inserted and inflated, but shield 85 could also be inserted into the joint prior to that if desired. Shield 85 could be made out of a material similar to the puncture-resistant structure 80 described above.

Alternatively, and looking now at FIGS. 64-68, a balloon-within-a-balloon configuration can be used to provide one or more secondary "fail-safe" (or "safety") balloons 90 within the primary balloon 15—such a construction can minimize the risk that complete joint distraction will be lost in the event that the primary balloon 15 is inadvertently deflated, e.g., by an accidental puncture. If desired, the inner balloon 90 can be made of a different material than the outer balloon 15. In one preferred construction, inner balloon 90 is non-compliant and outer balloon 15 is semi-compliant. The inner and outer balloons 90, 15 (respectively) could also have different wall thicknesses, geometries, or other aspects of construction as discussed above.

Figure 69:
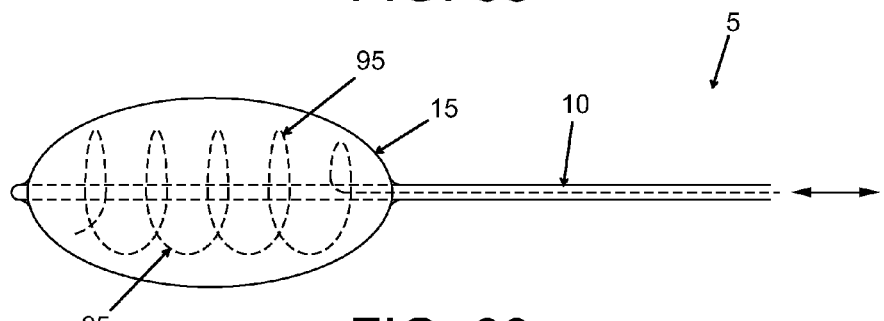
Figure 70:
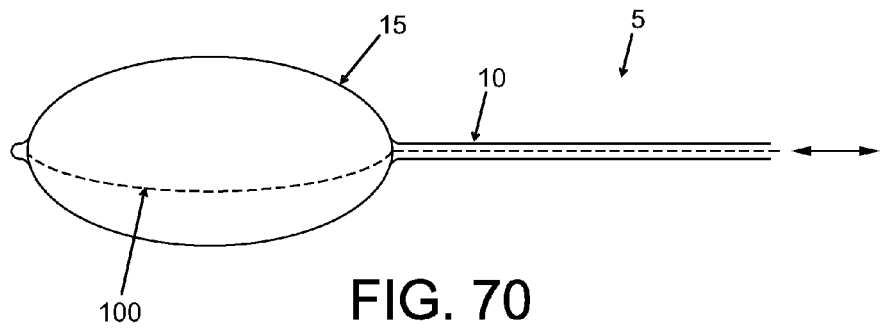
Figure 71:
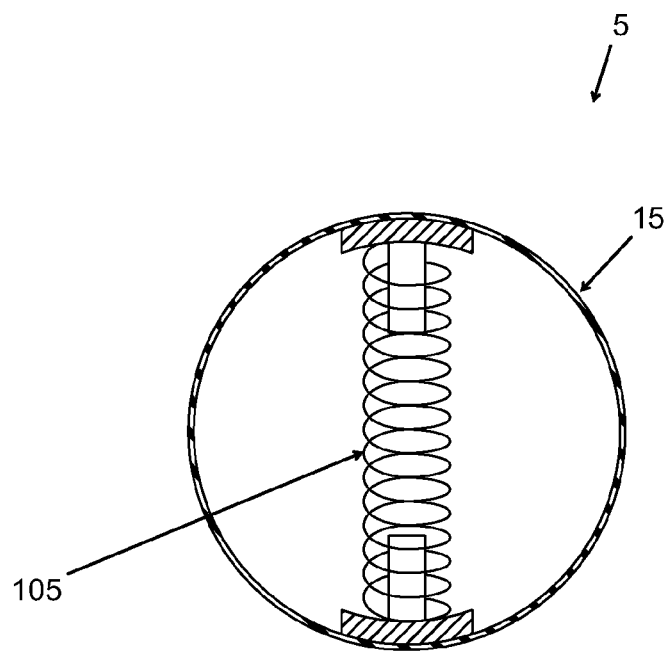
Figure 72:
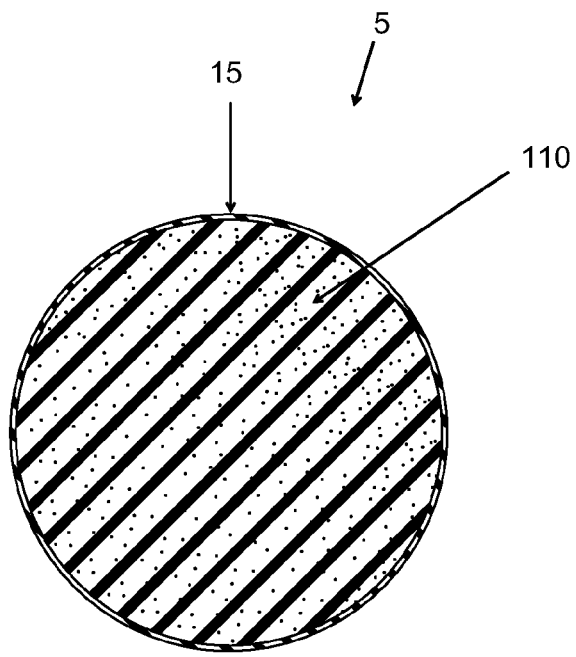

Alternatively, a different type of secondary structure can be deployed in balloon 15 in order to prevent balloon 15 from completely collapsing in the event that the balloon is punctured. In one embodiment, and looking now at FIG. 69, a wire 95 is delivered into the interior of the balloon and fills up a portion of the internal balloon volume; in the event that the balloon is punctured, wire 95 provides support to prevent the joint space from completely collapsing. Wire 95 is preferably made of Nitinol, but could also be formed out of another metal or polymer if desired. In another embodiment, and looking now at FIG. 70, a wire 100 is delivered across the length of the balloon and set in a bowed configuration. The bowed wire 100 provides mechanical support in the event that the balloon is punctured. In FIG. 71, an exemplary mechanical scaffold 105 is shown deployed in the interior of the balloon so as to provide a safety mechanical support. In FIG. 72, an expandable foam 110 is deployed within the interior of the balloon; foam 110 expands to fill some or most of the internal balloon space. In one embodiment, expandable foam 110 absorbs fluid and will therefore absorb saline which makes its way into the balloon, e.g., in the event of a balloon puncture. This construction can reduce the speed with which a punctured balloon will deflate.

Figure 73:
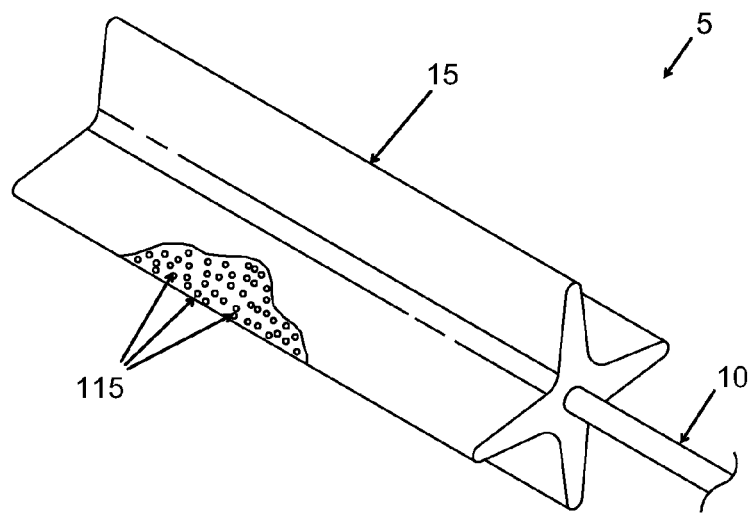
FIGS. 73-78 are schematic views showing additional mechanisms for expanding a balloon of the joint-spacing balloon catheter.
Figure 74:
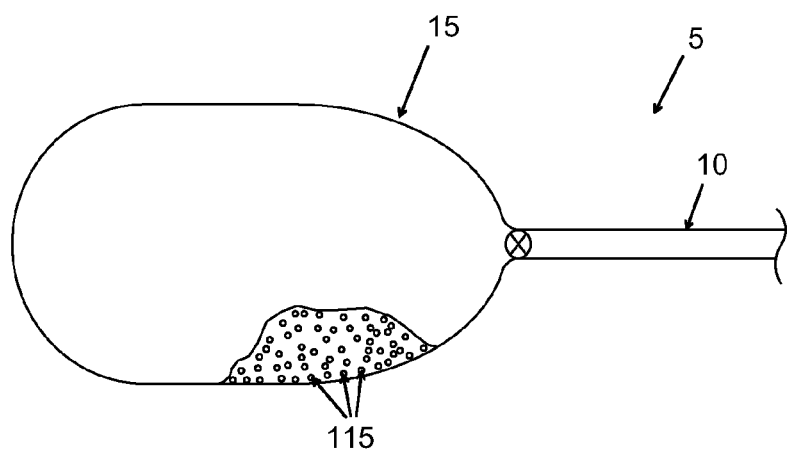
Figure 75:
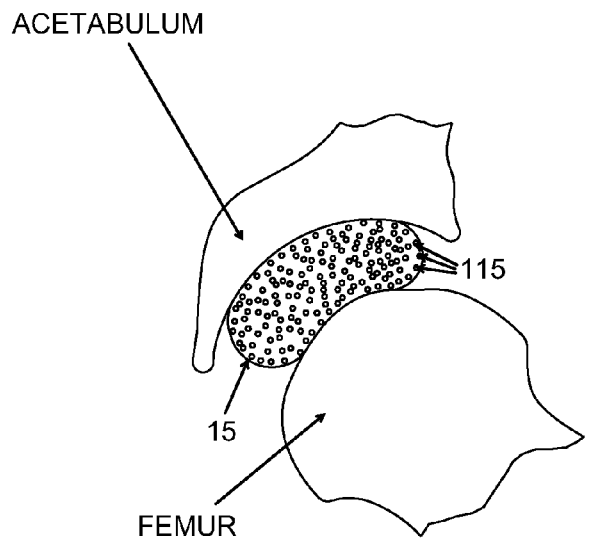
Figure 76:
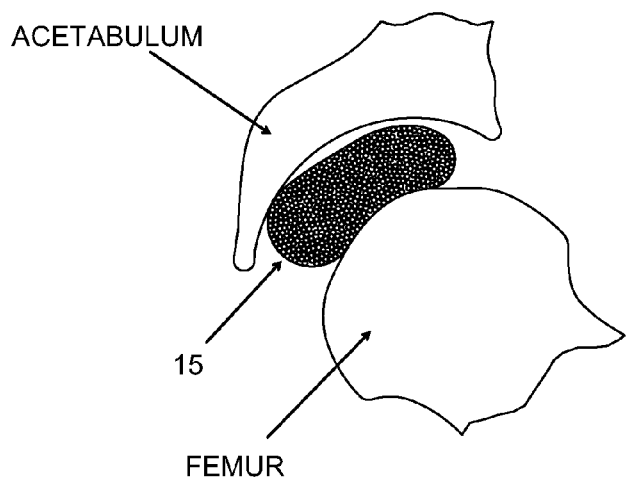
Figure 77:
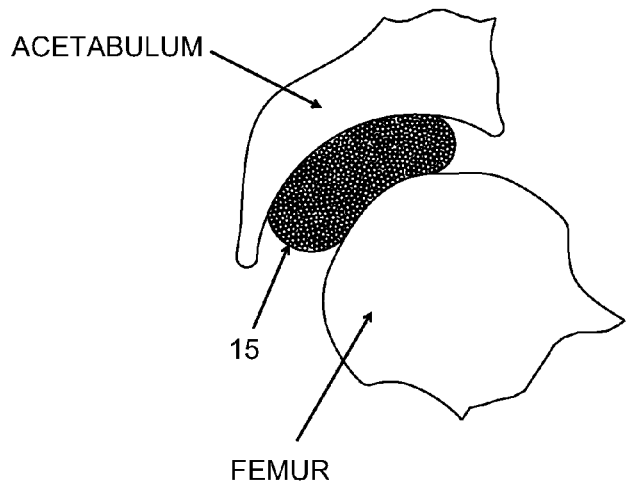
Figure 78:
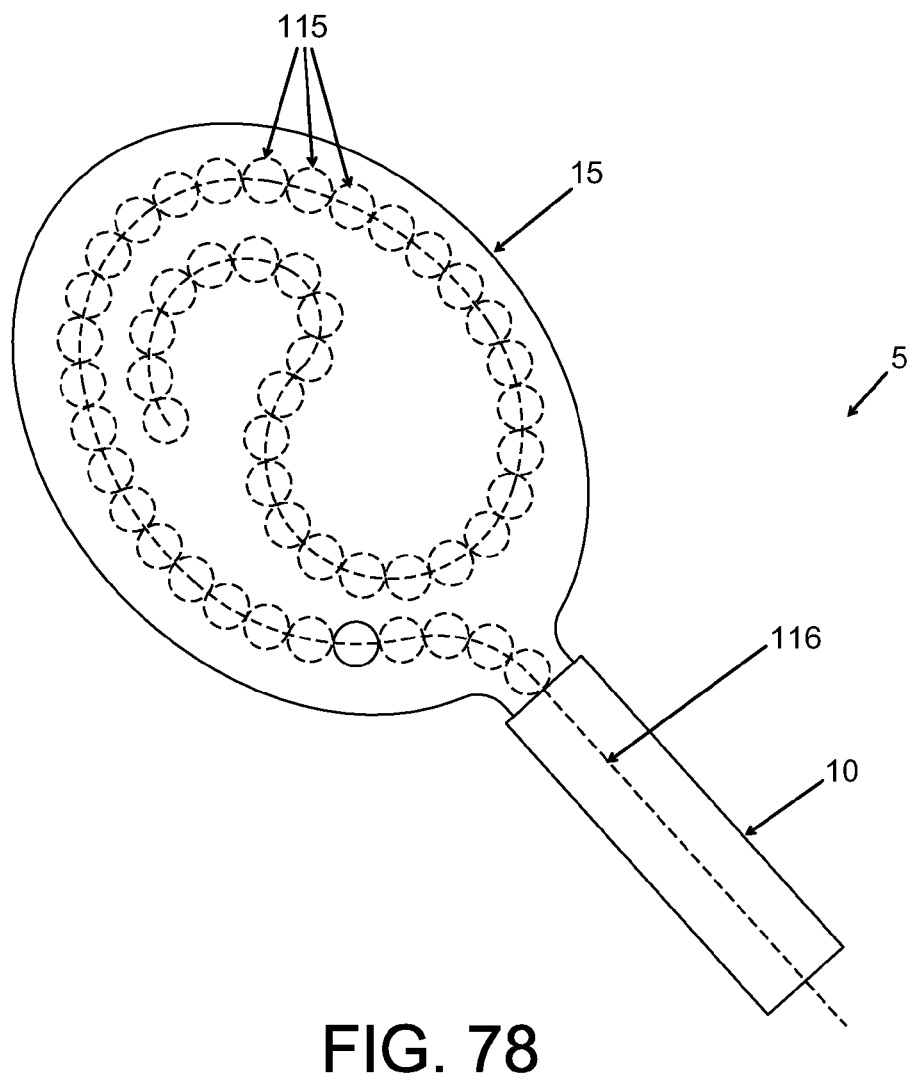

In yet another embodiment (FIGS. 73 and 74), the balloon is filled with beads 115. Beads 115 may be an absorbent polymer or foam, or non-absorbent. As shown in FIGS. 75-77, if beads 115 are non-absorbent, the balloon's inflation fluid can be evacuated from the balloon after beads 115 have been introduced into the inflated balloon, leaving a compact "bean bag" structure to maintain the joint space. As shown in FIG. 78, beads 115 may be delivered into the interior of the balloon in a strand configuration, i.e., mounted on a filament 116. This approach has the additional advantage that, in the event that the balloon should lose its integrity, beads 115 can be safely removed without leaving any beads in the hip joint, i.e., by pulling proximally on filament 116. If desired, beads 115 can be disposed between a primary outer balloon 15 and secondary inner balloon 90.

If desired, joint-spacing balloon catheter 5 can include pressure regulation, e.g., a relief valve (not shown) to ensure that a balloon is not inflated beyond a maximum level, or an alarm or other alert (not shown) to advise the user that a balloon has been inflated beyond a pre-determined level. This can be important to avoid damage to the patient's tissue or to reduce the risk of inadvertent balloon rupture.

Furthermore, a check valve (not shown) may be installed on the inflation port(s) 55 to enable joint-spacing balloon catheter 15 to be disconnected from the fluid reservoir while maintaining pressure in balloon 15.

It is also possible to place markings (e.g., longitudinal lines) along the body of balloon 15, or to color the balloon material, so as to improve endoscopic visualization of the balloon, including to show the degree of balloon inflation. Alternatively, the fluid used to inflate the balloon may be colored, or the balloon surface may have texture, in order to aid visualization of the balloon. Alternatively, a transparent, thick-walled balloon 15 can be used to increase visualization of the balloon by increasing the refraction of light, which will make the balloon foggy in appearance. Alternatively, a coating may be applied to the balloon in order to improve the endoscopic visualization of the balloon.
Alternatively, a second balloon or an expandable extrusion could be placed over the primary balloon so as to improve endoscopic visualization. The second balloon and/or expandable extrusion may be colored for improving endoscopic visualization. This configuration can also add to the puncture resistance of the primary balloon and assist in the delivery and retrieval of the primary balloon.

The joint-spacing balloon catheter 5 may also comprise a sensor (not shown). The sensor can measure the temperature of the surrounding tissue or fluid in the joint (e.g., the sensor may be a temperature sensor). The sensor may also detect characteristics of the adjacent cartilage, such as thickness, density, and/or quality (e.g., the sensor may be an ultrasound device, etc.). The sensor could be located on shaft 10 or on balloon 15, or on another portion of joint-spacing balloon catheter 5.

External Distraction of the Leg

In the foregoing description, the external distraction of the leg is generally discussed in the context of applying a distally-directed distraction force to the distal end of the leg. However, it should be appreciated that the distally-directed distraction force may be applied to another portion of the leg, e.g., to an intermediate portion of the leg, such as at or about the knee. Thus, as used herein, the term "distal end of the leg" is meant to include substantially any portion of the leg which is distal to the ball of the femur, such that by applying the external distraction force to the leg, a tension load is imposed on the intervening tissue. Furthermore, as used herein, the term "intervening tissue" is intended to mean the tissue which is interposed between the location where the external distraction force is applied to the leg and the ball of the femur.

Inflatable Perineal Post

The present invention also preferably comprises the provision and use of a novel inflatable perineal post for facilitating joint distraction.

Figure 79:
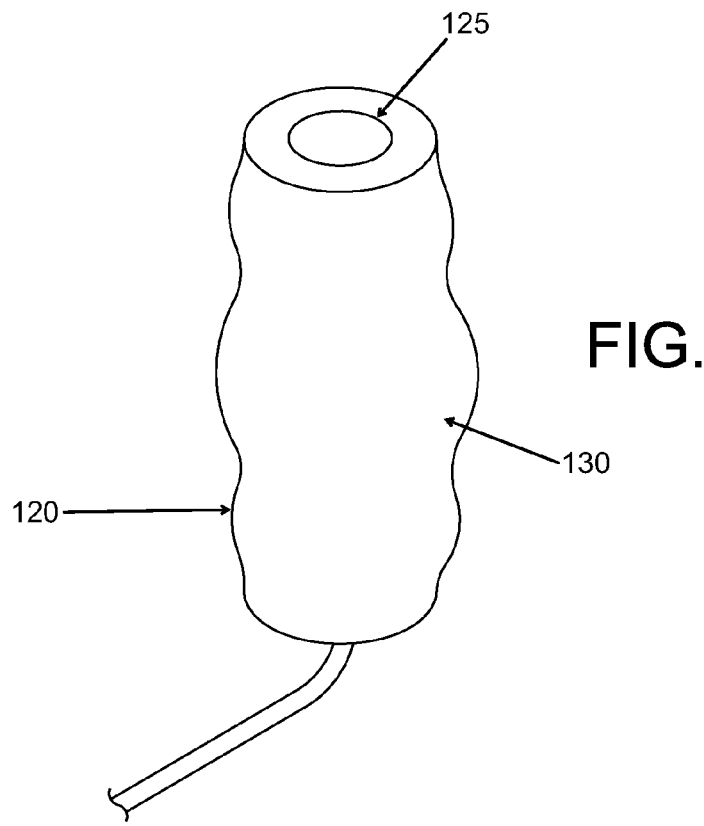
FIGS. 79 and 80 are schematic views showing an inflatable perineal post provided in accordance with the present invention.
Figure 80:
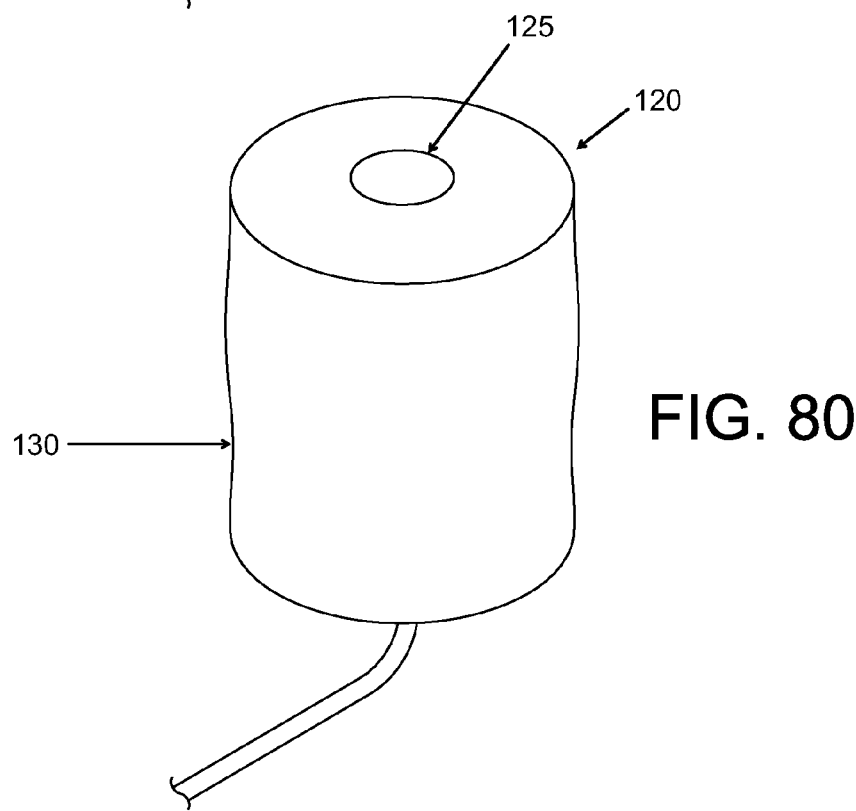
Figure 81:
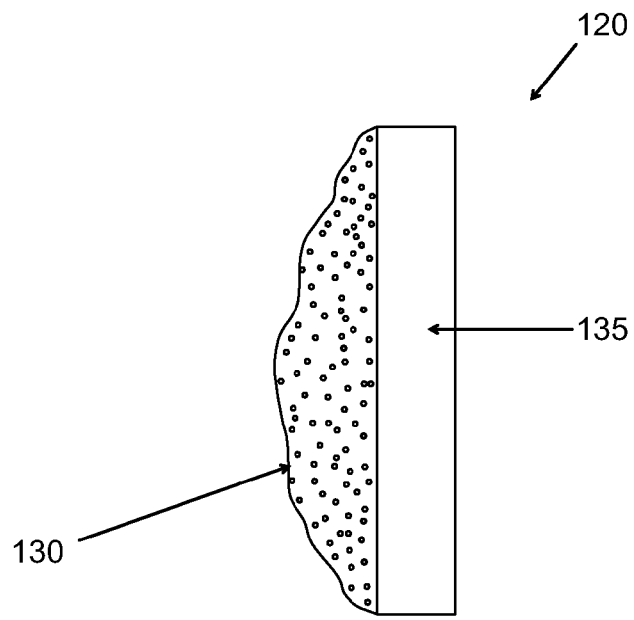
FIGS. 81 and 82 are schematic views showing another inflatable perineal post provided in accordance with the present invention.
Figure 82:
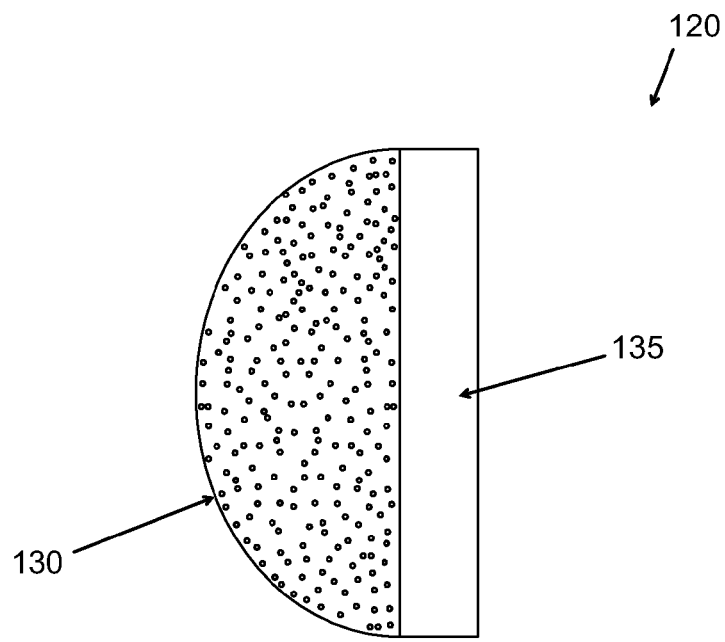

More particularly, and looking now at FIGS. 79 and 80, there is shown an inflatable perineal post 120 which generally comprises a relatively narrow, substantially rigid inner core 125 surrounded by a relatively wide, substantially soft inflatable balloon 130. In an alternative embodiment, and looking now at FIGS. 81 and 82, inflatable perineal post 120 comprises a soft inflatable balloon 130 which is supported on one or more sides by a substantially rigid support structure 135. Such a non-cylindrical construction, with inflation being directed along selected directions, can be highly beneficial, since it can reduce engagement of the non-working portions of the perineal post with patient anatomy (e.g., the genitalia). Still other post shapes and configurations will be apparent to one skilled in the art in view of the present disclosure.

The inflatable balloon 130 of the inflatable perineal post 120 is preferably constructed out of a semi-compliant material, but it may also be compliant or non-compliant. The inflatable balloon 130 of the inflatable perineal post 120 may involve a covering (not shown) for contact with the patient; this covering may be formed out of a non-slip material. The inflatable balloon 130 is preferably inflated with an appropriate fluid (e.g., air) using a manual or electric pump. The inflatable perineal post 120 could include a read-out panel displaying the balloon pressure.

The inflatable perineal post 120 may also comprise physiologic sensors (not shown) for monitoring parameters such as patient skin temperature and blood flow. Such parameters may be reflective of patient conditions of interest to the surgeon, e.g., a falling patient skin temperature is frequently indicative of reduced blood flow. These physiologic sensors may be incorporated into the surface of the inflatable balloon 130, or they could be separate sensors which are included as part of a kit provided with the inflatable perineal post. The physiologic sensors are adapted to be connected to a monitor so as to provide read-outs on the monitor.

In use, the inflatable perineal post 120 is positioned (in a deflated condition) between the patient's legs, the joint is distracted by pulling on the distal end of the leg so that the ball of the femur is spaced from the acetabular cup, the balloon 130 is inflated, a joint-spacing balloon catheter 5 is inserted into the distracted joint, the balloon 15 is inflated, the force applied to the distal end of the leg is relaxed so that the ball of the femur settles back down onto the one or more inflated balloons 15, and then the perineal post balloon 130 is at least partially deflated. At this point the arthroscopic surgery can be conducted without trauma to the patient's tissue, due to either the distal distraction of the leg or due to engagement of the perineal post with the tissue of the patient. At the conclusion of the surgery, the distal end of the leg is pulled distally again, the perineal post balloon 130 is inflated, the joint-spacing balloon 15 is deflated, the joint-spacing balloon catheter 5 is removed from the joint, and the joint is reduced. Alternatively, the balloon 130 could be inflated prior to pulling on the distal end of the leg. Or, alternatively, the perineal post balloon 130 could be deflated prior to withdrawal of the force being applied to the distal end of the leg. In some cases, only one of either (i) pulling on the leg, or (ii) inflating of the perineal post is performed in order to remove or re-position the joint-spacing balloon 15.

If desired the inflatable perineal post 120 may be used to replace a standard perineal post, and is used in conjunction with a standard traction table; in other words, in this form of the invention, the inflatable perineal post 120 is not used in conjunction with a joint-spacing balloon catheter 5.

One Preferred Form of the Invention

In one preferred form of the present invention, the aforementioned novel method for distracting the joint is implemented using the aforementioned novel joint-spacing balloon catheter 5 and the aforementioned inflatable perineal post 120.

More particularly, in this form of the invention, the hip joint is first distracted by pulling on the distal end of the leg just above the ankle, and then inflating the inflatable perineal post, where the perineal post is positioned between the patient's legs. The leg may be adducted so as to lever the femur laterally. Alternatively, the inflatable perineal post could be inflated prior to the distal end of the leg being pulled distally. In any case, this action separates the head of the femur from the acetabular cup by a distance which is greater than the distance that they are normally separated from one another when the joint is in a healthy state, whereby to distract the joint and create a substantial intrajoint space. By way of example but not limitation, the head of the femur may be separated from the acetabular cup by a distance of approximately 10-20 mm or more, and preferably in the range of approximately 15 mm.

Next, the surgeon identifies a portal location for delivery of joint-spacing balloon catheter 5. Then a stylet-filled needle is placed into the joint, the stylet is removed, a guidewire is delivered through the needle, and then the needle is removed. The guidewire can be placed so that it extends along the desired delivery path for the joint-spacing balloon catheter 5, whereby to facilitate proper deployment of the joint-spacing balloon catheter.

An arthroscopic cannula or outer guiding member may then be emplaced if desired; in this instance, the guidewire may be removed if desired.

Next, a joint-spacing balloon catheter 5 of the appropriate size is selected from a kit providing a range of differently-sized joint-spacing balloon catheters. Then the joint-spacing balloon catheter 5 is delivered over the guidewire (either percutaneously or through a cannula) to the target site between the femoral head and the acetabulum. The joint-spacing balloon catheter 5 may be rotated as appropriate if there is asymmetry in the balloon's shape. Alternatively, the joint-spacing balloon catheter 5 may be delivered through a cannula without the use of a guidewire.

Next, a syringe (or other inflation device) is secured to the joint-spacing balloon catheter 5, and the balloon 15 is inflated to the desired pressure and/or size. Balloon 15 may be inflated to a size and pressure such that when external distraction is reduced, the space in the joint remains substantially unchanged. Alternatively, balloon 15 may be inflated to a size and pressure such that when external distraction is reduced, the space in the joint is reduced by a small amount as the head of the femur settles back down on the balloon. In any case, this action keeps the head of the femur separated from the acetabular cup by a distance which is greater than the distance that they are normally separated from one another when the joint is in a healthy state, whereby to maintain a substantial intrajoint space which provides the surgeon with excellent access to the central compartment of the hip joint. By way of example but not limitation, the head of the femur may be maintained separated from the acetabular cup by a distance of approximately 10-20 mm or more, and preferably in the range of approximately 15 mm. The balloon 15 is preferably inflated to a pressure of less than 100 psi, and more preferably inflated to a pressure of approximately 30-75 psi. If there is more than one balloon 15, the additional balloon(s) 15 can be inflated. If the additional balloon(s) 15 are used to affect the direction of joint spacing, the pressure and/or size of each balloon 15 is adjusted so as to achieve the desired joint spacing direction.

Once the balloon(s) 15 have been inflated to the desired pressure and/or size, the distraction force applied to the leg is at least partially removed, allowing the head of the femur to rest on the inflated balloon(s) (which is/are itself/themselves supported by the acetabulum).

Additionally, the inflatable perineal post 120 is deflated as appropriate; this may occur before the external distraction force on the leg is released.

The balloon(s) 15 can be re-positioned by re-applying distraction force to the leg and/or re-inflating the inflatable perineal post 120, deflating balloon(s) 15 and re-positioning the joint-spacing balloon catheter 5, re-inflating the balloon(s) of the joint-spacing balloon catheter, then releasing the leg distraction and/or deflating the inflatable perineal post. The balloon(s) 15 may be placed in a location which directs the distraction in a preferred direction. Alternatively, where the joint-spacing balloon catheter comprises a plurality of balloons, the balloons may be inflated to different sizes and/or pressures in order to direct the joint distraction in a preferred direction.

With the balloon(s) maintaining the joint distraction, the leg may be manipulated (i.e. rotated, flexed, etc.) in order to visualize and access pathology through the established portals.

Then the arthroscopic surgery is conducted. The leg may be manipulated a number of times through the procedure in order to visualize, access and treat various pathologies. In this respect it should be appreciated that while the femoral head is supported on the balloon(s), manipulating the leg of the patient can change the relative spacing within the joint in general, and at the acetabular rim in particular. Furthermore, different manipulations of the leg can change the spacing at different regions of the acetabular rim. This can be extremely helpful in order to increase space at a specific location, whereby to improve visualization and/or increase working space. By way of example but not limitation: (i) extension of the leg closes the anterior/superior rim space, while flexion of the leg opens the anterior/superior rim space, and (ii) internal rotation of the leg opens the anterior/superior rim space, while external rotation of the leg closes the anterior/superior rim space. Of course, the foregoing comments are general in nature and will vary depending on the specific locations of the hip joint relative to the perineal post and the traction table pivot, as well as the position of the device within the joint and the patients' capsular ligament constitution. Also, combinations of the foregoing manipulations may be used, e.g., flexion plus internal rotation may be used to create lateral space which is of key importance to the hip arthroscopist.

At the conclusion of the arthroscopic surgery, the hip joint is distracted again, e.g., by pulling on the distal end of the leg just above the ankle, so as to lift the head of the femur off the balloon(s). The perineal post balloon may be inflated. The balloon(s) 15 of the joint-spacing balloon catheter is/are deflated and the joint-spacing balloon catheter is removed. Thereafter, the external distraction force applied to the leg may be removed, allowing the head of the femur to settle back on the acetabulum.

In another form of the invention, while the distal end of the leg is held stationary, the perineal post 120 is inflated to break the suction seal of the hip joint and enable the joint-spacing balloon catheter 5 to be placed in the joint and inflated. In this case, no pulling on the leg is performed. This would have the benefit of eliminating a piece of equipment from the surgery and reducing the corresponding surgical time associated with using that equipment.

Peripheral Spacer Balloon

Figure 83:
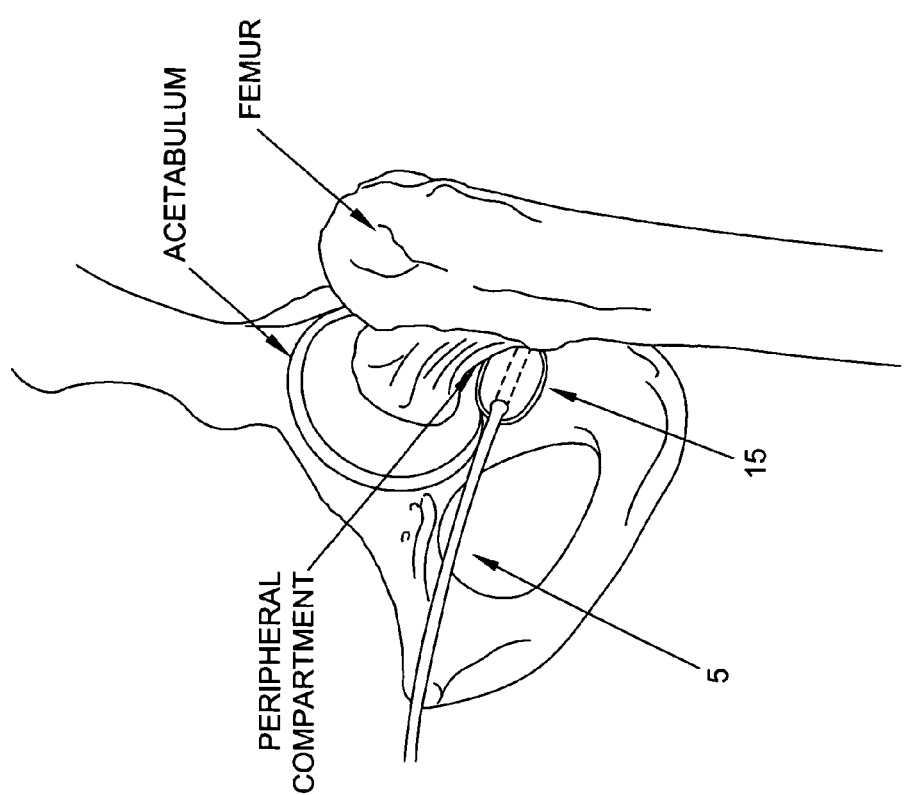
FIGS. 83-90 are schematic views showing how a joint-spacing balloon catheter may be placed in the peripheral compartment of the hip joint as well as in the central compartment of the hip joint.
Figure 84:
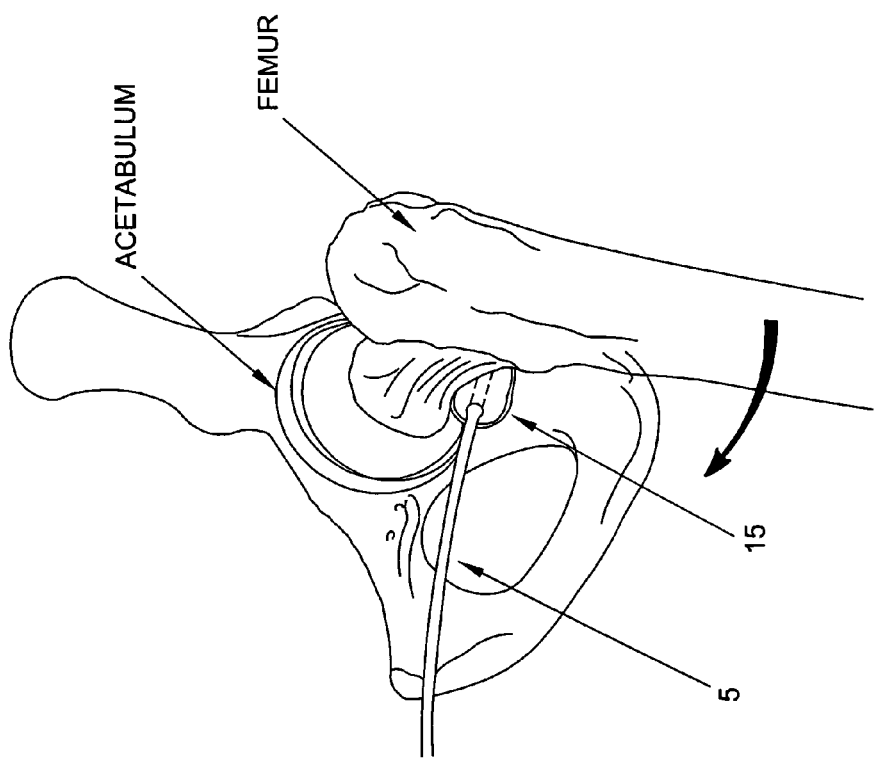
Figure 85:
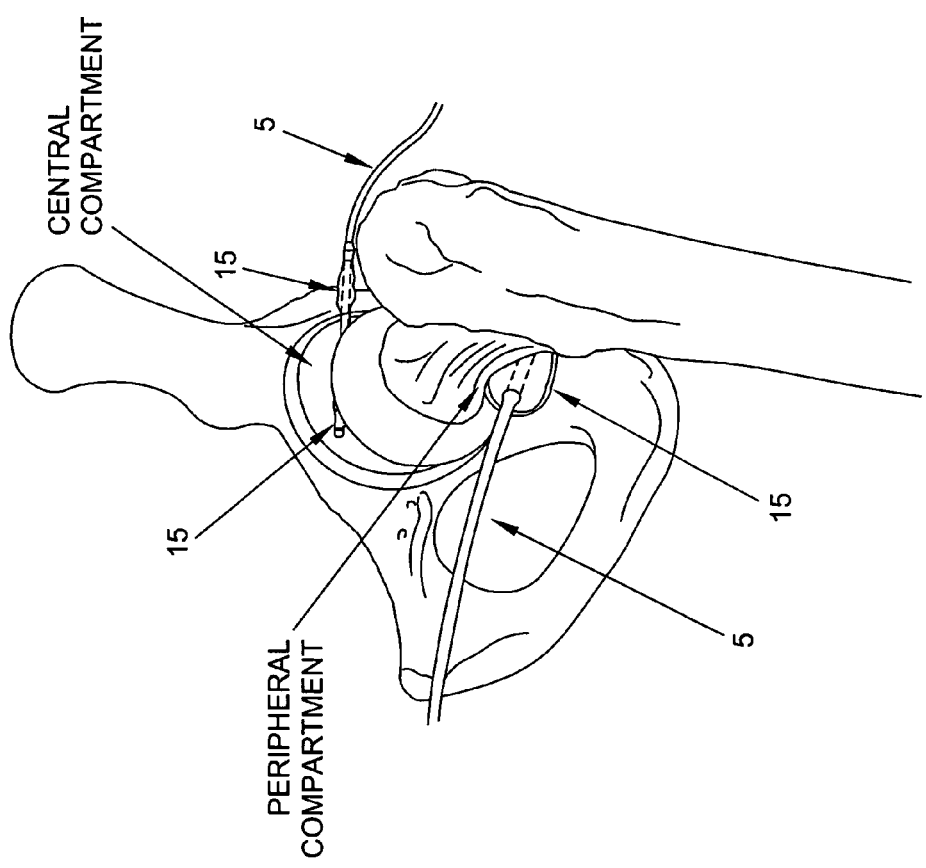
Figure 86:
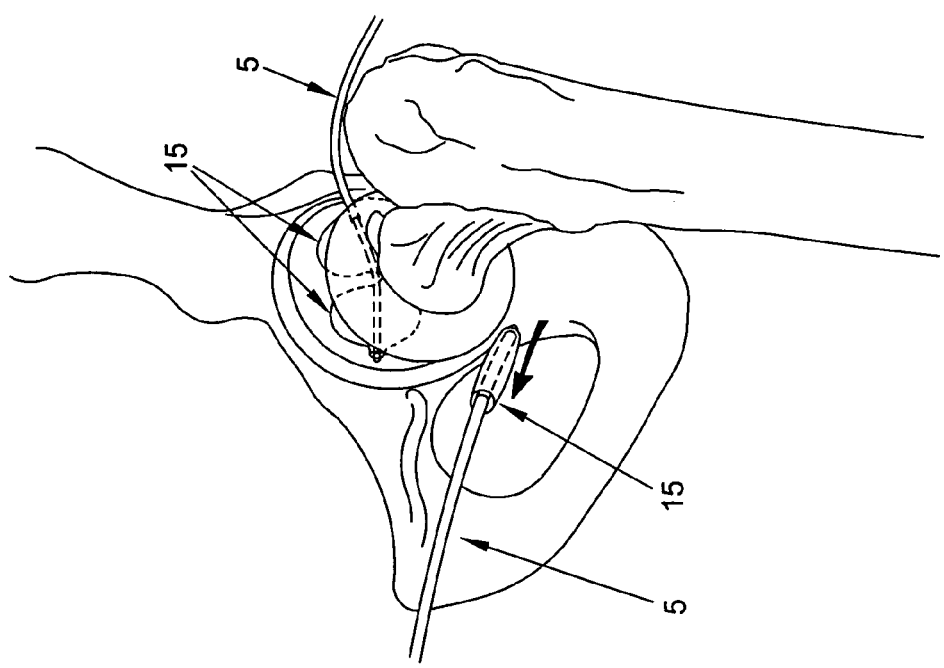
Figure 87:
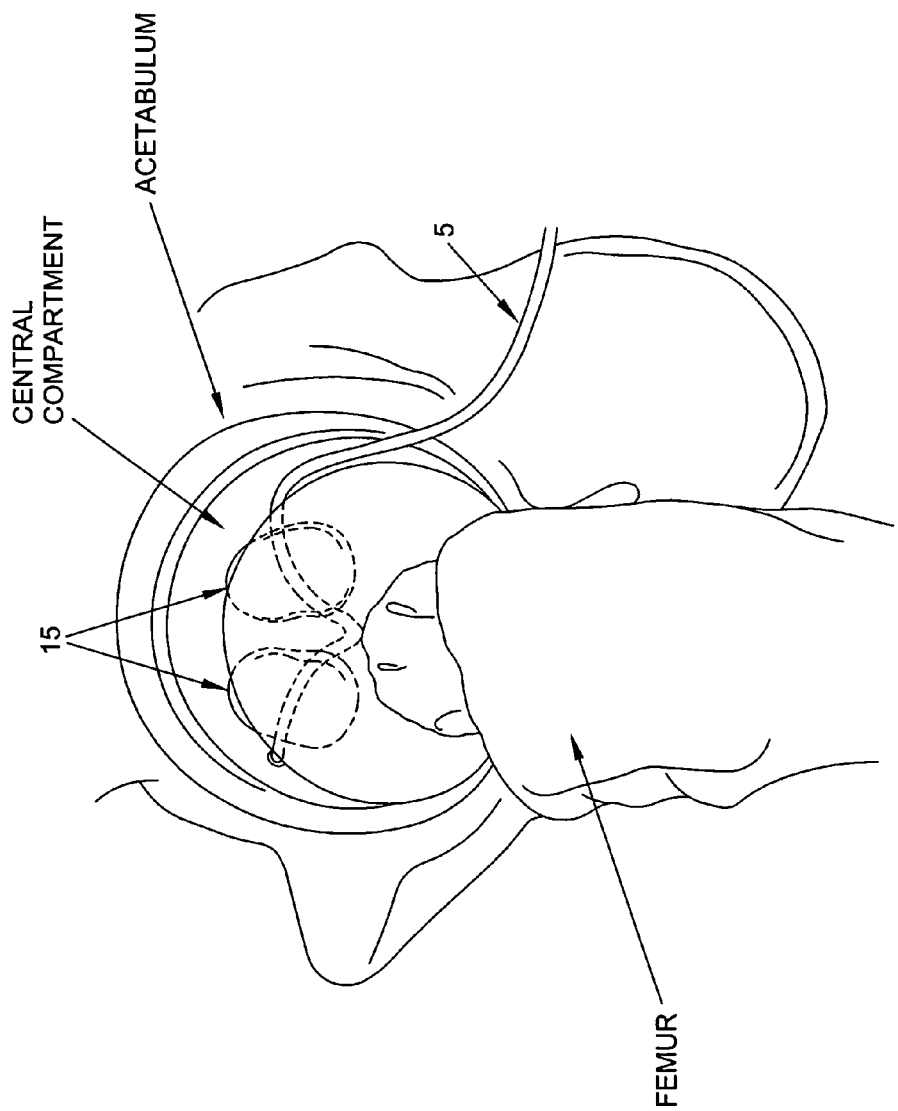

In yet another form of the invention, and looking now at FIGS. 83-87, the joint-spacing balloon catheter 5 can be used to perform some or all of the joint distraction. In one embodiment, a first joint-spacing balloon catheter 5 is placed adjacent to the femoral head (e.g., in the peripheral compartment) and the balloon is inflated (FIG. 83). The leg is then manipulated in abduction or adduction (FIG. 84), depending on balloon location, thus levering the femoral neck against the balloon. This levering action opens the central compartment (i.e., the space between the femoral head and the acetabulum) and creates a gap at the acetabular rim. A second joint-spacing balloon catheter 5 is then inserted into the gap (FIG. 85) and delivered into the central compartment of the joint (i.e., the space between the femoral head and the acetabulum). In one preferred form of the invention, this second joint-spacing balloon catheter comprises two balloons 15 disposed in a serial configuration. The balloons of the second joint-spacing balloon catheter 5 are then inflated (FIG. 86) to distract the joint; that is, to open up the joint space. In one embodiment, the balloon of the first joint-spacing balloon catheter 5 is placed on the lateral/superior aspect of the femoral neck. Once the balloons of the second joint-spacing balloon catheter 5 have been inflated, the balloon of the first joint-spacing balloon catheter 5 can be deflated and withdrawn (FIG. 87). The balloon of the first joint-spacing balloon catheter 5 may be of a different size and shape than the balloons of the second joint-spacing balloon catheter 5. It also may be inflated to a different pressure.

Use of Multiple Joint-Spacing Balloon Catheters

Figure 88:
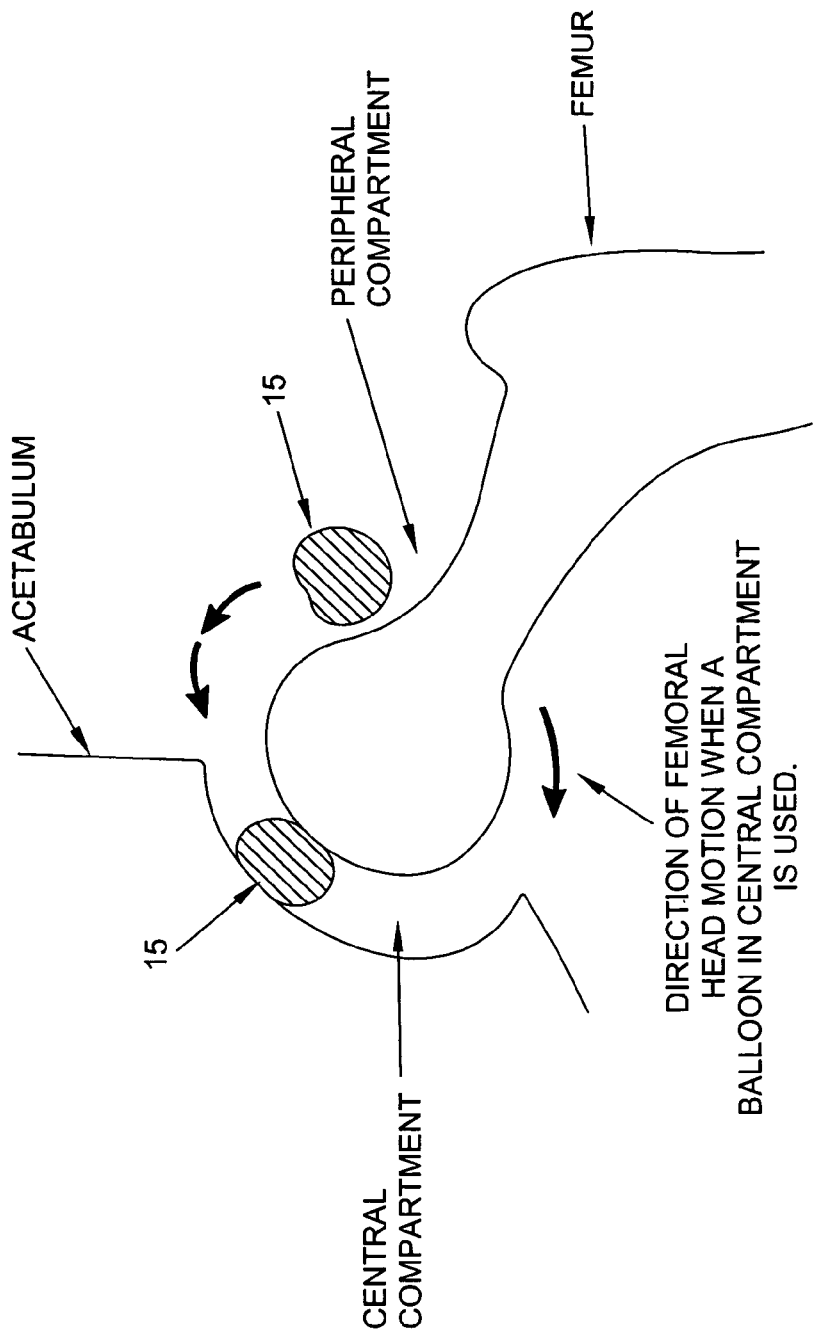
Figure 89:
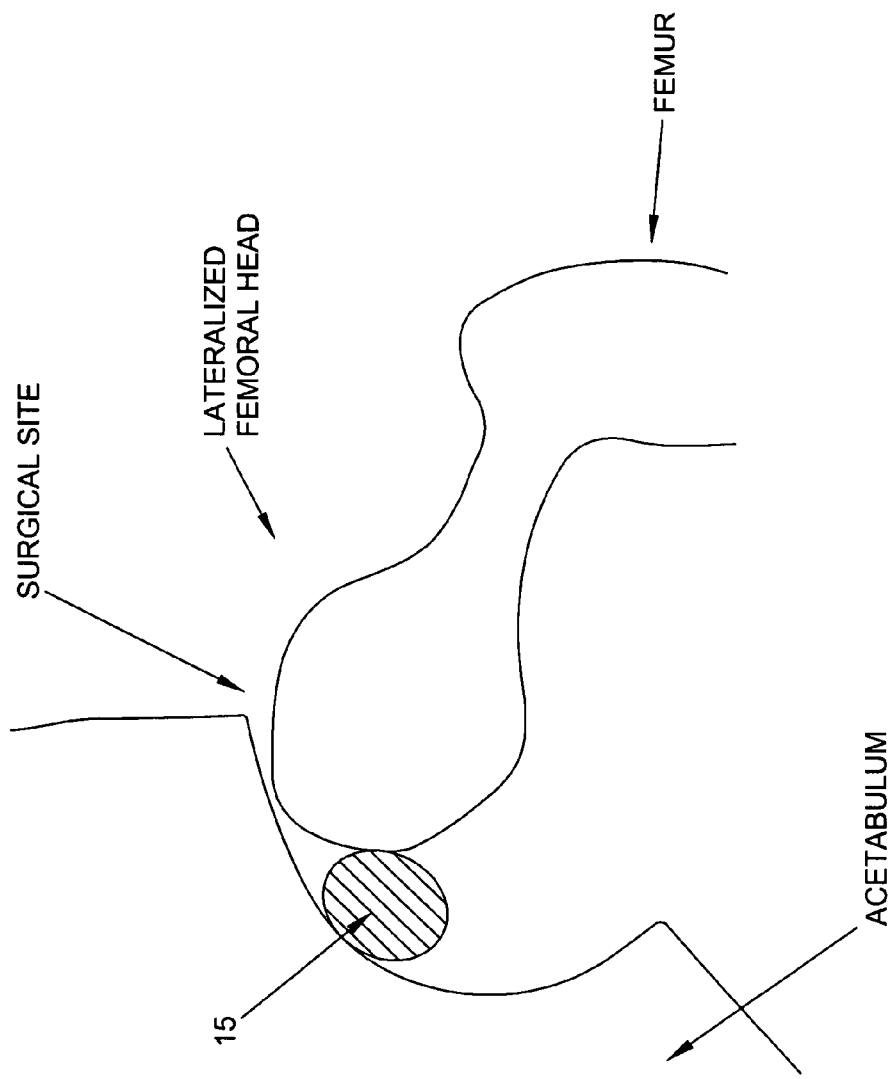
Figure 90:
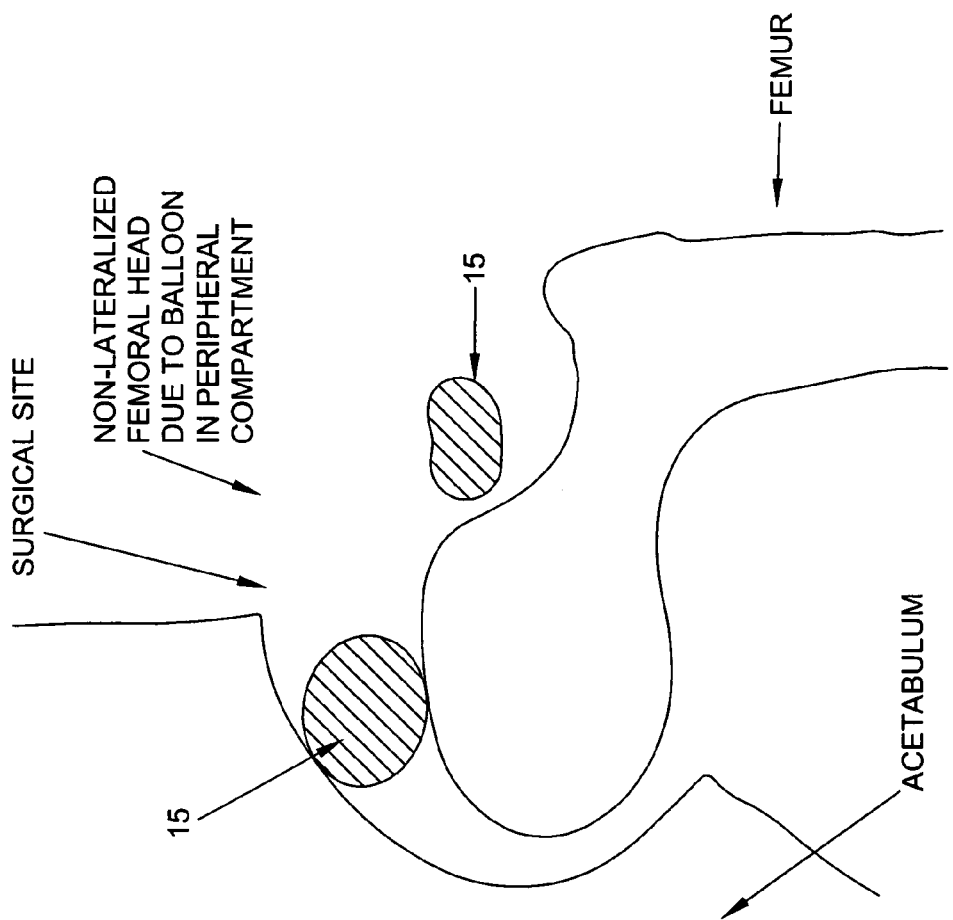

In one preferred form of the invention, multiple joint-spacing balloon catheters 5 are simultaneously used within the joint so as to achieve the desired distraction maintenance. More particularly, in one preferred manner of use, and looking now at FIG. 88, one joint-spacing balloon catheter 5 is disposed so that its balloon(s) 15 are disposed in the central compartment (for ease of illustration, only one balloon 15 is shown in the central compartment in FIG. 88), and one joint-spacing balloon catheter 5 is disposed in the peripheral compartment (for ease of illustration, only one balloon 15 is shown in the peripheral compartment in FIG. 88). As a result, when the external distraction is released, the balloon(s) 15 in the peripheral compartment will cooperate with the balloon(s) 15 in the central compartment so as to provide distraction maintenance with minimal lateralization of the femoral head relative to the acetabulum. More particularly, when distraction maintenance is provided using balloon(s) 15 in only the central compartment (FIG. 89), the femoral head may try to move superiorly and laterally when the external distraction is released, which can inhibit the surgeon's view of the central compartment. But if balloon(s) 15 are erected in the peripheral compartment (e.g., against the femoral neck) as well as in the central compartment (e.g., in the manner shown in FIG. 88), the femoral head will try to move downwardly and medially when the external distraction is released due to the presence of the balloons in the peripheral compartment, whereby to push the femoral head below the balloon(s) in the central compartment and avoid lateralization. See FIG. 90. Avoidance of such lateralization provides a more stable distraction maintenance.

Although balloon(s) 15 have been described here as being used to avoid lateralization of the femoral head, they can also be used to move the femoral head in a preferential direction relative to the acetabular cup. For example, if the surgeon has a anteriorly/medially located pincer impingement, it may be desirable to move the femoral head more posterior to increase surgical access. By placing and inflating balloon(s) 15 in the anterior region of the femoral neck, the femoral head can be moved more posterior, thus creating more space to access and treat the pincer impingement pathology. There may also be situations where balloons 15 are placed elsewhere in the joint to preferentially shift the location of the femoral head.

In an alternative embodiment, the balloon in the peripheral compartment is deflated but remains in position to be used at a later point in the procedure. For example, when the surgeon desires to operate in the peripheral compartment, the surgeon can re-inflate the balloon located in the peripheral compartment. This will push the capsule away from the femoral neck, thus creating operative space.

Kits

The joint-spacing balloon catheter 5 and the inflatable perineal post 120 may be offered as part of a single kit. A guidewire or obturator, outer guiding member, beveled cannula and a balloon inflation device may additionally be provided.

Preferred Construction

In General

Looking next at FIG. 91, there is shown a joint-spacing balloon catheter 200 which comprises one preferred form of the present invention. Joint-spacing balloon catheter 200 generally comprises an elongated shaft 205 having a distal end 210 and a proximal end 215.

Figure 94:
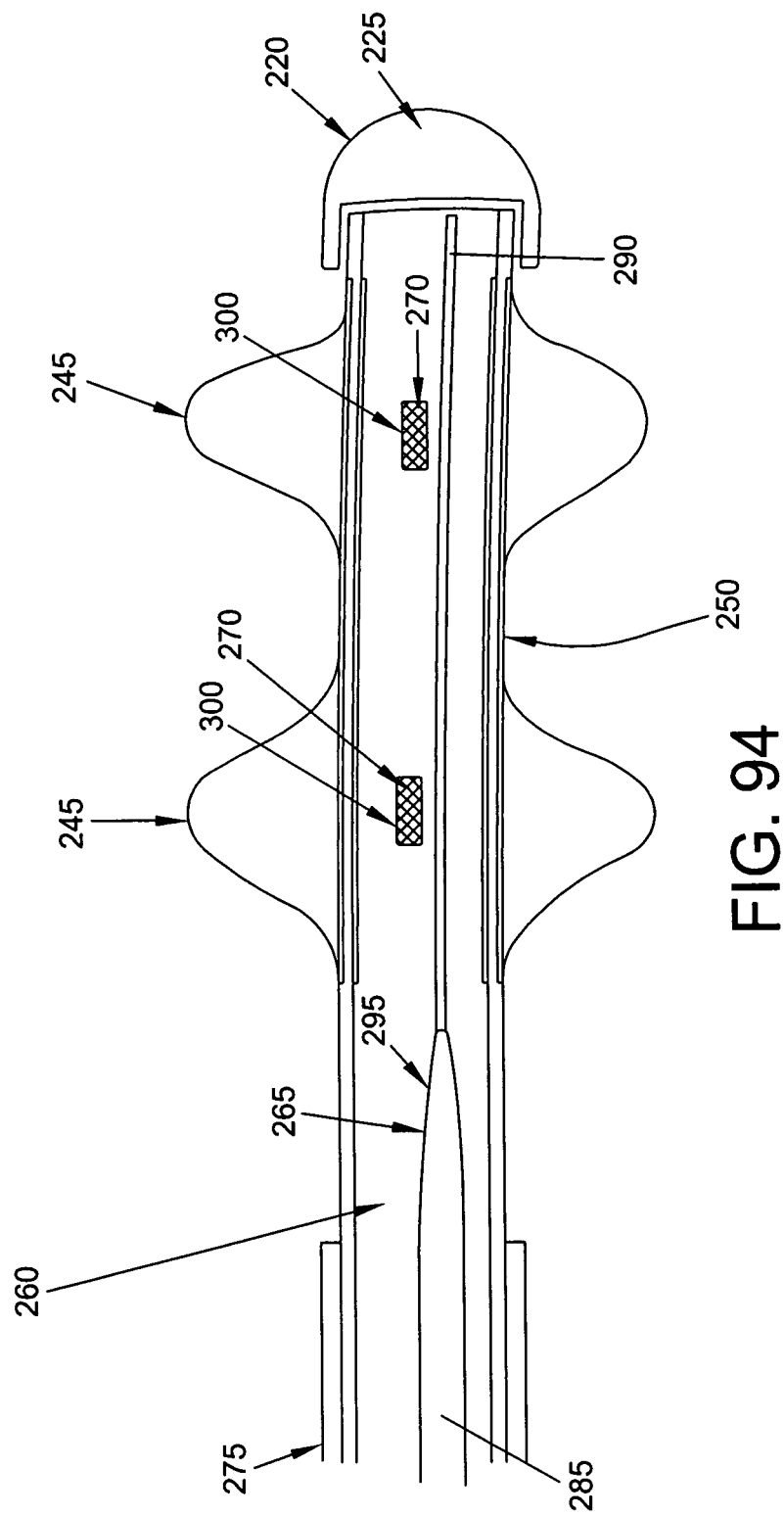

Distal end 210 of elongated shaft 205 comprises an atraumatic tip 220. In one preferred form of the present invention, and looking now at FIG. 94, atraumatic tip 220 comprises a silicone cap 225. Silicone cap 225 is constructed so as to have a very soft durometer, so that inadvertent engagement of atraumatic tip 220 with tissue (e.g., articular cartilage, labrum, etc.) will minimize any trauma to the tissue. Silicone cap 225 is preferably made of an elastomer (e.g., silicone rubber). Silicone cap 225 preferably has a radius of approximately 0.01" to 0.25", and more preferably has a radius of about 0.09".

Referring again to FIG. 91, the proximal end of shaft 205 is secured to a handle 230. Handle 230 preferably comprises a grip 235 and a spring-return trigger 240, whereby pulling spring-return trigger 240 towards grip 235 causes the distal end of elongated shaft 205 to articulate (i.e., bend), e.g., in the manner shown in FIG. 92 or in the manner shown in FIG. 93.

If desired, handle 230 may be provided with a releasable locking mechanism for releasably locking spring-return trigger 240 in position relative to grip 235, whereby to releasably lock elongated shaft 205 in a particular articulated position. In this respect it should be appreciated that locking spring-return trigger 240 in position relative to grip 235 (and hence locking elongated shaft 205 in a particular articulated position) can be advantageous, since it relieves the user of the need to continuously squeeze spring-return trigger 240 toward grip 235 in order to maintain a particular articulated position for elongated shaft 205. By way of example but not limitation, and looking now at FIG. 93A, spring-return trigger 240 may be provided with a ratchet mechanism 242 which releasably engages a finger (not shown in FIG. 93A) on grip 235, whereby to releasably lock spring-return trigger 240 in position relative to grip 235, and hence releasably lock elongated shaft 205 in a particular articulated position.

In one preferred form of the invention, joint-spacing balloon catheter 200 is intended to be used in the hip, and the distal end of elongated shaft 205 is configured to articulate about a radius of approximately 12-38 mm, and more preferably to articulate about a radius of approximately 25 mm. In this respect it should be appreciated that cadaver lab testing has shown that an articulation radius of larger than about 20-35 mm can result in the distal end of elongated shaft 205 colliding with the acetabulum, and an articulation radius of less than about 20-35 mm can result in the distal end of elongated shaft 210 colliding with the femoral head. The distal tip 220 of joint-spacing balloon catheter 200 is preferably able to articulate at least 90 degrees off the longitudinal axis of elongated shaft 205, and more preferably at least 120 degrees off the longitudinal axis of elongated shaft 205, and even more preferably about 180 degrees off the longitudinal axis of elongated shaft 205. In one preferred form of the present invention, the distal tip of elongated shaft 205 articulates 180 degrees about a one inch radius.

Handle 230 may also be detachable from shaft 205 after the balloons (see below) are inflated.

Figure 92:
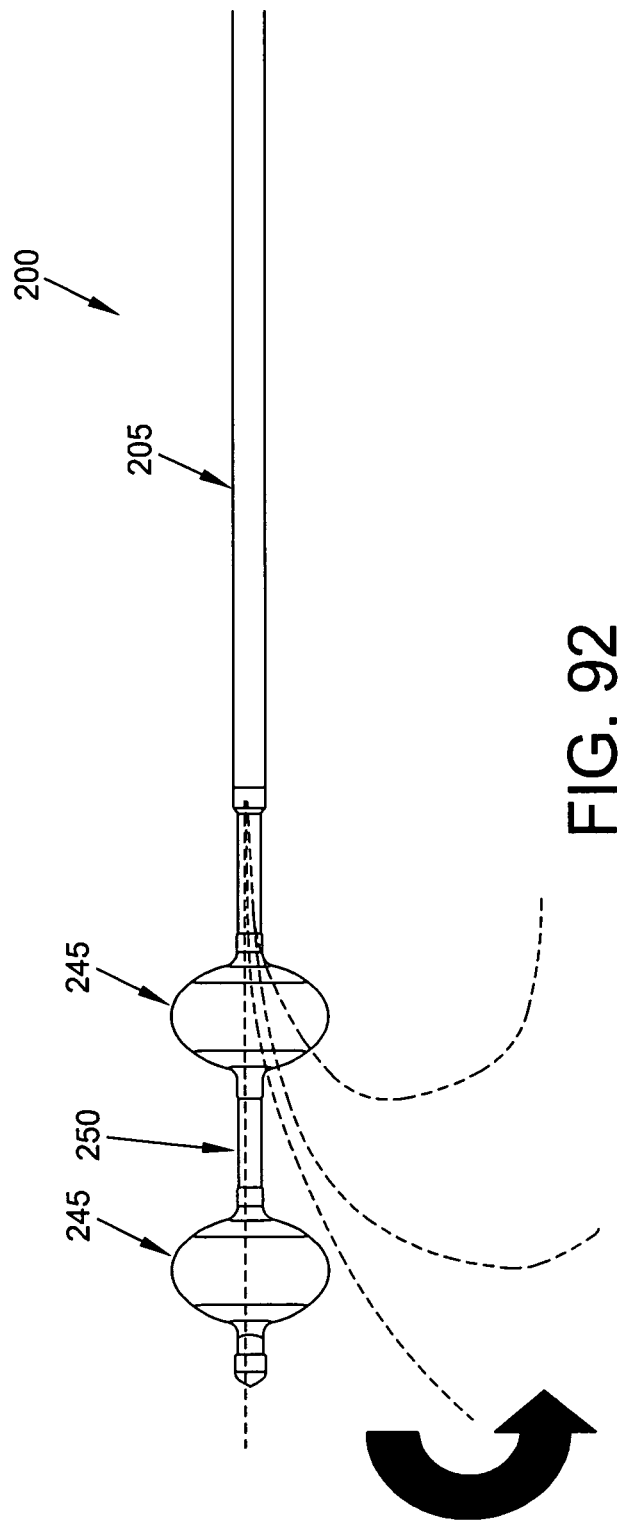
Figure 93A:
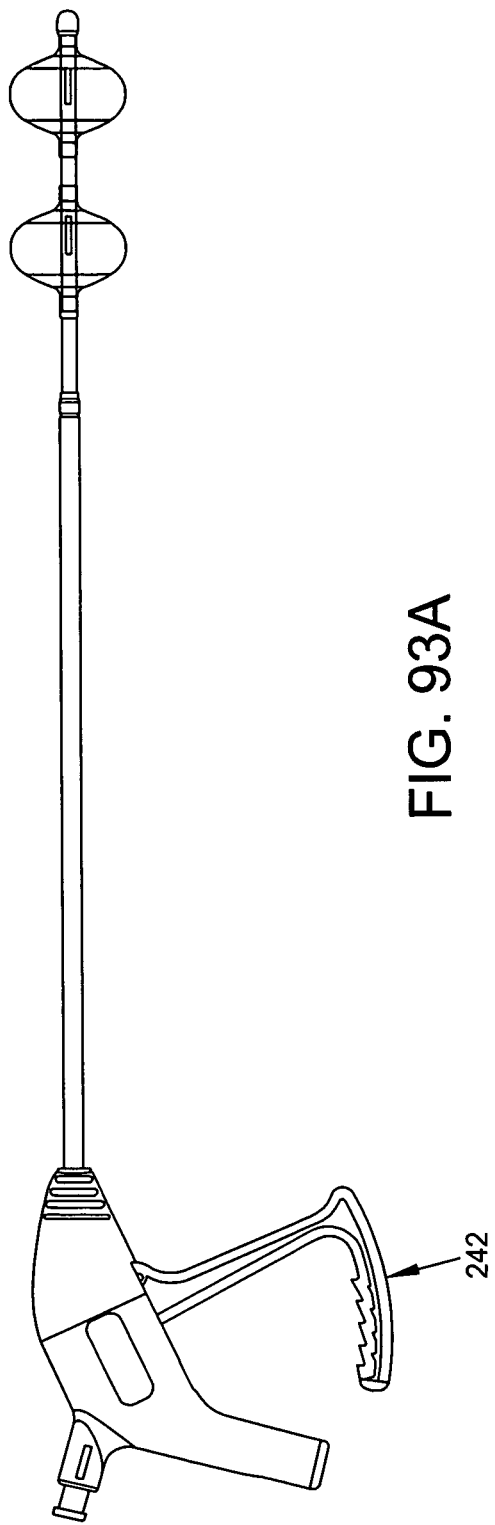

Joint-spacing balloon catheter 200 is preferably configured so as to articulate in the same plane as that of handle 230, e.g., in the manner shown in FIGS. 92 and 93, since such a construction is similar to other articulating surgical instruments commonly used in the field of hip arthroscopy. In addition, such a construction allows the joint-spacing balloon catheter 200 to be used on both right and left hips without modification.

Referring again to FIG. 91, a pair of balloons 245 are disposed adjacent to the distal end of the shaft. Balloons 245 are separated from one another by a shaft portion 250. Balloons 245 are inflatable/deflatable via a fluid fitting 246 provided on handle 230 and one or more lumens (not shown in FIG. 91) running through elongated shaft 205. Balloons 245 may be independently inflatable/deflatable or they may be inflatable/deflatable in a coordinated fashion. Preferably balloons 245 are constructed so that when the balloons are inflated and not subjected to any external forces, the balloons have a diameter which is larger than their length. Preferably, the balloons 245 are 0.39" to 1.57" in diameter, and more preferably about 1.10" in diameter. Preferably, the balloons 245 are 0.39" to 1.57" in length, and more preferably about 0.80" in length. Balloons 245 are preferably an ellipsoid shape. Balloons 245 are preferably constructed of Nylon 12 polymer material with a Shore D hardness of 79 to 115. Preferably the shaft portion 250 separating balloons 245 from one another is flexible. Preferably the gap between the two balloons 245 (i.e., the length of shaft portion 250) is approximately 0.5" to approximately 1.5".

Preferred Shaft Construction

Elongated shaft 205 of joint-spacing balloon catheter 200 is preferably constructed so as to provide substantial articulation, high torqueability and excellent column strength, so as to facilitate proper placement of the joint-spacing balloon catheter within the joint. This is preferably achieved by utilizing a unique construction for elongated shaft 205.

Figure 95:
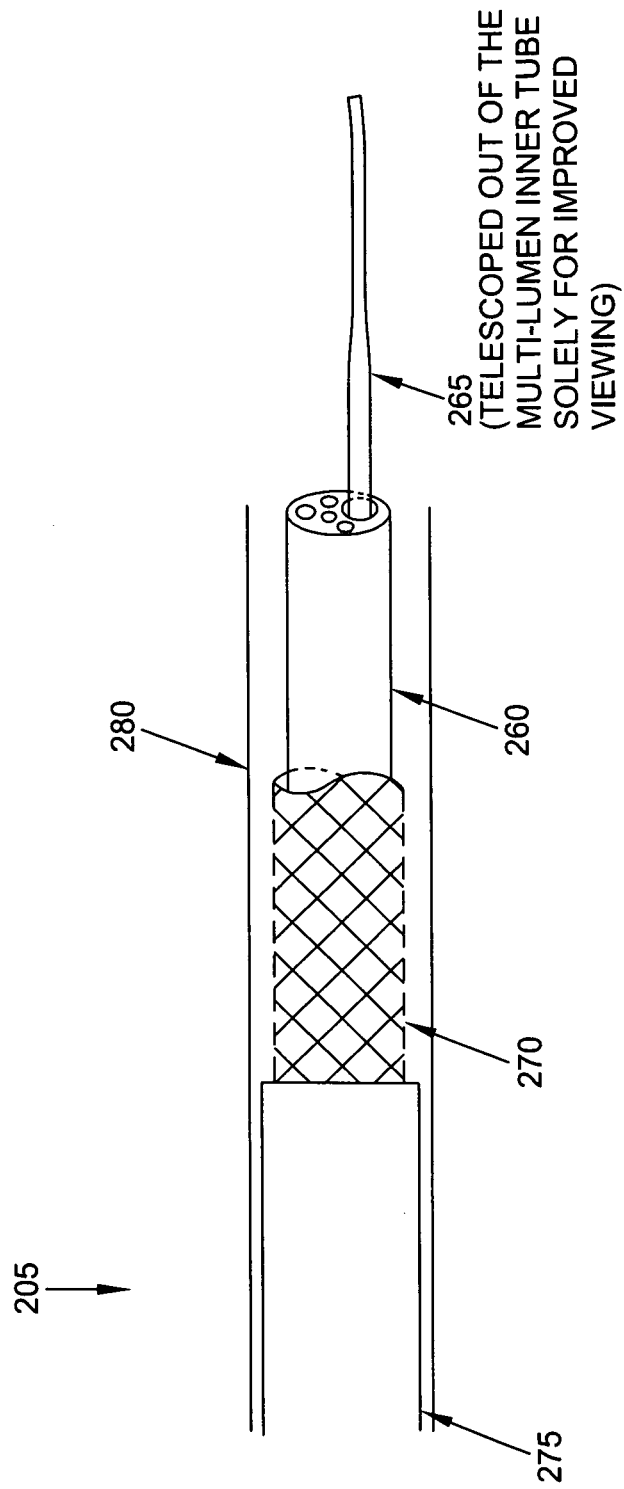
Figure 96:
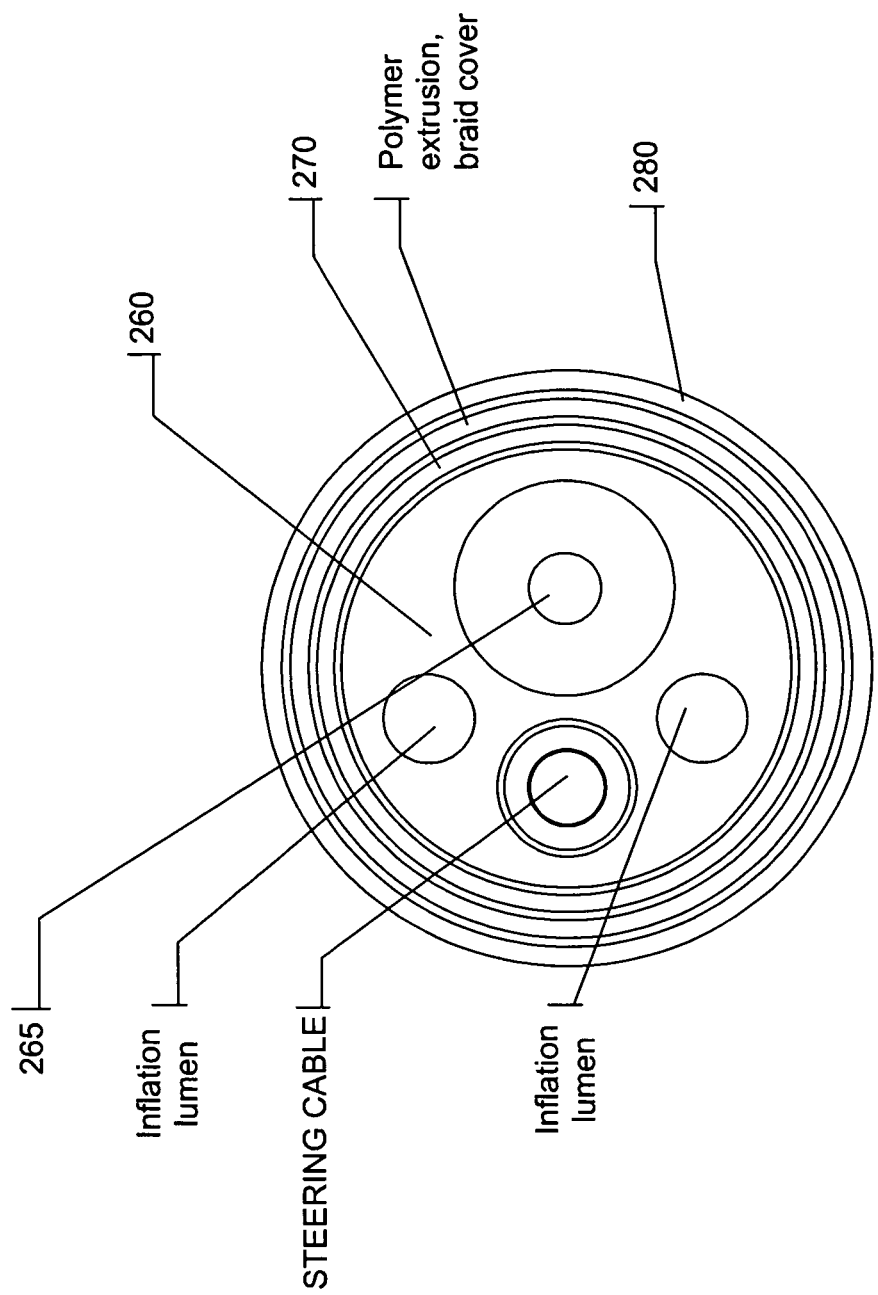
Figure 97:
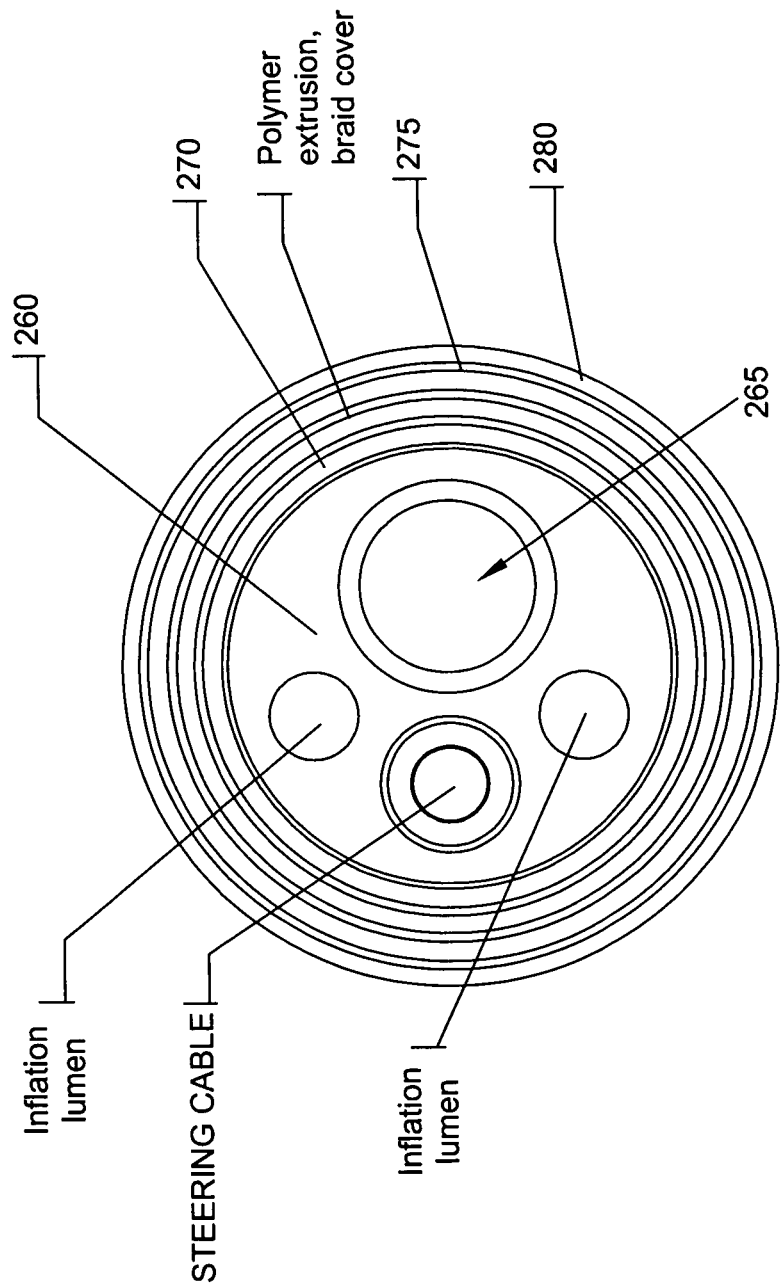

More particularly, and looking now at FIGS. 94-99, elongated shaft 205 preferably comprises a multi-lumen inner tube 260 which receives a nitinol stiffening rod 265 within one of its lumens. Multi-lumen inner tube 260 is preferably covered by a kink-resistant braid 270. Kink-resistant braid 270 is preferably covered by a rigid hypotube shaft 275 for part of its length. Rigid hypotube shaft 275, and the portion of kink-resistant braid 270 distal to rigid hypotube shaft 275, are preferably covered by a flexible polymer layer 280 (FIG. 95). Flexible polymer layer 280 is preferably 35 to 72 Shore D durometer, and more preferably 63 Shore D durometer. A second flexible polymer layer may cover the flexible polymer layer 280 along the shaft portion 250 extending between the balloons 245. This second flexible polymer layer helps contain the kink-resistant braid 270. The second flexible polymer layer is preferably 35 to 72 Shore D durometer, and more preferably 35 Shore D durometer.

Multi-lumen inner tube 260 is preferably formed from a polymer which is constructed so as to be highly elastic and, together with the remaining layers of the construction, can take on various shapes without permanent deformation.

Nitinol stiffening rod 265 is disposed within one of the lumens of multi-lumen inner tube 260 and provides stiffening for the multi-lumen inner tube. Nitinol stiffening rod 265 preferably has a variable diameter along its length. More particularly, and looking now at FIGS. 94-98, nitinol stiffening rod 265 preferably has a larger diameter proximal end 285 and a smaller diameter distal end 290, with a tapered transition zone 295 therebetween. The larger diameter proximal end 285 has a higher rigidity, which provides the proximal end of elongated shaft 205 with greater rigidity, whereby to enable transfer of forces to the distal end of the elongated shaft. The smaller diameter distal end 290 provides sufficient rigidity to transfer forces to the distal end of the elongated shaft, but it also provides flexibility so that the distal end of the elongated shaft can articulate. The Nitinol stiffening rod 265 can also provide sufficient spring action to return the shaft to a straight configuration. The preferred diameter of the distal end 290 of nitinol stiffening rod 265 is 0.020", but can preferably range from 0.010" to 0.030", or from 0.005" to 0.060". The tapered section 295, which is preferably located at the transition zone between rigid hypotube shaft 275 and multi-lumen inner tube 260, provides a gradual transition in rigidity from the rigid hypotube shaft to the flexible multi-lumen inner tube. See FIG. 98. This gradual reduction in rigidity is important in achieving the desired curvature when the articulation is activated. Without this gradual reduction, the shaft may kink at the distal end of the rigid hypotube shaft 275.

Kink-resistant braid 270 is provided to help distribute the forces created in elongated shaft 205 when the elongated shaft is articulated. More particularly, kink-resistant braid 270 allows the mechanical stresses in the bent shaft to redistribute evenly along the length of the elongated shaft rather than concentrate at the weakest point in the shaft. Kink-resistant braid 270 also provides flexibility that not only allows elongated shaft 205 to bend but also facilitates the shaft returning to a non-flexed position. Kink-resistant braid 270 also transfers torque from rigid hypotube shaft 275 to distal end 210; this enables the distal end of the joint-spacing balloon catheter 200 to be controllably steered during delivery into, and removal from, the joint. Kink-resistant braid 270 is preferably formed so that it can pass fluids therethrough, as will hereinafter be discussed in further detail.

Rigid hypotube shaft 275 is constructed so as to be substantially rigid, whereby to provide the desired structure for the proximal end of the elongated shaft 205. The rigid hypotube shaft 275 provides both the transfer of torque and push force from the proximal end of the joint-spacing balloon catheter 200 to the distal end of the joint-spacing balloon catheter 200. This provides the surgeon with good control in positioning the joint-spacing balloon catheter 200.

Flexible polymer layer 280 provides a smooth outer coating for elongated shaft 205. In one preferred form of the invention, flexible polymer layer 280 has a durometer which changes over the length of the device. By way of example but not limitation, flexible polymer layer 280 can have a higher durometer (stiffer) adjacent to the rigid hypotube shaft 275 and a lower durometer (softer) adjacent to balloons 245. The softer durometer enables the distal section to be more flexible, which is preferably for the articulation of the device.

Figure 98:
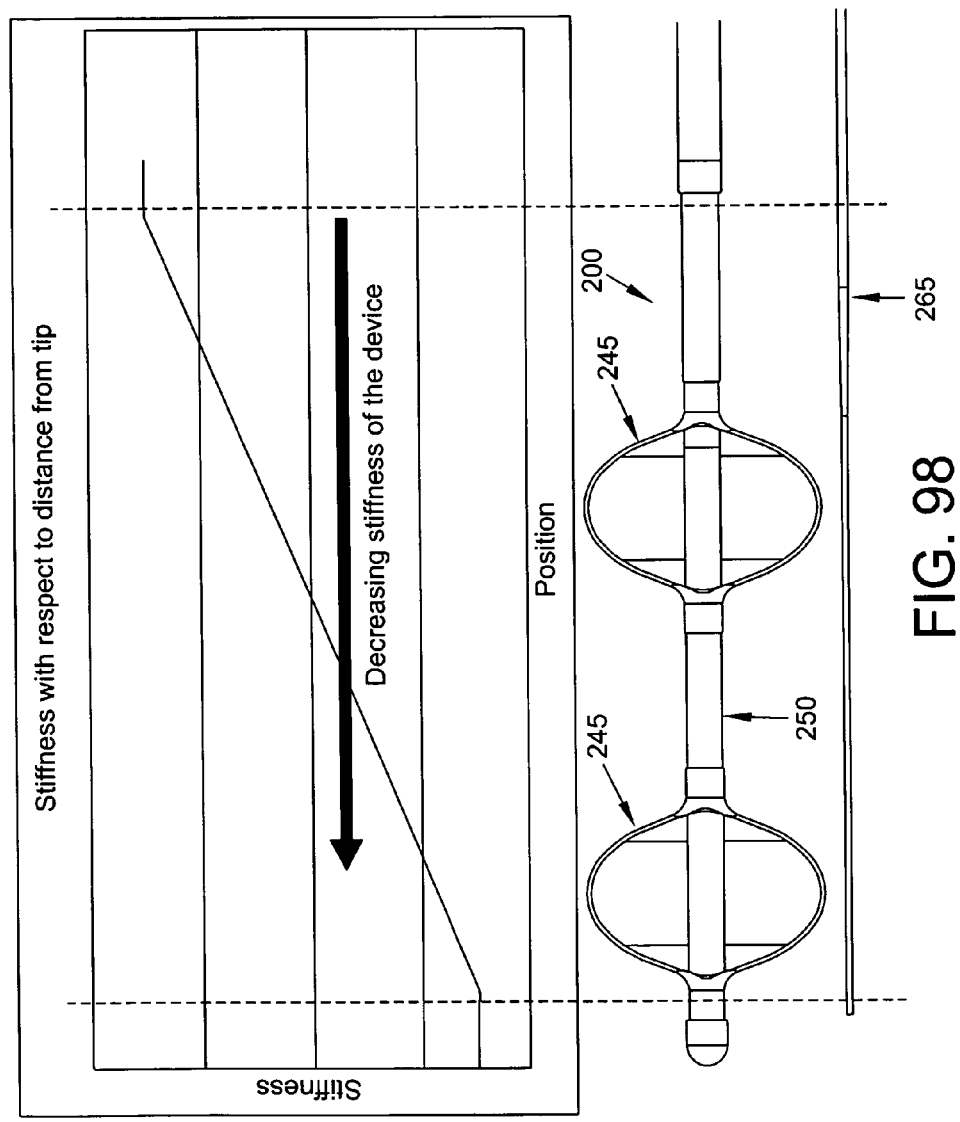

Since the flexible polymer layer 280, the kink-resistant braid 270, the nitinol stiffening rod 265 and the rigid hypotube shaft 275 are overlapping structures, their combined mechanical properties result in the overall flexibility of the system, which increases in flexibility along the length of the shaft (FIG. 98).

Preferably, one of the lumens of multi-lumen inner tube 260 is used to inflate/deflate the two balloons 245. To this end, windows 300 (FIGS. 94 and 99) are formed in multi-lumen inner tube 260 so as to connect the inflation/deflation lumen to the balloons 245. Significantly, kink-resistant braid 270 overlies these windows 300, interposed between the interior of the inflation/deflation lumen and the interior of the balloon, so that inflation/deflation takes place through the kink-resistant braid itself. By allowing fluid flow through the kink-resistant braid 270 and not removing that portion of the braid, the mechanical properties of the braid can be maintained while still enabling inflation/deflation of balloons 245. Alternatively, two of the lumens of multi-lumen inner tube 260 may be used to inflate/deflate the two balloons 245. To this end, windows 300 (FIGS. 94 and 99) are formed in multi-lumen inner tube 260 so as to connect a specific inflation/deflation lumen with its corresponding balloon 245.

Figure 99:
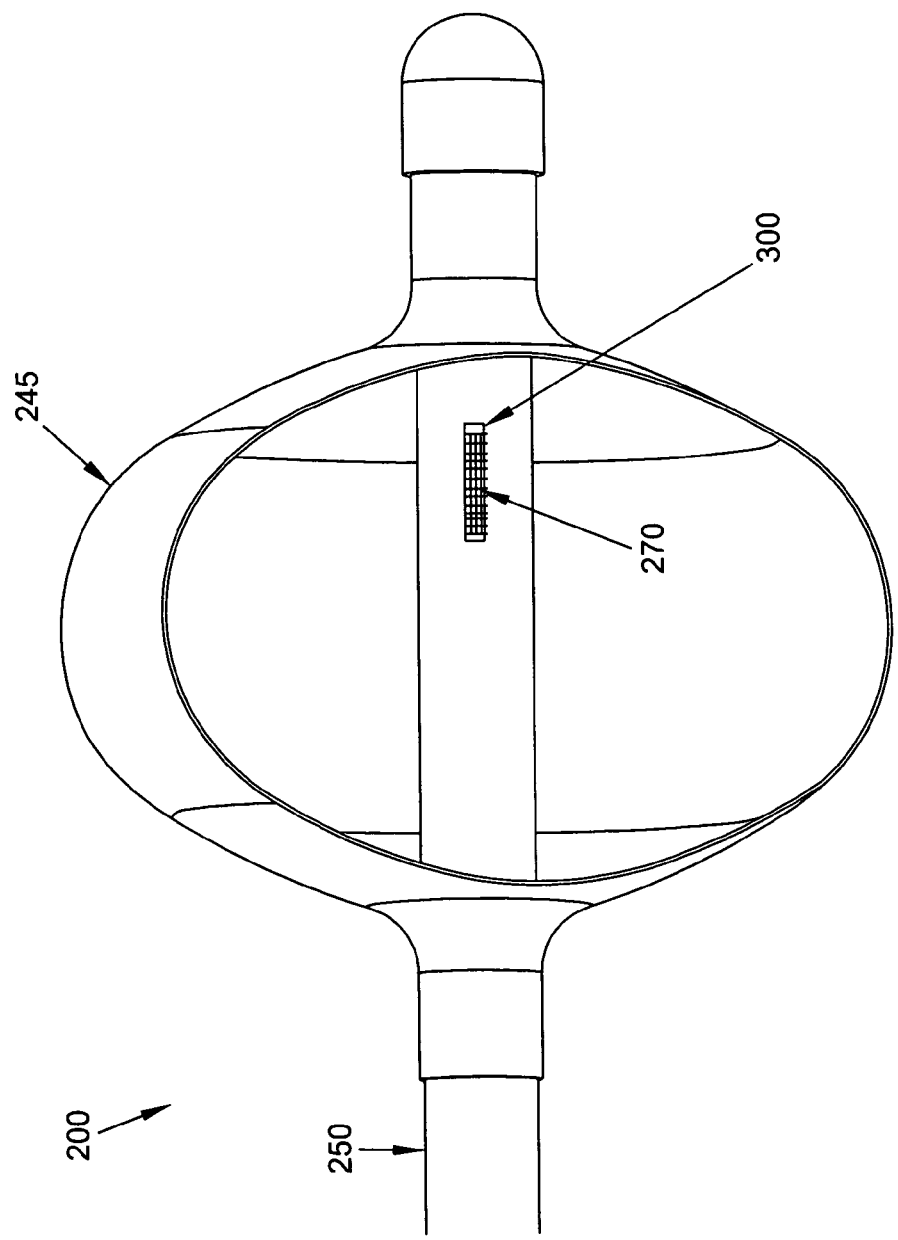
Figure 99A:
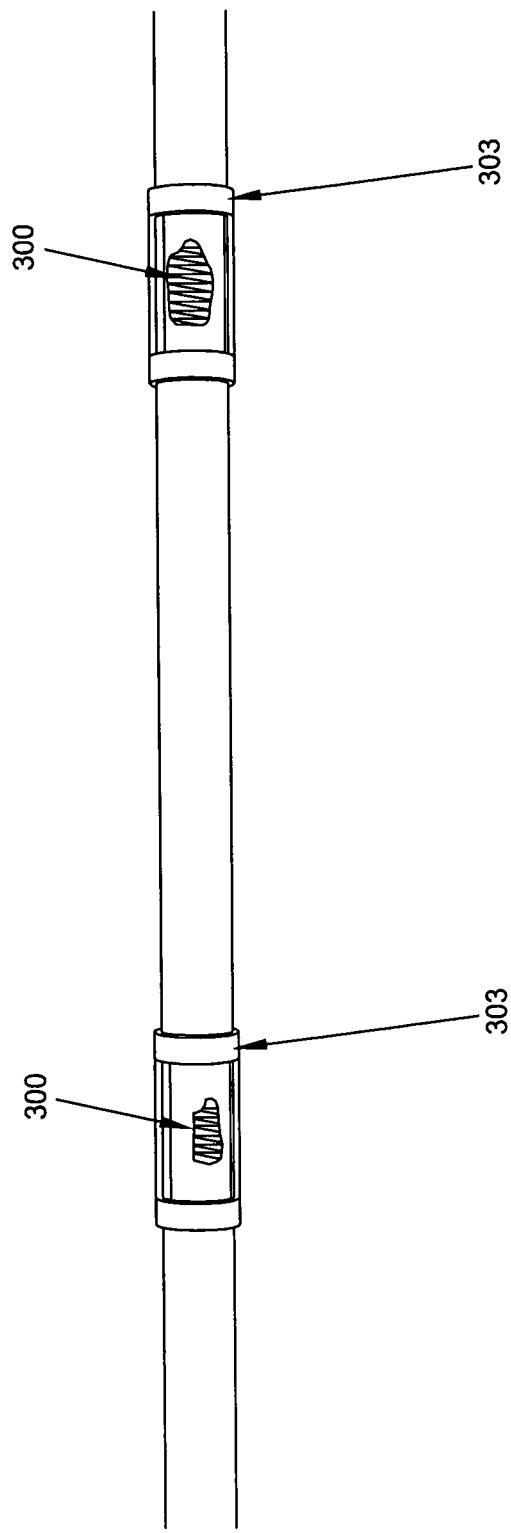

If desired, elongated shaft 205 may be reinforced in the vicinity of windows 300 so as to minimize the possibility that one or more of the windows 300 may unintentionally close down (either partially or completely) when the elongated shaft is torqued (e.g., such as where elongated shaft 205 is torqued about its longitudinal axis). By way of example but not limitation, and looking now at FIG. 99A, a collar 303 may be fitted about each of the windows 300, with the collars 303 reinforcing elongated shaft 205 in the region around the windows 300 such that the windows will not close down when the elongated shaft is torqued.

Cannula

In practice, it has been found that it is generally desirable to facilitate easy introduction of joint-spacing balloon catheter 200 into the joint, and easy removal of joint-spacing balloon catheter 200 from the joint.

Figure 100:
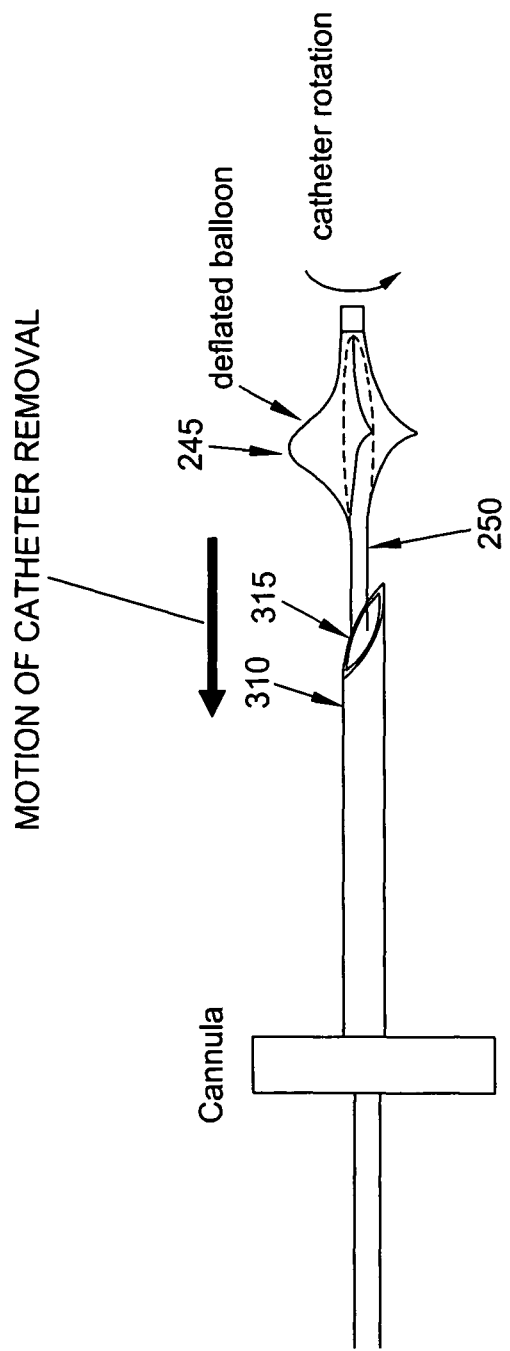
FIGS. 100 and 101 are schematic views showing means for folding a balloon of the joint-spacing balloon catheter and withdrawal of the joint-spacing balloon catheter from a joint through a beveled cannula.
Figure 101:
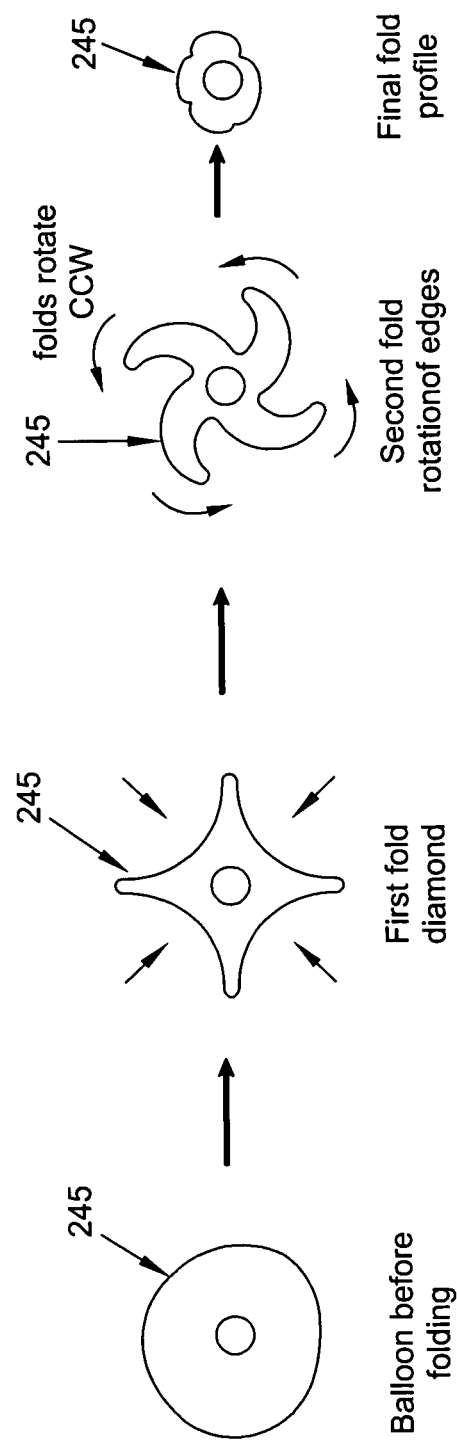

More particularly, and looking now at FIG. 100, joint-spacing balloon catheter 200 is preferably introduced into a surgical site by passing the distal end of the balloon catheter through a cannula 310, which is provided with a beveled distal end 315. Furthermore, balloons 245 are preferably configured into a reduced-profile condition so as to facilitate their delivery through the cannula 310. By way of example but not limitation, FIG. 101 shows a unique 3-step method for folding balloons 245. In Step 1, the balloon is deflated (e.g., vacuum is pulled from the inflation/deflation portal); the balloon is then formed into a diamond-shaped cross-sectional condition. In Step 2, the balloon is folded from a diamond-shaped cross-sectional condition to a pinwheel-shaped cross-sectional condition by rotating the edges of the balloon around the center axis of the balloon shaft. And in Step 3, the balloon is further folded from a pinwheel cross-sectional condition to a collapsed cross-sectional configuration. Once the balloon has been folded in the manner shown in FIG. 101, a sheath (e.g., the peel-away sheath 56 shown in FIG. 23') may be placed over the folded balloon so as to maintain the balloon in its collapsed cross-sectional configuration until the time of use.

As discussed above, cannula 310 comprises a beveled distal end 315 as shown in FIG. 100. The beveled distal end 315 enables the balloon to be more easily withdrawn back through cannula 310 for removal from the joint. By way of example but not limitation, the balloon 245 is deflated prior to removal from the joint. Once deflated, balloon 245 is drawn back through cannula 310; as it is drawn back, the balloon 245 is rotated so that the beveled distal end 315 of cannula 310 collapses and folds the balloon 245. In this way, the balloon 245 achieves a reduced profile which enables it to pass through the lumen of cannula 310.

Force Balancing

Figure 102:
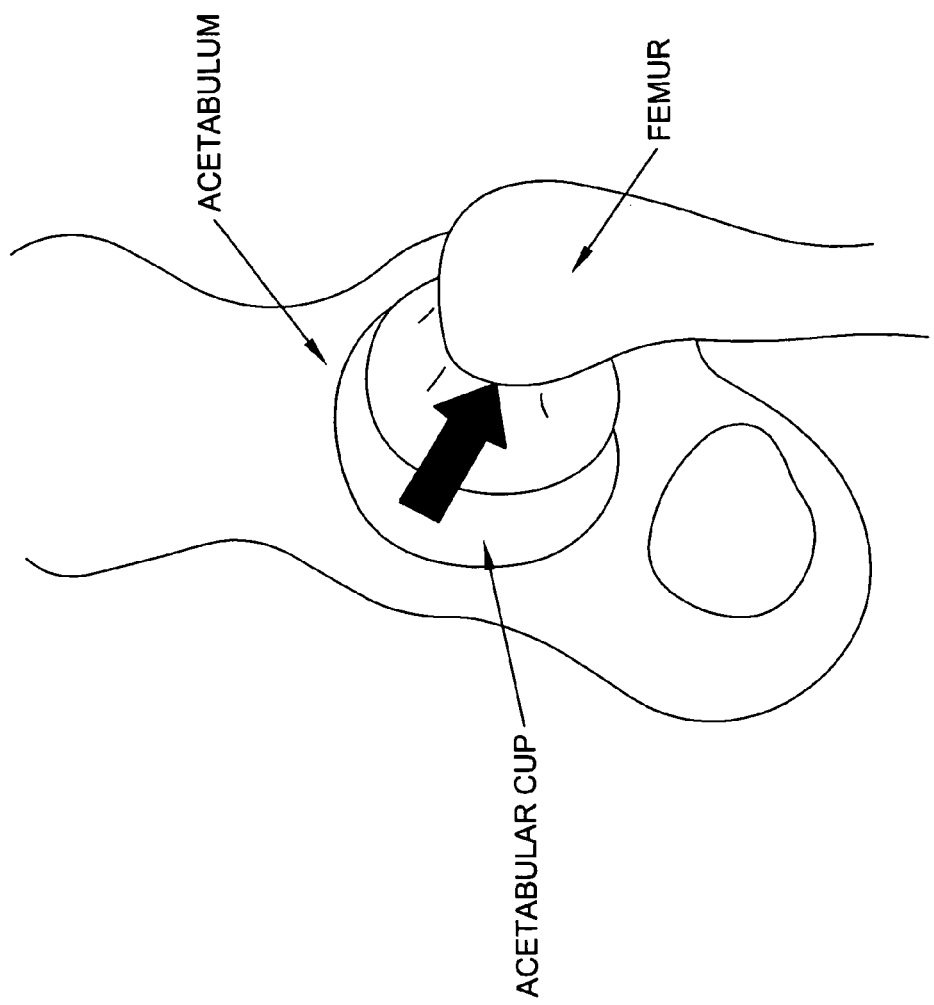
FIGS. 102, 103, 104 and 104A are schematic views showing how the joint-spacing balloon catheter is used to provide a counterforce to the force returning the ball of the femur to the acetabular cup when external distraction is reduced.
Figure 103:
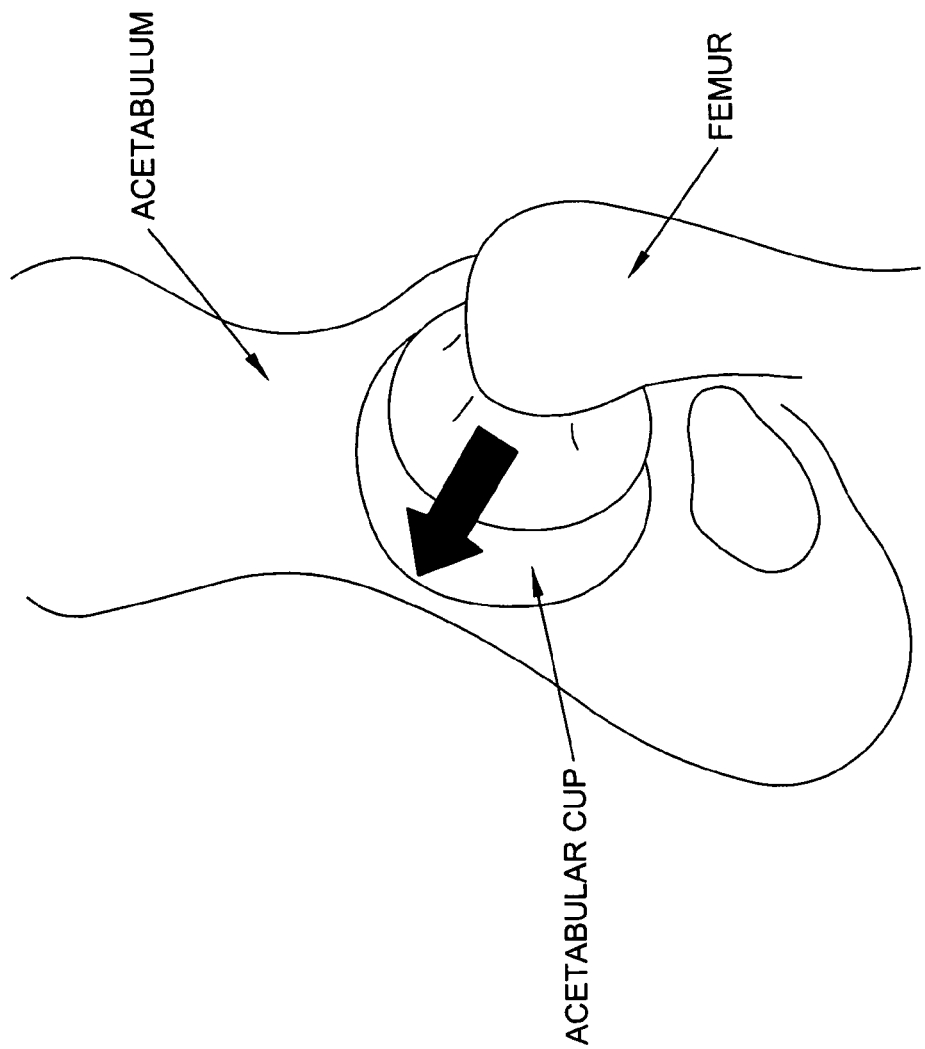
Figure 104:
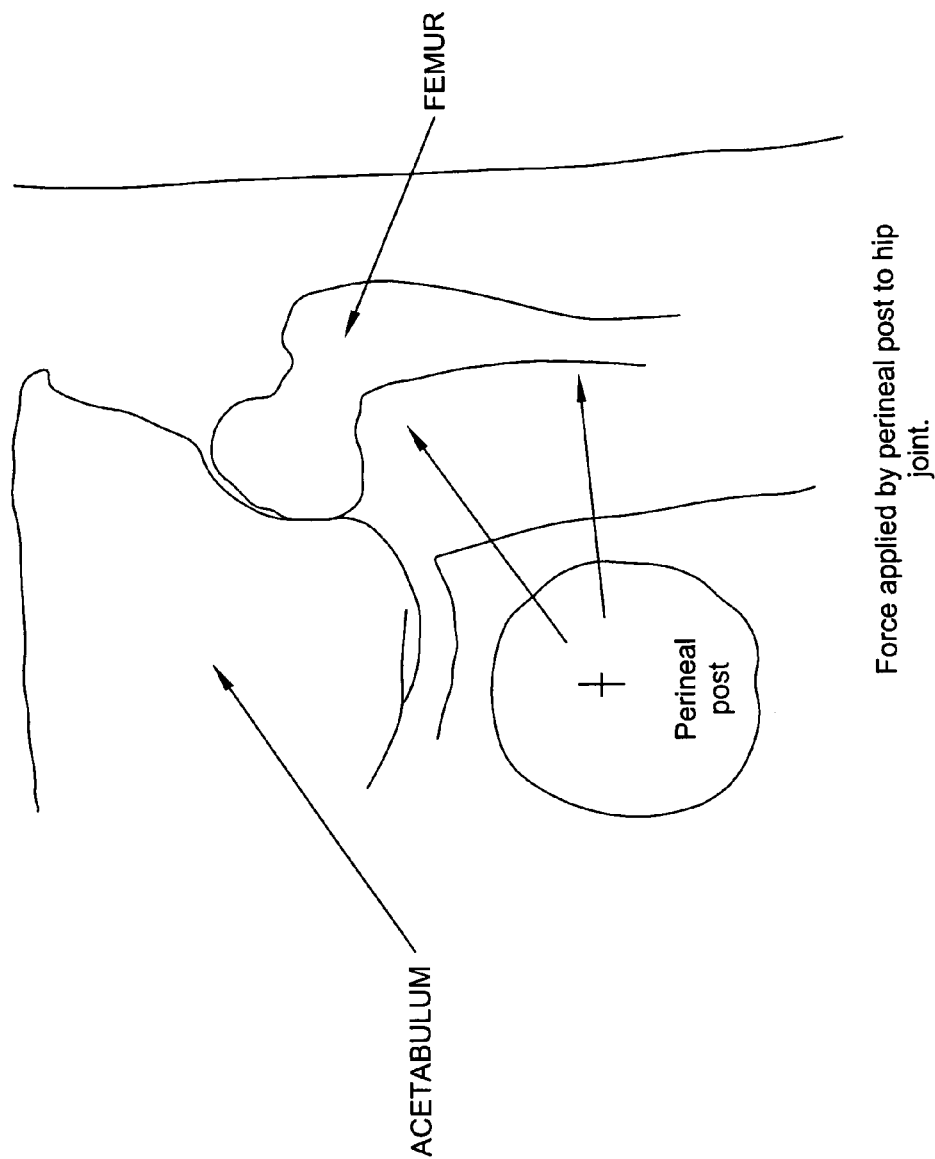

It will be appreciated that, in order for balloons 245 to maintain space within the joint, it is necessary for balloons 245 to provide a counterforce to the force returning the ball of the femur to the acetabular cup when external traction is relaxed. Thus, when placing balloons 245 in the central compartment, the balloons should be placed so as to provide the desired counterforce to the femur, taking into account the direction of the returning force vector and also the geometry of the space which is to be maintained. See FIGS. 102 and 103. In this respect it will be appreciated that where the patient's joint is distracted with the use of external distraction and a perineal post (FIGS. 104 and 17), the returning force vector may be approximately the inverse of the vector $V_D$ and so the balloons 245 will be set within the joint with this in mind.

Figure 104A:
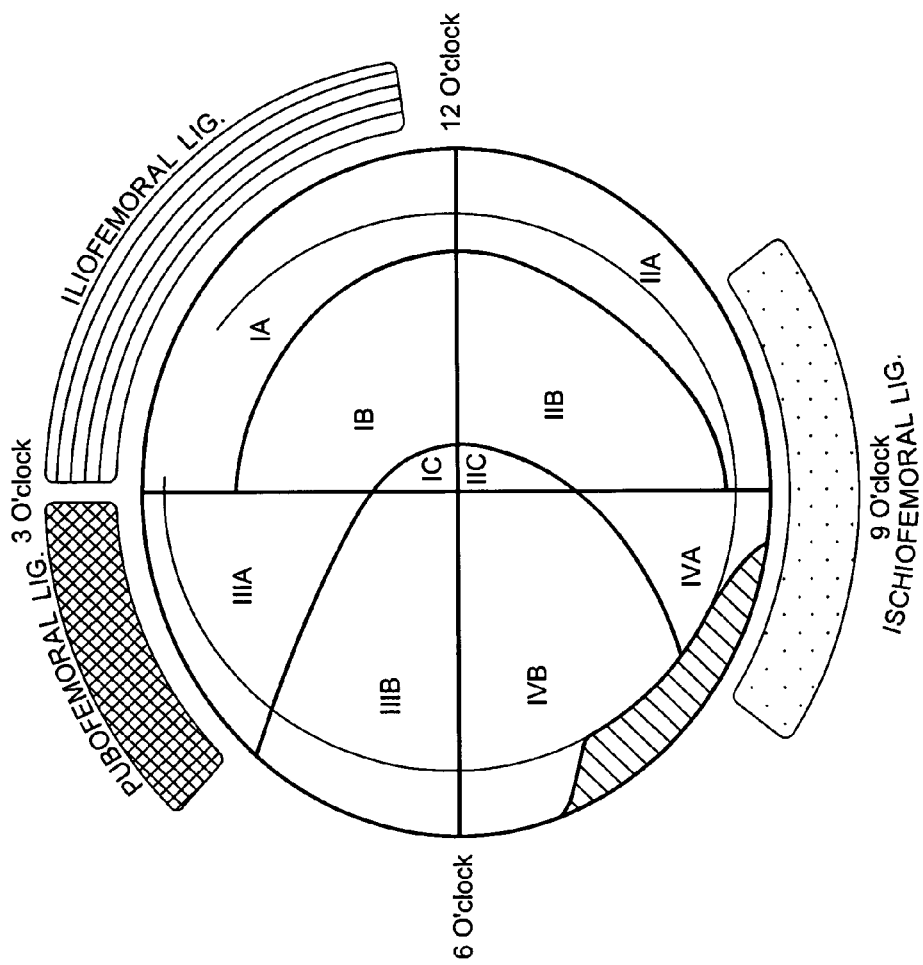

It is also understood that the principal forces which resist distraction in the surgical setting relate to the primary ligaments of the hip (i.e., the iliofemoral, ischiofemoral and pubofemoral ligaments) which form a circumferential mesh of tissue around the joint, with connections on the acetabular and femoral sides. The general position of these attachments on the acetabular side is shown in FIG. 104A. The unique structure of the capsule in each person determines that person's ability to move and perform various activities and can also be influential in how the hip will distract, especially with an in-situ distractor. It can be appreciated that someone with a larger or stronger iliofemoral ligament than normal may have the hip respond differently as the hip is surgically distracted than a person who has a smaller or weaker iliofemoral ligament. With an in-situ device such as a balloon spacer, the femoral head may be more inclined to shift as a result of the different strengths of the ligaments than in traditional distraction. In traditional distraction, the vector of the distraction force and the hip distraction are congruent because the distracting device overwhelms the anatomy by driving distraction in a constant direction. However, when using a joint-spacing balloon catheter to create and/or maintain distraction, the femur and acetabulum are forced apart without a specific, overwhelming mechanical force creating the distraction vector. Therefore, a joint-spacing balloon catheter 5 must be provided and used as described herein to achieve proper distraction.

Access Portals

Figure 105:
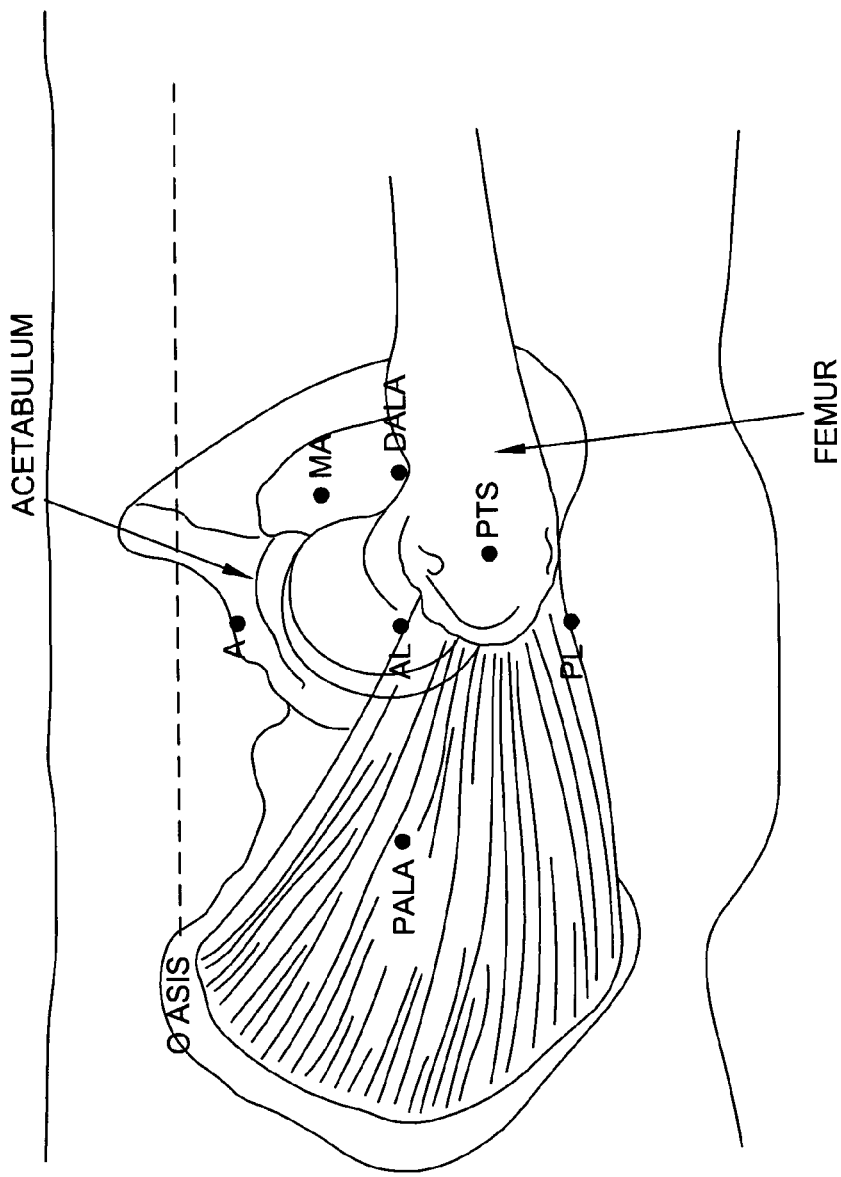
FIG. 105 is a schematic view showing the access portals commonly used in arthroscopic hip surgery.

In addition to the foregoing, and as noted above, hip arthroscopy is complicated by the fact that access to the interior of the hip joint is limited by the location of various bones and neurovascular structures. In practice, only a few locations are available to place the portals needed to gain arthroscopic entry into the hip joint. In practice, and as shown in FIG. 105, these are the AL (anterolateral), PL (posterolateral), A (anterior), PALA (proximal anterolateral accessory), MA (mid-anterior), DALA (distal anterolateral accessory) and PTS (peritrochanteric space) portals. In this respect it will be appreciated that while each of these portals provides access to the hip joint, they tend to provide only limited access to the hip joint, i.e., the PL portal provides good access to one portion of the hip joint but not to another portion of the hip joint, etc.

Disposition within the Joint

In one preferred form of the invention, joint-spacing balloon catheter 200 is intended to be used in the hip, with balloons 245 and portion 250 of shaft 205 (i.e., the portion of the shaft extending between the two balloons 245) forming a "3-point contact" with the acetabular cup and femoral head.

Figure 106:
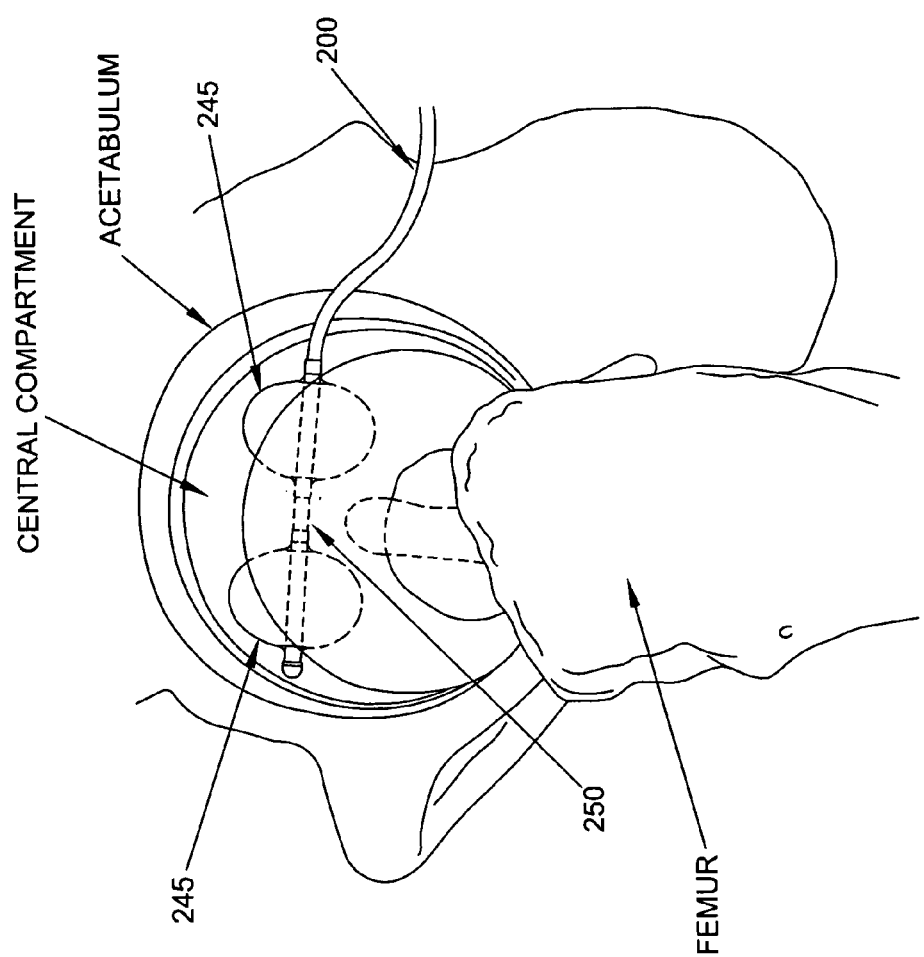
FIGS. 106-112 are schematic views showing various ways in which the balloons of the joint-spacing balloon catheter may be disposed within a hip joint.

More particularly, and looking now at FIG. 106, joint-spacing balloon catheter 200 is intended to be positioned within the externally-distracted hip joint, and its balloons 245 thereafter inflated, so that, prior to the external distraction being released, balloons 245 and portion 250 of elongated shaft 205 all sit spaced from the ligamentum teres. However, when the external distraction is thereafter released, the femoral head causes joint-spacing balloon catheter 200 to reconfigure in the manner shown in FIGS. 107 and 108, with distal balloon 245 moving towards the proximal balloon 245, and with portion 250 of elongated shaft 205 resting against the ligamentum teres, or against the acetabular fossa, or against another portion of the acetabular cup, or otherwise disposed in the central compartment, or extending out of the central compartment, etc. In fact, this action actually occurs in 3 dimensions, with balloons 245 positioning themselves close to the rim of the concave acetabular cup and portion 250 of elongated shaft 205 engaging the ligamentum teres, deeper in the cup. Thus, with the external distraction removed, balloons 245 and portion 250 of elongated shaft 205 form a so-called "3 point contact" with the adjacent hip structures.

This "3-point contact" arrangement has proven to be extremely advantageous, since it reliably creates stable distraction maintenance for a wide range of joint sizes, joint shapes and joint forces. In addition, this arrangement is stable when either articular surface is moved with respect to the other articular surface; for example, movement of the leg while the balloon is maintaining joint distraction. In addition, this "3 point contact" arrangement is believed to be equally applicable to other joints within the body.

The joint-spacing balloon catheter 200 is preferably positioned along the line of the 9 o'clock (posterior) position to the 3 o'clock (anterior) position in the acetabluar cup (where the "12 o'clock position" is in the superior portion in the acetabular cup). In this position, the joint-spacing balloon catheter 200 will have minimal obstruction to the portion of the anatomy which is typically accessed during femoroacetabular impingement arthroscopic surgery.

Figure 107:
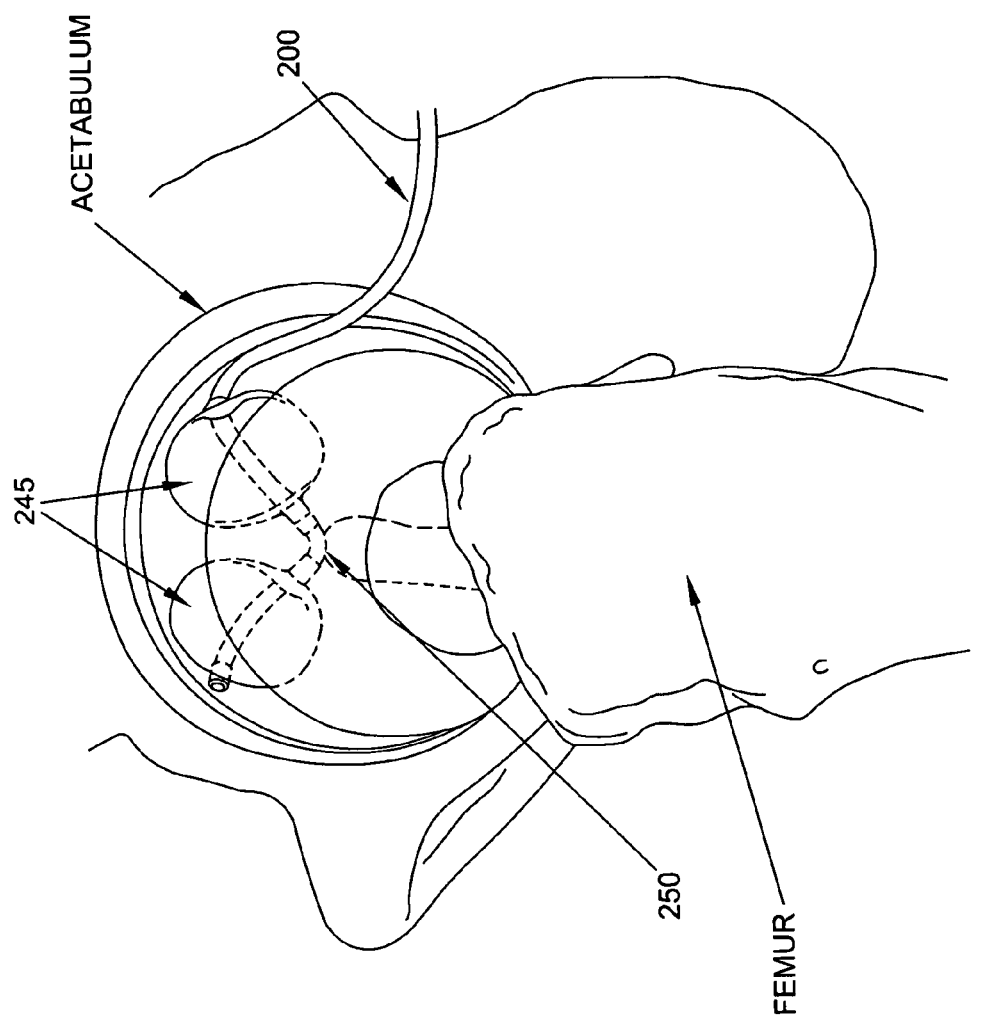
Figure 108:
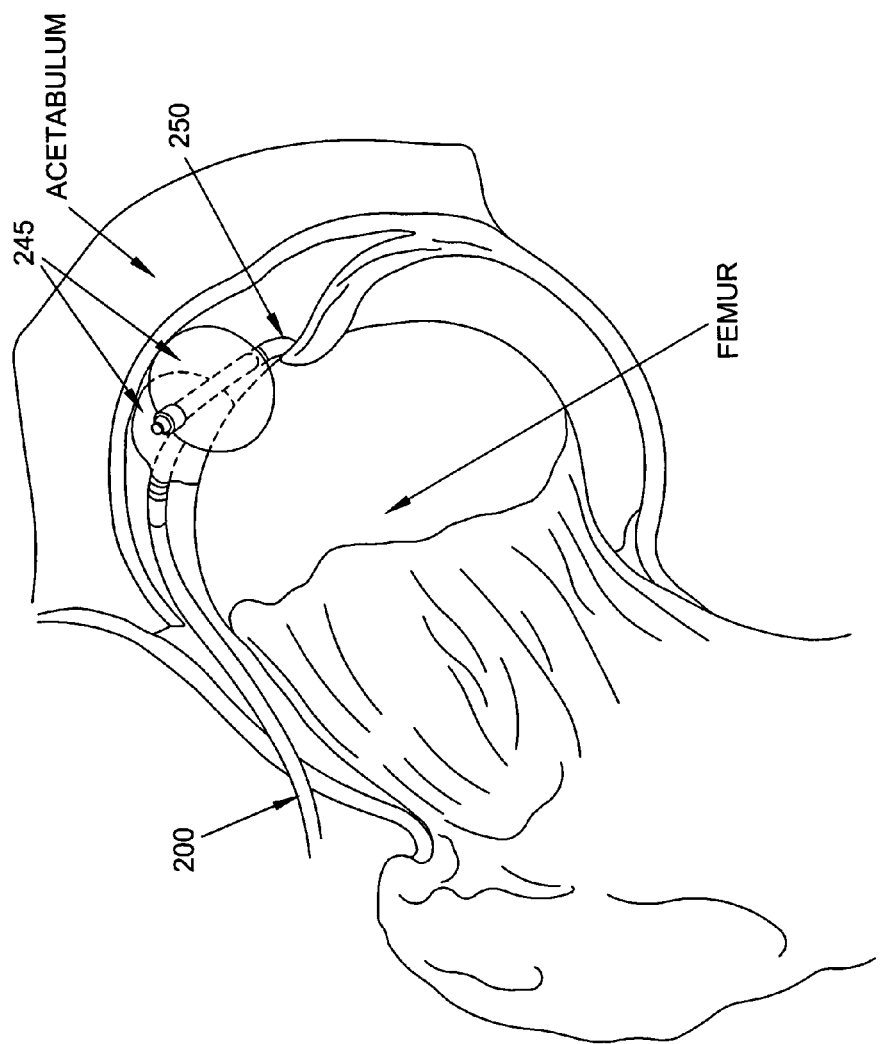

FIGS. 106-108 show balloons 245 being set through the PL portal, with the balloons 245 being disposed in the "10 o'clock" and "2 o'clock" positions.

Figure 109:
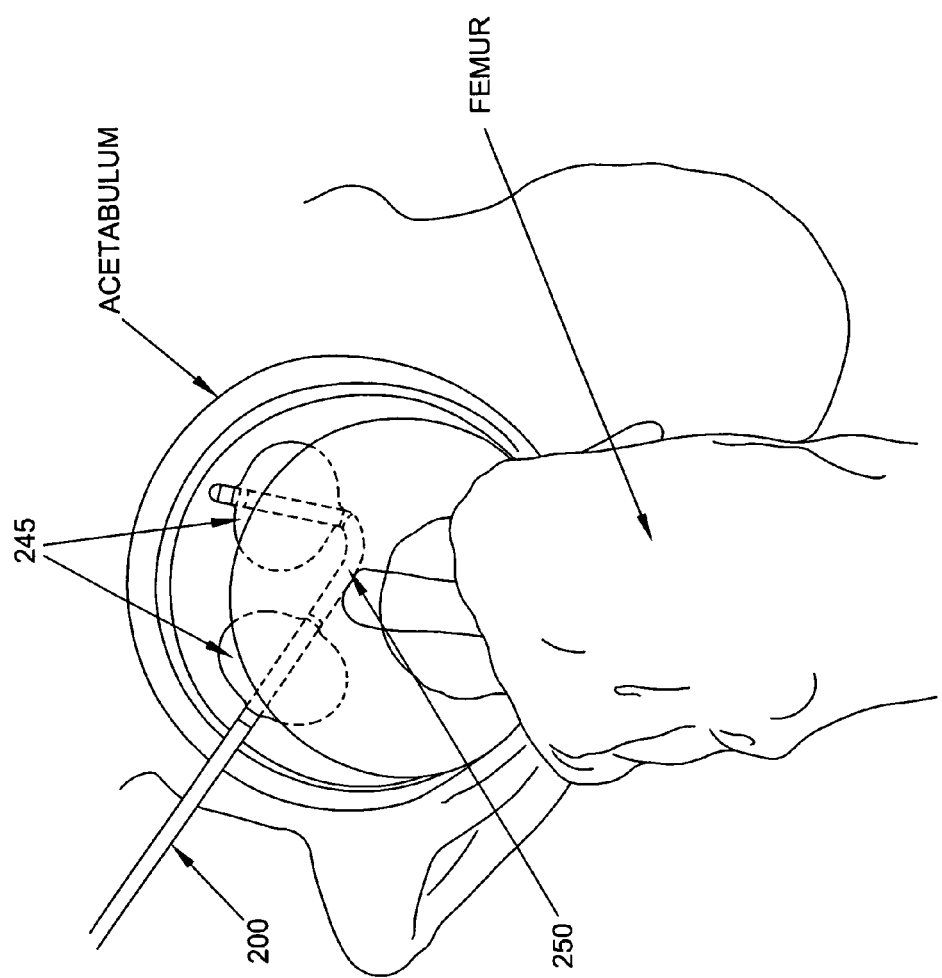

FIG. 109 shows balloons 245 being set through the A portal, with the balloons 245 being set in the "10 o'clock" and "2 o'clock" positions (the figures show the joint after external distraction has been released).

Thus it will be appreciated that providing a novel joint spacer comprising two balloons 245 connected to one another by a flexible shaft 250, provides a highly stable space maintenance structure which is a significant improvement in the art.

Figure 110:
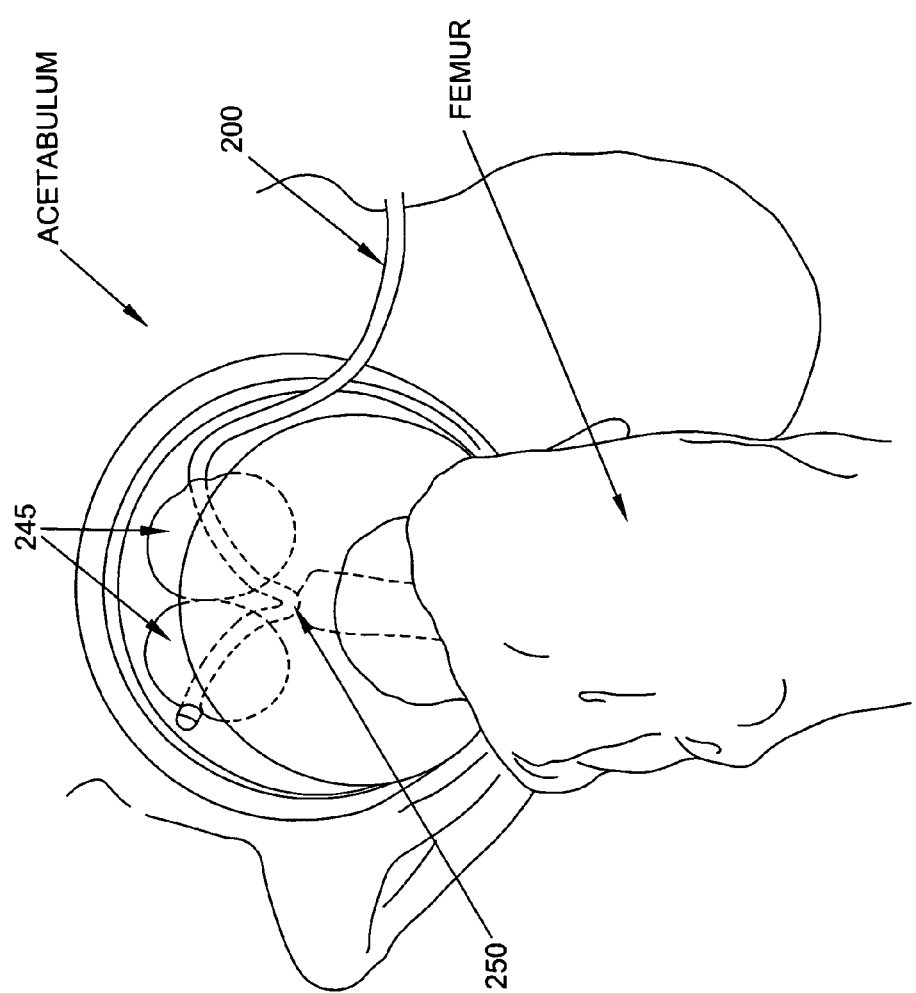

In another embodiment of the invention, an additional step can be performed during balloon delivery to more optimally place the balloons 245 in the joint space. In this embodiment, the distance between the balloons 245 is adjusted using the articulation of the distal end of the shaft; more articulation brings the balloons 245 closer together (as depicted in FIG. 110). This may be preferable, for example, when closer proximity of the balloons 245 to each other results in better stability of the femoral head (once external traction has been removed and the femoral head is resting on the balloons 245). Articulation of the balloons 245 for purposes of controlling their spacing to each other (as opposed to guiding the joint-spacing balloon catheter 200 into the joint as described above) would typically be performed after balloons 245 have been placed into the joint space but prior to inflation of the balloons 245. The operation sequence would be as follows: (1) joint-spacing balloon catheter 5, with balloon 15 set in its deflated state, is inserted into the space created between the ball of the femur and the acetabular cup (articulation of the distal end of the shaft can be used to facilitate guiding the device into the joint space); (2) the distal end of the shaft is rotated to orient the articulation in a different plane; (3) the distal end of the shaft is articulated to bring the balloons closer together; (4) the balloons are then inflated; and (5) the distal force which was previously applied to the leg is partially or fully released.

FIG. 110 shows balloons 245 being set through the PL portal with the balloons being set in the "10 o'clock" and "2 o'clock" positions, but with the shaft being bent prior to release of the external traction so as to get the balloons closer to each other.

Figure 111:
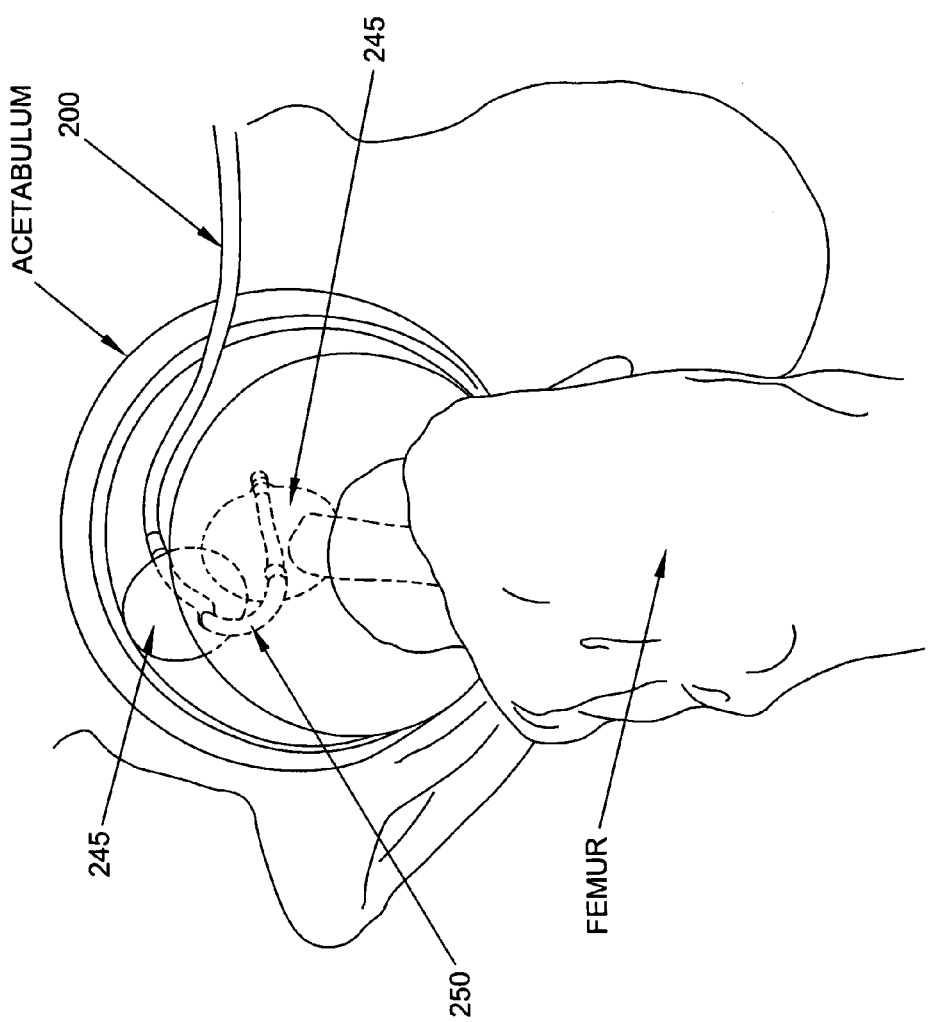

FIG. 111 shows balloons 245 being set through the PL portal, with the balloons being set in the so-called "fossa" and "1 o'clock" positions, but with the shaft being bent prior to release of the external traction.

Figure 112:
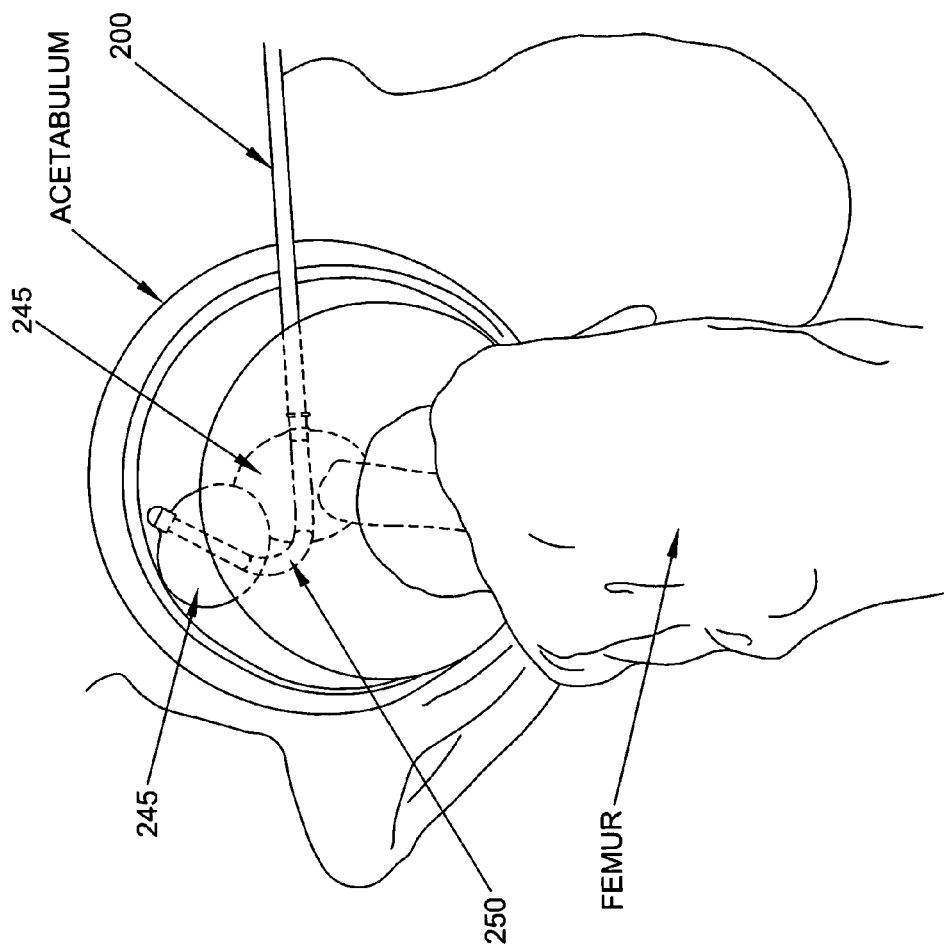

FIG. 112 shows balloons 245 being set through the PL portal, with the balloons being set in the "1 o'clock" and "fossa" positions, but with the shaft being bent prior to release of the external traction.

Figure 112A:
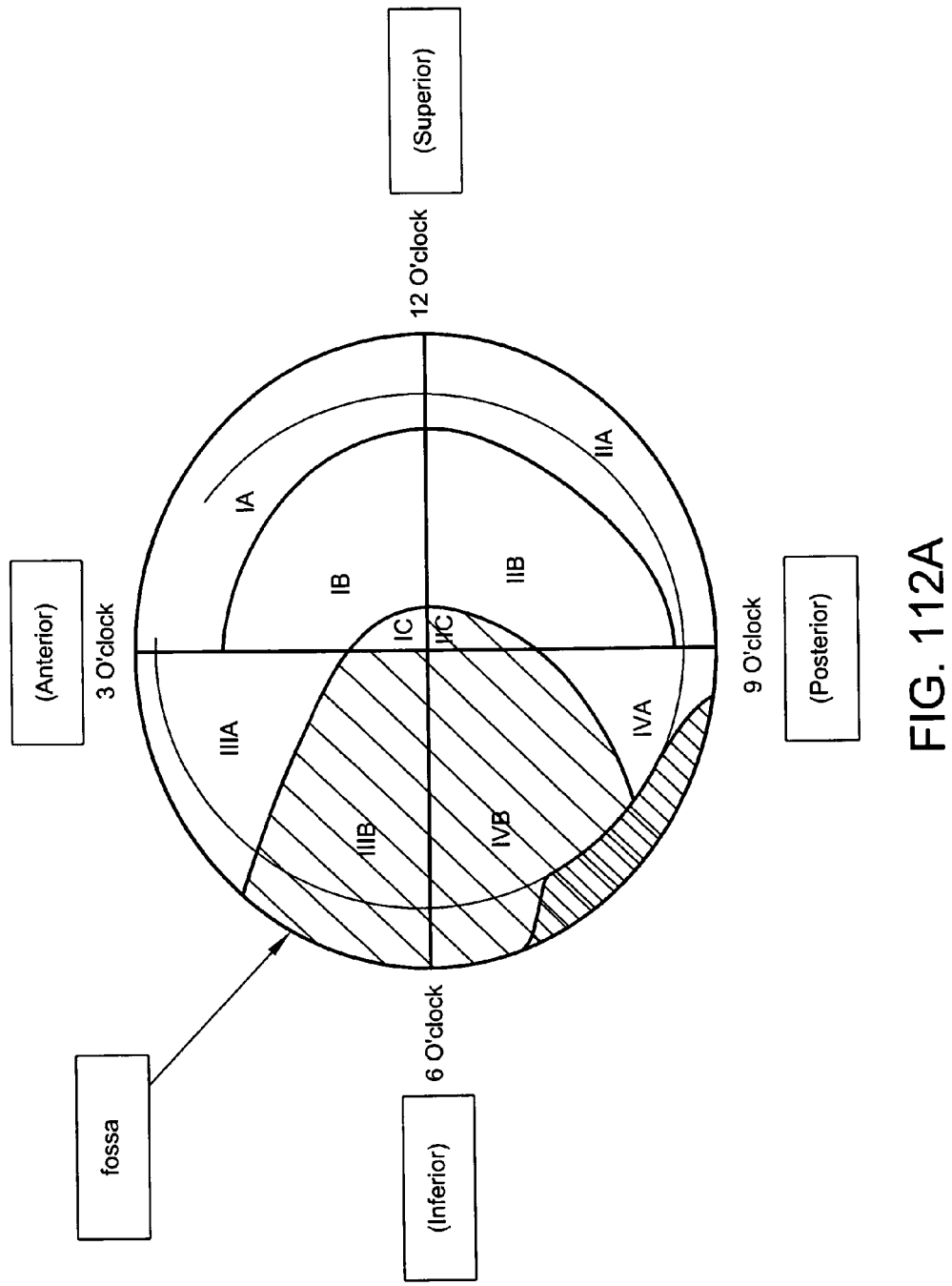
FIGS. 112A-112D are schematic views showing exemplary dispositions of the balloons of the joint-spacing balloon catheter within the hip joint.

FIG. 112A is a schematic view showing the acetabular cup of the left hip, with the cup being divided into quadrants (i.e., I, II, III and IV), with the quadrants divided into zones (i.e., A, B and, in some quadrants, C), and with the acetabular fossa being demarcated. In one preferred form of the invention, joint-spacing balloon catheter 5 is disposed in the joint so that one balloon is disposed in the fossa, with one or more balloons being disposed extra-fossa. The balloon disposed in the fossa is stable in the fossa depression, and can help prevent the other balloon(s) from moving deeper into the joint space and/or shifting position in the joint (i.e., the balloon in the fossa can help anchor the other balloon(s) in the joint). And in one preferred form of the present invention, the balloon disposed in the fossa is relatively large so as to fill a large portion of the fossa, and the extra-fossa balloon(s) are placed in locations between the fossa and the rim where space is desired (e.g., with reference to FIG. 112A, at around the "12 o'clock" position where labral defects are typically found). Alternatively, two balloons may be disposed in the fossa, with additional balloon(s) being disposed extra-fossa so as to provide stability for the femoral head and/or to create space on the rim of the acetabular cup for visualization and instrument access. In still another form of the present invention, a small balloon may be disposed in the fossa—with one or more larger balloons disposed extra-fossa—so as to limit the extent to which the head of the femur is pushed towards the lateral wall of the acetabulum. The balloon in the fossa may also be designed to self-locate on the fossa. As such it may have a profile, when viewed from the side, that has a maximum diameter at the center of its length and tapers at an advantageous, constant angle away from that point in either direction. The balloon in the fossa may also be of a different durometer and/or be separately controlled for inflation than the other balloons. As such the pressure and conformance of that balloon can be independently varied. If the balloon is more compliant it can be over-filled and achieve a variable filling of the volumetric space which is useful when considering different patients may have different sizes of their anatomy.

Figure 112B:
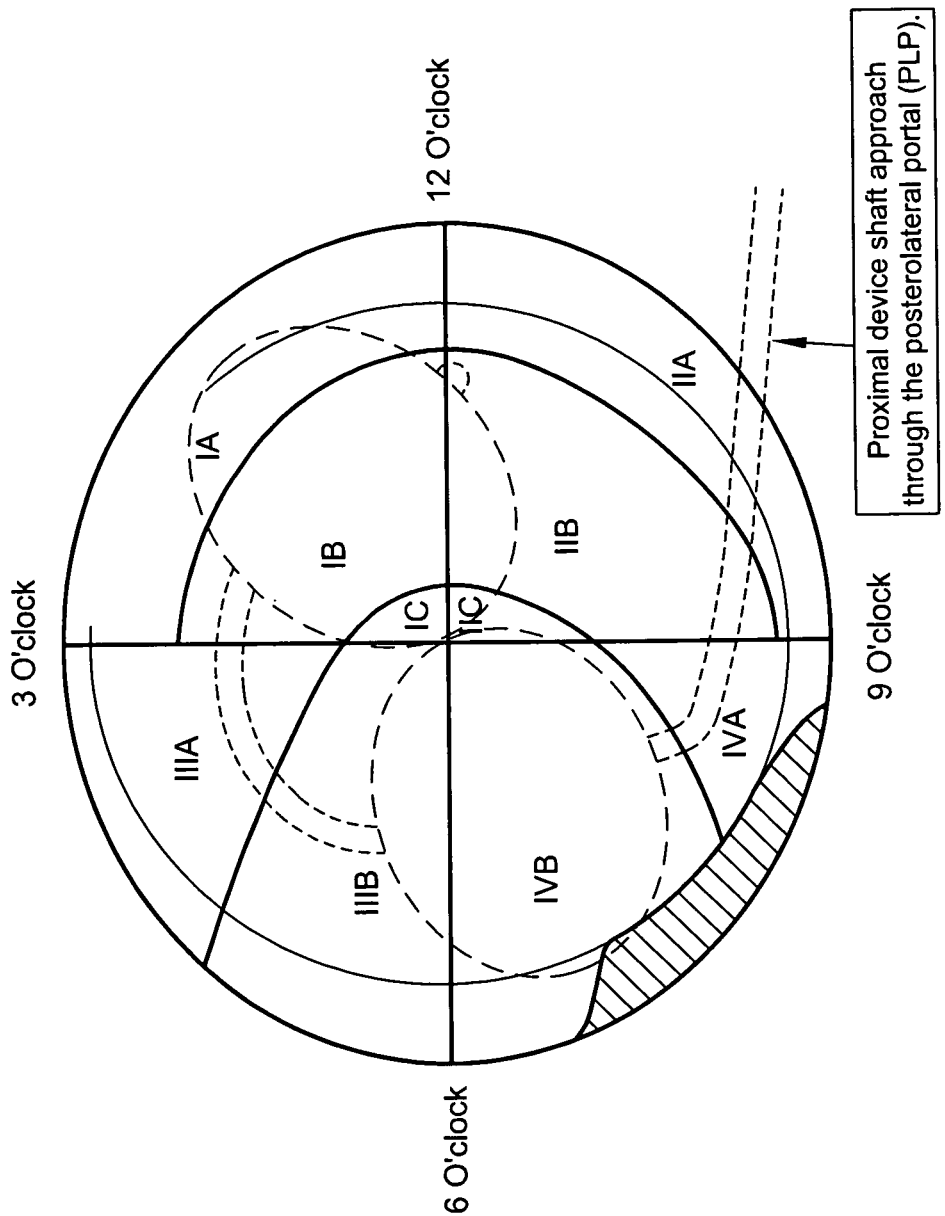

FIG. 112B is a schematic view showing two 28 mm diameter balloons disposed in the hip joint, with access being effected through the posterolateral portal (PLP). The proximal balloon is positioned in the fossa and the distal balloon is positioned in the quadrant between the "3 o'clock" position and the "12 o'clock" position. With the balloons in these positions, the femoral head is stable and sufficient space can be maintained between the femoral head and the acetabular rim in the region between the "12 o'clock" position and the "3 o'clock" position (i.e., where pathology is typically found).

Figure 112C:
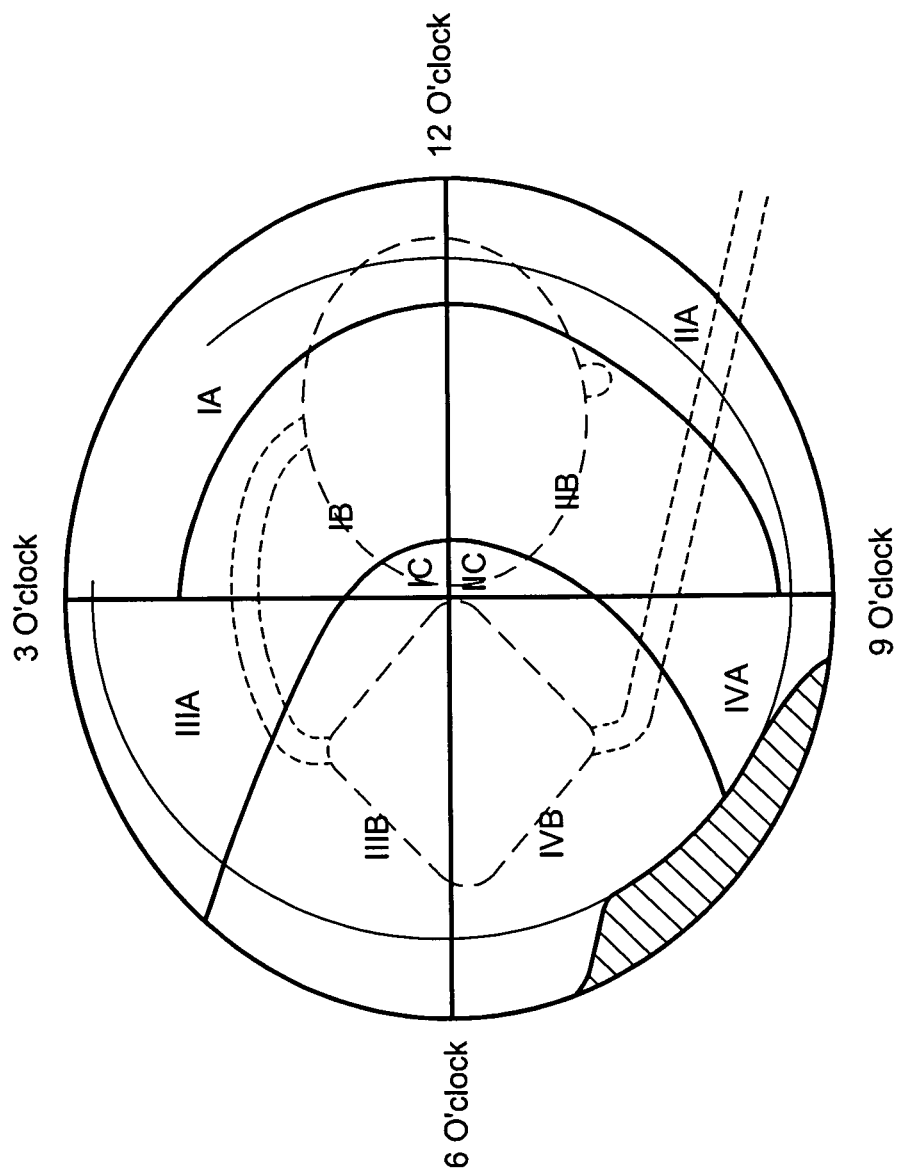

FIG. 112C is a schematic view showing two balloons disposed in different positions within the acetabular cup. The proximal balloon, preferably 21 mm in diameter, is disposed in the fossa. The distal balloon, preferably 28 mm in diameter, is positioned between the fossa and the "12 o'clock" position. With the balloons in these positions, the femoral head is stable and sufficient space can be maintained between the femoral head and the acetabular rim in the region around the "12 o'clock" position.

Figure 112D:
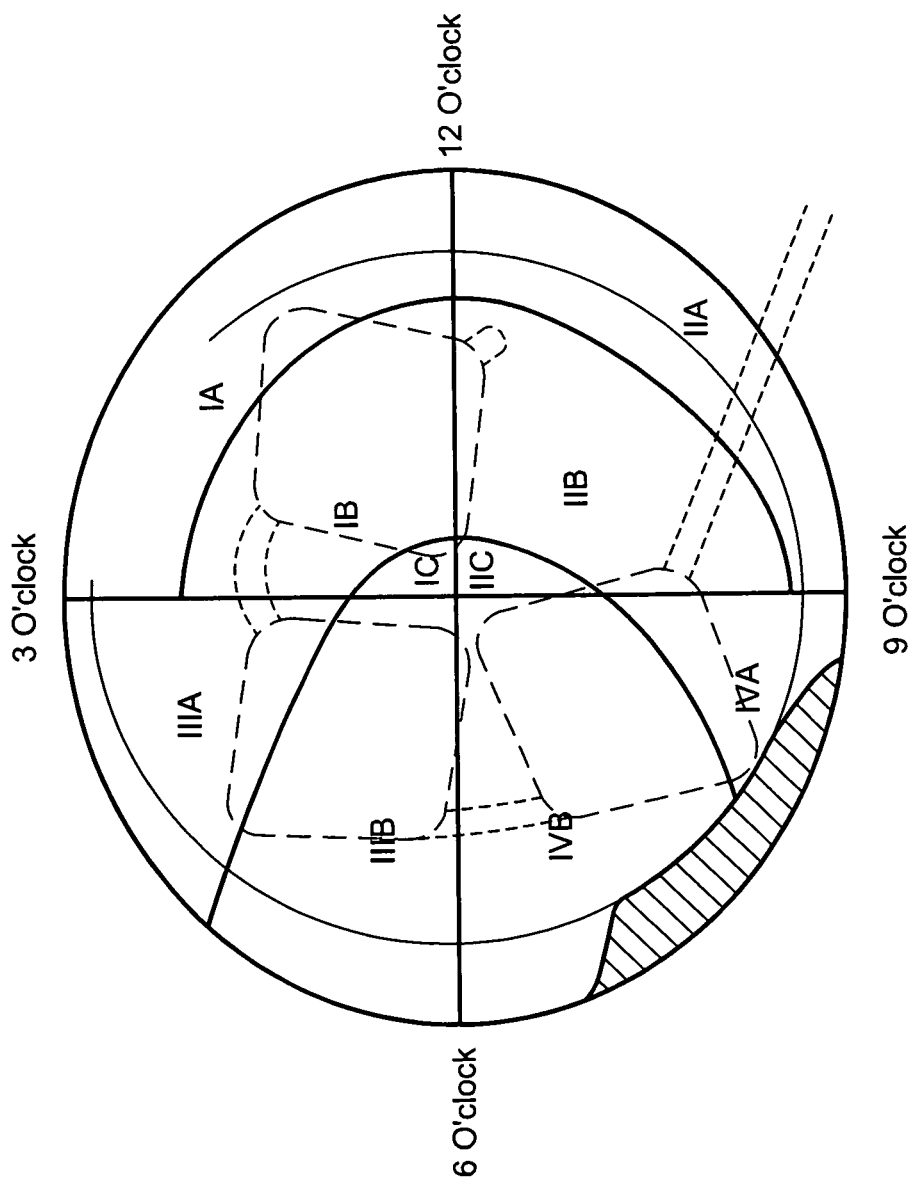

FIG. 112D is a schematic view showing three 21 mm diameter balloons disposed in the acetabular cup. The proximal balloon and the intermediate balloon are preferably positioned at least partially in the fossa, preferably with at least 50% of each balloon in the fossa. The distal balloon is preferably positioned between the fossa and the rim, between the "3 o'clock" position and the "12 o'clock" position.

It should be appreciated that where joint-spacing balloon catheter 5 comprises multiple balloons, the multiple balloons may have different or similar sizes, and the various balloons may be inflated to the same or different target pressures, and these balloon sizes and/or pressures may be coordinated with the disposition and/or function of the various balloons. By way of example but not limitation, one large balloon may be disposed in the fossa and two or more smaller balloons may be disposed extra-fossa, with the large balloon being inflated to a lower pressure for purposes of acting as an anchor for the smaller balloons, and with the smaller balloons being inflated to a higher pressure for the purpose of creating or maintaining space in the joint.

Figure 113:
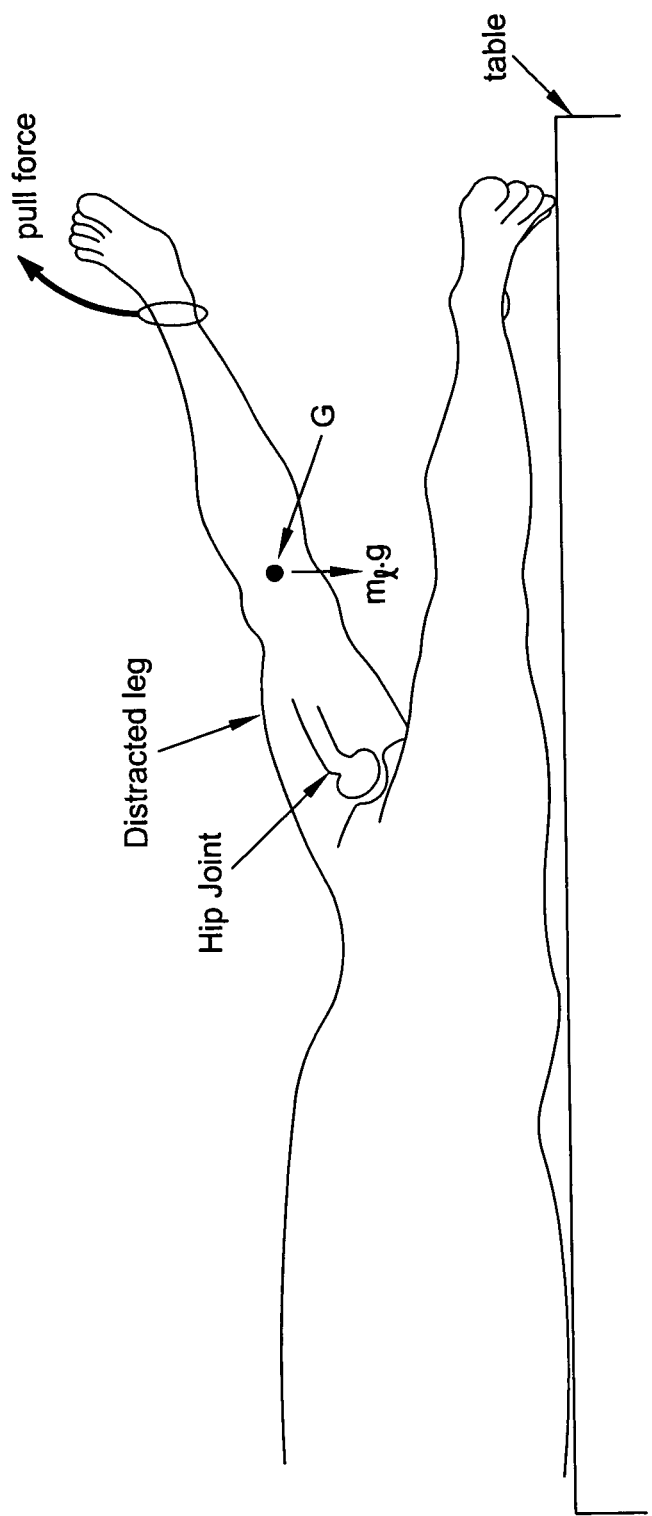
FIGS. 113-115 are schematic views showing additional ways in which the balloons of the joint-spacing balloon catheter may be disposed within a hip joint.
Figure 114:
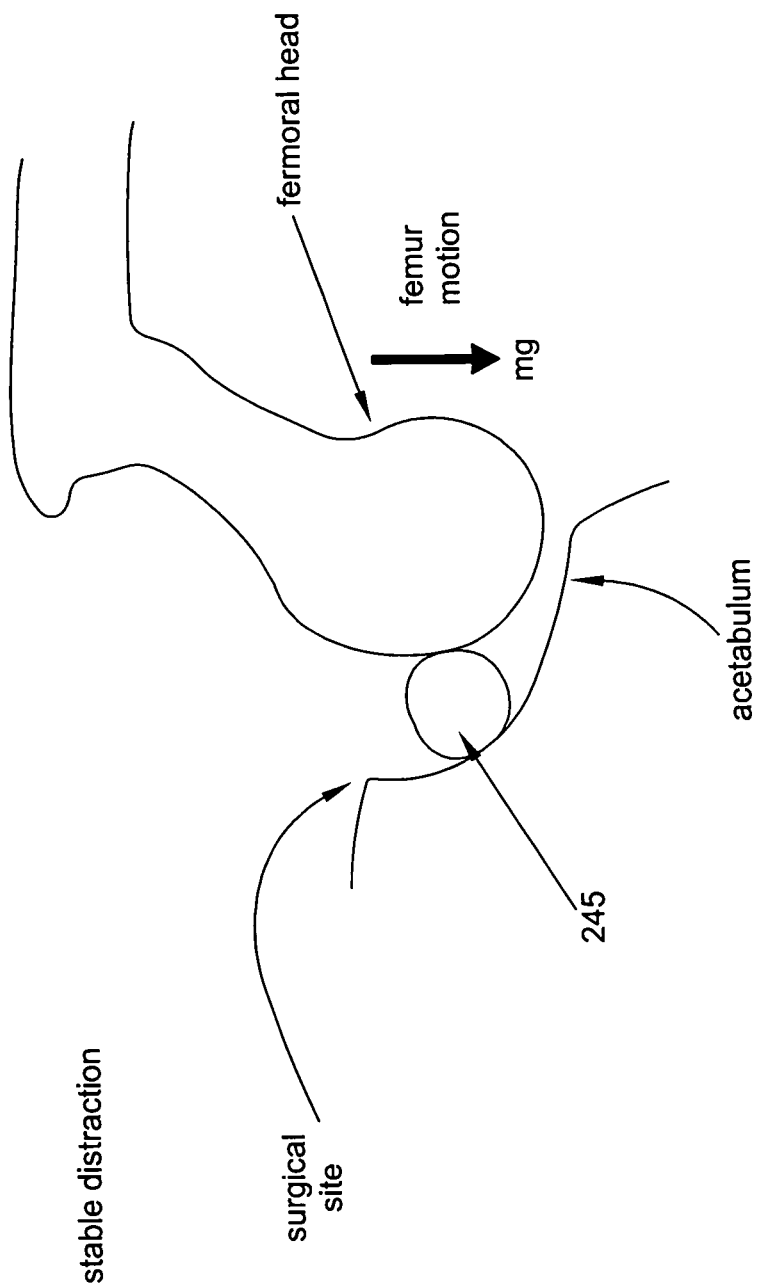
Figure 115:
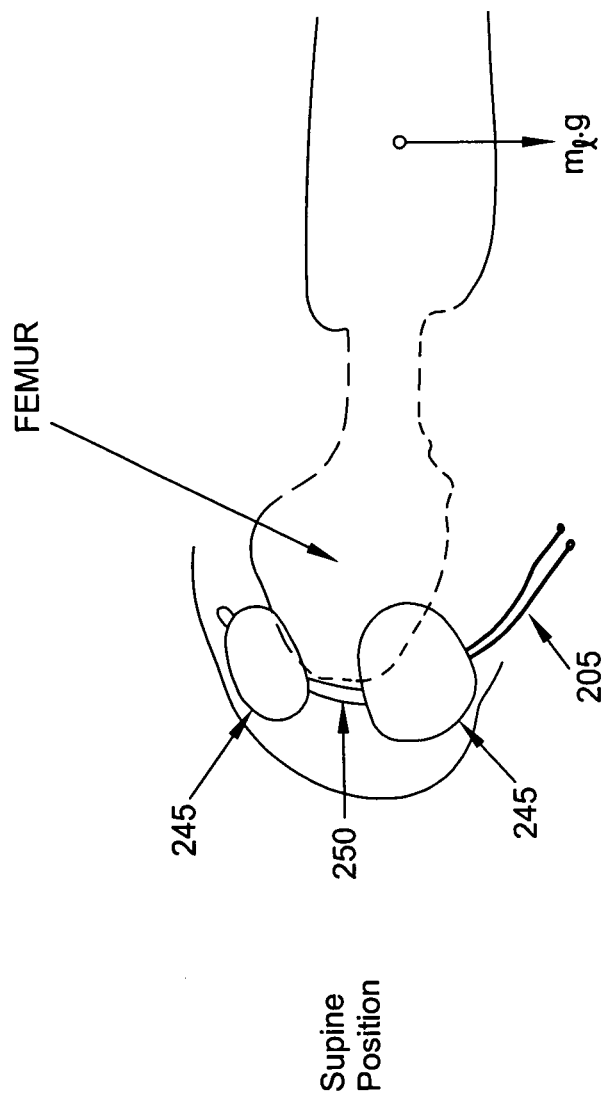

Among other things, when joint-spacing balloon catheter 200 is used with a patient in a lateral decubitus position (FIG. 113), the forces acting on the balloons after the external distraction has been released assist in creating stable distraction maintenance with excellent access to the labrum. More particularly, in this situation, gravity will force the femur downwardly and balloons 245 will force the femur distally, away from the labrum, in the manner shown in FIG. 114 (which is an anterior-posterior view of joint). Correspondingly, when joint-spacing balloon catheter 200 is used during a supine approach, the forces acting on the balloons after the external distraction has been released less reliably assist in creating stable distraction maintenance. More particularly, gravity will force the femur downwardly, and balloons 245 will force the femur distally, away from the labrum, in the manner shown in FIG. 115 (which is a lateral view of joint).

Figure 116:
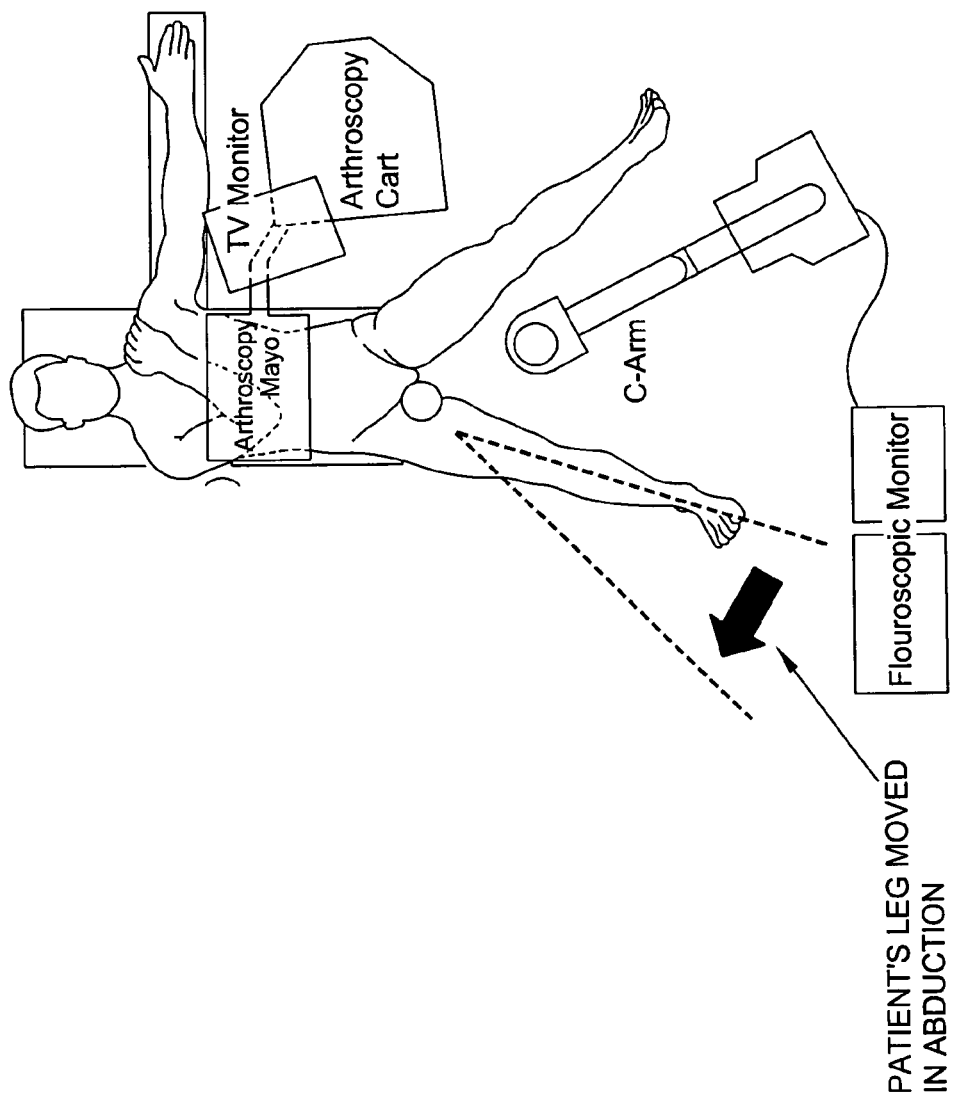
FIG. 116 is a schematic view showing abduction of the leg prior to release of the external traction.

In another preferred form of the invention, and looking now at FIG. 116, the patient's leg may be moved in abduction prior to releasing the external traction. This approach helps orient the femur so that it settles more securely onto the balloons 245 disposed in the acetabular cup when external distraction is released. It has been shown that this can more reliably assist in creating stable distraction maintenance with a patient situated in the supine position. Abducting the leg also displaces the leg off the perineal post which may partially or fully relieve any lateral force which the post may be placing on the leg and thus the femoral head (which could push the femoral head in a lateral direction and thereby reduce access to the labrum).

Visibility Under X-Ray

While it is anticipated that joint-spacing balloon catheter 200 will normally be set under direct visualization from an arthoscope, it is also desirable that the joint-spacing balloon catheter be visible under X-ray, since this will allow the user to confirm proper catheter placement before balloon inflation, and also confirm proper balloon seating as the external distraction is released. This is preferably achieved by forming some or all of elongated shaft 205 out of a material which is at least somewhat X-ray opaque. For example, the shaft 205 could comprise a plastic material filled with $BaSO_4$ (barium sulfate). In addition, some or all of one or both balloons 245 may also be formed out of a material which is at least somewhat X-ray opaque. By way of example but not limitation, a platinum O-ring (not shown) may be incorporated under the proximal end of the proximal balloon 245.

Method of Using Adjustable Balloon Inflation

Figure 117:
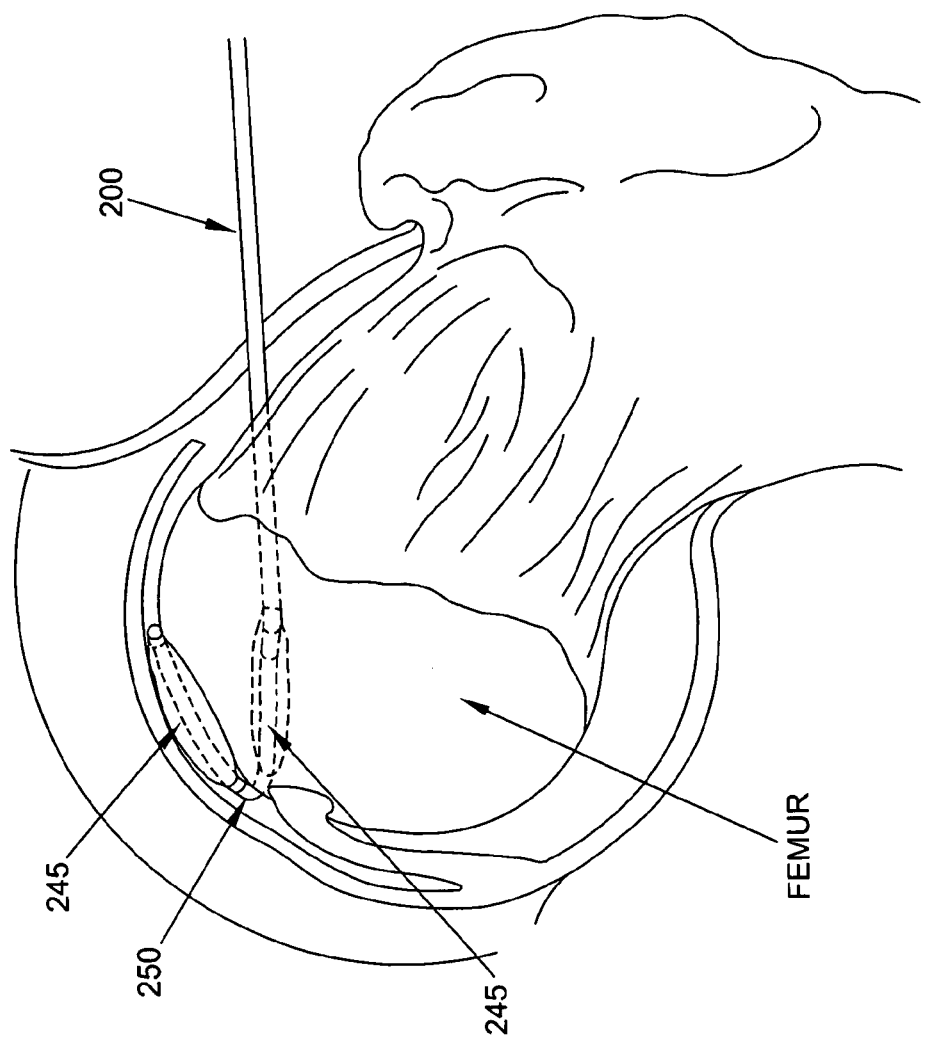
FIG. 117 is a schematic view showing intra-procedure deflation of the balloons of the joint-spacing balloon catheter in order to evaluate progress of the therapy.

It should be appreciated that balloons 245 do not need to remain completely inflated at all times during the surgery. For example, balloons 245 could be initially fully inflated prior to releasing the external distraction, and they could thereafter have their inflation adjusted so that they are thereafter only partially inflated, or they could be entirely deflated. This could be beneficial if, for example, the surgeon is performing labral refixation and wants to assess how well the labrum forms a suction seal with the femoral head. In this example, the surgeon would partially or fully deflate the balloons 245 (FIG. 117) so as to reduce or completely eliminate joint distraction. More particularly, by partial or full deflation of the balloons 245, the femoral head would settle back into the acetabular cup, enabling the surgeon to assess the repair and plan and/or perform additional refixation if necessary.

As has been disclosed, once the balloons 245 are inflated and external traction is released, the femur/leg can pivot on the balloons 245. This allows the surgeon to re-position the leg while maintaining distraction, something that is not possible with external traction because the patient's leg is secured to the traction table. In this respect it should be appreciated that the femoral head can also freely rotate on a partially or fully deflated balloons 245. This could be useful, for example, in diagnosing and treating femoroacetabular impingement (FAI). For example, if the surgeon is performing pincer decompression, with the joint-spacing balloon catheter 200 maintaining the joint space, the surgeon may want to assess whether further decompression is needed. By partially or fully deflating the balloons, the femoral head settles back into the acetabular cup. By then rotating the leg (for example, flexing and internally rotating), the surgeon can assess whether sufficient bone has been removed. The balloon can then be re-inflated to continue the decompression or other central compartment treatment.

Flexible/Rigid Shaft

Figure 118:
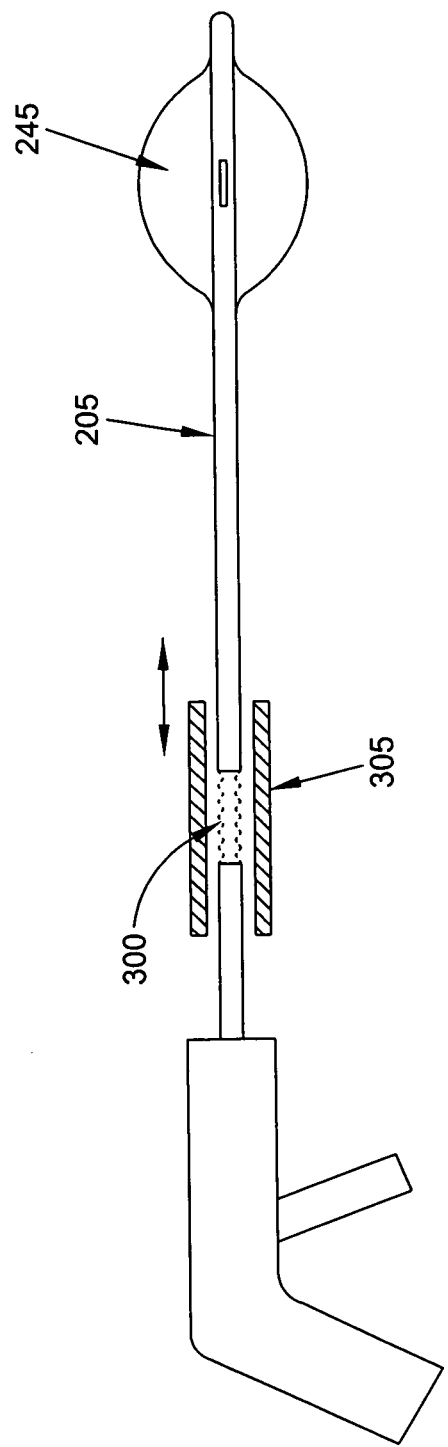
FIGS. 118 and 119 are schematic views showing a rigid/flexible shaft coupling in the proximal portion of the shaft to enable the handle to be selectively moved out of the way.
Figure 119:
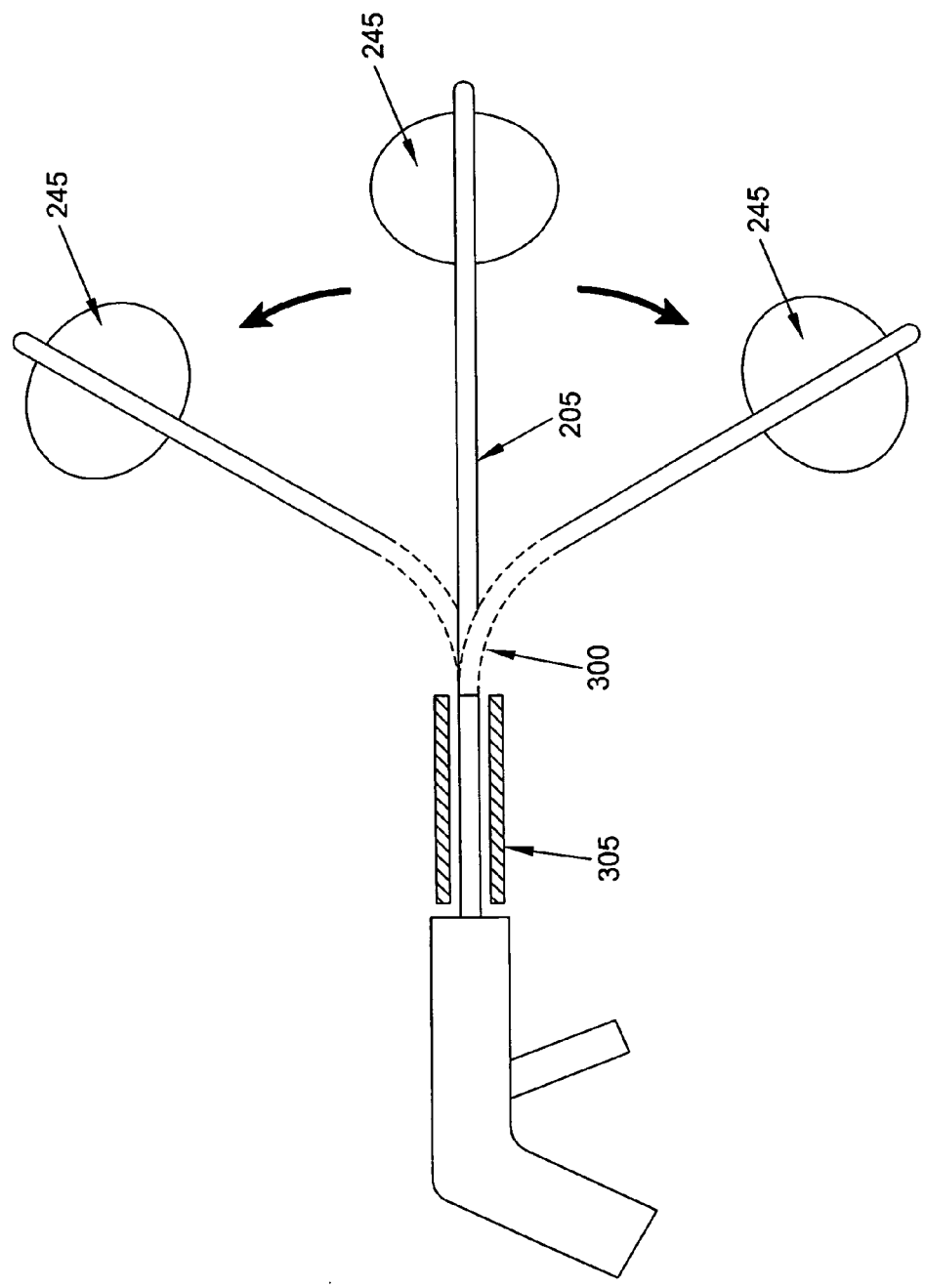

FIGS. 118 and 119 show another catheter construction. In this form of the invention, the proximal portion of elongated shaft 205 includes a flexible section 300 over which slides a rigid collar 305. When the rigid collar 305 is moved proximally away from the flexible section 300, the shaft can bend at the location of the flexible tube, however, when rigid collar 305 is set to span flexible section 300, elongated shaft 205 is rigid. A flexible/rigid shaft of the aforementioned sort can be highly advantageous in hip arthroscopy, since it enables the catheter to be in a rigid condition during entry into the joint so as to facilitate passage through intervening tissue, but then converted into a flexible condition so that the proximal (i.e., handle) end of the catheter can be moved out of the way during the surgery itself. By way of example but not limitation, in one form of the invention, the catheter is first rendered rigid and the distal end of the catheter is introduced into the joint; then the catheter is rendered flexible and the proximal end of the catheter is laid on the surgical drape adjacent to the portal so that the proximal end of the catheter is out of the way during surgery.

Figure 120:
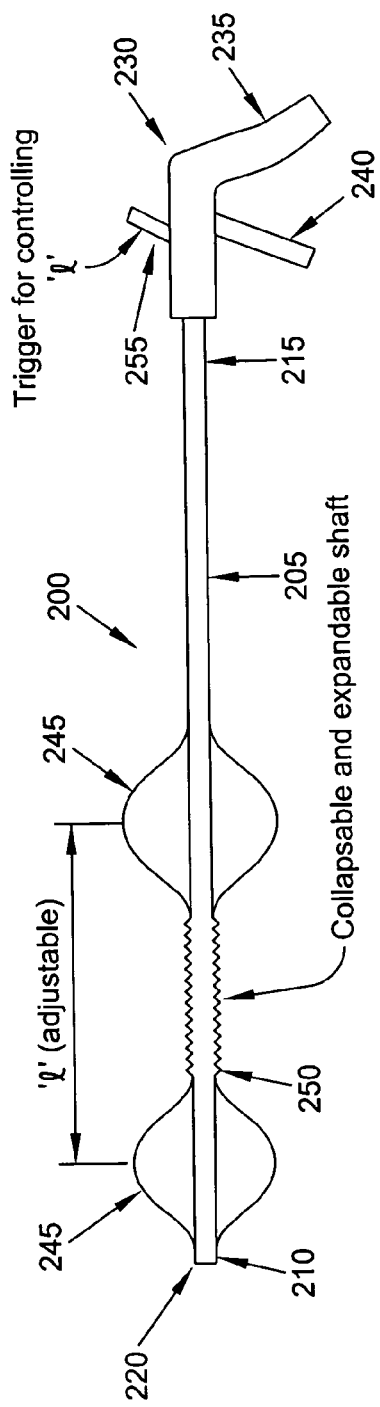
FIGS. 120 and 121 are schematic views showing a construction in which the distance between the two balloons is variable.
Figure 121:
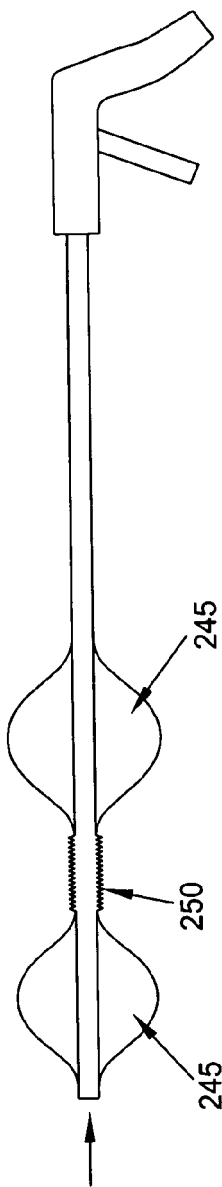

In one preferred form of the invention, the distance between the two balloons 245 is fixed. This distance is preferably 0.01" to 1.50", and more preferably 0.30" to 0.65". In another preferred form of the invention (FIGS. 120, 121), the portion 250 of elongated shaft 205 which is disposed between balloons 245 can vary in length. Such an arrangement can be extremely helpful in facilitating optimal placement of balloons 245 within the joint. For example, a larger joint size may require greater spacing between the two balloons 245. Other examples of situations where it may be desirable to adjust the spacing between balloons 245 may include anatomical variations of the joint like protrusio, profunda, etc. By way of example but not limitation, in one form of the invention, portion 250 of elongated shaft 205 is expandable/collapsible in the manner of a bellows (see FIGS. 120, 121), and in another form of the invention, portion 250 of elongated shaft 205 is telescoping in the manner of two concentric tubes, etc. Preferably a lever or plunger or other mechanism 255 (FIG. 120) is provided on handle 230 to permit the user to adjust the length of portion 250, whereby to set the spacing between balloons 245. Alternatively, the length of portion 250 can be self-adjusting once inside the joint, as balloons 245 and elongated shaft 205 are subjected to anatomical forces within the joint. In one such exemplary construction, portion 250 can comprise a spring-like element.

Tractionless Distraction of a Joint Using the Joint-Spacing Balloon Catheter In the preceding disclosure, the hip joint is initially distracted by external traction so as to create a space between the head of the femur and the acetabular cup, then the joint-spacing balloon catheter 5 is inserted (with its balloons in their deflated condition) into the space created between the head of the femur and the acetabular cup, then the balloons of the joint-spacing balloon catheter are inflated, and then the external traction is released so that the head of the femur settles down onto the inflated balloons.

However, it is also possible to use joint-spacing balloon catheter 5 to distract a joint without first requiring the use of external traction. In this approach, the joint-spacing balloon catheter 5 is inserted (with its balloons in their deflated condition) so that the deflated balloons are disposed between the head of the femur and the acetabular cup, and then the balloons are inflated so as to force the head of the femur away from the acetabular cup.

Figure 122:
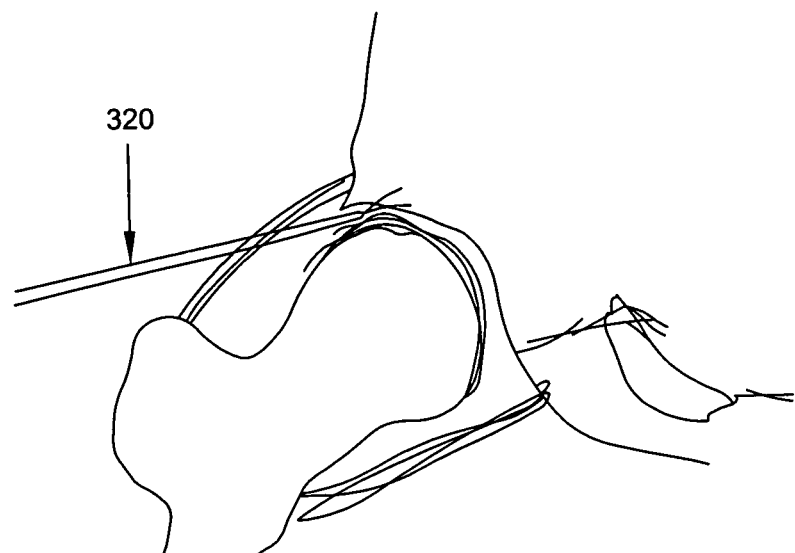
FIGS. 122 and 123 are schematic views showing how saline may be injected within the capsule of the joint, under pressure, so as to release the suction seal established by the labrum and thereby open the joint.
Figure 123:
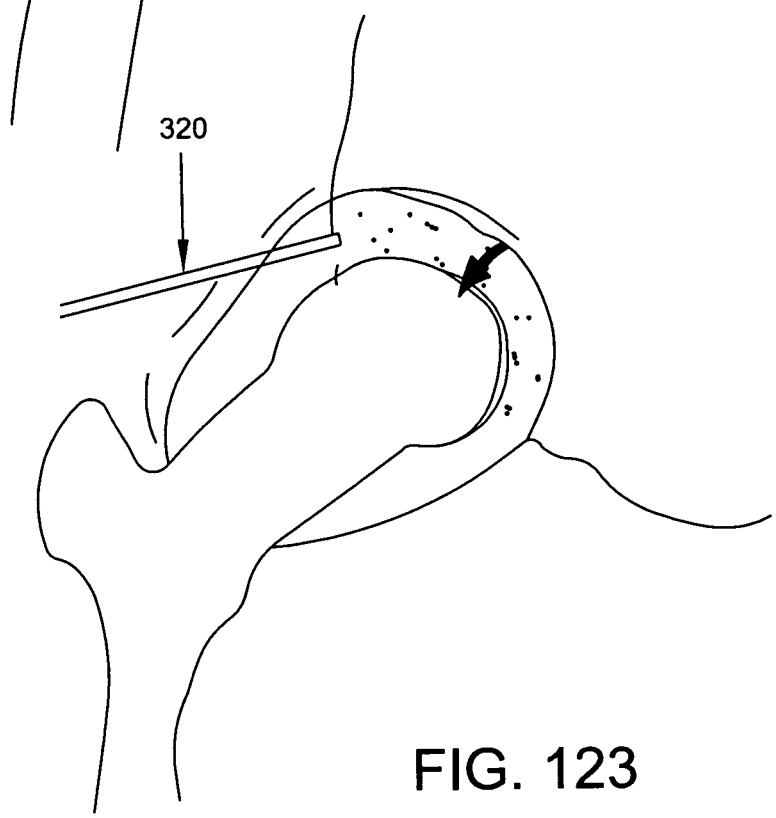

In order to facilitate positioning the joint-spacing balloon catheter 5 between the head of the femur and the acetabular cup, without first requiring the use of external traction to create a space between the head of the femur and the acetabular cup, it can be helpful to inject saline, under pressure, into the region inside of the capsule and outside of the labrum, whereby to release the suction seal created by the labrum and thereby open the joint. More particularly, in this form of the invention, and looking now at FIGS. 122 and 123, a needle 320 is inserted so that its distal end is located inside of the capsule, but outside of the labrum, and then saline is injected under pressure (preferably at about 10 psi). The pressurized saline passes between the labrum and the femur and fills the central compartment, thereby breaking (or disrupting) the suction seal created by the labrum and preferably creating a gap between the femoral head and acetabulum. The joint-spacing balloon catheter 5 may then be inserted (with its balloon(s) in its/their deflated condition) so that the deflated balloon(s) is/are disposed between the head of the femur and the acetabular cup, and then the balloon(s) is/are inflated so as to force the head of the femur away from the acetabular cup. It can be appreciated that more than one joint-spacing balloon catheter may be used to complete the full joint distraction. In one embodiment, a first joint-spacing balloon catheter 5 with a small balloon is inserted and inflated, followed by a second joint-spacing balloon catheter 5 with a larger balloon which is inserted and inflated. Thus each subsequent joint-spacing balloon catheter 5 incrementally opens the joint a greater distance.

In addition to the foregoing, the leg of the patient can be manipulated so as to create a gap between the head of the femur and the acetabular cup, and this gap can be used to insert joint-spacing balloon catheter 5 into the central compartment without first applying external traction. More particularly, moving the leg of the patient places tension on some ligaments and reduces tension on other ligaments. The direction in which the leg is manipulated will determine which ligaments are tensed and which ligaments are relaxed, and hence will determine where the gap is created about the rim of the acetabular cup. By way of example but not limitation, (i) flexion relaxes the anterior and lateral ligaments of the capsule, (ii) extension tenses the anterior and lateral ligaments of the capsule, (iii) internal rotation relaxes the anterior and lateral ligaments of the capsule (and opens anterior joint space), and (iv) external rotation tenses the anterior and lateral ligaments of the capsule (and closes the anterior joint space and opens the posterior joint space).

Use of the Present Invention for Other Applications

It should be appreciated that the present invention may be used for distracting the hip joint in an open, more invasive procedure. The present invention can also be used in hip joint pathologies where joint distraction is not needed but space creation is needed, e.g., to visualize and/or to address pathologies in the peripheral compartment or pathologies in the peritrochanteric space. Additionally, the present invention may be used for distracting joints other than the hip joint (e.g., it may be used to distract the shoulder joint).

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for creating space in a joint formed at the convergence of two bones, the method comprising: applying force to a body part at a location remote from the joint so as to separate the two bones from one another by a distance which is greater than the distance that they are normally separated from one another when the joint is in a healthy state, whereby to distract the joint and create an intrajoint space; inserting an assembly of three balloons into the intrajoint space while the assembly of three balloons is in a contracted condition; expanding the assembly of three balloons within the intrajoint space; and reducing the force applied to the body part at the location remote from the joint so that the joint is supported on the assembly of three balloons, with the two bones remaining separated from one another by a distance which is greater than the distance that they are normally separated from one another when the joint is in a healthy state.

2. A method according to claim 1 wherein the two bones move substantially toward one another when the force applied to the body part is reduced.

3. A method according to claim 1 wherein the two bones do not move substantially toward one another when the force applied to the body part is reduced.

4. A method according to claim 1 including the further step of performing a surgical procedure on the joint after the force applied to the body part has been reduced.

5. A method according to claim 1 including the further step of moving the body part after the force applied to the body part has been reduced, so that the joint articulates on the assembly of three balloons.

6. A method according to claim 5 including the additional step of performing a surgical procedure on the joint after the joint articulates on the assembly of three balloons.

7. A method according to claim 1 wherein the assembly of three balloons comprises a shaft.

8. A method according to claim 1 wherein the portions of the shaft located between the three balloons are flexible.

9. A method according to claim 8 wherein the joint comprises the hip joint, and further wherein the shaft is disposed in the hip joint so that one of the three balloons is located substantially in the acetabular fossa.

10. A method according to claim 8 wherein the portions of the shaft located between the three balloons bend when the force applied to the body part is reduced.

11. A method according to claim 8 wherein the portions of the shaft located between the three balloons are bent before the force applied to the body part is reduced.

12. A method according to claim 11 wherein the portions of the shaft located between the three balloons are bent by steering the distal end of the shaft.

13. A method according to claim 1 wherein a distalmost balloon is disposed in a location adjacent to a rim of the joint space.

14. A method for treating a patient, the method comprising: applying force to a body part at a location remote from a Joint so as to separate two bones from one another by a distance which is greater than distance that they are normally separated from one another when the joint is in a healthy state, whereby to distract the joint and create an joint space; providing a balloon catheter comprising a shaft having a distal tip and a balloon mounted to the shaft proximal to the distal tip; inserting the balloon into a joint space while the balloon is in a contracted condition; securing the distal tip of the shaft to a portion of the shaft proximal to the balloon; expanding the balloon within the joint space; and reducing the force applied to the body part at the location remote from the joint so that the joint is supported on the balloon, with the two bones remaining separated from one another by a distance which is greater than the distance that they are normally separated from one another when the joint is in a healthy state.

15. A method according to claim 14 wherein the distal tip of the shaft is releasably secured to the portion of the shaft proximal to the balloon.

16. A method according to claim 14 wherein the balloon comprises a substantially cylindrical shape, and further wherein the balloon assumes a substantially toroidal shape when the distal tip of the shaft is releasably secured to the portion of the shaft proximal to the balloon.

17. A method according to claim 14 wherein the shaft is steerable.

* * * * *